US011312668B2

(12) United States Patent
Braje et al.

(10) Patent No.: US 11,312,668 B2
(45) Date of Patent: *Apr. 26, 2022

(54) ORGANIC REACTIONS CARRIED OUT IN AQUEOUS SOLUTION IN THE PRESENCE OF A HYDROXYALKYL(ALKYL)CELLULOSE OR AN ALKYLCELLULOSE

(71) Applicants: AbbVie Deutschland GmbH & Co. KG, Wiesbaden (DE); AbbVie Inc., North Chicago, IL (US)

(72) Inventors: Wilfried Braje, Ludwigshafen (DE); Katarina Britze, Ludwigshafen (DE); Justin D. Dietrich, North Chicago, IL (US); Anais Jolit, Ludwigshafen (DE); Johannes Kaschel, Ludwigshafen (DE); Johanna Klee, Ludwigshafen (DE); Tanja Lindner, Ludwigshafen (DE)

(73) Assignees: ABBVIE INC., North Chicago, IL (US); ABBVIE DEUTSCHLAND GMBH & CO. KG, Wiesbaden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/060,801

(22) Filed: Oct. 1, 2020

(65) Prior Publication Data

US 2021/0017100 A1   Jan. 21, 2021

Related U.S. Application Data

(63) Continuation of application No. 16/742,523, filed on Jan. 14, 2020, now Pat. No. 10,836,688, which is a
(Continued)

(30) Foreign Application Priority Data

Feb. 16, 2016  (WO) ................. PCT/EP2016/053238

(51) Int. Cl.

| | | |
|---|---|---|
| C07D 213/74 | (2006.01) |
| C07D 215/227 | (2006.01) |
| C07D 239/26 | (2006.01) |
| C07D 239/42 | (2006.01) |
| C07D 307/36 | (2006.01) |
| C07D 307/81 | (2006.01) |
| C07D 311/58 | (2006.01) |
| C07D 405/04 | (2006.01) |
| C07D 409/04 | (2006.01) |
| C07D 471/04 | (2006.01) |
| C07D 495/04 | (2006.01) |
| C07B 63/04 | (2006.01) |
| C07B 43/06 | (2006.01) |
| C07F 5/02 | (2006.01) |
| C07B 43/04 | (2006.01) |
| C07B 37/04 | (2006.01) |
| C07C 41/46 | (2006.01) |
| C07C 67/62 | (2006.01) |
| C07C 209/90 | (2006.01) |
| C07C 213/10 | (2006.01) |
| C07C 231/22 | (2006.01) |
| C07C 253/32 | (2006.01) |
| C07C 269/08 | (2006.01) |
| C07C 273/18 | (2006.01) |
| C07C 303/42 | (2006.01) |
| C07C 319/26 | (2006.01) |
| C07D 205/04 | (2006.01) |
| C07D 207/34 | (2006.01) |

(Continued)

(52) U.S. Cl.
CPC .............. *C07B 63/04* (2013.01); *C07B 37/04* (2013.01); *C07B 43/04* (2013.01); *C07B 43/06* (2013.01); *C07C 41/46* (2013.01); *C07C 67/62* (2013.01); *C07C 209/90* (2013.01); *C07C 213/10* (2013.01); *C07C 231/22* (2013.01); *C07C 253/32* (2013.01); *C07C 269/08* (2013.01); *C07C 273/189* (2013.01); *C07C 303/42* (2013.01); *C07C 319/26* (2013.01); *C07D 205/04* (2013.01); *C07D 207/34* (2013.01); *C07D 209/08* (2013.01); *C07D 209/48* (2013.01); *C07D 211/06* (2013.01); *C07D 213/74* (2013.01); *C07D 215/227* (2013.01); *C07D 239/26* (2013.01); *C07D 239/42* (2013.01); *C07D 307/36* (2013.01); *C07D 307/81* (2013.01); *C07D 311/58* (2013.01); *C07D 405/04* (2013.01); *C07D 409/04* (2013.01); *C07D 471/04* (2013.01); *C07D 495/04* (2013.01); *C07F 5/02* (2013.01); *C07F 5/025* (2013.01)

(58) Field of Classification Search
None
See application file for complete search history.

(56) References Cited

U.S. PATENT DOCUMENTS 10,836,688 B2 * 11/2020 Braje .................... C07C 269/08

OTHER PUBLICATIONS

Azetsu A., et al., "Synthesis and Catalytic Features of Hybrid Metal Nanoparticles Supported on Cellulose Nanofibers," Catalysts, 2011, vol. 1 (1), pp. 83-96.
(Continued)

*Primary Examiner* — Joseph R Kosack
(74) *Attorney, Agent, or Firm* — Neal, Gerber & Eisenberg LLP

(57) ABSTRACT

The present invention relates to a method of carrying out an organic reaction in aqueous solution in the presence of a hydroxyalkyl(alkyl)cellulose or an alkylcellulose.

40 Claims, No Drawings

Related U.S. Application Data continuation of application No. 16/434,900, filed on Jun. 7, 2019, now abandoned, which is a continuation of application No. 15/417,806, filed on Jan. 27, 2017, now abandoned.

(60) Provisional application No. 62/288,890, filed on Jan. 29, 2016.

(51) Int. Cl.
 C07D 209/08 (2006.01)
 C07D 209/48 (2006.01)
 C07D 211/06 (2006.01)

(56) References Cited

OTHER PUBLICATIONS

Baruah D., et al., "Cellulose Supported Copper Nanoparticles as a Versatile and Efficient Catalyst for the Protodecarboxylation and Oxidative Decarboxylation of Aromatic Acids Under Microwave Heating," Catalysis Communications, Sep. 5, 2015, vol. 69, pp. 68-71.

Baruah D., et al., "Cu-Nanoparticles on Cellulose/H2O-CH3CN/microwave: A Green System for the Selective Oxidation of Alcohols to Aldehydes," Tetrahedron Letters, May 13, 2015, vol. 56 (20), pp. 2543-2547.

Baruah D., et al., "Deprotection of Oximes, Imines, and Azines to the Corresponding Carbonyls Using Cu-nanoparticles on Cellulose Template as Green Reusable Catalyst," RSC Advances, 2014, vol. 4, p. 59338-59343.

Bhardwaj M., et al., "Novel Heterogeneous Catalyst Systems Based on Pd(0) Nanoparticles Onto Amine Functionalized Silica-cellulose Substrates [pd(0)-eda/scs]: Synthesis, Characterization and Catalytic Activity Toward C—C and C—S Coupling Reactions in Water Under Limiting Basic Conditions," Journal of Molecular Catalysis A: Chemical, Nov. 2015, vol. 408, pp. 48-59.

Chavan P.V., et al., "Cellulose Supported Cuprous Iodide Nanoparticles (Cell-cui Nps): A New Heterogeneous and Recyclable Catalyst for the One Pot Synthesis of 1,4-disubstituted-1,2,3-triazoles in Water," RSC Advances, 2014, vol. 4, p. 42137-42146.

Faria V.W., et al., "Palladium Nanoparticles Supported in a Polymeric Membrane: An Efficient Phosphine-free "green" Catalyst for Suzuki-miyaura Reactions in Wate," RSC Advances, 2014, vol. 4, p. 13446-13452.

Harrad M.A., et al., "Colloidal Nickel(0)-carboxymethyl Cellulose Particles: A Biopolymer-inorganic Catalyst for Hydrogenation of Nitro-aromatics and Carbonyl Compounds," Catalysis Communications, Feb. 5, 2013, vol. 32, pp. 92-100.

Huang J.L., et al., "A3-coupling Catalyzed by Robust Au Nanoparticles Covalently Bonded to HS-functionalized Cellulose Nanocrystalline Films," Beilstein Journal of Organic Chemistry, 2013, vol. 9, pp. 1388-1396.

International Search Report and Written Opinion for Application No. mailed on PCT/EP2017/051858, dated Mar. 17, 2017, 6 pages.

Jamwal N., et al., "Nano Pd(0) Supported on Cellulose: A Highly Efficient and Recyclable Heterogeneous Catalyst for the Suzuki Coupling and Aerobic Oxidation of Benzyl Alcohols Under Liquid Phase Catalysis," International Journal of Biological Macromolecules, Dec. 1, 2011, vol. 49 (5), pp. 930-935.

Keshipour S., et al., "Palladium Nano-particles Supported on Ethylenediamine-functionalized Cellulose as a Novel and Efficient Catalyst for the Heck and Sonogashira Couplings in Water," Cellulose, Apr. 2013, vol. 20 (2), pp. 973-980.

Lam E., et al., "Catalysis Using Gold Nanoparticles Decorated on Nanocrystalline Cellulose," Nanoscale, 2012, vol. 4, pp. 997-1002.

Lipshutz B.H., et al., "TPGS-750-M: A Second-Generation Amphiphile for Metal-Catalyzed Cross-Couplings in Water at Room Temperature," The Journal of Organic Chemistry, Jun. 3, 2011, vol. 76 (11), pp. 4379-4391.

Lipshutz B.H., et al., "Transitioning Organic Synthesis From Organic Solvents to Water. What's Your E Factor?," Green Chemistry, Aug. 1, 2014, vol. 16 (8), pp. 3660-3679.

Xiao J., et al., "Carboxymethylcellulose-supported Palladium Nanoparticles Generated in Situ From Palladium(Ii) Carboxymethylcellulose: An Efficient and Reusable Catalyst for Suzuki-miyaura and Mizoroki-heck Reactions," Applied Organometallic Chemistry, Sep. 2015, vol. 29 (9), pp. 646-652.

Zhang H., et al., "An Aqueous-phase Catalytic Process for the Selective Hydrogenation of Acetylene With Monodisperse Water Soluble Palladium Nanoparticles as Catalyst," Catalysis Science & Technology, 2012, vol. 7, pp. 1319-1323.

* cited by examiner

ORGANIC REACTIONS CARRIED OUT IN AQUEOUS SOLUTION IN THE PRESENCE OF A HYDROXYALKYL(ALKYL)CELLULOSE OR AN ALKYLCELLULOSE

CROSS-REFERENCE TO RELATED APPLICATIONS

This application is a continuation of U.S. patent application Ser. No. 16/742,523, filed Jan. 14, 2020, which is a continuation of U.S. patent application Ser. No. 16/434,900, filed Jun. 7, 2019, which is a continuation of U.S. patent application Ser. No. 15/417,806, filed Jan. 27, 2017, which claims the benefit of U.S. Patent Application No. 62/288,890, filed Jan. 29, 2016, and International Patent Application No. PCT/EP2016/053238, filed Feb. 16, 2016, the contents of all of which are fully incorporated herein by reference.

FIELD OF THE INVENTION

The present invention relates to a method of carrying out an organic reaction in aqueous solution in the presence of a hydroxyalkyl(alkyl)cellulose or an alkylcellulose.

BACKGROUND OF THE INVENTION

With the growing concern for environmental protection, chemical synthesis and process chemistry are increasingly scrutinized with respect to sustainability. The term "green chemistry" illustrates the goal to provide a more resource-efficient and inherently safer design of molecules, materials, products, and processes. One goal is to provide chemical processes which minimize the use of substances which do not origin from renewable sources and/or cause disposal problems. Especially reducing or avoiding the use of organic solvents is the primary objective, as these account for the major part of the feedstock used in many chemical processes. Most organic solvents are of mineral origin and thus not from a renewable source. They are rather expensive, not only because of their production costs, but also because of the costs related with their disposal. They often pose significant risks to the environment and humans handling them, being mostly flammable or even explosive, and need to be handled and stored with precaution.

Many efforts have therefore been made to replace at least a part of the organic solvents with water. Water is readily available, cheap, neither flammable nor explosive, and non-toxic. Unfortunately however, it has only poor solubility for most organic compounds, so that reaction times and yields are generally inefficient. Many reactants agglomerate in aqueous medium, which hampers their efficient reaction and makes their processing, especially stirring, difficult.

To enhance conversion rates and reduce reaction times in aqueous medium, surfactants and emulsifiers are often used. Lipshutz and coworkers developed surfactants based on polyoxyethanyl-α-tocopheryl succinate (TPGS-750-M and TPGS-1000) or sebacate (PTS-600) which in aqueous solution forms micelles in which organic reactions can take place. TPGS-750-M, which is the most promising, is a polyoxyethanyl-α-tocopheryl succinate derivative of following formula:

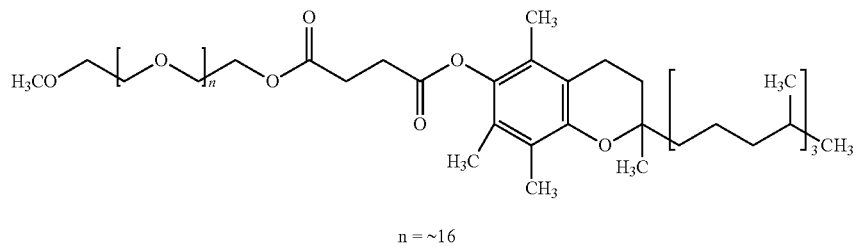

n = ~16

The use of these micelle-forming surfactants is described, for example, in J. Org. Chem., 2011, 76 (11), 4379-4391 or Green Chem. 2014, 16, 3660-3679, where the authors report the performance of various reactions, including Heck, Suzuki-Miyaura, Sonogashira, and Negishi-like couplings, as well as aminations, C—H activations, and olefin metathesis reactions in water in the presence of TPGS-750-M.

While the results obtained with this surfactant are impressive, TPGS-750-M as well as the other polyoxyethanyl-α-tocopheryl derivatives are a rather expensive and sophisticated material. Moreover, they tend to agglomerate in the aqueous reaction medium, which hampers the efficient reaction of the reactants and makes their processing, especially stirring, difficult.

Cellulose and its derivatives are inexpensive and biodegradable. Organic reactions in water catalyzed by a transition metal and carried out in the presence of cellulosic material have been reported.

Cellulose as such is not water-soluble or swellable and thus cannot act as a surfactant. It is used as carrier for transition metal catalysts; see for example Baruah et al., Catalysis Commun. 2015, 69, 68-71, where cellulose-supported copper nanoparticles are used as a catalyst for the protodecarboxylation and oxidative decarboxylation of aromatic acids; water or acetonitrile being used as solvents;

Baruah et al., Tetrahedron Lett. 2015, 56, 2543-2547, where cellulose-supported copper nanoparticles are used as a catalyst for the selective oxidation of alcohols to aldehydes; water or acetonitrile being used as solvents;

Baruah et al., RSC Adv. 2014, 4, 59338-59343, where cellulose-supported copper nanoparticles are used as a catalyst for the deprotection of oximes, imines and azines to carbonyl; water being used as solvent;

Chavan et al., RSC Adv. 2014, 4, 42137-42146, where cellulose-supported CuI nanoparticles are used as a catalyst for the one-pot synthesis of 1,4-disubstituted 1,2,3-triazoles in water; and Jamwal et al., Internat. J. Biol. Macromolecules 2011, 49, 930-935, where cellulose-supported Pd(0) is used as a catalyst for Suzuki coupling and aerobic oxidation of benzyl alcohols in water.

Modified celluloses are also used as carriers for transition metal catalysts; see for example

- Bhardwaj et al., where Pd(0) nanoparticles supported on ethylene diamine functionalized silica cellulose is used as a catalyst for C—C and C—S coupling reactions in water;
- Faria et al., RSC Adv. 2014, 4, 13446-13452, where cellulose acetate-supported Pd(0) nanoparticles are used as a catalyst for Suzuki reactions in water,
- Xiao et al., Appl. Organometal Chem. 2015, 29, 646-652, where carboxymethyl cellulose-supported Pd nanoparticles are used as a catalyst for Suzuki and Heck couplings in water;
- Huang et al., Beilstein J. Org. Chem. 2013, 9, 1388-1396, where Au nanoparticles covalently bonded to thiol-functionalized nanocrystalline cellulose films are used as a catalyst for $A^3$ coupling in water;
- Keshipour et al., Cellulose 2013, 20, 973-980, where Pd(0) nanoparticles supported on ethylene diamine functionalized cellulose is used as a catalyst for Heck and Sonogashira couplings in water;
- Harrad et al., Catalysis Commun. 2013, 32, 92-100, where colloidal Ni(0) carboxymethyl cellulose particles are used as a catalyst for hydrogenation of nitro aromatic compounds and carbonyl compounds in aqueous medium;
- Zhang et al., Catal. Sci. Technol. 2012, 2, 1319-1323, where sodium carboxymethyl cellulose-stabilized Pd is used as a catalyst for the selective hydrogenation of acetylene in water;
- Azetsu et al., Catalysis 2011, 1, 83-96, where Au/Pd bimetallic nanoparticles supported on TEMPO-oxidized cellulose nanofibers are used as a catalyst in the aqueous reduction of 4-nitrophenol; and
- Lam et al., Nanoscale 2012, 4, 997, where Au nanoparticles supported on poly(diallyldimethylamoniumchloride)-coated nanocrystalline cellulose are used as a catalyst in the aqueous reduction of 4-nitrophenol.

These documents do however not use the modified celluloses as surfactants.

It was the object of the present invention to provide a surfactant which allows the performance of organic reactions in water with good yields and short reaction times, but which is less expensive than TPGS-750-M and the other polyoxyethanyl-α-tocopheryl derivatives described above, and which is readily available. Moreover, this surfactant should not be restricted to the application in transition metal-catalyzed reactions, but should be widely applicable. Furthermore, the surfactant should be easily separable from the reaction medium after completion of the reaction.

The present invention is based on the finding that hydroxyalkyl(alkyl)celluloses and alkylcelluloses solve this task.

SUMMARY OF THE INVENTION

The invention relates to a method of carrying out an organic reaction in a solvent containing at least 90% by weight, in particular at least 97% by weight, based on the total weight of the solvent, of water, which method comprises reacting the reagents in said solvent in the presence of a cellulose derivative which is selected from the group consisting of cellulose modified with one or more alkylene oxides or other hydroxyalkyl precursors, and alkylcellulose; where the organic reaction is not a polymerization or oligomerization reaction of olefinically unsaturated compounds.

The invention also relates to the use of a cellulose derivative which is selected from the group consisting of cellulose modified with one or more alkylene oxides or other hydroxyalkyl precursors, and alkylcellulose, as a surfactant in organic reactions carried out in a solvent containing at least 90% by weight, in particular at least 97% by weight, based on the total weight of the solvent, of water, where the organic reactions are not a polymerization or oligomerization reaction of olefinically unsaturated compounds.

DETAILED DESCRIPTION

The below remarks and details of suitable and preferred or particular embodiments of the method of the invention are valid both alone, taken per se, and in particular in any conceivable combination with one another.

"Carrying out an organic reaction in a solvent containing at least 90% by weight, in particular at least 97% by weight, based on the total weight of the solvent, of water" means that at least the principal reaction step of the organic reaction is carried out in said aqueous medium. The aqueous medium is not limited to be used in a work-up or purification or separation step.

Work-up, separation and purification can however encompass the use of organic solvents.

The term "organic reaction" relates to all types of chemical reactions involving at least one organic compound. Organic compounds in turn are gaseous, liquid, or solid chemical compounds whose molecules contain carbon. Exceptions are carbides, carbonates (in the sense of salts of carbonic acid), carbon oxides (CO and $CO_2$), and cyanides (in the sense of salts of HCN), which for historical reasons are considered as inorganic. The basic types of organic reactions are addition reactions, elimination reactions, substitution reactions, pericyclic reactions, rearrangement reactions, photochemical reactions and redox reactions. Further details will become evident in the detailed description below.

In terms of the present invention, the organic reactions do not include polymerization or oligomerization reactions of olefinically unsaturated compounds, such as the polymerization of olefins (e.g. ethylene) to polyolefins (e.g. polyethylene), of acrylic acid (esters) to polyacrylates etc. In particular, in the present invention, the organic reactions do not include any type of polymerization or oligomerization, be it the polymerization of olefinically unsaturated molecules, polycondensations (like the formation of polyesters from diols and diacids or derivatives thereof, or of polyamides from diamines and diacids or derivatives thereof), or polyadditions (like the formation of polyurethanes). Polymerizations are reactions in which polymers are formed. Polymers in turn are high molecular mass compounds formed by polymerization of monomers and contain repeating units of the same or similar structure. In terms of the present invention, polymers are compounds formed of at least 11 monomers in polymerized form. Oligomers, too, are formed by polymerization of monomers and contain repeating units of the same or similar structure. They differ from polymers in being shorter-chained. In terms of the present invention, oligomers contain 3 to 10 monomers in polymerized form.

Organic reactions which do not include any polymerization or oligomerization reaction yield compounds with a discrete (i.e. well-defined) molar mass. In contrast thereto, oligomers and polymers do not have a discrete molar mass, but a mass distribution. The ratio of weight-average molecular weight and number average molecular weight $M_w/M_n$ for polymers and oligomers is >1. Thus, the particular embodiment of the present method which excludes any type of polymerization or oligomerization, yields compounds with a well-defined molar mass, and not with a molar mass distribution.

Apart from not including polymerization and oligomerization reactions of olefinically unsaturated compounds and especially not including any type of polymerization and oligomerization reactions at all, one other limiting factor imposed to the organic reactions which can be used in the method of the present invention is reactants, intermediates and products which are too hydrolabile, i.e. which are too easily deteriorated (e.g. hydrolyzed) by water to give satisfactory yields (as compared to non-aqueous systems) under the given reaction conditions. Thus, the present method does not include organic reactions using or yielding compounds which are easily deteriorated by water under the given reaction conditions. It has has however to be noticed that not all reactions usually known to use or yield hydrolabile compounds are excluded: Surprisingly, the method of the invention leads to good yields in a number of reactions which a skilled person would normally have carried out under the exclusion of water. Another limiting factor imposed to the organic reactions which can be used in the method of the present invention is reaction temperatures distinctly below 0° C. (it has to be mentioned that the addition of salts such as NaCl may allow to carry out the reactions at temperatures somewhat below 0° C. as they lower the freezing point, e.g. to as low as −5° C. or even −10° C.) as well as above the gelling or gelation point of the cellulose derivative used (if this has a gelation point at all) under the respective reaction conditions (especially concentration of the cellulose derivative). When the solutions of certain cellulose derivatives heat up to a critical temperature, the solutions congeal into a non-flowable, semi-flexible mass and the reactions cannot proceed in an optimum way. Thus, the present method does not include organic reactions mandatorily and inevitably requiring reaction temperatures of distinctly below 0° C. (i.e. of below −10° C. or in particular of below −5° C. or specifically of below 0° C.) or above the gelling point of the cellulose derivative used (of course only if the respective cellulose derivative has a gelling point under the given reaction conditions, especially the concentration in which the cellulose derivative is used).

"Solvent" is a liquid substance that dissolves a solute (a chemically different liquid, solid or gas), resulting in a solution. In terms of the present invention, the solvent is not restricted to a compound or medium which dissolves the reagents in the proper sense: This compound or medium may be more generally a dispersing medium, and thus the "solution" might be a suspension, emulsion or solution in the proper sense (solution in the proper sense being a homogeneous mixture composed of two or more substances, where the particles of the solute cannot be seen by naked eye and which does not scatter light).

As a matter of course, the term "solvent" in the terms of the present invention does not include the stoichiometric amounts of liquid reactants (i.e. those amounts theoretically needed for the reaction with respect to the amount of the other reactant(s)) which may principally act as a solvent for other reagent(s). By way of example, in a Heck reaction of 1 mole of chlorobenzene and 1 mole of methylacrylate, chlorobenzene may principally act as solvent for the acrylate. However, this 1 mole of chlorobenzene is not considered as belonging to the solvent in the terms of the present invention and thus is not part of the 10% by weight or in particular 3% by weight of the solvent which may be different from water. The term "solvent" in the terms of the present invention does moreover not include the excess amount of any liquid reactant which may principally act as a solvent for other reagent(s). For instance, if in the above example chlorobenzene is used in excess, for example here in an amount of 1.2 mole, this excess of 0.2 mole is not considered as part of the solvent, although chlorobenzene may principally act as solvent for the acrylate, and thus is not part of the 10% by weight or in particular 3% by weight of the solvent which may be different from water. See however the below restrictions.

The term "solvent" in the terms of the present invention does furthermore not include auxiliary reagents (other than reactants; i.e. reagents which do not appear in the net reaction equation) which are liquid and can principally act as solvents, such as liquid bases (e.g. liquid amines or basic N-heterocycles, e.g. triethylamine, pyridine or lutidine). See however the below restrictions.

If the solvent contains, apart from water, a supplementary solvent, this is usually present because it is necessary for bringing one or more reagents into the reaction vessel, e.g. if these are oily and stick to the container in which they are kept before being introduced into the reaction. The supplementary solvent is generally chosen for its property to bring the reagent(s) into the reaction vessel and of course for being inert in the reaction mixture, i.e. for not interfering with the desired reaction. Generally, water miscible solvents which do not interfere with the reaction are preferred. Examples are protic solvents, such as $C_1$-$C_3$-alkanols, e.g. methanol, ethanol, propanol or isopropanol, or glycols, such as ethylene glycol, diethylene glycol, triethylene glycol or polyethyleneglycol, and polar aprotic solvents, such as N,N-dimethylformamide (DMF), N,N-dimethylacetamide (DMA), dimethylsulfoxide (DMSO), tetrahydrofuran (THF), 1,4-dioxane, acetone, methylethylketone or acetonitrile. If these polar solvents are however not useful for the intended purpose, i.e. for bringing the reagents into the reaction vessel, less polar solvents can be used, too.

In some very few instances the presence of a supplementary solvent might be useful for improving the yield of the reaction. In such cases the solvent can be selected from any solvent type useful for the specific surface.

These supplementary solvents are of course used in such an amount that their amount does not exceed 10% by weight, preferably does not exceed 3% by weight, of the total weight solvent (composed of water and optionally said supplementary solvent).

The term "solvent" in the terms of the present invention is thus restricted to water and optionally another solvent which is inert in the reaction and generally has no other role but to bring one or more reagents into the reaction vessel.

In particular, the amount of optionally present excess liquid reactant suitable to act as solvent for the other reagent(s) plus the amount of optionally present liquid auxiliary reagent(s) plus the amount of optionally present supplementary solvent does not exceed 35% by weight, preferably does not exceed 30% by weight, in particular does not exceed 25% by weight, more particularly does not exceed 20% by weight, specifically does not exceed 15% by weight, very specifically does not exceed 10% by weight, more specifically does not exceed 8% by weight, of the total weight of water plus excess liquid reactant suitable to act as solvent for the other reagent(s) plus liquid auxiliary reagent(s) plus supplementary solvent.

In terms of the present invention, "cellulose modified with one or more alkylene oxides or other hydroxyalkyl precursors" relates to hydroxyalkylcelluloses; i.e. to celluloses in which a part of the hydrogen atoms of the OH groups is replaced by hydroxyalkyl groups. In these hydroxyalkylcelluloses another part of the hydrogen atoms of the OH groups may be replaced by alkyl groups. Such derivatives are termed hydroxyalkyl(alkyl)celluloses.

The term "alkylcellulose" relates to celluloses in which a part of the hydrogen atoms of the OH groups are replaced by alkyl groups. In terms of the present invention, in alkylcelluloses, hydrogen atoms of the OH groups are not replaced by hydroxyalkyl groups.

The term "reagents" means starting compounds (also termed starting materials or reactants), and also catalysts, catalyst ligands, coupling agents and other compounds which do not appear in the net reaction equation. The cellulose derivative is however not considered as a reagent. Generally, the solvent is not considered a reagent, either, except in cases where it is consumed, such as water in a hydrolyzation reaction.

The term "starting compound" or "starting material" or "reactant" relates to those substances which are consumed in the course of a chemical reaction and which are indispensable yet for the "paper" or net reaction (e.g. alcohol and acid or acid derivative for an esterification, amine and acid or acid derivative for an amide synthesis, diene and dienophile for a Diels-Alder reaction, organoboron compound and halide or sulfonate compound for a Suzuki reaction, etc.). Thus, catalysts, catalyst ligands, coupling agents and the like are no "starting compounds" or "starting materials" or "reactants" in the terms of the present invention.

The method of the invention is suitable for reactions in which all the reagents are water-miscible or water-soluble under the given reaction conditions (e.g. reaction temperature, degree of dilution of the reagents, etc.); its advantages become however especially manifest in reactions in which at least one of the reagents is not or only scarcely water-soluble or water-miscible. "Miscible" generally refers to two liquids; thus the term water miscibility relates to liquid reagents. "Soluble" generally refers to a property of a gas or a solid in a liquid; thus the term water-solubility relates to gaseous or solid reagents. In the present invention, however, the term "water solubility" is used indiscriminately both for water miscibility and solubility, and thus independently of the physical state of the reagent(s).

In one embodiment, at least one of the reagents has a water solubility of at most 100 g per 1 l of water, in particular at most 50 g per 1 l of water, more particularly at most 10 g per 1 l of water, and specifically at most 5 g per 1 l of water at 20° C.+/−20% and 101325 Pascal+/−20%. In another embodiment, at least one of the starting compounds has a water solubility of at most 100 g per 1 l of water, in particular at most 50 g per 1 l of water, more particularly at most 10 g per 1 l of water, and specifically at most 5 g per 1 l of water at 20° C.+/−20% and 101325 Pascal+/−20%.

Cellulose Derivative

Without wishing to be bound by theory, it is assumed that the cellulose derivatives form in the aqueous medium a three-dimensional hollow structure inside which or at the interface (phase boundary) of which at least a part of the organic reaction takes place.

As said above, "cellulose modified with one or more alkylene oxides or other hydroxyalkyl precursors" relates to hydroxyalkylcelluloses; i.e. to celluloses in which a part of the hydrogen atoms of the OH groups is replaced by a hydroxyalkyl group, in particular by a $C_2$-$C_4$-hydroxyalkyl group, especially by a $C_2$-$C_3$-hydroxyalkyl group. Suitable alkylene oxides for modifying celluloses are ethylene oxide and 1,2-propylene oxide. Other hydroxyalkyl precursors are for example tetrahydrofuran. Preferably, ethylene oxide and/or 1,2-propylene oxide and especially 1,2-propylene oxide are used for modifying cellulose, and thus the cellulose modified with one or more alkylene oxides or other hydroxyalkyl precursors is preferably a hydroxyethylcellulose, a 2-hydroxypropylcellulose or a mixed hydroxyethyl-2-hydroxypropylcellulose; i.e. a cellulose in which a part of the hydrogen atoms of the OH groups is replaced by hydroxyethyl- and/or 2-hydroxypropyl groups.

In these hydroxyalkylcelluloses another part of the hydrogen atoms of the OH groups may be replaced by alkyl groups, especially by $C_1$-$C_3$-alkyl groups, such as methyl, ethyl or propyl groups, especially by methyl or ethyl groups. Such derivatives are termed "hydroxyalkyl(alkyl)celluloses". Derivatives in which another part of the hydrogen atoms of the OH groups is indeed replaced by alkyl groups are termed "hydroxyalkylalkylcelluloses".

The term "alkylcellulose" relates to celluloses in which a part of the hydrogen atoms of the OH groups are replaced by alkyl groups, especially by $C_1$-$C_3$-alkyl groups, such as methyl, ethyl or propyl groups, especially by methyl groups. In terms of the present invention, in order to distinguish them from hydroxyalkylalkylcelluloses, in alkylcelluloses, hydrogen atoms of the OH groups are not replaced by hydroxyalkyl groups.

Alkylcelluloses can be prepared by reacting cellulose, generally after a pretreatment with a base, with an alkylation agent, such as a methyl, ethyl or propyl halide, e.g. methyl chloride, bromide or iodide, dimethyl sulfate, ethyl chloride, bromide or iodide, diethyl sulfate and the like.

Hydroxyalkylcelluloses can be prepared by reacting cellulose, generally after a pretreatment with a base, with an alkylene oxide, such as ethylene oxide or 1,2-propylene oxide, or with another hydroxyalkyl precursors, such as tetrahydrofuran.

Hydroxyalkylalkylcelluloses can be prepared by reacting alkylcelluloses, generally after a pretreatment with a base, with an alkylene oxide, such as ethylene oxide or 1,2-propylene oxide, or with another hydroxyalkyl precursors, such as tetrahydrofuran, or by reacting cellulose, also generally after a pretreatment with a base, with an alkylene oxide, such as ethylene oxide or 1,2-propylene oxide, or with another hydroxyalkyl precursors, such as tetrahydrofuran, and simultaneously with an alkylation agent, such as a methyl, ethyl or propyl halide, e.g. methyl chloride, bromide or iodide, dimethyl sulfate, ethyl chloride, bromide or iodide, diethyl sulfate and the like.

Under the reaction conditions alkylene oxides or other hydroxyalkyl precursors might react with hydroxyalkyl groups already bound to the celluloses, thus yielding oligoether groups terminated by OH. Such compounds are also enclosed in the present cellulose derivatives, more precisely in the terms "hydroxyalkylcelluloses", "hydroxyalkyl(alkyl)celluloses" and "hydroxyalkylalkylcelluloses".

The cellulose derivatives may also be used in quaternized form; i.e. may contain an ammonium or (di/tri)alkylammonium group. Such ammonium groups may for example be introduced by reacting a hydroxyl group of the cellulose derivative with an epoxide containing an ammonium group or an amino group which is then quaternized via alkylation.

Cellulose derivatives are generally characterized by their size and the degree of substitution. The cellulose derivatives are generally macromolecules, and thus their size or weight has to be determined by methods suitable for characterizing polymers. Generally, cellulose derivatives are characterized by their viscosity. Viscosity can be determined by various methods, for example with a Brookfield LV or RV, Höppler falling ball, Haake Rotovisco, and the like. If not indicated otherwise, in the present invention, viscosity values of up to (and including) 70 mPa·s are values obtained with a 2% by weight solution of the cellulose derivative in water, relative to the weight of water, at 25° C., as determined when using a Malvern Instruments Viscosizer 200 and an uncoated glass capillary (Art.-Nr. PRY2007, Malvern Instruments) and applying following protocol:

| Step | Solution | Pressure (mBar) | Duration (min) |
|---|---|---|---|
| wash | 3% Mucasol ™ universal detergent | 2000 | 1 |
| rinse | water | 2000 | 4 |
| fill | water | 2000 | 1 |
| reset baseline | water | 1000 | 1 |
| load sample | sample | 1000 | auto |
| dip (clean inlet) | water | 0 | 0.15 |
| ran | water | 1000 | auto |

A 1 mg/mL caffeine in water solution is used as viscosity reference at 0.8905 mPa·s. Raw data is fitted using the trailing region of the detector trace with a sampling interval of 55 and peak region threshold of 30%.

If not indicated otherwise, in the present invention, viscosities of above 70 mPa·s and up to (and including) 4000 mPa·s are values obtained with a 2% by weight solution of the cellulose derivative in water, relative to the weight of water, at 25° C., as determined when using a falling-sphere viscosimeter: First, sample density is determined with an Anton Paar DMA 4100 densitometer. Sample density is used to determine dynamic viscosity with an Anton Paar AMVn viscosimeter equipped with an 1.8 mm capillary or an Anton Paar Lovis 2000 ME viscosimeter equipped with a 2.5 mm capillary. Measurements are performed as quadruplicates at 25° C. with capillaries tilted to 70°.

If not indicated otherwise, in the present invention, viscosities of above 4000 mPa·s are values obtained with a 2% by weight solution of the cellulose derivative in water, relative to the weight of water, at 20° C., as described in European Pharmacopoeia 8.6, 01/2016:0348, Chapter "Hypromellose", Method 2, using a single-cylinder type spindle viscosimeter. For viscosities below 9500 mPa·s, following specifications apply: rotor number: 4; revolutions. 60 r/min; calculation multiplier: 100; for viscosities of from 9500 to <99500 mPa·s, following specifications apply: rotor number 4; revolutions. 6 r/min; calculation multiplier: 1000; and for viscosities of 99500 mPa·s and above, following specifications apply: rotor number: 4; revolutions. 3 r/min; calculation multiplier: 2000.

In a preferred embodiment, the cellulose derivative has a viscosity of from 1 to 150000 mPa·s, more preferably 2 to 100000 mPa·s, in particular 2 to 10000 mPa·s, more particularly 2 to 6000 mPa·s, even more particularly 2 to 1000 mPa·s, specifically 2 to 100 mPa·s, more specifically 2 to 80 mPa·s, very specifically 3 to 70 mPa·s, determined as a 2% by weight aqueous solution, relative to the weight of water, at the temperature and with the method as described above (viscosities of 1 to 70 mPa·s determined at 25° C. with a Malvern Instruments Viscosizer 200 according to the above-described method; viscosities of >70 to 4000 mPa·s determined at 25° C. with a falling-sphere viscosimeter according to the above-described method; viscosities of >4000 mPa·s determined at 20° C. with a single-cylinder type spindle viscosimeter according to the above-described method (in the case of viscosities of >4000 mPa·s as given by the respective suppliers). In a specific embodiment, the cellulose derivative has a viscosity of from 2 to 7 mPa·s, specifically from 3 to 6 mPa·s, very specifically from 3.5 to 6 mPa·s or from 3.8 to 5 mPa·s, determined as a 2% by weight aqueous solution, relative to the weight of water, at 25° C. with a Malvern Instruments Viscosizer 200 according to the above-described method. In another specific embodiment, the cellulose derivative has a viscosity of from 10 to 20 mPa·s, determined as a 2% by weight aqueous solution, relative to the weight of water, at 25° C. with a Malvern Instruments Viscosizer 200 according to the above-described method. In another specific embodiment, the cellulose derivative has a viscosity of from 30 to 70 mPa·s, specifically from 40 to 60 mPa·s, very specifically from 40 to 50 mPa·s, determined as a 2% by weight aqueous solution, relative to the weight of water, at 25° C. with a Malvern Instruments Viscosizer 200 according to the above-described method. In another specific embodiment, the cellulose derivative has a viscosity of from 70 to 150 mPa·s, specifically from 75 to 120 or 75 to 100 mPa·s, determined as a 2% by weight aqueous solution, relative to the weight of water, at 25° C. with a falling-sphere viscosimeter according to the above-described method. In another specific embodiment, the cellulose derivative has a viscosity of from 100 to 600 mPa·s, specifically from 100 to 500 mPa·s, determined as a 2% by weight aqueous solution, relative to the weight of water, at 25° C. with a falling-sphere viscosimeter according to the above-described method. In another specific embodiment, the cellulose derivative has a viscosity of from 2000 to 6000 mPa·s, specifically from 2500 to 5700 mPa·s, very specifically from 3000 to 4000 mPa·s, determined at 20° C. with a single-cylinder type spindle viscosimeter according to the above-described method. 1 mPa·s is 1 cP (cP=centipoise; also abbreviated as cps).

In an alternatively preferred embodiment, the cellulose derivative has a molecular weight of from 5000 to 1500000, more preferably from 6000 to 1000000, in particular from 7000 to 500000, more particularly from 8000 to 250000, even more particularly from 8000 to 100000, specifically from 8000 to 50000 Dalton. The molecular weight values relate to the weight average molecular weight.

The degree of substitution is the average level of alkyl and/or hydroxyalkyl substitution on the cellulose chain. The degree of substitution is often expressed in percentages.

In a preferred embodiment, in the cellulose derivative 5 to 70%, in particular 10 to 60%, specifically 15 to 50%, more specifically 20 to 45%, very specifically 25 to 45% of the hydrogen atoms in the hydroxyl groups of the cellulose on which the cellulose derivative is based are replaced by a hydroxyalkyl and/or alkyl group.

In particular, the cellulose derivative is selected from the group consisting of hydroxypropylmethylcellulose, hydroxypropylcellulose, hydroxyethylmethylcellulose, ethylhydroxyethylcellulose, hydroxyethylcellulose and methylcellulose, and especially from hydroxypropylmethylcellulose, hydroxyethylcellulose, and methylcellulose. Particularly, however, the cellulose derivative is a hydroxyalkylcellulose. Thus, more particularly, the cellulose derivative is selected from the group consisting of hydroxypropylmethylcellulose, hydroxypropylcellulose, hydroxyethylmethylcellulose, ethylhydroxyethylcellulose and hydroxyethylcellulose and especially from hydroxypropylmethylcellulose and hydroxyethylcellulose.

Specifically, the cellulose derivative is hydroxypropylmethylcellulose.

Various viscosities and substitution degrees of the above hydroxyalkyl(alkyl)-celluloses and alkylcelluloses are commercially available.

In a preferred embodiment, the cellulose derivative is used in an amount of from 0.01 to 15% by weight, in particular 0.05 to 10% by weight, more particularly 0.1 to 7% by weight, specifically 0.2 to 5% by weight, based on the weight of the solvent.

In another preferred embodiment, the cellulose derivative is used in an amount of from 0.01 to 15% by weight, in particular 0.05 to 10% by weight, more particularly 0.1 to 7% by weight, specifically 0.2 to 5% by weight, based on the weight of water (water being the only solvent or making up at least 90% by weight of the solvent, in particular at least 97% by weight of the solvent, the percentages being based on the total weight of the solvent).

In a preferred embodiment, the weight ratio of the cellulose derivative and all reagents is of from 1:1 to 1:200, in particular 1:1 to 1:100, more particularly 1:2 to 1:70, specifically 1:5 to 1:60. The term "reagents" is as defined above, i.e. it includes catalysts, catalyst ligands, coupling agents and other compounds which do not appear in the net reaction equation.

In a preferred embodiment, the weight ratio of the cellulose derivative and the starting compounds, i.e. those compounds indispensable for the respective reaction (e.g. alcohol and acid or acid derivative for an esterification, amine and acid or acid derivative for an amide synthesis, diene and dienophile for a Diels-Alder reaction, organoboron compound and halide or sulfonate compound for a Suzuki reaction, etc.), i.e. exclusive of any catalysts, ligands therefor, coupling agents and other compounds which do not appear in the net reaction equation, is of from 1:1 to 1:150, in particular 1:1 to 1:100, more particularly 1:2 to 1:50, specifically 1:2 to 1:30.

In cases in which high dilution is not important (high dilution is for example advantageous in intramolecular reactions, like lactone or lactam formation, in order to suppress competing intermolecular reactions), it is preferred to carry out the present organic reactions in rather high concentration. Preferably the reaction is carried out in such a way that the reactant used in substoichiometric amounts is present in the reaction medium in a concentration of from 0.1 to 5 mol per l of solvent, more preferably from 0.2 to 4 mol per l of solvent, in particular from 0.3 to 3 mol per l of solvent, more particularly from 0.5 to 3 mol per l of solvent and specifically from 0.8 to 3 mol per l of solvent. In case that the reactants are used in equimolar amounts, the above concentrations apply of course simply to one of these reactants. Alternatively preferably the reaction is carried out in such a way that the overall concentration of all reagents (i.e. reactants, catalysts, ligands, coupling agents) is of from 0.2 to 10 mol per l of solvent, more preferably from 0.4 to 8 mol per l of solvent, in particular from 0.8 to 6 mol per l of solvent and specifically from 1 to 4 mol per l of solvent.

Reaction Temperature

As indicated above, the limiting factor of reaction temperature is on the lower side the temperature at which the reaction mixture solidifies (0° C. or somewhat lower, e.g. −10° C. or −5° C.) and on the upper side the gelation point, i.e. the temperature at which the reaction mixture gels, or, if the cellulose derivative does not gel, the boiling point of the reaction mixture at the given pressure. Preferably the reaction is carried out at of from 5° C. to 80° C., more preferably from 10° C. to 70° C., in particular from 20° C. to 70° C., more particularly from 20° C. to 65° C. and specifically from 20° C. to 55° C., e.g. at from 20 to 25° C. or at from 45 to 55° C. or at from 48 to 52° C. The reaction temperature will be chosen according to the specific aim of the specific reaction. Higher reaction temperatures, e.g. around 50° C. to 70° C., will generally shorten reaction times significantly, but lower temperatures might lead to a more selective formation of the desired product, which advantage may overweigh longer reaction times.

Organic Reactions

As said above, basic types of organic reactions are addition reactions, elimination reactions, substitution reactions, pericyclic reactions, rearrangement reactions, photochemical reactions and redox reactions. Thus, in one aspect, the organic reactions of the present invention are selected from the group consisting of addition reactions, elimination reactions, substitution reactions, pericyclic reactions, rearrangement reactions, photochemical reactions and redox reactions.

Addition Reactions:

In this reaction type two or more molecules combine to form a larger one (the adduct). Addition reactions are limited to chemical compounds that have multiple bonds, such as molecules with carbon-carbon double bonds (alkenes, alkadienes, cycloalkenes, cycloalkadienes and other olefinic compounds) or triple bonds (alkynes, alkadiynes, cycloalkynes etc.), or with carbon-heteroatom double bonds, like carbonyl (C=O) groups or imine (C=N) groups or carbon-heteroatom triple bonds, like cyano (C≡N). Addition can take place by initial attack of a nucleophile, an electrophile or a free radical. Examples are the addition of hydrogen halides, other acids, like sulfuric acid or carboxylic acids, halogens, hydrogen, water, alcohols, hydrogen sulfide, thiols, ammonia, amines, hydroazoic acid to C—C double or triple bonds, the addition of hydrogen to C=O, C=N or C≡N bonds to give the reduced species, pericyclic reactions like Diels-Alder and various other cycloadditions, and many more. See for example J. March, Advanced Organic Chemistry, $3^{rd}$ ed., John Wiley & Sons, p. 657 et seq.

Elimination Reactions:

In this reaction type two substituents are removed from a molecule in either a one or two-step mechanism. Examples are dehydration (α,β-hydro-hydroxy elimination), α,β-hydro-alkoxy elimination, α,β-hydro-halo elimination, intramolecular condensation reactions etc. Elimination in α,β-position normally leads to unsaturated compounds, e.g. olefins, alkynes or aromatic compounds. Intramolecular condensation normally leads to a cyclic system, e.g. to a lactone or lactam.

Substitution Reactions

In substitution reactions one functional group in a chemical compound is replaced by another functional group. Depending on the substituent type, substitution reactions are classified as nucleophilic ($S_N$), electrophilic ($S_E$) or radical ($S_R$). Examples are $S_N1$ and $S_N2$ reactions of aliphatic or cycloaliphatic compounds, $S_E$, $S_N$ reactions on (hetero) aromatic compounds, $S_R$ on aromatic compounds like the Sandmeyer reaction, transition metal catalyzed C—C, C—O, C—N or C—S coupling reactions, etc.

Pericyclic Reactions

In pericyclic reactions the transition state of the molecule has a cyclic geometry, the reaction progresses in a concerted fashion and no radical or ionic intermediates are formed. Examples are concerted cycloadditions, like Diels-Alder reaction, Paterno Büchi reactions or 1,3-cycloadditons; sigmatropic rearrangements, cheletropic reactions etc.

Rearrangement Reactions

In rearrangement reactions, the carbon skeleton of a molecule is rearranged to give a structural isomer of the original molecule. Often a substituent moves from one atom to another atom in the same molecule.

Photochemical Reactions

In photochemical reactions, a chemical reaction is caused by absorption of ultraviolet (wavelength from 100 to 400 nm), visible light (400-750 nm) or infrared radiation (750-2500 nm). Examples are [2+2] and other thermally forbidden cycloadditions, di-pi-methane rearrangement, Norrish type I and II reactions, photoredox reactions etc.

Redox Reactions

Redox reactions encompass oxidations and reductions.

As many reactions cannot be categorized to belong to only one of the above types, in the following other categories will be used.

Thus, the organic reactions of the present invention are in particular selected from the group consisting of
- transition metal catalyzed reactions, especially transition metal catalyzed C—C coupling reactions, and transition metal catalyzed reactions involving C—N, C—O, C—S, C—B or C-halogen bond formation,
- C—C coupling reactions not requiring transition metal catalysis, such as the Wittig reaction, pericyclic reactions like the Diels-Alder reaction or photochemically induced reactions like [2+2] cycloaddition or cyclopropanation reactions, or reaction of carbonyl compounds with CH acidic compounds, such as in the aldol reaction or the Knoevenagel reaction or Michael addition and the like,
- reactions involving C—N bond formation and not requiring transition metal catalysis, such as carboxamide bond formation (amidation; synthesis of amides/peptides), urea formation, carbamate formation (formation of C(O)—N bond in the carbamate), amination (in the sense of nucleophilic substitution), reductive amination, Michael addition with N nucleophiles or nitration,
- reactions involving C—O bond formation and not requiring transition metal catalysis, such as esterification or etherification or carbamate formation (formation of C(O)—O bond in the carbamate) or Michael addition with O nucleophiles,
- reactions involving C-halogen bond formation and not requiring transition metal catalysis, such as halogenation of e.g. aromatic compounds,
- reactions involving S—N bond formation and not requiring transition metal catalysis, such as sulfonamide bond formation (synthesis of sulfonamides) or Michael addition with S nucleophiles,
- substitution reactions, such as (cyclo)aliphatic nucleophilic substitution, aromatic nucleophilic, electrophilic or radical substitution,
- reductions and oxidations (redox reactions),
- protection and deprotection reactions,
- photochemically induced reactions, and
- combined forms of the above reaction types.

The method of the invention also allows to carry out a chain of different organic reactions as a one pot reaction, such as protection of a functional group, reaction at another functional group, deprotection and, where expedient, further reaction of the deprotected functional group.

Transition Metal-Catalyzed Reactions

In one particular embodiment of the invention, in the organic reaction a transition metal catalyst is used; i.e. the organic reaction is a transition metal-catalyzed reaction.

Transition metal-catalyzed reactions are all organic reactions which involve the use of one or more transition metals as catalysts. Typically, they result in C—C, C—N, C—O, C—S, C—B or C-halogen bond formation. C—C bond formation is also called coupling reaction. If the two substrates to be coupled are different, the coupling reaction is termed cross coupling, while in case of identical substrates it is termed homocoupling.

Most transition metals are useful as catalysts; however, due to their availability and acceptable toxicity, the following metals are mostly used: Fe, Ru, Co, Rh, Ir, Ni, Pd, Pt, Cu, Ag, Au, and Zn. Thus, in a preferred embodiment, the transition metal is selected from the group consisting of Fe, Ru, Co, Rh, Ir, Ni, Pd, Pt, Cu, Ag, Au, and Zn. In particular, the transition metal is selected from the group consisting of Ru, Rh, Ni, Pd, Pt, Cu and Au. In another particular embodiment, the transition metal is Fe.

Transition metals can be used with an oxidation state of 0 or in oxidized form. In an oxidation state of 0, the transition metals are generally used as complexes to make their homogeneous distribution in the reaction medium possible. Alternatively they can be used as such (i.e. in elementary form), advantageously in a finely divided form, or supported on a carrier, to act as a heterogeneous catalyst. In oxidized form, the transition metals can be used in form of their salts, oxides or, mostly, in form of their complexes. The transition metal catalysts can also be used in form of their precursors, i.e. the active form forms in situ. For instance, in reactions requiring the metal in an oxidation state of 0 the transition metal can be introduced into the reaction in oxidized form and be reduced before or in the course of the reaction by a reduction agent present in the reaction.

In a particular embodiment, the transition metal catalyst is not a catalyst supported on a cellulose derivative or on cellulose.

In another particular embodiment the catalyst is used as a catalyst complex. Suitable complex ligands are well known and often contain phosphorus. Examples for phosphorus ligands are di-tert-butyl(1-methyl-2,2-diphenylcyclopropyl)phosphine (cBRIDP; Mo-Phos), 2-di-tert-butylphosphino-2',4',6'-triisopropylbiphenyl (t-Bu XPhos, tBuXPhos, tert-Butyl XPhos), 1,1'-bis(diphenylphosphino)ferrocene (dppf), 1,1'-bis(di-tert-butylphosphino)ferrocene (dtbpf), 1,2-bis(diphenylphosphino)ethane (dppe), 1,3-bis(diphenylphosphino)propane (dppp), 1,4-bis(diphenylphosphino)butane (dppb), (2,3-O-isopropylidene-2,3-dihydroxy-1,4-bis(diphenylphosphino)butane (diop), bis(di-tert-butyl(4-dimethylaminophenyl)phosphine) (Amphos), (2S,3S)-(–)-bis(diphenylphosphino)butane (Chiraphos), di-(tert-butyl)phenylphosphine, 2,2'-bis(diphenylphosphino)-1,1'-binaphthyl (BINAP), [1,1'-biphenyl]-2-diisopropyl phosphine, 2-dicyclohexylphosphino-2',4',6'-triisopropylbiphenyl (X-phos), 9,9-dimethyl-4,5-bis(diphenylphosphino)xanthene (Xantphos), 4,5-bis-(di-1-(3-methylindolyl)-phosphoramidit)-2,7,9,9-tetramethylxanthene (MeSkatOX), 2-dicyclohexylphosphino-2',6'-dimethoxybiphenyl (S-phos), 2-(2-dicyclohexyl-phosphanylphenyl)-N1,N1,N3,N3-tetramethyl-benzene-1,3-diamine (C-phos), 6,6'-dimethoxy-[1,1'-biphenyl]-2,2'-diyl)bis(bis(3,5-dimethylphenyl) phosphine, [(4R)-(4,4'-bis-1,3-benzodioxole)-5,5'-diyl]bis[bis(3,5-di-tert-butyl-4-methoxyphenyl)phosphine]((R)-DTBM-SEGPHOS®), (R)- or (S)-3,5-Xyl-MeO-BIPHEP, (R,S)- or (S,R)-PPF-P(t-Bu)$_2$, the Josiphos ligands, triphenylphosphite, tri-(2-(1,1-dimethylethyl)-4-methoxy-phenyl)-phosphite, tricyclohexylphosphine, tri(tert-butyl)phosphine, butyldi-1-adamantylphosphine (cataCXium), 1,6-bis (diphenylphosphino)hexane (DPPH), 2,6-bis(2,5-dimethylphenyl)-1-octyl-4-phenylphosphacyclohexan (PCH), tris(3-sulfophenyl)phosphine trisodium salt (TPPTS) and the like.

Non-phosphorus ligands are for example bis(dibenzylideneacetone) (dba), acetonitrile, bisoxazoline and the like. Further, Pd catalysts with non-phosphorus ligands are for example the PEPPSI catalysts (PEPPSI=Pyridine-Enhanced Precatalyst Preparation Stabilization and Initiation)

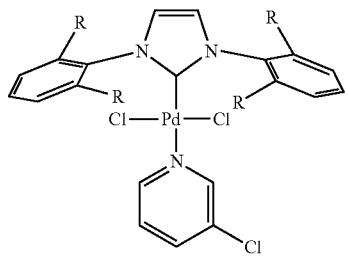

in which R is a small organic fragment, e.g. methyl, ethyl, isopropyl, isopentyl, or isoheptyl. The corresponding catalysts are labeled as PEPPSI-IMes, PEPPSI-IEt, PEPPSI-IPr, PEPPSI-IPent, and PEPPSI-IHept respectively, with or without "Pd-" added in front.

Also new generation PEPPSI catalysts are suitable:

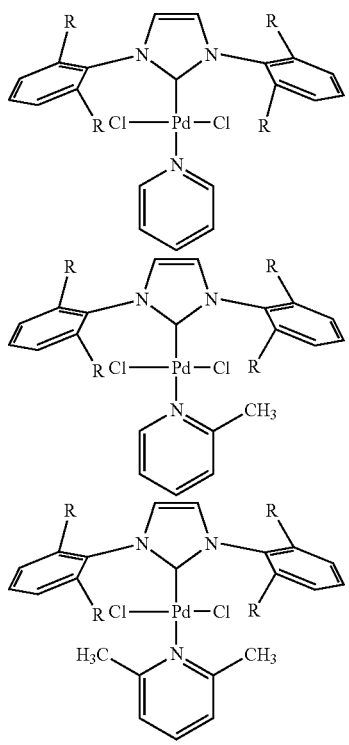

Here, too, R is a small organic fragment, e.g. methyl, ethyl, isopropyl, isopentyl, or isoheptyl.

Other suitable non-phosphorus ligands are for example porphyrins, such as shown in the following formula. They are mostly used with Fe, Ru, Rh or Ir as central metal, but Zn may also be used.

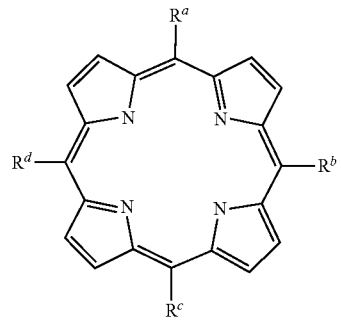

Generally, at least one of $R^a$, $R^b$, $R^c$ and $R^d$ is an aromatic group, such as phenyl, optionally substituted by 1, 2 or 3 substituents selected from the group consisting of methyl, methoxy, hydroxyl, amino, alkylcarbonyl, alkoxycarbonyl and the like. For sterically selective reactions, expediently, at least one of $R^a$, $R^b$, $R^c$ and $R^d$ is a chiral group, such as a BINAP radical, a phenyl ring carrying one or more chiral substituents or a phenyl ring fused to one or more rings resulting in a chiral system. Radicals $R^a$, $R^b$, $R^c$ and $R^d$ which are not an aromatic group are generally selected from the group consisting of alkyl groups, alkoxy groups, alkyl carbonyl groups and alkoxycarbonyl groups. They can however also be hydrogen.

Transition metal complexes of these porphyrin ligands, in particular complexes with Fe, Ru, Rh or Ir as central metal, are especially useful in cyclopropanation reactions.

Other suitable ligands are the following semicorrin or bis-oxazolin (BOX and PyBOX) ligands:

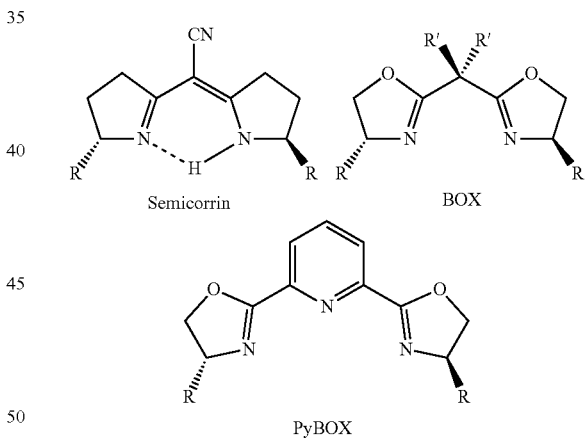

R can have various meanings, such as $C_1$-$C_4$-alkyl, $C_1$-$C_4$-alkyl substituted by OH, tri-$C_1$-$C_4$-alkyl-silyloxy, $C_1$-$C_4$-alkylcarbonyl, $C_1$-$C_4$-alkoxycarbonyl or phenyl; $C_1$-$C_4$-alkylcarbonyl, $C_1$-$C_4$-alkoxycarbonyl or phenyl. Each R' is generally independently H or $C_1$-$C_4$-alkyl, in particular H or methyl.

These ligands are generally used with Cu as central metal. Copper complexes of these ligands are especially useful in cyclopropanation reactions.

a) C—C Coupling Reactions

In a particular embodiment, the transition metal catalyzed reaction is a C—C coupling reaction. Transition metal catalyzed C—C coupling reactions are well known, and are often named reactions. Examples are the Suzuki-Miyaura reaction (or Suzuki-Miyaura coupling or just Suzuki reaction or just Suzuki coupling), Negishi coupling, Heck reaction, C—C coupling reactions involving C—H activation (different from Heck reaction), Sonogashira coupling, Stille coupling, Grubbs olefin metathesis, 1,4-additions of organoborane compounds to α,β-olefinically unsaturated carbonyl compounds, in particular Rh-catalyzed 1,4-additions, Kumada coupling, Hiyama coupling, Ullmann reaction, Glaser coupling (inclusive the Eglinton and the Hay coupling), Cadiot-Chodkiewicz coupling, the Fukuyama coupling, hydroformylations or cyclopropanations.

The Suzuki reaction is a cross coupling reaction in which an organoboron compound is reacted with an organic halogenide or sulfonate [the sulfonate being in particular a fluorinated alkylsulfonate or tosylate, specifically triflate (trifluoromethylsulfonate) or nonaflate (nonafluorobutylsulfonate)], e.g. with an alkyl, alkenyl, alkynyl, aryl or heteroaryl halogenide or sulfonate (the sulfonate being in particular a fluorinated alkylsulfonate or tosylate, specifically triflate or nonaflate), in the presence of a transition metal catalyst, mostly a Pd or Ni catalyst, and in general also of a base.

The Negishi reaction is a cross coupling reaction in which an organozinc compound is reacted with an organic halogenide or sulfonate (the sulfonate being in particular a fluorinated alkylsulfonate or tosylate, specifically triflate or nonaflate), e.g. with an alkyl, alkenyl, alkynyl, aryl or heteroaryl halogenide or sulfonate (the sulfonate being in particular a fluorinated alkylsulfonate or tosylate, specifically triflate or nonaflate), in the presence of a transition metal catalyst, mostly a Pd or Ni catalyst. Organoaluminum or organozirconium compounds can be used instead of the organozinc compound.

In Heck reactions an aryl, heteroaryl, benzyl, vinyl or alkyl halogenide or sulfonate (the sulfonate being in particular a fluorinated alkylsulfonate or tosylate, specifically triflate, nonaflate or tosylate) (the alkyl group must not contain any β-hydrogen atoms) is reacted with an olefinically unsaturated compound in the presence of a transition metal catalyst, mostly a Pd catalyst, and generally also in the presence of a base.

C—C coupling reactions involving C—H activation are coupling reactions in which one of the reactants reacts via a C—H bond and not via a specific activating group. The Heck reaction is such a reaction involving C—H activation. In the present case, in the C—C coupling reactions involving C—H activation two aromatic or heteroaromatic compounds are coupled.

The Sonogashira reaction is a cross coupling reaction in which an aryl, heteroaryl or vinyl halogenide or sulfonate (the sulfonate being in particular a fluorinated alkylsulfonate or tosylate, specifically triflate or nonaflate) is reacted with a terminal alkyne in the presence of a transition metal catalyst, mostly a Pd catalyst, generally also of a base and optionally of a Cu(I) salt (also in catalytic amounts).

The Stille reaction, also termed Migita-Kosugi-Stille coupling, is a cross coupling reaction in which an organotin compound (organostannane) is reacted with an alkenyl, aryl, heteroaryl or acyl halide, sulfonate (the sulfonate being in particular a fluorinated alkylsulfonate or tosylate, specifically triflate or nonaflate) or phosphate in the presence of a Pd catalyst.

Grubbs olefin metathesis is an olefin metathesis in which a Grubbs catalyst is used. An olefin metathesis is an organic reaction that entails the redistribution of fragments of alkenes (olefins) by the scission and regeneration of carbon-carbon double bonds. Grubbs catalysts are Ruthenium carbene complexes. For further details see below.

Rh-catalyzed 1,4-additions in the terms of the present invention are 1,4 additions of organoborane compounds, in particular of aryl or heteroaryl boronic acids, to α,β-olefinically unsaturated carbonyl compounds, in particular to α,β-unsaturated carboxylic acids or acid derivatives, in the presence of a rhodium catalyst to give 3-(het)arylpropionic acids or acid derivatives. However, Pd and Ru catalysts are principally also suitable for such 1,4 additions of organoborane compounds to α,β-olefinically unsaturated carbonyl compounds.

The Kumada reaction is a cross coupling reaction in which a vinyl halide or sulfonate (the sulfonate being in particular a fluorinated alkylsulfonate or tosylate, specifically triflate or nonaflate) is reacted with a Grignard reagent or a lithium organyl in the presence of a transition metal catalyst, mostly a Pd or Ni catalyst.

The Hiyama reaction is cross-coupling reaction in which an aryl, heteroaryl, alkenyl or alkynyl silane is reacted with an organic halide or sulfonate (the sulfonate being in particular a fluorinated alkylsulfonate or tosylate, specifically triflate or nonaflate), e.g. an alkyl, alkenyl, alkynyl, aryl or heteroaryl halide or sulfonate (the sulfonate being in particular a fluorinated alkylsulfonate or tosylate, specifically triflate or nonaflate), in the presence of a transition metal catalyst, mostly a Pd catalyst.

The Ullmann reaction or Ullmann coupling is a cross coupling or homocoupling reaction in which two aryl or heteroaryl halides or pseudohalogenides (e.g. —SCN) are reacted to biaryl compounds in the presence of copper, a Cu(I) salt or a Ni catalyst.

The Glaser coupling is homocoupling reaction in which a terminal alkyne is treated with a copper(I) salt and oxidized to give a symmetrical conjugated diyne. The original Glaser reaction was carried out in aqueous ammonia, and air or oxygen was used as oxidation agent, but in terms of the present invention the Glaser coupling comprises all variants of Cu-catalyzed homocoupling of terminal alkynes, e.g. the use of $CuCl_2$ or $K_3Fe(CN)_6$ as oxidizing agents, the Eglinton variant (Eglinton coupling), in which Cu(II) acetate and methanolic pyridine is used, or the Hay variant (Hay coupling), in which tertiary amines, like pyridine, or TMEDA are used as complexing agents for the Cu(I) salt, and air or oxygen is used as oxidizing agent.

The Cadiot-Chodkiewicz coupling is a cross coupling in which a terminal alkyne and an 1-bromoalkyne are reacted in the presence of a Cu(I) catalyst and an aliphatic amine.

The Fukuyama coupling is a cross coupling reaction in which a thioester and an organozinc halide are reacted in the presence of a transition metal catalyst, mostly a Pd catalyst, to give a ketone.

In a transition metal catalyzed cyclopropanation an olefinically unsaturated compound is reacted with a diazo compound to a cyclopropane in the presence of a transition metal catalyst. The reaction is formally a [1+2] ring forming reaction of a carbene (formed after $N_2$ elimination) and an olefin; therefore cyclopropanations are herein formally considered as a pericyclic reaction.

In a hydroformylation, also known as oxo synthesis or oxo process, formally a formyl group (CHO) and a hydrogen atom add to a carbon-carbon double bond, thus giving an aldehyde. The reaction is generally catalyzed by a Rh or Ru catalyst, mostly by a homogeneous Rh or Ru catalyst.

Particularly, the transition metal catalyzed C—C coupling reaction is selected from the group consisting of the Suzuki-Miyaura reaction (or just Suzuki reaction), Negishi coupling, Heck reaction, C—C coupling reactions involving C—H activation other than Heck reaction (see above and below definition), Sonogashira coupling, Stille coupling, Grubbs olefin metathesis, 1,4-additions of organoborane compounds to α,β-olefinically unsaturated carbonyl compounds, in particular Rh-catalyzed 1,4-additions, hydroformylations and cyclopropanations. Specifically, the transition metal catalyzed C—C coupling reaction is selected from the group consisting of the Suzuki-Miyaura reaction (or just Suzuki reaction), Heck reaction, C—C coupling reactions involving C—H activation other than Heck reaction, Sonogashira coupling, Stille coupling, Grubbs olefin metathesis, Rh-catalyzed 1,4-additions and cyclopropanations. In another specific embodiment the transition metal catalyzed C—C coupling reaction is selected from the group consisting of the Suzuki-Miyaura reaction (or just Suzuki reaction), Heck reaction, C—C coupling reactions involving C—H activation other than Heck reaction, Sonogashira coupling, Stille coupling, Grubbs olefin metathesis and Rh-catalyzed 1,4-additions.

Suzuki-Miyaura Reaction

In a particular embodiment the transition metal catalyzed C—C coupling reaction is a Suzuki-Miyaura reaction. As said, in Suzuki reactions an organoboron compound is reacted with an organic halogenide or sulfonate (the sulfonate being in particular a fluorinated alkylsulfonate or tosylate, specifically triflate or nonaflate), in particular with a halogenide or sulfonate (the sulfonate being in particular a fluorinated alkylsulfonate or tosylate, specifically triflate or nonaflate) $R^2—(Z)_n$, where $R^2$ is an alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl or heteroaryl group, Z is a halogenide or sulfonate (the sulfonate being in particular a fluorinated alkylsulfonate or tosylate, specifically triflate or nonaflate) group, especially Cl, Br, I, triflate or nonaflate, and n is 1, 2, 3 or 4, in the presence of a transition metal catalyst, mostly a Pd or Ni catalyst, and in general also of a base.

Preferably, the organoboron compound is a compound of formula $R^1—BY_2$, where $R^1$ is an alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl or heteroaryl group and Y is an alkyl, O-alkyl or hydroxyl group, or the two substituents Y form together with the boron atom they are bound to a mono-, bi- or polycyclic ring; or the organoboron compound is a compound of formula $R^1—BF_3M$, where M is a metal equivalent. The reaction of the organoboron compound with $R^2—(Z)_n$ yields a compound $(R^1)_n—R^2$. Examples of suitable organoboron compounds $R^1—BY_2$ are $R^1—B(OH)_2$, $R^1—B(O—C_1-C_4\text{-alkyl})_2$, $R^1—B(C_1-C_4\text{-alkyl})_2$, or the MIDA ester of $R^1—B(OH)_2$ (MIDA=N-methyliminodiacetic acid; HO—C(=O)—CH$_2$—N(CH)—CH$_2$—C(=O)—OH; i.e. the two Y form together —O—C(=O)—CH$_2$—N(CH$_3$)—CH$_2$—C(=O)—O—). The alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl or heteroaryl halide or sulfonate can contain more than one halide or sulfonate group (when n is 2, 3 or 4), so that multiply coupled compounds can form, especially if the organoboron compound is used in excess. For instance, a difunctional compound $R^2—(Z)_2$ can yield a twofold coupled compound $R^1—R^2—R^1$. In case that n is 2, 3 or 4 and the reaction is intended to couple 2, 3 or 4 organic radicals deriving from the organoboron compound (e.g. 2, 3 or 4 $R^1$ deriving from $R^1—BY_2$), Z in $(Z)_n$ is preferably always the same; i.e. all groups Z in $R^2—(Z)_n$ have the same meaning.

Due to the tolerance of the Suzuki reaction to a wide variety of functional groups, the alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl or heteroaryl groups $R^1$ and $R^2$ can carry one or more substituents, e.g. halogen (provided that this not more reactive than the halogen atom or sulfonate group on the desired reaction site of the $R^2—(Z)_n$ compound), cyano, nitro, azido, —SCN, —SF$_5$, OR$^{11}$ (provided that this not more reactive than the halogen atom or sulfonate group on the desired reaction site of the $R^2—(Z)_n$ compound), $S(O)_mR^{11}$, $NR^{12a}R^{12b}$, $C(=O)R^{13}$, $C(=S)R^{13}$, $C(=NR^{12a})R^{13}$, —Si(R$^{14}$)$_3$, cycloalkyl, cycloalkenyl, cycloalkynyl, mixed cycloalkenyl/cycloalkynyl, polycarbocyclyl, where the five last-mentioned cyclic substituents may carry one or more substituents selected from $R^{15}$; aryl which may be substituted by one or more radicals $R^{15}$; heterocyclyl which may be substituted by one or more radicals $R^{15}$; heteroaryl which may be substituted by one or more radicals $R^{15}$; oxo (=O), =S, or =NR$^{12a}$;

and in case of cycloalkyl, cycloalkenyl, cycloalkynyl, mixed cycloalkenyl/cycloalkynyl, polycarbocyclyl, aryl and heteroaryl groups $R^1$ and $R^2$, optional substituents on these groups can additionally be alkyl, alkenyl, alkapolyenyl, alkynyl, alkapolyynyl and mixed alkenyl/alkynyl, where these six radicals may in turn be substituted by one or more radicals, e.g. by halogen (provided that this not more reactive than the halogen atom or sulfonate group on the desired reaction site of the $R^2—(Z)_n$ compound), cyano, nitro, azido, —SCN, —SF$_5$, OR$^{11}$, $S(O)_mR^{11}$, $NR^{12a}R^{12b}$, $C(=O)R^{13}$, $C(=S)R^{13}$, $C(=NR^{12a})R^{13}$, —Si(R$^{14}$)$_3$, cycloalkyl, cycloalkenyl, cycloalkynyl, mixed cycloalkenyl/cycloalkynyl, polycarbocyclyl, where the five last-mentioned cyclic substituents may carry one or more substituents selected from $R^{15}$; aryl which may be substituted by one or more radicals $R^{15}$; heterocyclyl which may be substituted by one or more radicals $R^{15}$; heteroaryl which may be substituted by one or more radicals $R^{15}$; oxo (=O), =S, and =NR$^{12a}$;

where each $R^{11}$ is independently selected from the group consisting of hydrogen, cyano, alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, where the aliphatic and cycloaliphatic moieties in the 11 last-mentioned radicals may be partially or fully halogenated and/or may be substituted by one or more radicals $R^{17}$, -alkyl-C(=O)OR$^{18}$, -alkyl-C(=O)N(R$^{12a}$)R$^{12b}$,
-alkyl-C(=S)N(R$^{12a}$)R$^{12b}$, -alkyl-C(=NR$^{12}$)N(R$^{12a}$)R$^{12b}$,
—Si(R$^{14}$)$_3$, —S(O)$_m$R$^{18}$, —S(O)$_m$N(R$^{12a}$)R$^{12b}$,
—N(R$^{12a}$)R$^{12b}$, —N=C(R$^{16}$)$_2$, —C(=O)R$^{13}$,
—C(=O)N(R$^{12a}$)R$^{12b}$, —C(=S)N(R$^{12a}$)R$^{12b}$,
—C(=O)OR$^{18}$, aryl, optionally substituted with one or more substituents $R^{15}$;

heterocyclyl, optionally substituted with one or more substituents $R^{15}$; and heteroaryl, optionally substituted with one or more substituents $R^{15}$; and $R^{11}$ in the group —S(O)$_m$R$^{11}$ is additionally selected from the group consisting of alkoxy and haloalkoxy;

$R^{12}$, $R^{12a}$ and $R^{12b}$, independently of each other and independently of each occurrence, are selected from the group consisting of hydrogen, cyano, alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, wherein the 11 last-mentioned aliphatic and cycloaliphatic radicals may be partially or fully halogenated and/or may be substituted by one or more, preferably 1, 2 or 3, in particular 1, substituents $R^{19}$,
—$OR^{20}$, —$NR^{21a}R^{21b}$, —$S(O)_m R^{20}$, —$C(=O)N(R^{21a}R^{21b})$, —$C(=O)NR^{21}N(R^{21a}R^{21b})$, —$Si(R^{14})_3$, —$C(=O)R^{13}$,
aryl which may be substituted with 1, 2, 3, 4, or 5, preferably 1, 2 or 3, in particular 1, substituents $R^{15}$, heterocyclyl which may be substituted with one or more, preferably 1, 2 or 3, in particular 1, substituents $R^{15}$; and heteroaryl which may be substituted with one or more, preferably 1, 2 or 3, in particular 1, substituents $R^{15}$; and or $R^{12a}$ and $R^{12b}$, together with the nitrogen atom to which they are bound, form a saturated, partially unsaturated or maximally unsaturated heterocyclic or heteroaromatic ring, where the ring may further contain 1, 2, 3 or 4 heteroatoms or heteroatom-containing groups selected from the group consisting of O, S, N, SO, $SO_2$, C=O and C=S as ring members, wherein the heterocyclic or heteroaromatic ring may be substituted with 1, 2, 3, 4 or 5, preferably 1, 2 or 3, in particular 1, substituents independently selected from $R^{15}$;
or $R^{12a}$ and $R^{12b}$ together form a group =$C(R^{22})_2$, =$S(O)_m(R^{20})_2$, =$NR^{21a}$ or =$NOR^{20}$;
each $R^{13}$ is independently selected from the group consisting of hydrogen, alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, where the aliphatic and cycloaliphatic moieties in the 11 last-mentioned radicals may be partially or fully halogenated and/or may be substituted by one or more radicals $R^{17}$; aryl, optionally substituted with one or more radicals $R^{15}$; heterocyclyl, optionally substituted with one or more radicals $R^{15}$; heteroaryl, optionally substituted with one or more radicals $R^{15}$; $OR^{20}$, —$S(O)_m R^{20}$, —$N(R^{21a})R^{21b}$, —$C(=O)N(R^{21a})R^{21b}$, —$C(=S)N(R^{21a})R^{21b}$ and —$C(=O)OR^{20}$;
each $R^{14}$ is independently selected from the group consisting of hydrogen, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, and phenyl, optionally substituted with 1, 2, 3, 4, or 5 radicals $R^{15}$;
each $R^{15}$ is independently selected from the group consisting of halogen, azido, nitro, cyano, —OH, —SH, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —$Si(R^{23})_3$;
$C_1$-$C_{20}$-alkyl, $C_2$-$C_{20}$-alkenyl, $C_2$-$C_{20}$-alkapolyenyl, $C_2$-$C_{20}$-alkynyl, $C_2$-$C_{20}$-alkapolyynyl, mixed $C_2$-$C_{20}$-alkenyl/alkynyl, wherein the six last-mentioned aliphatic radicals may be partially or fully halogenated and/or may carry one or more radicals selected from the group consisting of OH, $C_1$-$C_{20}$-alkoxy, $C_1$-$C_{20}$-haloalkoxy, SH, $C_1$-$C_{20}$-alkylthio, $C_1$-$C_{20}$-haloalkylthio, $C_1$-$C_{20}$-alkylsulfinyl, $C_1$-$C_{20}$-haloalkylsulfinyl, $C_1$-$C_{20}$-alkylsulfonyl, $C_1$-$C_{20}$-haloalkylsulfonyl, —$Si(R^{23})_3$, oxo, $C_3$-$C_8$-cycloalkyl, $C_3$-$C_8$-cycloalkenyl, $C_8$-$C_{20}$-cycloalkynyl, mixed $C_3$-$C_{20}$-cycloalkenyl/cycloalkynyl, polycarbocyclyl, aryl, heterocyclyl and heteroaryl, wherein the 8 last-mentioned cyclic radicals may in turn be partially or fully halogenated and/or may carry one or more radicals selected from the group consisting of OH, $C_1$-$C_{20}$-alkoxy, $C_1$-$C_{20}$-haloalkoxy, SH, $C_1$-$C_{20}$-alkylthio, $C_1$-$C_{20}$-haloalkylthio, $C_1$-$C_{20}$-alkylsulfinyl, $C_1$-$C_{20}$-haloalkylsulfinyl, $C_1$-$C_{20}$-alkylsulfonyl, $C_1$-$C_{20}$-haloalkylsulfonyl, —$Si(R^{23})_3$, oxo, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-cycloalkenyl, $C_8$-$C_{20}$-cycloalkynyl, mixed $C_3$-$C_{20}$-cycloalkenyl/cycloalkynyl, polycarbocyclyl, aryl, heterocyclyl and heteroaryl, wherein the 8 last mentioned radicals may in turn be unsubstituted, partially or fully halogenated and/or carry 1, 2 or 3 substituents selected from the group consisting of cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl and $C_1$-$C_6$-haloalkoxycarbonyl; $C_3$-$C_8$-cycloalkyl, $C_3$-$C_8$-cycloalkenyl, $C_8$-$C_{20}$-cycloalkynyl, mixed $C_3$-$C_{20}$-cycloalkenyl/cycloalkynyl, polycarbocyclyl, wherein the 5 last-mentioned cycloaliphatic radicals may be partially or fully halogenated and/or may carry one or more radicals selected from the group consisting of cyano, $C_1$-$C_4$-alkyl, $C_1$-$C_4$-haloalkyl, $C_1$-$C_4$-alkoxy, $C_1$-$C_4$-haloalkoxy and oxo;
aryl, O-aryl, heterocyclyl, O-heterocyclyl, heteroaryl and O-heteroaryl, wherein the cyclic moieties in the 6 last mentioned radicals may be unsubstituted, partially or fully halogenated and/or carry 1, 2 or 3, in particular 1, substituents selected from the group consisting of $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl and $C_1$-$C_6$-haloalkoxycarbonyl;
or
two $R^{15}$ present together on the same atom of an unsaturated or partially unsaturated ring may be =O, =S, =$N(C_1$-$C_6$-alkyl), =$NO(C_1$-$C_6$-alkyl), =$CH(C_1$-$C_4$-alkyl) or =$C(C_1$-$C_4$-alkyl)C_1$-$C_4$-alkyl;
or
two $R^{15}$ on two adjacent carbon or nitrogen atoms form together with the carbon or nitrogen atoms they are bonded to a 4-, 5-, 6-, 7- or 8-membered saturated, partially unsaturated or maximally unsaturated, including heteroaromatic, ring, wherein the ring may contain 1, 2, 3 or 4 heteroatoms or heteroatom groups selected from the group consisting of N, O, S, NO, SO and $SO_2$, as ring members, and wherein the ring optionally carries one or more, preferably 1, 2 or 3, in particular 1, substituents selected from the group consisting of halogen, cyano, $C_1$-$C_4$-alkyl, $C_1$-$C_4$-haloalkyl, $C_1$-$C_4$-alkoxy and $C_1$-$C_4$-haloalkoxy;
each $R^{16}$ is independently selected from the group consisting of hydrogen, halogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl and $C_2$-$C_6$-haloalkynyl, wherein the six last-mentioned aliphatic radicals may carry 1 or 2 radicals selected from the group consisting of CN, $C_3$-$C_4$-cycloalkyl, $C_1$-$C_4$-alkoxy, $C_1$-$C_4$-haloalkoxy and oxo;
each $R^{17}$ is independently selected from the group consisting of cyano, nitro, —OH, —SH, —SCN, —$SF_5$, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —$Si(R^{14})_3$,
$C_3$-$C_8$-cycloalkyl which may be unsubstituted, partially or fully halogenated and/or may carry 1 or 2 radicals selected from the group consisting of $C_1$-$C_4$-alkyl, $C_1$-$C_4$-haloalkyl, $C_3$-$C_8$-cycloalkyl, $C_3$-$C_8$-halocycloalkyl, $C_1$-$C_4$-alkoxy, $C_1$-$C_4$-haloalkoxy and oxo;
aryl, aryloxy, heterocyclyl, heterocyclyloxy, heteroaryl and heteroaryloxy, where the cyclic moiety in the 6 last-mentioned radicals may be unsubstituted, partially or fully halogenated and/or carry 1, 2, 3, 4 or 5 substituents $R^{15}$; or two $R^{17}$ present on the same carbon atom (of an alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl or polycarbocyclyl, group) may together be $=$O, $=$CH($C_1$-$C_4$-alkyl), $=$C($C_1$-$C_4$-alkyl)$C_1$-$C_4$-alkyl, $=$N($C_1$-$C_6$-alkyl) or $=$NO($C_1$-$C_6$-alkyl);

and $R^{17}$ as a substituent on a cycloalkyl, cycloalkenyl, cycloalkynyl, mixed cycloalkenyl/cycloalkynyl or polycarbocyclyl ring is additionally selected from the group consisting of $C_1$-$C_6$-alkyl, $C_2$-$C_6$-alkenyl and $C_2$-$C_6$-alkynyl, wherein the three last-mentioned aliphatic radicals may be unsubstituted, partially or fully halogenated and/or may carry 1 or 2 substituents selected from the group consisting of CN, $C_3$-$C_4$-cycloalkyl, $C_3$-$C_4$-halocycloalkyl, $C_1$-$C_4$-alkoxy, $C_1$-$C_4$-haloalkoxy and oxo;

each $R^{18}$ is independently selected from the group consisting of hydrogen, cyano, —Si($R^{14}$)$_3$, $C_1$-$C_{20}$-alkyl, $C_2$-$C_{20}$-alkenyl, $C_2$-$C_{20}$-alkynyl, wherein the three last-mentioned aliphatic radicals may be unsubstituted, partially or fully halogenated and/or may carry 1 or 2, in particular 1, radicals selected from the group consisting of $C_3$-$C_8$-cycloalkyl, $C_3$-$C_8$-halocycloalkyl, $C_1$-$C_{20}$-alkoxy, $C_1$-$C_{20}$-haloalkoxy, $C_1$-$C_{20}$-alkylthio, $C_1$-$C_{20}$-haloalkylthio, $C_1$-$C_{20}$-alkylsulfinyl, $C_1$-$C_{20}$-haloalkylsulfinyl, $C_1$-$C_{20}$-alkylsulfonyl, $C_1$-$C_{20}$-haloalkylsulfonyl and oxo;

$C_3$-$C_8$-cycloalkyl which may be unsubstituted, partially or fully halogenated and/or may carry 1 or 2, in particular 1, radicals selected from the group consisting of $C_1$-$C_4$-alkyl, $C_1$-$C_4$-haloalkyl, $C_3$-$C_4$-cycloalkyl, $C_3$-$C_4$-halocycloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl and oxo;

aryl, heterocyclyl and heteroaryl, wherein the 3 last-mentioned radicals may be unsubstituted, partially or fully halogenated and/or carry 1, 2 or 3, preferably 1 or 2 in particular 1, substituents selected from the group consisting of $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl and $C_1$-$C_6$-haloalkoxycarbonyl; and $R^{18}$ in the group S(O)$_m$$R^{18}$ is additionally selected from the group consisting of $C_1$-$C_6$-alkoxy, $C_1$-$C_6$-haloalkoxy, aryloxy, heterocyclyloxy and heteroaryloxy;

each $R^{19}$ is independently selected from the group consisting of halogen, nitro, cyano, —OH, —SH, $C_1$-$C_6$-alkoxy, $C_1$-$C_6$-haloalkoxy, $C_1$-$C_6$-alkylthio, $C_1$-$C_6$-haloalkylthio, $C_1$-$C_3$-alkylsulfinyl, $C_1$-$C_6$-haloalkylsulfinyl, $C_1$-$C_6$-alkylsulfonyl, $C_1$-$C_6$-haloalkylsulfonyl, Si($R^{14}$)$_3$;

$C_3$-$C_8$-cycloalkyl, $C_3$-$C_8$-halocycloalkyl, wherein the two last-mentioned cycloaliphatic radicals may carry one or more radicals selected from the group consisting of cyano, $C_1$-$C_4$-alkyl, $C_1$-$C_4$-haloalkyl, $C_3$-$C_8$-cycloalkyl, $C_3$-$C_8$-halocycloalkyl, $C_1$-$C_4$-alkoxy, $C_1$-$C_4$-haloalkoxy and oxo;

aryl, aryloxy, heterocyclyl, heterocyclyloxy, heteroaryl and heteroaryloxy, wherein the 6 last mentioned radicals may be unsubstituted, partially or fully halogenated and/or carry 1, 2 or 3, in particular 1, substituents selected from the group consisting of $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl and $C_1$-$C_6$-haloalkoxycarbonyl;

each $R^{20}$ is independently defined as $R^{18}$;

$R^{21}$, $R^{21a}$ and $R^{21b}$, independently of each other and independently of each occurrence, are selected from the group consisting of hydrogen, cyano, alkyl, cycloalkyl, alkenyl, alkynyl, wherein the four last-mentioned aliphatic and cycloaliphatic radicals may be partially or fully halogenated, and/or the four last-mentioned aliphatic and cycloaliphatic radicals carry one or more substituents selected from the group consisting of cyano, OH, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino;

aryl, aryl-$C_1$-$C_4$-alkyl, heterocyclyl, and heteroaryl, where the rings in the 4 last mentioned radicals may be substituted with 1, 2, 3, 4, or 5 substituents $R^{15}$;

or $R^{21a}$ and $R^{21b}$, together with the nitrogen atom to which they are bound, form a 3-, 4-, 5-, 6-, 7- or 8-membered saturated, partially unsaturated or maximally unsaturated heterocyclic, inclusive heteroaromatic, ring, where the ring may further contain 1, 2, 3 or 4 heteroatoms or heteroatom-containing groups selected from the group consisting of O, S, N, SO, SO$_2$, C$=$O and C$=$S as ring members, wherein the heterocyclic ring may be substituted with 1, 2, 3, 4 or 5 substituents independently selected from $R^{15}$;

each $R^{22}$ is independently defined as $R^{16}$;

each $R^{23}$ is independently selected from the group consisting of hydrogen, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, and phenyl, optionally substituted with 1, 2, 3, 4, or 5 radicals selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy; and m is 0, 1 or 2.

In the above radicals, all functional groups, especially halogen atoms and sulfonyloxy groups, have to be less reactive towards the organoboron compound than the halogen atom or sulfonate group on the desired reaction site of the $R^2$—(Z)$_n$ compound.

Specifically, $R^1$ and $R^2$ are aryl or heteroaryl groups, Y is OH or forms a MIDA ester, Z is a halide, especially Cl or Br, and n is 1 or 2.

The organoboron compounds are either commercially available or can be prepared by known methods; see e.g. the below-described Miyaura borylation.

The organoboron compound and the halogenide or sulfonate can be used in a molar ratio of from 10:1 to 1:10, e.g. from 7:1 to 1:7 or from 5:1 to 1:5. In case of di- or polyfunctional halides or sulfonates, the molar ratio relates of course to the number of halide or sulfonate groups in the molecule. The organoboron compounds are however generally used in at least equimolar amount (in case of di- or polyfunctional halides or sulfonates, the at least equimolar amount refers of course to the amount of halide or sulfonate groups; i.e. for 1 mol of Z—$R^2$—Z at least 2 mol of $R^1$—BY$_2$ are used), e.g. from equimolar amount to a fivefold or in particular threefold or especially twofold excess or 1.5-fold excess (again, in case of di- or polyfunctional halides or sulfonates, the excess amount refers of course to the amount of halide or sulfonate groups; i.e. for 1 mol of Z—R²—Z 10 mol of R¹—BY₂ are used for a fivefold excess). If however the halide or sulfonate is more easily available and/or less expensive than the organoboron compound, this can instead be used in excess, e.g. in a fivefold or threefold or twofold or 1.5-fold excess. Especially in case that the organoboron compound is a MIDA ester, the organoboron compound and the halide or sulfonate can be used in approximately equimolar amounts.

The Pd catalyst can generally either be used as a salt (e.g. Pd(II) acetate or Na₂PdCl₄) or, more often, as a Pd(II) complex which is either preformed or prepared in situ from a Pd(II) salt (e.g. Pd(II)acetate or PdCl₂) and the respective ligand. The same applies to Ni catalysts. Suitable ligands for the complex often contain phosphorus. Examples for phosphorus ligands are di-tert-butyl(1-methyl-2,2-diphenylcyclopropyl)-phosphine (cBRIDP; Mo-Phos), 2-di-tert-butylphosphino-2',4',6'-triisopropylbiphenyl (t-Bu XPhos, tBuXPhos, tert-Butyl XPhos), 1,1'-bis(diphenylphosphino) ferrocene (dppf), 1,1'-bis(di-tert-butylphosphino)ferrocene (dtbpf), 1,2-bis(diphenylphosphino)ethane (dppe), 1,3-bis (diphenylphosphino)propane (dppp), 1,4-bis(diphenylphosphino)butane (dppb), (2,3-O-isopropylidene-2,3-dihydroxy-1,4-bis(diphenylphosphino)butane (diop), bis(di-tert-butyl (4-dimethylaminophenyl)-phosphine) (Amphos), (2S,3S)-(−)-bis(diphenylphosphino)butane (Chiraphos), di-(tert-butyl)phenylphosphine, 2,2'-bis(diphenylphosphino)-1,1'-binaphthyl (BINAP), [1,1'-biphenyl]-2-diisopropyl phosphine, 2-dicyclohexylphosphino-2',4',6'-triisopropylbiphenyl (X-phos), 9,9-dimethyl-4,5-bis(diphenylphosphino) xanthene (Xantphos), 4,5-bis(di-1-(3-methylindolyl)-phosphoramidit)-2,7,9,9-tetramethylxanthene (MeSkatOX), 2-dicyclohexylphosphino-2',6'-dimethoxybiphenyl (S-phos), 2-(2-dicyclohexylphosphanylphenyl)-N1,N1,N3,N3-tetramethyl-benzene-1,3-diamine (C-phos), 6,6'-dimethoxy-[1,1'-biphenyl]-2,2'-diyl)bis(bis(3,5-dimethylphenyl) phosphine, [(4R)-(4,4'-bis-1,3-benzodioxole)-5,5'-diyl]bis [bis(3,5-di-tert-butyl-4-methoxyphenyl)phosphine] ((R)-DTBM-SEGPHOS®), (R)- or (S)-3,5-Xyl-MeO-BIPHEP, (R,S)- or (S,R)-PPF-P(t-Bu)₂, the Josiphos ligands, triphenylphosphine, triphenylphosphite, tri-(2-(1,1-dimethylethyl)-4-methoxy-phenyl)-phosphite, tricyclohexylphosphine, tri(tert-butyl)phosphine, butyldi-1-adamantylphosphine (cataCXium), 1,6-bis (diphenylphosphino)hexane (DPPH), 2,6-bis(2,5-dimethylphenyl)-1-octyl-4-phenylphosphacyclohexan (PCH), tris(3-sulfophenyl)phosphine trisodium salt (TPPTS) and the like.

Non-phosphorus ligands are for example bis(dibenzylideneacetone) (dba), acetonitrile, bisoxazoline and the like. Further, examples for Pd catalysts with ligands without phosphorus are the above-mentioned PEPPSI catalysts (inclusive the new generation).

Examples for catalysts are Pd(Cl)₂(dtbpf), PdCl₂(dppf), Pd(PPh₃)₄, Pd(Cl)₂(t-Bu₂PPh)₂, Pd(Cl)₂(Amphos)₂, Pd(OAc)₂-TPPTS, (OAc=acetate, Ph=phenyl), Pd(dba)₂, the above PEPPSI catalysts (inclusive the new generation), Ni(Cl)₂(dtbpf), Ni(Cl)₂(dppf), Ni(Cl)₂(dppp), and the like.

Suitable bases can be inorganic or organic. Examples for suitable inorganic bases are alkali metal carbonates, e.g. Li₂CO₃, Na₂CO₃, K₂CO₃ or Cs₂CO₃, alkali metal hydroxides, e.g. LiOH, NaOH or KOH, or phosphates, e.g. Li₃PO₄, Na₃PO₄, K₃PO₄ or Cs₃PO₄. Examples for suitable organic bases are open-chained amines, e.g. trimethylamine, triethylamine, tripropylamine, ethyldiisopropylamine and the like, basic N-heterocycles, such as morpoline, pyridine, lutidine, DABCO, DBU or DBN, alkoxylates, e.g. sodium or potassium methanolate, ethanolate, propanolate, isopropanolate, butanolate or tert-butanolate, especially sterically hindered alkoxylates, such as sodium or potassium tert-butanolate, silanolates, like sodium or potassium trimethylsilanolate ((CH₃)₃SiO⁻) or triisopropylsilanolate ((CH(CH₃)₂)₃SiO⁻), phosphazene bases (superbases), such as BEMP and t-Bu-P4

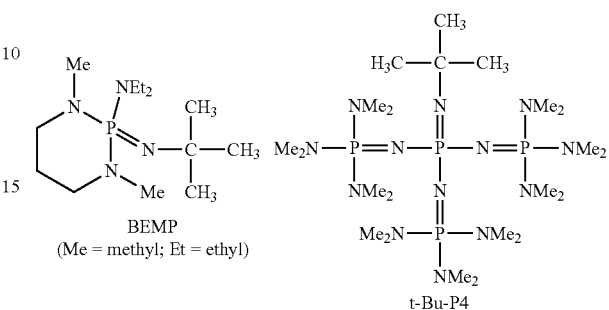

BEMP
(Me = methyl; Et = ethyl)

t-Bu-P4 or phenolates, especially sterically hindered phenolates, like the sodium or potassium salts of the following hydroxyaromatic compounds:

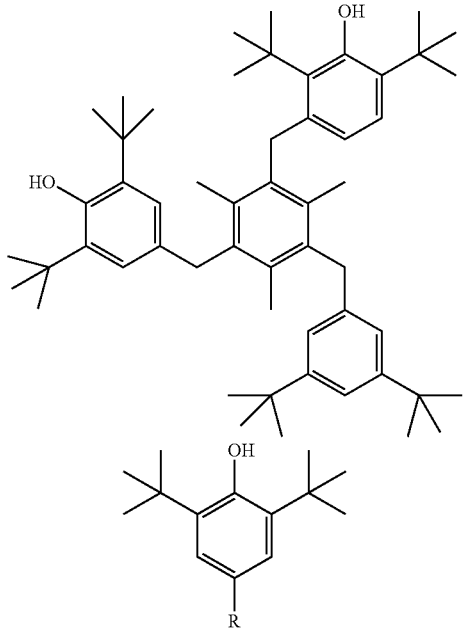

wherein R is H or optionally substituted C₁-C₂-alkyl, e.g. methyl, CH₂—N(CH₃)₂ or CH₂CH₂—C(O)—O—C₁₈H₂₁.

The alkoxylates, phenolates and silanolates are either commercially available or can be prepared shortly before starting the reaction or in situ by reaction of the respective alcohol/hydroxyaromatic compound/silanol with NaOH or KOH.

Specifically, the present method relates to a Suzuki reaction in which an aromatic or heteroaromatic halide R²—(Z)ₙ, where R² is a mono-, bi- or polycyclic, especially a mono-, bi- or tricyclic aryl or heteroaryl group, Z is a halogen atom, especially Cl, Br or I, and n is 1 or 2, is reacted with an aromatic or heteroaromatic boron compound R¹—BY₂, wherein R¹ is a mono-, bi- or polycyclic, especially a mono-, bi- or tricyclic aryl or heteroaryl group and Y is OH or the two Y form together a group —O—C(=O)—

CH$_2$—N(CH$_3$)—CH$_2$—C(=O)—O—, in the presence of a Pd catalyst, specifically of PdCl$_2$(dtbpf), and in the presence of a base, specifically of an organic base, very specifically an amine.

In a particular embodiment aryl groups R$^1$ and R$^2$ are mono-, bi- or tricyclic and are specifically selected from the group consisting of phenyl and naphthyl; and heteroaryl groups R$^1$ and R$^2$ are in particular mono-, bi- or tricyclic and are specifically selected from the group consisting of 5- or 6-membered heteroaromatic monocyclic rings and 9- or 10-membered heteroaromatic bicyclic rings containing 1, 2, 3 or 4 heteroatoms selected from the group consisting of N, O and S as ring members. Mono- or bicyclic aryl or heteroaryl groups R$^1$ and R$^2$ are for example phenyl, naphthyl, furanyl, thienyl, pyrrolyl, pyrazolyl, imidazolyl, oxazoyl, isoxazoyl, thiazoyl, isothiazolyl, [1,2,3]triazolyl, [1,2,4]triazolyl, [1,3,4]triazolyl, the oxadiazolyls, the thiadiazolyls, the tetrazolyls, pyridyl, pyrazinyl, pyrimidyl, pyridazinyl, 1,2,4-triazinyl, 1,3,5-triazinyl, indolyl, benzofuranyl, benzothienyl, quinolinyl, isoquinolinyl, quinazalinyl and the like. More particularly, they are for example phenyl, naphthyl, 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 3-isothiazolyl, 4-isothiazolyl, 5-isothiazolyl, 1,3,4-triazol-1-yl, 1,3,4-triazol-2-yl, 1,3,4-triazol-3-yl, 1,2,3-triazol-1-yl, 1,2,3-triazol-2-yl, 1,2,3-triazol-4-yl, 1,2,5-oxadiazol-3-yl, 1,2,3-oxadiazol-4-yl, 1,2,3-oxadiazol-5-yl, 1,3,4-oxadiazol-2-yl, 1,2,5-thiadiazol-3-yl, 1,2,3-thiadiazol-4-yl, 1,2,3-thiadiazol-5-yl, 1,3,4-thiadiazol-2-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, 1,2,3,4-tetrazin-1-yl, 1,2,3,4-tetrazin-2-yl, 1,2,3,4-tetrazin-5-yl, indolyl, benzofuranyl, benzothienyl, benzopyrazolyl, benzimidazolyl, benzoxazolyl, benzisoxazolyl, benzothiazolyl, benzisothiazolyl, quinolinyl, isoquinolinyl, quinazalinyl and other heteroaromatic bicyclic rings shown below in the "general definitions".

The aryl and heteroaryl groups R$^1$ and R$^2$ can carry one or more substituents, e.g. 1, 2, 3 or 4, in particular 1, 2 or 3, specifically 1 or 2 substituents. Suitable substituents are listed above in context with aryl and heteroaryl groups R$^1$ and R$^2$ in the Suzuki reaction. In a particular embodiment, the substituents on the aryl and heteroaryl groups R$^1$ and R$^2$ are selected from the group consisting of fluorine, cyano, nitro, OH, SH, C$_1$-C$_6$-alkyl, C$_1$-C$_6$-haloalkyl, C$_2$-C$_6$-alkenyl, C$_2$-C$_6$-haloalkenyl, C$_2$-C$_6$-alkynyl, C$_2$-C$_6$-haloalkynyl, C$_3$-C$_8$-cycloalkyl, C$_3$-C$_8$-halocycloalkyl, C$_1$-C$_6$-alkoxy, C$_1$-C$_6$-haloalkoxy, C$_1$-C$_6$-alkoxy-C$_1$-C$_6$-alkyl, C$_1$-C$_6$-haloalkoxy-C$_1$-C$_6$-alkyl, C$_1$-C$_6$-alkylthio, C$_1$-C$_6$-haloalkylthio, C$_1$-C$_6$-alkylsulfinyl, C$_1$-C$_6$-haloalkylsulfinyl, C$_1$-C$_6$-alkylsulfonyl, C$_1$-C$_6$-haloalkylsulfonyl, formyl, C$_1$-C$_4$-alkylcarbonyl, C$_1$-C$_4$-haloalkylcarbonyl, C$_1$-C$_4$-alkoxycarbonyl, C$_1$-C$_4$-haloalkoxycarbonyl, amino, C$_1$-C$_4$-alkylamino, di-(C$_1$-C$_4$-alkyl)amino, phenyl, a 5- or 6-membered heteroaromatic monocyclic ring containing 1, 2, 3 or 4 heteroatoms selected from the group consisting of N, O and S as ring members and a 9- or 10-membered heteroaromatic bicyclic ring containing 1, 2, 3 or 4 heteroatoms selected from the group consisting of N, O and S as ring members, where phenyl and the heteroaromatic rings may carry one or more substituents selected from the group consisting of fluorine, cyano, nitro, OH, SH, C$_1$-C$_6$-alkyl, C$_1$-C$_6$-haloalkyl, C$_2$-C$_6$-alkenyl, C$_2$-C$_6$-haloalkenyl, C$_2$-C$_6$-alkynyl, C$_2$-C$_6$-haloalkynyl, C$_3$-C$_8$-cycloalkyl, C$_3$-C$_8$-halocycloalkyl, C$_1$-C$_6$-alkoxy, C$_1$-C$_6$-haloalkoxy, C$_1$-C$_6$-alkoxy-C$_1$-C$_6$-alkyl, C$_1$-C$_6$-haloalkoxy-C$_1$-C$_6$-alkyl, C$_1$-C$_6$-alkylthio, C$_1$-C$_6$-haloalkylthio, C$_1$-C$_6$-alkylsulfinyl, C$_1$-C$_6$-haloalkylsulfinyl, C$_1$-C$_6$-alkylsulfonyl, C$_1$-C$_6$-haloalkylsulfonyl, formyl, C$_1$-C$_4$-alkylcarbonyl, C$_1$-C$_4$-haloalkylcarbonyl, C$_1$-C$_4$-alkoxycarbonyl, C$_1$-C$_4$-haloalkoxycarbonyl, amino, C$_1$-C$_4$-alkylamino and di-(C$_1$-C$_4$-alkyl)amino. Specifically, the substituents on the aryl and heteroaryl groups R$^1$ and R$^2$ are selected from the group consisting of fluorine, cyano, C$_1$-C$_6$-alkyl, C$_1$-C$_6$-haloalkyl, C$_3$-C$_8$-cycloalkyl, C$_3$-C$_8$-halocycloalkyl, C$_3$-C$_8$-cycloalkyl-C$_1$-C$_6$-alkyl, C$_3$-C$_8$-halocycloalkyl-C$_1$-C$_6$-alkyl, C$_1$-C$_6$-alkoxy, C$_1$-C$_6$-haloalkoxy, C$_1$-C$_6$-alkoxy-C$_1$-C$_6$-alkyl, C$_1$-C$_6$-haloalkoxy-C$_1$-C$_6$-alkyl, C$_1$-C$_6$-alkylthio, C$_1$-C$_6$-haloalkylthio, C$_1$-C$_6$-alkylsulfinyl, C$_1$-C$_6$-haloalkylsulfinyl, C$_1$-C$_6$-alkylsulfonyl, C$_1$-C$_6$-haloalkylsulfonyl, formyl, C$_1$-C$_4$-alkylcarbonyl, C$_1$-C$_4$-haloalkylcarbonyl, C$_1$-C$_4$-alkoxycarbonyl, C$_1$-C$_4$-haloalkoxycarbonyl, amino, C$_1$-C$_4$-alkylamino and di-(C$_1$-C$_4$-alkyl)amino.

The reaction is preferably carried out at from 10° C. to 60° C., in particular from 20° C. to 55° C., specifically from 25° C. to 55° C. and very specifically from 40° C. to 50° C.

If n is 1, R$^2$—(Z)$_n$ and R$^1$—BY$_2$ are in particular used in a molar ratio of from 0.8:1 to 1:4, more particularly from 1:1 to 1:3 and specifically from 1:1 to 1:2. If n is 2, R$^2$—(Z)$_n$ and R$^1$—BY$_2$ are in particular used in a molar ratio of from 1:1.5 to 1:8, more particularly from 1:2 to 1:6 and specifically from 1:2 to 1:5.

The catalyst is used in catalytic, i.e. substoichiometric amounts, e.g. in an amount of from 0.001 to 0.1 mol per mol of that reactant which not used in excess (here mostly the compound R$^2$—(Z)$_n$), in particular 0.005 to 0.07 mol per mol of the reactant not used in excess, specifically 0.01 to 0.05 mol per mol of the reactant not used in excess. If the reactants are used in equimolar ratio, the above amounts of catalyst apply of course to either of the reactants.

The base is generally used in excess, i.e. in overstoichiometric amounts with respect to that reactant not used in excess, e.g. in an amount of from 1.5 to 5 mol per mol of the reactant not used in excess, in particular 2 to 4 mol per mol of the reactant not used in excess. If the reactants are used in equimolar ratio, the above amounts of base apply of course to either of the reactants.

The reaction can be carried out by standard proceedings for Suzuki reactions, e.g. by mixing all reagents, inclusive catalyst or catalyst precursor and ligand(s) and base, water and the cellulose derivative and reacting them at the desired temperature. Alternatively the reagents can be added gradually, especially in the case of a continuous or semicontinuous process.

If the catalyst ligand or any reactant is prone to oxidation by air (such as is the case, for example, for triphenylphosphine, tri(tert-butyl)phosphine, X-Phos, 6,6-dimethoxy-[1,1'-biphenyl]-2,2'-diyl)bis(bis(3,5-dimethylphenyl)phosphine and several others), the reaction is preferably carried out in an inert atmosphere in order to avoid the presence of oxygen, e.g. under an argon or nitrogen atmosphere. Preferably, moreover, the solvent is used in degassed form. On a laboratory scale this is e.g. obtained by freezing, applying a vacuum and unfreezing under an inert atmosphere or by bubbling a vigorous stream of argon or nitrogen through the solvent or by ultrasonification under an inert atmosphere. On an industrial scale other methods known in the art can be applied.

Workup proceedings will be described below, as they are similar for most reactions.

Sonogashira Reaction

In another particular embodiment the transition metal catalyzed C—C coupling reaction is a Sonogashira reaction. In Sonogashira reactions an aryl, heteroaryl or vinyl halogenide or sulfonate (the sulfonate being in particular a fluorinated alkylsulfonate or tosylate, specifically triflate or nonaflate) is reacted with a terminal alkyne. Preferably, a halogenide or sulfonate $R^2$—$(Z)_n$, where $R^2$ is an alkenyl (especially a terminal alkenyl; i.e. Z is bound to a carbon atom of a C—C double bond), aryl or heteroaryl group, Z is a halogenide or sulfonate (the sulfonate being in particular a fluorinated alkylsulfonate or tosylate, specifically triflate or nonaflate) group and n is 1, 2, 3 or 4, is reacted with a terminal alkyne H—C≡C—$R^1$, where $R^1$ is hydrogen or an alkyl, alkenyl, alkapolyenyl, alkynyl (provided that the C—C triple bond is not terminal), alkapolyynyl (provided there is no terminal C—C triple bond (—C≡C—H) in this radical), mixed alkenyl/alkynyl (provided there is no terminal C—C triple bond (—C≡C—H) in this radical), cycloalkyl, cycloalkenyl, cycloalkynyl, mixed cycloalkenyl/cycloalkynyl, polycarbocyclyl, heterocyclyl, aryl, heteroaryl or silyl group $Si(R^{14})_3$, in the presence of a transition metal catalyst, mostly a Pd catalyst, optionally of a copper(I) salt, and in general also of a base. Each $R^{14+}$ has independently one of the meanings given above in context with the Suzuki reaction for $R^{14}$. Classically, the Sonogashira coupling involves the use of a copper salt. In the present invention, however, the term "Sonogashira reaction" or "Sonogashira coupling" is also used for the coupling of an aryl, heteroaryl or vinyl halogenide or sulfonate with a terminal alkyne in the presence of a transition metal catalyst, mostly a Pd catalyst, and in general also of a base, but without copper (salts/complexes).

The reaction of the terminal alkyne with $R^2$—$(Z)_n$ yields a compound $(R^1)_n$—$R^2$. The alkenyl, aryl or heteroaryl halide or sulfonate can contain more than one halide or sulfonate group (when n is 2, 3 or 4), so that multiply coupled compounds can form, especially if the alkyne compound is used in excess. For instance, a difunctional compound $R^2$—$(Z)_2$ can yield a twofold coupled compound $R^1$—$R^2$—$R^1$.

Due to the tolerance of the Sonogashira reaction to a wide variety of functional groups, the alkyl, alkenyl, alkapolyenyl, alkynyl, mixed alkenyl/alkynyl, alkapolyynyl, cycloalkyl, cycloalkenyl, cycloalkynyl, mixed cycloalkenyl/cycloalkynyl, polycarbocyclyl, heterocyclyl, aryl or heteroaryl groups $R^1$ and $R^2$ can carry one or more substituents. Suitable substituents for the alkyl, alkenyl, alkapolyenyl, alkynyl, mixed alkenyl/alkynyl, alkapolyynyl, cycloalkyl, cycloalkenyl, cycloalkynyl, mixed cycloalkenyl/cycloalkynyl, polycarbocyclyl, aryl or heteroaryl groups correspond to those listed above in context with substituents on the alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling. Suitable substituents for heterocyclyl groups $R^1$ and $R^2$ correspond to those listed above in context with substituents on the cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling.

In these substituents, however, all functional groups, especially halogen atoms and sulfonyloxy groups, have to be less reactive towards the alkyne compound than the halogen atom or sulfonate group on the desired reaction site of the $R^2$—$(Z)_n$ compound.

Suitable Pd catalysts (inclusive ligands) are those mentioned above in context with the Suzuki coupling.

Suitable Cu(I) salts are CuI and CuBr.

Suitable bases are those mentioned above in context with the Suzuki coupling.

Specifically, the present method relates to a Sonogashira reaction in which an aromatic or heteroaromatic halogenide $R^2$—$(Z)_n$, where $R^2$ is a mono-, bi- or polycyclic aryl or heteroaryl group, Z is a halogen atom, especially Cl, Br or I, more specifically Br or I, and n is 1, is reacted with a terminal alkyne H—C≡C—$R^1$, where $R^1$ is a mono-, bi- or polycyclic aryl or heteroaryl group, in the presence of a Pd catalyst, specifically of $PdCl_2(CH_3CN)_2$ or $PdCl_2(X\text{-Phos})_2$, and in the presence of a base, specifically of an alkali metal carbonate, very specifically $Cs_2CO_3$, or an organic base, specifically an amine.

In a particular embodiment aryl groups $R^1$ and $R^2$ are mono-, bi- or tricyclic and are specifically selected from the group consisting of phenyl and naphthyl; and heteroaryl groups $R^1$ and $R^2$ are in particular mono-, bi- or tricyclic and are specifically selected from the group consisting of 5- or 6-membered heteroaromatic monocyclic rings and 9- or 10-membered heteroaromatic bicyclic rings containing 1, 2, 3 or 4 heteroatoms selected from the group consisting of N, O and S as ring members. Mono- or bicyclic aryl or heteroaryl groups $R^1$ and $R^2$ are for example phenyl, naphthyl, furanyl, thienyl, pyrrolyl, pyrazolyl, imidazolyl, oxazoyl, isoxazoyl, thiazoyl, isothiazolyl, [1,2,3]triazolyl, [1,2,4]triazolyl, [1,3,4]triazolyl, the oxadiazolyls, the thiadiazolyls, the tetrazolyls, pyridyl, pyrazinyl, pyrimidyl, pyridazinyl, 1,2,4-triazinyl, 1,3,5-triazinyl, indolyl, benzofuranyl, benzothienyl, quinolinyl, isoquinolinyl, quinazalinyl and the like. More particularly, they are for example phenyl, naphthyl, 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 3-isothiazolyl, 4-isothiazolyl, 5-isothiazolyl, 1,3,4-triazol-1-yl, 1,3,4-triazol-2-yl, 1,3,4-triazol-3-yl, 1,2,3-triazol-1-yl, 1,2,3-triazol-2-yl, 1,2,3-triazol-4-yl, 1,2,5-oxadiazol-3-yl, 1,2,3-oxadiazol-4-yl, 1,2,3-oxadiazol-5-yl, 1,3,4-oxadiazol-2-yl, 1,2,5-thiadiazol-3-yl, 1,2,3-thiadiazol-4-yl, 1,2,3-thiadiazol-5-yl, 1,3,4-thiadiazol-2-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, 1,2,3,4-tetrazin-1-yl, 1,2,3,4-tetrazin-2-yl, 1,2,3,4-tetrazin-5-yl, indolyl, benzofuranyl, benzothienyl, benzopyrazolyl, benzimidazolyl, benzoxazolyl, benzisoxazolyl, benzothiazolyl, benzisothiazolyl, quinolinyl, isoquinolinyl, quinazalinyl and other heteroaromatic bicyclic rings shown below in the "general definitions".

The aryl and heteroaryl groups $R^1$ and $R^2$ can carry one or more substituents, e.g. 1, 2, 3 or 4, in particular 1, 2 or 3, specifically 1 or 2 substituents. Suitable substituents are listed above in context with aryl and heteroaryl groups $R^1$ and $R^2$ in the Suzuki reaction. In a particular embodiment, the substituents on the aryl and heteroaryl groups $R^1$ and $R^2$ are selected from the group consisting of fluorine, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino, di-($C_1$-$C_4$-alkyl)amino, phenyl, a 5- or 6-membered heteroaromatic monocyclic ring containing 1, 2, 3 or 4 heteroatoms selected from N, O and S as ring members and a 9- or 10-membered heteroaromatic bicyclic ring containing 1, 2, 3 or 4 heteroatoms selected from the group consisting of N, O and S as ring members, where phenyl and the heteroaromatic rings may carry one or more substituents selected from the group consisting of fluorine, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino. Specifically, the substituents on the aryl and heteroaryl groups $R^1$ and $R^2$ are selected from the group consisting of fluorine, cyano, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino.

Very specifically, $R^1$ and $R^2$ are selected from the group consisting of phenyl and naphthyl, where phenyl and naphthyl may carry 1, 2 or 3, specifically 1 or 2 substituents as defined above.

The reaction is preferably carried out at from 10° C. to 60° C., in particular from 20° C. to 55° C., specifically from 20° C. to 50° C. and very specifically from 20° C. to 30° C.

The halogenide or sulfonate and the terminal alkyne can be used in a molar ratio of from 10:1 to 1:10, e.g. from 7:1 to 1:7 or from 5:1 to 1:5. In case of di- or polyfunctional halides or sulfonates, the molar ratio relates of course to the number of halide or sulfonate groups in the molecule. If n is 1, $R^2$—$(Z)_n$ and H—C≡C—$R^1$ are preferably used in a molar ratio of from 2:1 to 1:2, more preferably from 1.5:1 to 1:1.5 and specifically in approximately equimolar amounts. If n is 2, $R^2$—$(Z)_n$ and H—C≡C—$R^1$ are preferably used in a molar ratio of from 1:1 to 1:4, more preferably from 1:1.5 to 1:3 and specifically in a molar ratio of ca. 1:2. "ca." and "approximately" include weighing errors of +/−10%.

The catalyst is used in catalytic, i.e. substoichiometric amounts, e.g. in an amount of from 0.001 to 0.1 mol per mol of that reactant which is not used in excess, in particular 0.005 to 0.07 mol per mol of the reactant not used in excess, specifically 0.005 to 0.05 mol per mol of the reactant not used in excess. If the reactants are used in equimolar ratio, the above amounts of catalyst apply of course to either of the reactants.

The base is generally used in excess, i.e. in overstoichiometric amounts with respect to that reactant not used in excess, e.g. in an amount of from 1.5 to 5 mol per mol of the reactant not used in excess, in particular 1.5 to 4 mol per mol of the reactant not used in excess, specifically 1.5 to 3 mol per mol of the reactant not used in excess. If the reactants are used in equimolar ratio, the above amounts of base apply of course to either of the reactants.

The reaction can be carried out by standard proceedings for Sonogashira reactions, e.g. by mixing all reagents, inclusive catalyst or catalyst precursor and ligand(s) and base, water and the cellulose derivative and reacting them at the desired temperature. Alternatively the reagents can be added gradually, especially in the case of a continuous or semicontinuous process.

If the catalyst ligand or any reactant is prone to oxidation by air (such as is the case, for example, for triphenylphosphine, tri(tert-butyl)phosphine, X-Phos, 6,6'-dimethoxy-[1,1'-biphenyl]-2,2'-diyl)bis(bis(3,5-dimethylphenyl)phosphine and several others), the reaction is preferably carried out in an inert atmosphere in order to avoid the presence of oxygen, e.g. under an argon or nitrogen atmosphere. Preferably, moreover, the solvent is used in degassed form. On a laboratory scale this is e.g. obtained by freezing, applying a vacuum and unfreezing under an inert atmosphere or by bubbling a vigorous stream of argon or nitrogen through the solvent or by ultrasonification under an inert atmosphere. On an industrial scale other methods known in the art can be applied.

Workup proceedings will be described below, as they are similar for most reactions.

Heck Reaction

In another particular embodiment the transition metal catalyzed C—C coupling reaction is a Heck reaction. In Heck reactions an aryl, heteroaryl, benzyl, vinyl or alkyl halogenide or sulfonate (the alkyl group must not contain any β-hydrogen atoms) is reacted with an olefinically unsaturated compound in the presence of a transition metal catalyst, mostly a Pd catalyst, and generally also in the presence of a base. The sulfonate is in particular a fluorinated alkylsulfonate or tosylate, specifically triflate, nonaflate or tosylate.

Preferably, a halogenide or sulfonate $R^2$—$(Z)_n$, where $R^2$ is an aryl, heteroaryl, benzyl, vinyl or alkyl group (the alkyl group must however not contain any β-hydrogen atoms), Z is a halogen atom or a sulfonate group (the sulfonate being in particular a fluorinated alkylsulfonate or tosylate, specifically triflate, nonaflate or tosylate), preferably a Cl, Br, I, triflate, nonaflate or tosylate group, and n is 1, 2, 3 or 4, is reacted with an olefin $R^1$(H)C=C($R^3$)($R^4$) where $R^1$, $R^3$, and $R^4$, independently of each other, are hydrogen, alkyl, alkenyl, alkapolyenyl, alkynyl, alkapolynyl, mixed alkenyl/alkynyl, cycloalkyl, cycloalkenyl, cycloalkynyl, mixed cycloalkenyl/cycloalkynyl, polycarbocyclyl, heterocyclyl, aryl, heteroaryl, or are one of the substituents listed in context with the Suzuki reaction as suitable radicals on alkyl, alkenyl, alkapoyenyl, alkynyl, alkapolyynyl or mixed alkenyl/alkynyl groups (however except for oxo (=O), =S, and =$NR^{12a}$), in the presence of a transition metal catalyst, mostly a Pd catalyst, and in general also of a base. More precisely, $R^1$, $R^3$ and $R^4$, independently of each other, are hydrogen, alkyl, alkenyl, alkapolyenyl, alkynyl, alkapolynyl, mixed alkenyl/alkynyl, cycloalkyl, cycloalkenyl, cycloalkynyl, mixed cycloalkenyl/cycloalkynyl, polycarbocyclyl, heterocyclyl, aryl, heteroaryl, halogen, cyano, nitro, azido, —SCN, —$SF_5$, $OR^{11}$, $S(O)_m R^{11}$, $NR^{12a}R^{12b}$, C(=O)$R^{13}$, C(=S)$R^{13}$, C(=$NR^{12a}$)$R^{13}$ or —Si($R^{14}$)$_3$; where $R^{11}$, $R^{12a}$, $R^{12b}$, $R^{13}$, $R^{14}$ and $R^{15}$ are independently as defined above in context with the Suzuki reaction. The reaction yields a compound $(R^1)_n$—$R^2$. The halogenide or sulfonate can contain more than one halogenide or sulfonate group (when n is 2, 3 or 4), so that multiply coupled compounds can form, especially if the olefinic compound is used in excess. For instance, a difunctional compound $R^2$—$(Z)_2$ can yield a twofold coupled compound $R^1$—$R^2$—$R^1$.

Due to the tolerance of the Heck reaction to a wide variety of functional groups, the alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl, heteroaryl, benzyl, vinyl groups $R^1$, $R^2$, $R^3$ and $R^4$ can carry one or more substituents. Suitable substituents for the on the alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl or heteroaryl groups correspond to those listed above in context with substituents on the alkyl, alkenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling. Suitable substituents for heterocyclyl groups correspond to those listed above in context with substituents on the cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling. Specifically, the cycloalkenyl, cycloalkynyl, mixed cycloalkenyl/cycloalkynyl, polycarbocyclyl, aryl, heterocyclyl and heteroaryl groups $R^1$, $R^3$ and $R^4$ may be substituted by one or more radicals $R^{15}$.

In these substituents, however, all functional groups, especially halogen atoms and sulfonyloxy groups, have to be less reactive towards the olefinic compound than the halogen atom or sulfonate group on the desired reaction site of the $R^2$—$(Z)_n$ compound. Analogously, if in the olefinic compound $R^1(H)C=C(R^3)(R^4)$ the radicals $R^1$, $R^3$, and/or $R^4$ contain C—C double (or also triple) bonds, these have to be less reactive towards Z than the C—C double bond at the desired reaction site of $R^1(H)C=C(R^3)(R^4)$.

Suitable Pd catalysts (inclusive ligands) are those mentioned above in context with the Suzuki coupling.

Suitable bases are those mentioned above in context with the Suzuki coupling.

Specifically, the present method relates to a Heck reaction in which an aromatic or heteroaromatic halogenide $R^2$—$(Z)_n$, where $R^2$ is a mono-, bi- or polycyclic aryl or heteroaryl group, Z is a halogen atom, especially Cl, Br or I, more specifically Br or I, and n is 1, is reacted with an olefinic compound $R^1(H)C=C(R^3)(R^4)$ where $R^1$ and $R^3$ are H and $R^4$ is hydrogen, alkyl, or is one of the substituents listed in context with the Suzuki reaction as suitable radicals on alkyl, alkenyl and alkynyl groups (and is more precisely hydrogen, alkyl, halogen, cyano, nitro, azido, —SCN, —SF$_5$, OR$^{11}$, S(O)$_m$R$^{11}$, NR$^{12a}$R$^{12b}$, C(=O)R$^{13}$, C(=S) R$^{13}$, C(=NR$^{12a}$)R$^{13}$ or —Si(R$^{14}$)$_3$), in the presence of a Pd catalyst, specifically of Pd(t-Bu$_3$P)$_2$, and in the presence of a base, specifically an amine.

In a particular embodiment the aryl group $R^2$ is mono-, bi- or tricyclic and is specifically selected from the group consisting of phenyl and naphthyl; and the heteroaryl group $R^2$ is in particular mono-, bi- or tricyclic and is specifically selected from the group consisting of 5- or 6-membered heteroaromatic monocyclic rings and 9- or 10-membered heteroaromatic bicyclic rings containing 1, 2, 3 or 4 heteroatoms selected from the group consisting of N, O and S as ring members. Mono- or bicyclic aryl or heteroaryl groups $R^2$ are for example phenyl, naphthyl, furanyl, thienyl, pyrrolyl, pyrazolyl, imidazolyl, oxazoyl, isoxazoyl, thiazoyl, isothiazolyl, [1,2,3]triazolyl, [1,2,4]triazolyl, [1,3,4]triazolyl, the oxadiazolyls, the thiadiazolyls, the tetrazolyls, pyridyl, pyrazinyl, pyrimidyl, pyridazinyl, 1,2,4-triazinyl, 1,3,5-triazinyl, indolyl, benzofuranyl, benzothienyl, quinolinyl, isoquinolinyl, quinazalinyl and the like. More particularly, they are for example phenyl, naphthyl, 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 3-isothiazolyl, 4-isothiazolyl, 5-isothiazolyl, 1,3,4-triazol-1-yl, 1,3,4-triazol-2-yl, 1,3,4-triazol-3-yl, 1,2,3-triazol-1-yl, 1,2,3-triazol-2-yl, 1,2,3-triazol-4-yl, 1,2,5-oxadiazol-3-yl, 1,2,3-oxadiazol-4-yl, 1,2,3-oxadiazol-5-yl, 1,3,4-oxadiazol-2-yl, 1,2,5-thiadiazol-3-yl, 1,2,3-thiadiazol-4-yl, 1,2,3-thiadiazol-5-yl, 1,3,4-thiadiazol-2-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, 1,2,3,4-tetrazin-1-yl, 1,2,3,4-tetrazin-2-yl, 1,2,3,4-tetrazin-5-yl, indolyl, benzofuranyl, benzothienyl, benzopyrazolyl, benzimidazolyl, benzoxazolyl, benzisoxazolyl, benzothiazolyl, benzisothiazolyl, quinolinyl, isoquinolinyl, quinazalinyl and other heteroaromatic bicyclic rings shown below in the "general definitions".

The aryl and heteroaryl groups $R^2$ can carry one or more substituents, e.g. 1, 2, 3 or 4, in particular 1, 2 or 3, specifically 1 or 2 substituents. Suitable substituents are listed above in context with aryl and heteroaryl groups $R^1$ and $R^2$ in the Suzuki reaction. In a particular embodiment, the substituents on the aryl and heteroaryl groups $R^2$ are selected from the group consisting of fluorine, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino, di-($C_1$-$C_4$-alkyl)amino, phenyl, a 5- or 6-membered heteroaromatic monocyclic ring containing 1, 2, 3 or 4 heteroatoms selected from N, O and S as ring members and a 9- or 10-membered heteroaromatic bicyclic ring containing 1, 2, 3 or 4 heteroatoms selected from the group consisting of N, O and S as ring members, where phenyl and the heteroaromatic rings may carry one or more substituents selected from the group consisting of fluorine, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino. Specifically, the substituents on the aryl and heteroaryl groups $R^2$ are selected from the group consisting of fluorine, cyano, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino.

Particular groups $R^4$ are halogen (provided that this not more reactive than the halogen atom or sulfonate group on the desired reaction site of the $R^2$—$(Z)_n$ compound) cyano, nitro, azido, —SCN, —SF$_5$, OR$^{11}$, S(O)$_m$R$^{11}$, NR$^{12a}$R$^{12b}$, C(=O)R$^{13}$, C(=S)R$^{13}$, C(=NR$^{12a}$)R$^{13}$, —Si(R$^{14}$)$_3$, alkyl, optionally substituted by one or more radicals R$^{17}$; cycloalkyl, cycloalkenyl, cycloalkynyl, mixed cycloalkenyl/cycloalkynyl, polycarbocyclyl, where the 5 last-mentioned substituents may carry one or more substituents selected from R$^{15}$; aryl which may be substituted by one or more radicals R$^{15}$, heterocyclyl may be substituted by one or more radicals R$^{15}$; and heteroaryl which may be substituted by one or more radicals R$^{15}$; where R$^{11}$, R$^{12a}$, R$^{12b}$, R$^{13}$, R$^{14}$, R$^{15}$ and R$^{17}$ are as defined above in context with the Suzuki reaction. Specifically, R$^4$ is C(=O)R$^{13}$, where R$^{13}$ is alkyl or alkoxy, specifically $C_1$-$C_6$-alkyl or $C_1$-$C_6$-alkoxy and very specifically $C_1$-$C_6$-alkoxy.

The reaction is preferably carried out at from 10° C. to 60° C., in particular from 20° C. to 55° C., specifically from 25° C. to 55° C. and very specifically from 40° C. to 50° C.

The halogenide or sulfonate and the olefinically unsaturated compound can be used in a molar ratio of from 10:1 to 1:10, e.g. from 7:1 to 1:7 or from 5:1 to 1:5. In case of di- or polyfunctional halogenides or sulfonates, the molar ratio relates of course to the number of halogenide or sulfonate groups in the molecule. If n is 1, $R^2$—$(Z)_n$ and R$^1$(H)C=C(R$^3$)(R$^4$) are preferably used in a molar ratio of from 0.8:1 to 1:4, more preferably from 1:1 to 1:3 and specifically from 1:1 to 1:2. If n is 2, $R^2$—$(Z)_n$ and R$^1$(H)C=C(R$^3$)R$^4$) are preferably used in a molar ratio of from 1:1.5 to 1:8, more preferably from 1:2 to 1:6 and specifically from 1:2 to 1:5.

The catalyst is used in catalytic, i.e. substoichiometric amounts, e.g. in an amount of from 0.001 to 0.1 mol per mol of that reactant which is not used in excess, in particular 0.005 to 0.07 mol per mol of the reactant not used in excess, specifically 0.01 to 0.05 mol per mol of the reactant not used in excess. If the reactants are used in equimolar ratio, the above amounts of catalyst apply of course to either of the reactants.

The base is generally used in excess, i.e. in overstoichiometric amounts with respect to that reactant not used in excess, e.g. in an amount of from 1.5 to 5 mol per mol of the reactant not used in excess, in particular 1.5 to 4 mol per mol of the reactant not used in excess, specifically 2 to 4 mol per mol of the reactant not used in excess. If the reactants are used in equimolar ratio, the above amounts of base apply of course to either of the reactants.

The reaction can be carried out by standard proceedings for Heck reactions, e.g. by mixing all reagents, inclusive catalyst or catalyst precursor and ligand(s) and base, water and the cellulose derivative and reacting them at the desired temperature. Alternatively the reagents can be added gradually, especially in the case of a continuous or semicontinuous process.

If the catalyst ligand or any reactant is prone to oxidation by air (such as is the case, for example, for triphenylphosphine, tri(tert-butyl)phosphine, X-Phos, 6,6'-dimethoxy-[1,1'-biphenyl]-2,2'-diyl)bis(bis(3,5-dimethylphenyl)phosphine and several others), the reaction is preferably carried out in an inert atmosphere in order to avoid the presence of oxygen, e.g. under an argon or nitrogen atmosphere. Preferably, moreover, the solvent is used in degassed form. On a laboratory scale this is e.g. obtained by freezing, applying a vacuum and unfreezing under an inert atmosphere or by bubbling a vigorous stream of argon or nitrogen through the solvent or by ultrasonification under an inert atmosphere. On an industrial scale other methods known in the art can be applied.

Workup proceedings will be described below, as they are similar for most reactions.

C—C Coupling Reactions Involving C—H Activation

In another particular embodiment the transition metal catalyzed C—C coupling reaction is C—C coupling reaction involving C—H activation. Such reactions are coupling reactions in which one of the reactants reacts via a C—H bond and not via a specific activating group. The Heck reaction is such a reaction involving C—H activation. In the present case however, in the C—C coupling reactions involving C—H activation two aromatic or heteroaromatic compounds are coupled.

In a particular embodiment of the present invention, a halogenide or sulfonate $R^2$—Z, where $R^2$ is an aryl or heteroaryl group, Z is a halogen atom (Cl, Br and I being preferred) or a sulfonate group (the sulfonate being in particular a fluorinated alkylsulfonate or tosylate, specifically triflate, nonaflate or tosylate), and is preferably I, is reacted with a compound $R^1$—H, where $R^1$ is an aryl or heteroaryl group, in the presence of a transition metal catalyst, mostly a Pd catalyst, often under acidic conditions. If Z is Cl, Br or I, it may be advantageous to carry out the reaction in the presence of a water-soluble silver(I) salt, which precipitates the eliminated chloride, bromide or iodide ion as AgCl, AgBr or AgI and draws the reaction to the product side. The reaction yields a compound $R^1$—$R^2$. Preferably, $R^1$ carries in ortho position to the shown hydrogen atom a heteroatom-directing group. This group helps the transition metal to coordinate to the substrate. Such heteroatom-directing groups are for example amino groups, carbonylamino groups, urea groups, carbonyl groups, carboxyl groups, carboxylic ester groups, carboxamide groups and the like. Particularly useful are urea groups, especially urea groups with electron-donating groups, e.g. alkyl-substituted urea groups, such as ($C_1$-$C_4$-alkyl)$_2$N—C(O)—NH—.

In a particular embodiment aryl groups $R^1$ and $R^2$ are mono-, bi- or tricyclic and are specifically selected from the group consisting of phenyl and naphthyl; and heteroaryl groups $R^1$ and $R^2$ are in particular mono-, bi- or tricyclic and are specifically selected from the group consisting of 5- or 6-membered heteroaromatic monocyclic rings and 9- or 10-membered heteroaromatic bicyclic rings containing 1, 2, 3 or 4 heteroatoms selected from the group consisting of N, O and S as ring members. Mono- or bicyclic aryl or heteroaryl groups $R^1$ and $R^2$ are for example phenyl, naphthyl, furanyl, thienyl, pyrrolyl, pyrazolyl, imidazolyl, oxazoyl, isoxazoyl, thiazoyl, isothiazolyl, [1,2,3]triazolyl, [1,2,4]triazolyl, [1,3,4]triazolyl, the oxadiazolyls, the thiadiazolyls, the tetrazolyls, pyridyl, pyrazinyl, pyrimidyl, pyridazinyl, 1,2,4-triazinyl, 1,3,5-triazinyl, indolyl, benzofuranyl, benzothienyl, quinolinyl, isoquinolinyl, quinazalinyl and the like. More particularly, they are for example phenyl, naphthyl, 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 3-isothiazolyl, 4-isothiazolyl, 5-isothiazolyl, 1,3,4-triazol-1-yl, 1,3,4-triazol-2-yl, 1,3,4-triazol-3-yl, 1,2,3-triazol-1-yl, 1,2,3-triazol-2-yl, 1,2,3-triazol-4-yl, 1,2, 5-oxadiazol-3-yl, 1,2,3-oxadiazol-4-yl, 1,2,3-oxadiazol-5-yl, 1,3,4-oxadiazol-2-yl, 1,2,5-thiadiazol-3-yl, 1,2,3-thiadiazol-4-yl, 1,2,3-thiadiazol-5-yl, 1,3,4-thiadiazol-2-yl, 2-pyridinyl, 3-pyridinyl, 4-pyridinyl, 1-oxopyridin-2-yl, 1-oxopyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, 1,2,3,4-tetrazin-1-yl, 1,2,3,4-tetrazin-2-yl, 1,2,3,4-tetrazin-5-yl, indolyl, benzofuranyl, benzothienyl, benzopyrazolyl, benzimidazolyl, benzoxazolyl, benzisoxazolyl, benzothiazolyl, benzisothiazolyl, quinolinyl, isoquinolinyl, quinazalinyl and other heteroaromatic bicyclic rings shown below in the "general definitions".

The aryl and heteroaryl groups $R^1$ and $R^2$ can carry one or more substituents, e.g. 1, 2, 3 or 4, in particular 1, 2 or 3, specifically 1 or 2 substituents. Suitable substituents are listed above in context with aryl and heteroaryl groups $R^1$ and $R^2$ in the Suzuki reaction.

In these substituents, however, all functional groups, especially halogen atoms and sulfonyloxy groups, have to be less reactive towards the alkyne compound than the halogen atom or sulfonate group on the desired reaction site of the $R^2$—Z compound.

In a particular embodiment, the substituents on the aryl and heteroaryl groups $R^1$ and $R^2$ are selected from the group consisting of fluorine, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino, di-($C_1$-$C_4$-alkyl)amino, phenyl, a 5- or 6-membered heteroaromatic monocyclic ring containing 1, 2, 3 or 4 heteroatoms selected from the group consisting of N, O and S as ring members and a 9- or 10-membered heteroaromatic bicyclic ring containing 1, 2, 3 or 4 heteroatoms selected from the group consisting of N, O and S as ring members, where phenyl and the heteroaromatic rings may carry one or more substituents selected from the group consisting of fluorine, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino. Specifically, the substituents on the aryl and heteroaryl groups $R^1$ and $R^2$ are selected from the group consisting of fluorine, cyano, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino.

Very specifically, $R^1$ and $R^2$ are selected from the group consisting of phenyl and naphthyl, where phenyl and naphthyl may carry 1, 2 or 3, specifically 1 or 2 substituents as defined above. As said, preferably, $R^1$ carries in ortho position to the shown hydrogen atom a heteroatom-directing group.

Suitable Pd catalysts (inclusive ligands) are those mentioned above in context with the Suzuki coupling. Particularly, however, the Pd catalyst is used in form of a salt, e.g. as $PdCl_2$ or, in particular $Pd(OAc)_2$ (OAc=acetate).

The Ag salt, if present, is in particular used as a water-soluble salt, e.g. $AgNO_3$ or, in particular, AgOAc.

The reaction is preferably carried out in acidic medium, so that the electrophilic attack on the (het)aryl ring is facilitated. Suitable acids are for example $HBF_4$, trifluoroacetic acid, toluenesulfonic acid and acetic acid.

The reaction is preferably carried out at from 10° C. to 60° C., in particular from 20° C. to 55° C., specifically from 20° C. to 50° C. and very specifically from 20° C. to 30° C.

The halogenide or sulfonate and the C—H compound can be used in a molar ratio of from 10:1 to 1:10, e.g. from 7:1 to 1:7 or from 5:1 to 1:5; preferably from 4:1 to 1:4, in particular from 3:1 to 1:3 and specifically from 2:1 to 1:2.

The catalyst is used in catalytic, i.e. substoichiometric amounts, e.g. in an amount of from 0.001 to 0.5 mol per mol of that reactant which is not used in excess, in particular 0.01 to 0.5 mol per mol of the reactant not used in excess, specifically 0.05 to 0.3 mol per mol of the reactant not used in excess. If the reactants are used in equimolar ratio, the above amounts of catalyst apply of course to either of the reactants.

The silver(I) salt is preferably used in such an amount that it can precipitate all the theoretically eliminated halide ions. Accordingly, it is preferably used in at least equimolar amounts with respect to the halide $R^2$—Z, e.g. in a weight ratio of Ag salt to halide of from 1:1 to 2:1, in particular 1:2 to 1.5:1 and specifically in approximately equimolar amounts "Approximately" includes weighing errors of +/−10%.

The acid is generally used in excess, i.e. in overstoichiometric amounts with respect to that reactant not used in excess, e.g. in an amount of from 1.5 to 5 mol per mol of the reactant not used in excess, in particular 1.5 to 4 mol per mol of the reactant not used in excess, specifically 2 to 4 mol per mol of the reactant not used in excess. If the reactants are used in equimolar ratio, the above amounts of base apply of course to either of the reactants.

The reaction can be carried out by standard proceedings for C—C coupling reactions reactions involving C—H activation, e.g. by mixing all reagents, inclusive catalyst or catalyst precursor and ligand(s), silver salt, if used, acid, if used, water and the cellulose derivative and reacting them at the desired temperature. Alternatively the reagents can be added gradually, especially in the case of a continuous or semicontinuous process.

If the catalyst ligand or any reactant is prone to oxidation by air (such as is the case, for example, for triphenylphosphine, tri(tert-butyl)phosphine, X-Phos, 6,6'-dimethoxy-[1,1'-biphenyl]-2,2'-diyl)bis(bis(3,5-dimethylphenyl)phosphine and several others), the reaction is preferably carried out in an inert atmosphere in order to avoid the presence of oxygen, e.g. under an argon or nitrogen atmosphere. Preferably, moreover, the solvent is used in degassed form. On a laboratory scale this is e.g. obtained by freezing, applying a vacuum and unfreezing under an inert atmosphere or by bubbling a vigorous stream of argon or nitrogen through the solvent or by ultrasonification under an inert atmosphere. On an industrial scale other methods known in the art can be applied.

Workup proceedings will be described below, as they are similar for most reactions.

Negishi Reaction

In another particular embodiment the transition metal catalyzed C—C coupling reaction is a Negishi reaction. In classical Negishi reactions an organozinc compound is reacted with a halogenide, sulfonate (the sulfonate being in particular a fluorinated alkylsulfonate or tosylate, specifically triflate or nonaflate) or acetate in the presence of a transition metal catalyst, mostly a Pd or Ni catalyst, where the Pd catalyst is often better suited. The reaction does not need the presence of a further booster, such as the base in the Suzuki coupling. Instead of organozinc compounds organoaluminum or organozirconium compounds can be used. If these are not reactive enough they can be transmetallated to the corresponding zinc compounds by addition of zinc salts ("double metal catalysis").

In the present case, however, the organozinc compound (or the organoaluminum or organozirconium compound) need not be preformed. Instead the precursor halide (of which the organozinc compound would normally be formed), the other halogenide, sulfonate or acetate, a transition metal catalyst (mostly a Pd or Ni catalyst, better a Pd catalyst) and Zn dust or powder are mixed in water in the presence of the cellulose derivative. It is assumed that the corresponding organozinc compound is formed in situ and reacts then with the halogenide, sulfonate or acetate. Preferably, a halide $R^1$—Z, where $R^1$ is an alkyl, alkenyl, alkynyl, aryl or heteroaryl group and Z is a halogen atom, especially Cl, Br or I, is reacted with a compound $R^2$—$(Z)_n$, where $R^2$ is an alkyl, alkenyl, alkynyl, aryl or heteroaryl group, Z is a halogen atom, a sulfonate (the sulfonate being in particular a fluorinated alkylsulfonate or tosylate, specifically triflate or nonaflate) or an acetate group and n is 1, 2, 3 or 4, in the presence of a transition metal catalyst, mostly a Pd or Ni catalyst, where the Pd catalyst is often better suited, Zn powder or dust to a compound $(R^1)_n$—$R^2$. The halogenide, sulfonate or acetate can contain more than one halogenide, sulfonate or acetate group (when n is 2, 3 or 4), so that multiply coupled compounds can form, especially if the organozine compound is used in excess. For instance, a difunctional compound $R^2$—$(Z)_2$ can yield a twofold coupled compound $R^1$—$R^2$—$R^1$. In a particular embodiment the reaction is moreover carried out in the presence of TMEDA (tetramethylethylendiamine), which presumably activates the Zn surface.

Due to the tolerance of the Negishi reaction to a wide variety of functional groups, the alkyl, alkenyl, alkynyl, aryl or heteroaryl groups $R^1$ and $R^2$ can carry one or more substituents. Suitable substituents correspond to those listed above in context with substituents on the alkyl, alkenyl, alkynyl, aryl or heteroaryl groups $R^1$ and $R^2$ in the Suzuki coupling.

In these substituents, however, all functional groups, especially halogen atoms and sulfonyloxy groups, have to be less reactive towards the organozinc compound (formed in situ) than the halogen atom or sulfonate or acetate group on the desired reaction site of the $R^1$—Z and $R^2$—$(Z)_n$ compounds.

Suitable Pd and Ni catalysts (inclusive ligands) are those mentioned above in context with the Suzuki coupling.

The precursor halide (of which the organozinc compound would normally be formed) or the organizing compound, if preformed, and the other halogenide, sulfonate or acetate can be used in a molar ratio of from 10:1 to 1:10, e.g. from 7:1 to 1:7 or from 5:1 to 1:5. In case of di- or polyfunctional halogenides, sulfonates or acetates, the molar ratio relates of course to the number of halogenide, sulfonate or acetate groups in the molecule.

The catalyst is used in catalytic, i.e. substoichiometric amounts, e.g. in an amount of from 0.001 to 0.1 mol per mol of that reactant which is not used in excess, in particular 0.005 to 0.07 mol per mol of the reactant not used in excess, specifically 0.01 to 0.05 mol per mol of the reactant not used in excess. If the reactants are used in equimolar ratio, the above amounts of catalyst apply of course to either of the reactants.

If the catalyst ligand or any reactant is prone to oxidation by air (such as is the case, for example, for triphenylphosphine, tri(tert-butyl)phosphine, X-Phos, 6,6'-dimethoxy-[1,1'-biphenyl]-2,2'-diyl)bis(bis(3,5-dimethylphenyl)phosphine and several others), the reaction is preferably carried out in an inert atmosphere in order to avoid the presence of oxygen, e.g. under an argon or nitrogen atmosphere. Preferably, moreover, the solvent is used in degassed form. On a laboratory scale this is e.g. obtained by freezing, applying a vacuum and unfreezing under an inert atmosphere or by bubbling a vigorous stream of argon or nitrogen through the solvent or by ultrasonification under an inert atmosphere. On an industrial scale other methods known in the art can be applied.

Workup proceedings will be described below, as they are similar for most reactions.

Stille Coupling

In another particular embodiment the transition metal catalyzed C—C coupling reaction is a Stille reaction. In the Stille reaction, also termed Migita-Kosugi-Stille coupling, an organotin compound (organostannane) is reacted with an alkenyl, aryl, heteroaryl or acyl halide, sulfonate (the sulfonate being in particular a fluorinated alkylsulfonate or tosylate, specifically triflate or nonaflate) or phosphate in the presence of a transition metal catalyst, mostly a Pd catalyst, and sometimes also in the presence of a base.

Preferably, the organostannane compound is a compound of formula $R^1$—$Sn(R^a)_3$, where $R^1$ is a an alkenyl, aryl or heteroaryl group and $R^a$ is an alkyl group, mostly butyl. The alkenyl, aryl, heteroaryl or acyl halide, sulfonate or phosphate is preferably a compound $R^2$—$(Z)_n$, where $R^2$ is an alkenyl, aryl, heteroaryl or acyl group, Z is a halogen atom, sulfonate (the sulfonate being in particular a fluorinated alkylsulfonate or tosylate, specifically triflate or nonaflate) or phosphate group, preferably a Cl, Br, I, triflate, nonaflate or phosphate group, and n is 1, 2, 3 or 4. The reaction yields a compound $(R^1)_n$—$R^2$. The halogenide, sulfonate or phosphate can contain more than one halogenide, sulfonate or phosphate group (when n is 2, 3 or 4), so that multiply coupled compounds can form, especially if the organostannane compound is used in excess. For instance, a difunctional compound $R^2$—$(Z)_2$ can yield a twofold coupled compound $R^1$—$R^2$—$R^1$.

Due to the tolerance of the Stille reaction to a wide variety of functional groups, the alkenyl, aryl and heteroaryl groups $R^1$ and $R^2$ can carry one or more substituents. Suitable substituents correspond to those listed above in context with substituents on the alkyl, alkenyl, aryl or heteroaryl groups $R^1$ and $R^2$ in the Suzuki coupling.

In these substituents, however, all functional groups, especially halogen atoms and sulfonyloxy groups, have to be less reactive towards the organotin compound than the halogen atom or sulfonate or phosphate group on the desired reaction site of the $R^2$—$(Z)_n$ compound.

Suitable Pd catalysts (inclusive ligands) are those mentioned above in context with the Suzuki coupling.

Suitable bases are those mentioned above in context with the Suzuki coupling.

Specifically, the present method relates to a Stille reaction in which an aromatic or heteroaromatic halogenide $R^2$—$(Z)_n$, where $R^2$ is a mono-, bi- or polycyclic aryl or heteroaryl group, Z is a halogen atom, especially Cl, Br or I, more specifically Br or I, and n is 1, is reacted with an organostannane $R^1$—$Sn(R^a)_3$, where $R^1$ is an aryl or in particular an alkenyl group and $R^a$ is butyl, a Pd catalyst, specifically of $Pd(t-Bu_3P)_2$, and in the presence of a base, specifically a basic heterocycle.

In a particular embodiment aryl groups $R^1$ and $R^2$ are mono-, bi- or tricyclic and are specifically selected from the group consisting of phenyl and naphthyl; and heteroaryl groups $R^1$ and $R^2$ are in particular mono-, bi- or tricyclic and are specifically selected from the group consisting of 5- or 6-membered heteroaromatic monocyclic rings and 9- or 10-membered heteroaromatic bicyclic rings containing 1, 2, 3 or 4 heteroatoms selected from the group consisting of N, O and S as ring members. Mono- or bicyclic aryl or heteroaryl groups $R^1$ and $R^2$ are for example phenyl, naphthyl, furanyl, thienyl, pyrrolyl, pyrazolyl, imidazolyl, oxazoyl, isoxazoyl, thiazoyl, isothiazolyl, [1,2,3]triazolyl, [1,2,4]triazolyl, [1,3,4]triazolyl, the oxadiazolyls, the thiadiazolyls, the tetrazolyls, pyridyl, pyrazinyl, pyrimidyl, pyridazinyl, 1,2,4-triazinyl, 1,3,5-triazinyl, indolyl, benzofuranyl, benzothienyl, quinolinyl, isoquinolinyl, quinazalinyl and the like. More particularly, they are for example phenyl, naphthyl, 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 3-isothiazolyl, 4-isothiazolyl, 5-isothiazolyl, 1,3,4-triazol-1-yl, 1,3,4-triazol-2-yl, 1,3,4-triazol-3-yl, 1,2,3-triazol-1-yl, 1,2,3-triazol-2-yl, 1,2,3-triazol-4-yl, 1,2,5-oxadiazol-3-yl, 1,2,3-oxadiazol-4-yl, 1,2,3-oxadiazol-5-yl, 1,3,4-oxadiazol-2-yl, 1,2,5-thiadiazol-3-yl, 1,2,3-thiadiazol-4-yl, 1,2,3-thiadiazol-5-yl, 1,3,4-thiadiazol-2-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, 1,2,3,4-tetrazin-1-yl, 1,2,3,4-tetrazin-2-yl, 1,2,3,4-tetrazin-5-yl, indolyl, benzofuranyl, benzothienyl, benzopyrazolyl, benzimidazolyl, benzoxazolyl, benzisoxazolyl, benzothiazolyl, benzisothiazolyl, quinolinyl, isoquinolinyl, quinazalinyl and other heteroaromatic bicyclic rings shown below in the "general definitions".

The aryl and heteroaryl groups $R^1$ and $R^2$ can carry one or more substituents, e.g. 1, 2, 3 or 4, in particular 1, 2 or 3, specifically 1 or 2 substituents. Suitable substituents are listed above in context with aryl and heteroaryl groups $R^1$ and $R^2$ in the Suzuki reaction. In a particular embodiment, the substituents on the aryl and heteroaryl groups $R^1$ and $R^2$ are selected from the group consisting of fluorine, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino, di-($C_1$-$C_4$-alkyl)amino, phenyl, a 5- or 6-membered heteroaromatic monocyclic ring containing 1, 2, 3 or 4 heteroatoms selected from N, O and S as ring members and a 9- or 10-membered heteroaromatic bicyclic ring containing 1, 2, 3 or 4 heteroatoms selected from the group consisting of N, O and S as ring members, where phenyl and the heteroaromatic rings may carry one or more substituents selected from the group consisting of fluorine, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino. Specifically, the substituents on the aryl and heteroaryl groups $R^1$ and $R^2$ are selected from the group consisting of fluorine cyano, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino.

The alkenyl group $R^1$ may be substituted as described above in context of the Suzuki reaction for alkenyl groups $R^1$ and $R^2$. In particular, the alkenyl group has a terminal C—C double bond; i.e. Sn is bound to a C—C double bond. This C—C double bond may be substituted as described above in context of the Suzuki reaction for alkenyl groups $R^1$ and $R^2$. Examples for suitable substituents on this C—C double bond or on alkenyl in general are halogen (provided that this not more reactive than the group Z in the $R^2$—$(Z)_n$ compound) cyano, nitro, azido, —SCN, —$SF_5$, $OR^{11}$, $S(O)_m R^{11}$, $NR^{12a} R^{12b}$, $C(=O)R^{13}$, $C(=S)R^{13}$, $C(=NR^{12a})R^{13}$, —$Si(R^{14})_3$, alkyl, optionally substituted by one or more radicals $R^{17}$; cycloalkyl, cycloalkenyl, cycloalkynyl, mixed cycloalkenyl/cycloalkynyl, polycarbocyclyl, where the 5 last-mentioned substituents may carry one or more substituents selected from $R^{15}$; aryl which may be substituted by one or more radicals $R^{15}$, heterocyclyl may be substituted by one or more radicals $R^{15}$; and heteroaryl which may be substituted by one or more radicals $R^{15}$; where $R^{11}$, $R^{12a}$, $R^{12b}$, $R^{13}$, $R^{14}$, $R^{15}$ and $R^{17}$ are as defined above in context with the Suzuki reaction. Specifically, the substituent on the alkenyl group $R^1$ is $OR^{11}$, where $R^{13}$ is alkyl, specifically $C_1$-$C_6$-alkyl.

The reaction is preferably carried out at from 10° C. to 60° C., in particular from 20° C. to 55° C., and specifically from 20° C. to 50° C.

The halogenide, sulfonate or phosphate and the organostannane compound can be used in a molar ratio of from 10:1 to 1:10, e.g. from 7:1 to 1:7 or from 5:1 to 1:5. In case of di- or polyfunctional halogenides, sulfonates or phosphates, the molar ratio relates of course to the number of halogenide, sulfonate or phosphate groups in the molecule. If n is 1, $R^2$—$(Z)_n$ and $R^1$—$Sn(R^a)_3$ are preferably used in a molar ratio of from 0.8:1 to 1:2, more preferably from 1:1 to 1:1.5 and specifically from 1:1 to 1:1.2. If n is 2, $R^2$—$(Z)_n$ and $R^1$—$Sn(R^a)_3$ are preferably used in a molar ratio of from 0.4:1 to 1:4, more preferably from 0.5:1 to 1:3 and specifically from 0.5:1 to 1:2.5.

The catalyst is used in catalytic, i.e. substoichiometric amounts, e.g. in an amount of from 0.001 to 0.1 mol per mol of that reactant which is not used in excess, in particular 0.005 to 0.07 mol per mol of the reactant not used in excess, specifically 0.007 to 0.05 mol per mol of the reactant not used in excess. If the reactants are used in equimolar ratio, the above amounts of catalyst apply of course to either of the reactants.

The base is generally used in excess, i.e. in overstoichiometric amounts with respect to that reactant not used in excess, e.g. in an amount of from 1.1 to 5 mol per mol of the reactant not used in excess, in particular 1.2 to 4 mol per mol of the reactant not used in excess, specifically 1.3 to 2 mol per mol of the reactant not used in excess. If the reactants are used in equimolar ratio, the above amounts of base apply of course to either of the reactants.

The reaction can be carried out by standard proceedings for Stille reactions, e.g. by mixing all reagents, inclusive catalyst or catalyst precursor and ligand(s) and base, water and the cellulose derivative and reacting them at the desired temperature. Alternatively the reagents can be added gradually, especially in the case of a continuous or semicontinuous process.

If the catalyst ligand or any reactant is prone to oxidation by air (such as is the case, for example, for triphenylphosphine, tri(tert-butyl)phosphine, X-Phos, 6,6'-dimethoxy-[1,1'-biphenyl]-2,2'-diyl)bis(bis(3,5-dimethylphenyl)phosphine and several others), the reaction is preferably carried out in an inert atmosphere in order to avoid the presence of oxygen, e.g. under an argon or nitrogen atmosphere. Preferably, moreover, the solvent is used in degassed form. On a laboratory scale this is e.g. obtained by freezing, applying a vacuum and unfreezing under an inert atmosphere or by bubbling a vigorous stream of argon or nitrogen through the solvent or by ultrasonification under an inert atmosphere. On an industrial scale other methods known in the art can be applied.

Workup proceedings will be described below, as they are similar for most reactions.

Grubbs Olefin Metathesis

In another particular embodiment the transition metal catalyzed C—C coupling reaction is a Grubbs olefin metathesis. Olefin metathesis is an organic reaction in which fragments of alkenes (olefins) are redistributed by the scission and regeneration of carbon-carbon double bonds, as illustrated below (the regio- and steric arrangement of the groups is not necessarily as shown; $R^a$ and $R^e$ as well as $R^b$ and $R^g$ can be trans to each other, or an olefin $R^aR^dC=CR^fR^g$+an olefin $R^bR^cC=CR^eR^h$ can be formed instead of the below couple):

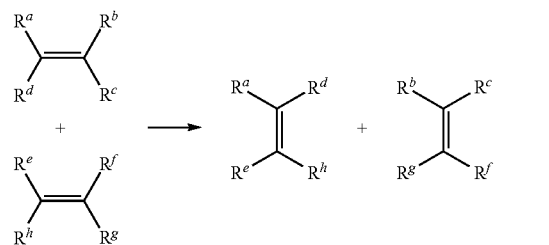

Olefin metathesis, which includes i.a. cross metathesis (CM), ring opening metathesis (ROM), ring closing metathesis RCM), acyclic diene metathesis (ADMET) and ethanolysis, is catalyzed by various transition metal catalysts, the most known being the Schrock and Grubbs metathesis catalysts. In the present case, the olefin metathesis is a Grubbs olefin metathesis, which means that it is catalyzed by a Grubbs catalyst. Grubbs catalysts are Ruthenium carbene complexes, especially complexes of the following formulae:

First generation Grubbs catalyst:

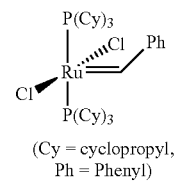

(Cy = cyclopropyl, Ph = Phenyl)

This first generation catalyst is e.g. prepared from $RuCl_2(PPh_3)_4$ and diphenylcyclopropene.

The second generation catalyst has following formula:

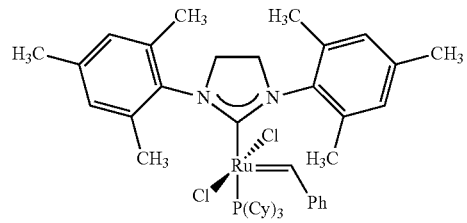

The Hoveyda Grubbs first generation catalyst has following formula:

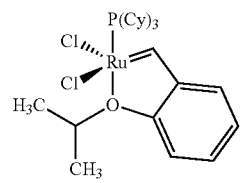

The Hoveyda Grubbs second generation catalyst has following formula:

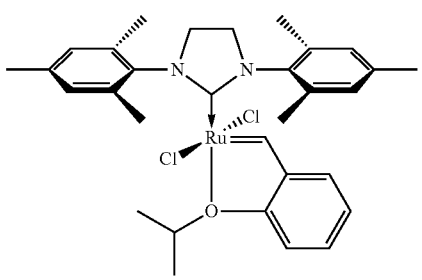

The Hoveyda Grubbs third generation catalyst has following formula:

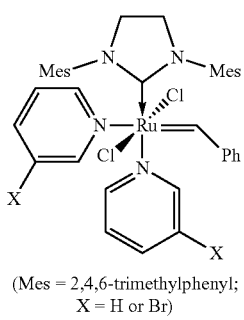

(Mes = 2,4,6-trimethylphenyl;
X = H or Br)

Grubbs catalysts in terms of the present invention also include the Hoveyda Grubbs I and II analogous catalysts from Zannan Pharma Ltd. with a sulfonamide on the phenyl ring:

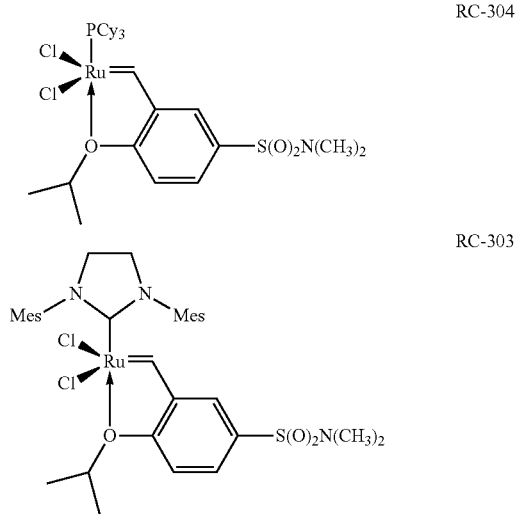

In a preferred embodiment, two olefinic compounds $R^1R^2C=CR^3R^4$ and $R^5R^6C=CR^7R^8$ are reacted with each other in the presence of a Grubbs catalyst, especially the Grubbs second generation catalyst. $R^1$, $R^2$, $R^3$, $R^4$, $R^5$, $R^6$, $R^7$ and $R^8$, independently of each other, are hydrogen, alkyl, alkenyl, alkynyl, cycloalkyl, cycloalkenyl, cycloalkynyl, mixed cycloalkenyl/cycloalkynyl, polycarbocyclyl, heterocyclyl, aryl, heteroaryl or are one of the substituents listed in context with the Suzuki reaction as suitable radicals on alkyl, alkenyl and alkynyl groups (however except for oxo (=O), =S and =NR$^{12a}$). More precisely, $R^1$, $R^2$, $R^3$, $R^4$, $R^5$, $R^6$, $R^7$ and $R^8$, independently of each other, are hydrogen, alkyl, alkenyl, alkynyl, cycloalkyl, cycloalkenyl, cycloalkynyl, mixed cycloalkenyl/cycloalkynyl, polycarbocyclyl, heterocyclyl, aryl, heteroaryl, halogen, cyano, nitro, azido, —SCN, —SF$_5$, OR$^{11}$, S(O)$_m$R$^{11}$, NR$^{12a}$R$^{12b}$, C(=O)R$^{13}$, C(=S)R$^{13}$, C(=NR$^{12a}$)R$^{13}$ or —Si(R$^{14}$)$_3$; where R$^{11}$, R$^{12a}$, R$^{12b}$, R$^{13}$ and R$^{14}$ are independently as defined above in context with the Suzuki reaction. The alkyl, alkenyl, alkynyl, cycloalkyl, cycloalkenyl, cycloalkynyl, mixed cycloalkenyl/cycloalkynyl, polycarbocyclyl, heterocyclyl, aryl or heteroaryl groups $R^1$, $R^2$, $R^3$, $R^4$, $R^5$, $R^6$, $R^7$ and $R^8$ can in turn carry one or more substituents. Suitable substituents for the alkyl, alkenyl, alkynyl, cycloalkyl, cycloalkenyl, cycloalkynyl, mixed cycloalkenyl/cycloalkynyl, polycarbocyclyl, aryl and heteroaryl groups correspond to those listed above in context with substituents on the alkyl, alkenyl, alkynyl, cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling. Suitable substituents for heterocyclyl groups correspond to those listed above in context with substituents on the aryl or heteroaryl groups $R^1$ and $R^2$ in the Suzuki coupling.

In particular $R^3$, $R^4$, $R^7$ and $R^8$ are hydrogen and at least one of $R^1$, $R^2$, $R^5$ and $R^6$ is not hydrogen. More particularly, $R^3$, $R^4$, $R^7$ and $R^8$ are hydrogen, one of $R^1$ and $R^2$ is not hydrogen and one of $R^5$ and $R^6$ is not hydrogen. In particular, the two radicals not being hydrogen are selected from the group consisting of halogen, cyano, nitro, azido, —SCN, —SF$_5$, OR$^{11}$, S(O)$_m$R$^{11}$, NR$^{12a}$R$^{12b}$, C(=O)R$^{13}$, C(=S)R$^{13}$, C(=NR$^{12a}$)R$^{13}$, —Si(R$^{14}$)$_3$, alkyl, optionally substituted by one or more radicals R$^{17}$; aryl which may be substituted by one or more radicals R$^{15}$, and a 3-, 4-, 5-, 6-, 7-, 8-, 9- or 10-membered saturated, partially unsaturated or maximally unsaturated (inclusive heteroaromatic) heteromonocyclic or heterobicyclic ring containing 1, 2, 3 or 4 heteroatoms or heteroatom groups selected from the group consisting of N, O, S, NO, SO and SO$_2$, as ring members, where the heteromonocyclic or heterobicyclic ring may be substituted by one or more radicals R$^{15}$; where R$^{11}$, R$^{12a}$, R$^{12b}$, R$^{13}$, R$^{14}$, R$^{15}$ and R$^{17}$ are as defined above in context with the Suzuki reaction. Specifically, one of R$^1$ and R$^2$ is alkyl, optionally substituted by one or more radicals R$^{17}$; and one of R$^5$ and R$^6$ is C(=O)R$^{13}$. More specifically one of R$^1$ and R$^2$ is C$_1$-C$_4$-alkyl substituted with an aryl group which may carry one or more substituents R$^{15}$ as defined in context with the Suzuki reaction, and one of R$^5$ and R$^6$ is C(=O)R$^{13}$, where R$^{13}$ is C$_1$-C$_6$-alkoxy.

The olefins $R^1R^2C=CR^3R^4$ and $R^5R^6C=CR^7R^8$ are used in a molar ratio of from 10:1 to 1:10, e.g. from 7:1 to 1:7 or 5:1 to 1:5, preferably 4:1 to 1:4, in particular 3:1 to 1:3 and specifically from 2:1 to 1:2.

The catalyst is generally used in catalytic, i.e. substoichiometric amounts, e.g. in an amount of from 0.0001 to 0.1 mol per mol of that reactant which is not used in excess, in particular 0.001 to 0.05 mol per mol of the reactant not used in excess, specifically 0.002 to 0.01 mol per mol of the reactant not used in excess. If the reactants are used in equimolar ratio, the above amounts of catalyst apply of course to either of the reactants.

It may be advantageous to carry out the reaction in the presence of a weak acid, such as acetic acid, citric acid, malic acid, oxalic acid or succinic acid. The acid is generally used in substoichiometric amounts, e.g. in an amount of from 0.0001 to 0.1 mol per mol of that reactant which is not used in excess, in particular 0.001 to 0.05 mol per mol of the reactant not used in excess, specifically 0.002 to 0.01 mol per mol of the reactant not used in excess. If the reactants are used in equimolar ratio, the above amounts of acid apply of course to either of the reactants.

The reaction is preferably carried out at from 10° C. to 60° C., in particular from 20° C. to 55° C., specifically from 20° C. to 50° C. and very specifically from 20° C. to 30° C.

The reaction can be carried out by standard proceedings for olefin metathesis reactions, e.g. by mixing all reagents, inclusive catalyst, water and the cellulose derivative and reacting them at the desired temperature. Alternatively the reagents can be added gradually, especially in the case of a continuous or semicontinuous process.

Although Grubbs catalysts are rather stable to oxidation by air, the reaction is nevertheless preferably carried out in an inert atmosphere. Preferably, moreover, the solvent is used in degassed form. On a laboratory scale this is e.g.

obtained by freezing, applying a vacuum and unfreezing under an inert atmosphere or by bubbling a vigorous stream of argon or nitrogen through the solvent or by ultrasonification under an inert atmosphere. On an industrial scale other methods known in the art can be applied.

Workup proceedings will be described below, as they are similar for most reactions.

1,4-Additions of an Organoborane Compounds to α,β-olefinically Unsaturated Carbonyl Compounds In another particular embodiment the transition metal catalyzed C—C coupling reaction is a 1,4-addition of an organoborane compound to an α,β-olefinically unsaturated carbonyl compound. This addition reaction resembles the well-known Michael addition, uses however an organoboron compound as nucleophile instead of a CH-acidic compound, and uses transition metal catalysis. Suitable catalysts are Pd, Ru and especially Rh catalysts.

Preferably, the organoboron compound is a compound of formula $R^1$—$BY_2$, where $R^1$ is an alkyl, alkenyl, alkynyl, aryl or heteroaryl group and Y is an alkyl, O-alkyl or hydroxyl group, or the two substituents Y form together with the boron atom they are bound to a mono-, bi- or polycyclic ring; or the organoboron compound is a compound of formula $R^1$—$BF_3M$, where M is a metal equivalent. Examples of suitable organoboron compounds $R^1$—$BY_2$ are $R^1$—$B(OH)_2$, $R^1$—$B(O$—$C_1$-$C_4$-alkyl$)_2$, $R^1$—$B(C_1$-$C_4$-alkyl$)_2$, or the MIDA ester of $R^1$—$B(OH)_2$ (MIDA=N-methyliminodiacetic acid; HO—C(=O)—$CH_2$—N($CH_3$)—$CH_2$—C(=O)—OH; i.e. the two Y form together —O—C(=O)—$CH_2$—N($CH_3$)—$CH_2$—C(=O)—O—).

The α,β-olefinically unsaturated carbonyl compound is preferably a compound of formula $R^2R^3C$=$CR^4$—C(=O)—$R^5$, where $R^2$, $R^3$ and $R^4$, independently of each other, are hydrogen, alkyl, cycloalkyl, heterocyclyl, aryl or heteroaryl and $R^5$ is hydrogen, alkyl, cycloalkyl, aryl, heteroaryl, OH, SH, alkoxy, alkylthio, $NH_2$, alkylamino or dialkylamino. The alkyl (also as part of alkoxy, alkylthio, alkylamino or dialkylamino), alkenyl, alkynyl, cycloalkyl, heterocyclyl, aryl or heteroaryl groups $R^1$, $R^2$, $R^3$, $R^4$ and $R^5$ can carry one or more substituents. Suitable substituents for the alkyl, alkenyl, alkynyl, cycloalkyl, aryl and heteroaryl groups correspond to those listed above in context with substituents on the alkyl, alkenyl, alkynyl, cycloalkyl, aryl or heteroaryl groups $R^1$ and $R^2$ in the Suzuki coupling. Suitable substituents for heterocyclyl groups correspond to those listed above in context with substituents on the cycloalkyl, aryl or heteroaryl groups $R^1$ and $R^2$ in the Suzuki coupling.

In these substituents, however, all functional groups have to be less reactive towards the organoboron compound than the desired reaction site on the C—C double bond of the α,β-olefinically unsaturated carbonyl compound.

Reaction of the organoboron compound with $R^2R^3C$=$CR$—C(=O)—$R^5$ yields a compound $R^1$—$(R^2)(R)^3C$—$CHR^4$—C(=O)—$R^5$.

Specifically $R^1$ is an aryl or heteroaryl group which may be substituted as described above in context with the Suzuki reaction.

In a particular embodiment the aryl group $R^1$ is mono-, bi- or tricyclic and is specifically selected from the group consisting of phenyl and naphthyl; and the heteroaryl group $R^1$ is in particular mono-, bi- or tricyclic and is specifically selected from the group consisting of 5- or 6-membered heteroaromatic monocyclic rings and 9- or 10-membered heteroaromatic bicyclic rings containing 1, 2, 3 or 4 heteroatoms selected from the group consisting of N, O and S as ring members. Mono- or bicyclic aryl or heteroaryl groups R are for example phenyl, naphthyl, furanyl, thienyl, pyrrolyl, pyrazolyl, imidazolyl, oxazoyl, isoxazoyl, thiazoyl, isothiazolyl, [1,2,3]triazolyl, [1,2,4]triazolyl, [1,3,4]triazolyl, the oxadiazolyls, the thiadiazolyls, the tetrazolyls, pyridyl, pyrazinyl, pyrimidyl, pyridazinyl, 1,2,4-triazinyl, 1,3,5-triazinyl, indolyl, benzofuranyl, benzothienyl, quinolinyl, isoquinolinyl, quinazalinyl and the like. More particularly, they are for example phenyl, naphthyl, 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 3-isothiazolyl, 4-isothiazolyl, 5-isothiazolyl, 1,3,4-triazol-1-yl, 1,3,4-triazol-2-yl, 1,3,4-triazol-3-yl, 1,2,3-triazol-1-yl, 1,2,3-triazol-2-yl, 1,2,3-triazol-4-yl, 1,2,5-oxadiazol-3-yl, 1,2,3-oxadiazol-4-yl, 1,2,3-oxadiazol-5-yl, 1,3,4-oxadiazol-2-yl, 1,2,5-thiadiazol-3-yl, 1,2,3-thiadiazol-4-yl, 1,2,3-thiadiazol-5-yl, 1,3,4-thiadiazol-2-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, 1,2,3,4-tetrazin-1-yl, 1,2,3,4-tetrazin-2-yl, 1,2,3,4-tetrazin-5-yl, indolyl, benzofuranyl, benzothienyl, benzopyrazolyl, benzimidazolyl, benzoxazolyl, benzisoxazolyl, benzothiazolyl, benzisothiazolyl, quinolinyl, isoquinolinyl, quinazalinyl and other heteroaromatic bicyclic rings shown below in the "general definitions".

The aryl and heteroaryl groups $R^1$ can carry one or more substituents, e.g. 1, 2, 3 or 4, in particular 1, 2 or 3, specifically 1 or 2 substituents. Suitable substituents are listed above in context with aryl and heteroaryl groups $R^1$ and $R^2$ in the Suzuki reaction. In a particular embodiment, the substituents on the aryl and heteroaryl groups $R^1$ are selected from the group consisting of fluorine, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino, di-($C_1$-$C_4$-alkyl)amino, phenyl, a 5- or 6-membered heteroaromatic monocyclic ring containing 1, 2, 3 or 4 heteroatoms selected from N, O and S as ring members and a 9- or 10-membered heteroaromatic bicyclic ring containing 1, 2, 3 or 4 heteroatoms selected from the group consisting of N, O and S as ring members, where phenyl and the heteroaromatic rings may carry one or more substituents selected from the group consisting of fluorine, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkycarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino. Specifically, the substituents on the aryl and heteroaryl groups $R^1$ are selected from the group consisting of fluorine, cyano, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy- $C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino.

In particular at least one of $R^2$ and $R^3$ is H. If one of $R^2$ and $R^3$ is not H, this is specifically alkyl. Specifically, $R^4$ is H. Specifically $R^5$ is alkoxy.

Suitable Pd catalysts correspond to those mentioned above in context with the Suzuki reaction.

Like Pd, Rh may be introduced as a salt into the reaction and converted in situ into a complex by reaction with suitable ligands. It is however more expedient to use preformed Rh catalysts.

Suitable Rh catalysts are e.g. [RhCl($C_2H_4$)$_2$]$_2$, [RhCl$_2$($C_2H_4$)$_2$], [Rh(nbd)]$_2$BF$_4$ (nbd=norbornadiene), [Rh(nbd)]$_2$CF$_3$SO$_3$, [Rh(cod)(CH$_3$CN)$_2$]BF$_4$ (cod=cyclooctadiene), [Rh(cod)$_2$]PF$_6$, [Rh(cod)$_2$]SbF$_6$, [Rh(cod)$_2$]BF$_4$, [Rh(cod)$_2$]CF$_3$SO$_3$, [Rh(OH)(cod)]$_2$, acetylacetonatobis(ethylene)rhodium(I), (acetylacetonato)(1,5-cyclooctadiene)rhodium(I), (acetylacetonato)dicarbonylrhodium(I), (acetylacetonatoxnorbornadiene)rhodium(I), (bicyclo[2.2.1]hepta-2,5-diene)[1,4-bis(diphenylphosphino)butane]rhodium(I) tetrafluoroborate, bicyclo[2.2.1]hepta-2,5-diene-rhodium(I) chloride dimer, [(bisacetonitrile)(norbornadiene)]rhodium(I) hexafluoroantimonate, bis(2,2-dimethylpropanoato)(4-methylphenyl)bis[tris[4-(trifluoromethyl)phenyl]phosphine]rhodium, [1,4-bis(diphenylphosphino)butane](1,5-cyclooctadiene)rhodium(I) tetrafluoroborate, bis(triphenylphosphine)rhodium(I) carbonyl chloride, chlorobis(cyclooctene)rhodium(I) dimer, and the like.

The organoboron compound and the unsaturated carbonyl compound can be used in a molar ratio of from 10:1 to 1:10, e.g. from 7:1 to 1:7 or from 5:1 to 1:5. The organoboron compounds are however generally used in at least equimolar amount, e.g. from equimolar amount to a fivefold or in particular threefold or especially twofold or 1.5-fold excess. If however the carbonyl compound is more easily available and/or less expensive than the organoboron compound, this can instead be used in excess, e.g. in a fivefold or threefold or twofold or 1.5-fold excess. Especially in case that the organoboron compound is a MIDA ester, the organoboron compound and the carbonyl compound can be used in approximately equimolar amounts.

The catalyst is used in catalytic, i.e. substoichiometric amounts, e.g. in an amount of from 0.001 to 0.1 mol per mol of that reactant which not used in excess (here mostly the α,β-olefinically unsaturated carbonyl compound), in particular 0.005 to 0.07 mol per mol of the reactant not used in excess, specifically 0.01 to 0.07 mol per mol of the reactant not used in excess. If the reactants are used in equimolar ratio, the above amounts of catalyst apply of course to either of the reactants.

The reaction can be carried out by standard proceedings for transition metal-catalyzed 1,4-coupling reactions, e.g. by mixing all reagents, inclusive catalyst or catalyst precursor and ligand(s), water and the cellulose derivative and reacting them at the desired temperature. Alternatively the reagents can be added gradually, especially in the case of a continuous or semicontinuous process.

If the catalyst ligand or any reactant is prone to oxidation by air, the reaction is preferably carried out in an inert atmosphere in order to avoid the presence of oxygen, e.g. under an argon or nitrogen atmosphere. Preferably, moreover, the solvent is used in degassed form. On a laboratory scale this is e.g. obtained by freezing, applying a vacuum and unfreezing under an inert atmosphere or by bubbling a vigorous stream of argon or nitrogen through the solvent or by ultrasonification under an inert atmosphere. On an industrial scale other methods known in the art can be applied.

Workup proceedings will be described below, as they are similar for most reactions.

Cyclopropanation

In another particular embodiment the transition metal catalyzed C—C coupling reaction is a cyclopropanation. Cyclopropanations without transition metal catalysis are also well-known reactions, but in this context, only transition metal catalyzed cyclopropanations are discussed. As said, in a transition metal catalyzed cyclopropanation an olefinically unsaturated compound is reacted with a diazo compound to a cyclopropane in the presence of a transition metal catalyst. The olefinically unsaturated compound is preferably a compound of formula $R^1R^2C$=$CR^3R^4$, and the diazo compound is preferably a compound of formula $N_2$=$CR^5R^6$; where $R^1$, $R^2$, $R^3$, $R^4$, $R^5$ and $R^6$, independently of each other, are selected from the group consisting of hydrogen, alkyl, alkenyl, alkynyl, cycloalkyl, cycloalkenyl, cycloalkynyl, mixed cycloalkenyl/cycloalkynyl, polycarbocyclyl, heterocyclyl, aryl, hetaryl, halogen, cyano, nitro, azido, —SCN, —SF$_5$, OR$^{11}$, S(O)$_m$R$^{11}$, NR$^{12a}$R$^{12b}$, C(=O)R$^{13}$, C(=S)R$^{13}$, C(=NR$^{12a}$)R$^{13}$ and —Si(R$^{14}$)$_3$; where $R^{11}$, $R^{12a}$, $R^{12b}$, $R^{13}$ and $R^{14}$ are independently as defined above in context with the Heck reaction; where the alkyl, alkenyl, alkynyl, cycloalkyl, cycloalkenyl, cycloalkynyl, mixed cycloalkenyl/cycloalkynyl, polycarbocyclyl, heterocyclyl, aryl and heteroaryl groups $R^1$, $R^2$, $R^3$, $R^4$, $R^5$ and $R^6$ can carry one or more substituents. Suitable substituents for the alkyl, alkenyl, alkynyl, cycloalkyl, cycloalkenyl, cycloalkynyl, mixed cycloalkenyl/cycloalkynyl, polycarbocyclyl, heterocyclyl, aryl and heteroaryl groups correspond to those listed above in context with substituents on the alkyl, alkenyl, alkynyl, cycloalkyl, cycloalkenyl, cycloalkynyl, mixed cycloalkenyl/cycloalkynyl, polycarbocyclyl, aryl and heteroaryl groups $R^1$ and $R^2$ in the Suzuki coupling. Suitable substituents for heterocyclyl groups correspond to those listed above in context with substituents on the cycloalkyl, aryl or heteroaryl groups $R^1$ and $R^2$ in the Suzuki coupling. Specifically, the cycloalkenyl, cycloalkynyl, mixed cycloalkenyl/cycloalkynyl, polycarbocyclyl, aryl, heterocyclyl and heteroaryl groups $R^1$, $R^2$, $R^3$ and $R^4$ may be substituted by one or more radicals $R^{15}$.

Suitable catalysts are all those customarily used for cyclopropanations, such as the following copper(II) complexes of Schiff's bases

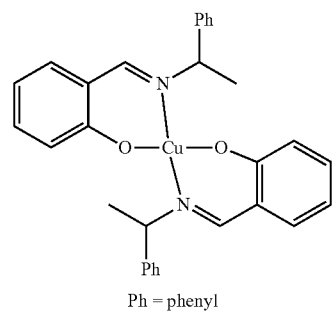

Ph = phenyl

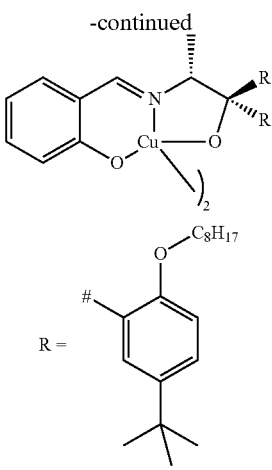

or the above-described semicorrin, bisoxazolin or porphyrin complexes. Among the above semicorrin and bis-oxazolin complexes, preference is given to following complexes of copper:

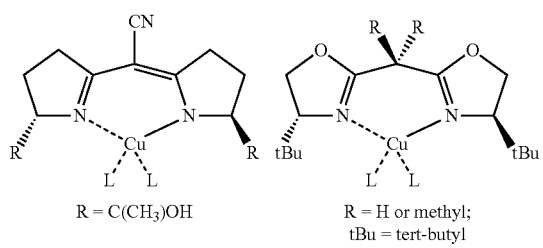

L is a simple ligand, such as Cl, or two L form together a usual bidentate ligand, such as acetylacetonate or methyl acetylacetate.

Preferably however, porphyrin complexes are used, in particular porphyrin complexes with Fe, Ru, Rh or Ir as central metal, but Zn may also be used.

The porphyrin ligand has preferably following structure:

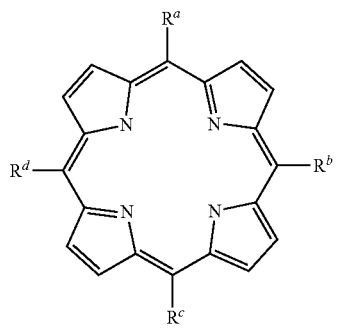

Generally, at least one of $R^a$, $R^b$, $R^c$ and $R^d$ is an aromatic group, such as phenyl, optionally substituted by 1, 2 or 3 substituents selected from the group consisting of methyl, methoxy, hydroxyl, amino and the like. For sterically selective reactions, expediently, at least one of $R^a$, $R^b$, $R^c$ and $R^d$ is a chiral group, such as a BINAP radical, a phenyl ring carrying one or more chiral substituents or a phenyl ring fused to one or more rings resulting in a chiral system. Radicals $R^a$, $R^b$, $R^c$ and $R^d$ which are not an aromatic group are generally selected from the group consisting of alkyl groups, alkoxy groups, alkyl carbonyl groups and alkoxycarbonyl groups. They can however also be hydrogen. In a specific embodiment, $R^a$, $R^b$, $R^c$ and $R^d$ are phenyl, and the central atom is Fe, in particular Fe(III). The charge of the central metal is generally neutralized by a halide, especially chloride, an acetate or other anions customary in such complexes.

In a particular embodiment, in the olefinically unsaturated compound $R^1R^2C=CR^3R^4$ the radicals $R^1$, $R^2$, $R^3$ and $R^4$ are not electron-withdrawing groups and are preferably selected from the group consisting of hydrogen, alkyl, alkenyl, alkynyl, cycloalkyl, cycloalkenyl, cycloalkynyl, mixed cycloalkenyl/cycloalkynyl, polycarbocyclyl, heterocyclyl, aryl and hetaryl, where these groups (apart from hydrogen, of course) may be substituted as described above. Specifically, the present method relates to a cyclopropanation reaction wherein in the olefinically unsaturated compound $R^1R^2C=CR^3R^4$ in two or three of $R^1$, $R^2$, $R^3$ and $R^4$ are hydrogen and the other is/are $C_1$-$C_4$-alkyl, $C_3$-$C_6$-cycloalkyl or aryl, specifically phenyl, where the alkyl, cycloalkyl and aryl radical may carry one or more substituents. Suitable substituents correspond to those listed above in context with substituents on the alkyl, cycloalkyl or aryl groups $R^1$ and $R^2$ in the Suzuki coupling. Very specifically, three of $R^1$, $R^2$, $R^3$ and $R^4$ are hydrogen and the other is phenyl which may be substituted as described above, specific substituents being selected from the group consisting of CN, halogen, $C_1$-$C_4$-alkyl, $C_1$-$C_4$-haloalkyl, $C_1$-$C_4$-alkoxy, $C_1$-$C_4$-haloalkoxy, $C_3$-$C_6$-cycloalkyl, $C_3$-$C_6$-halocycloalkyl and phenyl.

In the diazo compound $N_2=CR^5R^6$, $R^5$ is specifically H and $R^6$ is a $C_1$-$C_4$-alkoxycarbonyl group.

The diazocompound is prepared by known means, such as reaction of the $C_1$-$C_4$-alkyl ester of glycine with a nitrite, generally sodium nitrite, often in the presence of an acid. Suitable acids are inorganic acids which do not interfere with the diazonium formation, such as hydrochloric acid, and organic acids, such as acetic acid, trifluoroacetic acid, toluene sulfonic acid and the like. The diazo compound can be prepared in situ before the olefinic compound is added, i.e. in the aqueous solvent used in the method of the invention in the presence of the cellulose derivative, or, preferably, in the presence of the olefinic compound. For example, the olefinic compound, the $C_1$-$C_4$-alkyl ester of glycine, the transition metal catalyst, if desired the acid, water and the cellulose derivative are mixed and sodium nitrite is added. If desired, the reaction mixture can be heated before, during or after addition of sodium nitrite, e.g. to 30 to 60° C. or 35 to 50° C. or to 35 to 45° C.

The diazo compound is generally used in at least equivalent amounts, preferably in excess, with respect to the olefinic compound, the molar ratio of diazo compound and olefinic compound being preferably of from 1:1 to 10:1, in particular from 1.1:1 to 5:1 and specifically from 1.5:1 to 3:1.

The nitrite is generally used in at least equivalent amounts, often in slight excess, with respect to the diazo compound, the molar ratio of nitrite and diazo compound being preferably of from 1:1 to 5:1, in particular from 1:1 to 2:1 and specifically from 1.1:1 to 1.5:1.

The catalyst is used in catalytic, i.e. substoichiometric amounts, e.g. in an amount of from 0.001 to 0.1 mol per mol of that reactant which not used in excess (here mostly the olefinic compound), in particular 0.005 to 0.07 mol per mol of the reactant not used in excess, specifically 0.005 to 0.05 mol per mol of the reactant not used in excess. If the reactants are used in equimolar ratio, the above amounts of catalyst apply of course to either of the reactants.

Workup proceedings will be described below, as they are similar for most reactions.

b) C—N Coupling Reactions

In a particular embodiment, the transition metal catalyzed reaction is a C—N coupling reaction. Transition metal catalyzed C—N coupling reactions are well known. Examples are the Buchwald-Hartwig reaction and Au-catalyzed cyclodehydratizations of alkynes carrying in α-position to the alkyne group an OH group and in β-position a primary or secondary amino group to give pyrroles.

Buchwald-Hartwig Reaction

In a particular embodiment the transition metal catalyzed C—N coupling reaction is a Buchwald-Hartwig reaction. The Buchwald-Hartwig reaction is a transition metal-catalyzed, mostly a Pd catalyzed, C—N or C—O bond formation between an aryl or heteroaryl halogenide or sulfonate and a primary or secondary amine, carboxamide, sulfonamide, imide, urea or urethane (for C—N bond formation) or an alcohol (for C—O bond formation), generally in the presence of a base. In context with C—N coupling reactions, the Buchwald-Hartwig reaction is understood as a transition metal-catalyzed, mostly a Pd catalyzed, C—N bond formation between an aryl or heteroaryl halogenide or sulfonate (the sulfonate being in particular a fluorinated alkylsulfonate or tosylate, specifically triflate or nonaflate) and a primary or secondary amine, carboxamide, sulfonamide, imide, urea or urethane, generally in the presence of a base.

Preferably, a halogenide or sulfonate $R^2$—$(Z)_n$, where $R^2$ is an aryl or heteroaryl group, Z is a halogenide or sulfonate group (the sulfonate being in particular a fluorinated alkylsulfonate or tosylate, specifically triflate or nonaflate) and n is 1, 2, 3 or 4, is reacted with a compound H—$N(R^1)R^3$, where $R^1$ is H, alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl, heterocyclyl, heteroaryl or —C(O)—$R^4$, and $R^3$ is H, alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl, heterocyclyl, heteroaryl, —C(O)—$R^4$, —S(O)$_2$—$R^4$, —C(O)—O—$R^4$ or —C(O)—$N(R^4)R^5$, where $R^4$ and $R^5$ are independently H, alkyl, alkenyl, alkapolyenyl, alkynyl, alkapolyynyl, mixed alkenyl/alkynyl, cycloalkyl, mixed cycloalkenyl/cycloalkynyl, polycarbocyclyl, aryl, heterocyclyl or heteroaryl, or $R^4$ and $R^5$ form together with the nitrogen atom they are bound to a mono- bi- or polycyclic heterocyclic ring; or $R^1$ and $R^3$ form together with the nitrogen atom they are bound to a mono-, bi- or polycyclic heterocyclic ring. The reaction of the halogenide or sulfonate $R^2$—$(Z)_n$ and the amine (derivative) H—$N(R^1)R^3$ yields a compound $(R^3(R^1)N)_n$—$R^2$. The aryl or heteroaryl halide or sulfonate can contain more than one halide or sulfonate group (when n is 2, 3 or 4), so that multiply coupled compounds can form, especially if the amine compound is used in excess. For instance, a difunctional compound $R^2$—$(Z)_2$ can yield a twofold C—N coupled compound $R^3(R^1)N$—$R^2$—$N(R^1)R^3$.

Due to the tolerance of the Buchwald-Hartwig reaction to a wide variety of functional groups, the alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl or heteroaryl groups $R^1$, $R^2$, $R^3$, $R^4$, and $R^5$, as well as the mono- bi- or polycyclic heterocyclic ring formed by $R^4$ and $R^5$ or $R^1$ and $R^3$ together with the nitrogen atom they are bound to, can carry one or more substituents. Suitable substituents for alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl and heteroaryl correspond to those listed above in context with substituents on the alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling. Suitable substituents for heterocyclyl groups and for the mono- bi- or polycyclic heterocyclic ring formed by $R^4$ and $R^5$ together with the nitrogen atom they are bound to or by $R^1$ and $R^3$ together with the nitrogen atom they are bound to correspond to those listed above in context with substituents on the cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling.

In these substituents, however, all functional groups, especially halogen atoms and sulfonyloxy groups, have to be less reactive than the halogen atom or sulfonate group on the desired reaction site of the $R^2$—$(Z)_n$ compound; amino groups have to be less reactive than the amino group on the desired reaction site of the H—$N(R^1)R^3$ compound.

Suitable Pd catalysts (inclusive ligands) are those mentioned above in context with the Suzuki coupling.

Suitable bases are those mentioned above in context with the Suzuki coupling.

Specifically, the present method relates to a Buchwald-Hartwig reaction in which an aromatic or heteroaromatic halogenide $R^2$—$(Z)_n$, where $R^2$ is an optionally substituted mono-, bi- or polycyclic aryl or heteroaryl group, Z is a halogen atom, especially Cl, Br or I, and n is 1, is reacted with an amine (derivative) H—$N(R^1)R^3$, where $R^1$ is H and $R^3$ is optionally substituted alkyl, optionally substituted aryl, optionally substituted heteroaryl, —C(O)—$R^4$, —S(O)$_2$—$R^4$, —C(O)—O—$R^4$ or —C(O)—$N(R^4)R^5$, where $R^4$ and $R^5$ are independently of each other alkyl, optionally substituted aryl or optionally substituted heteroaryl, or $R^4$ and $R^5$ form together with the nitrogen atom they are bound to a monocyclic heterocyclic ring, in the presence of a Pd catalyst, specifically of a Pd catalyst with cBRIDP or t-BuXPhos as ligand, and in the presence of a base, specifically of an alkali metal alcoholate, especially an alkali metal tert-butanolate, or a silanolate, especially an alkali metal triisopropylsilanolate.

In a particular embodiment the aryl groups $R^1$, $R^2$, $R^3$, $R^4$, and $R^5$ are mono-, bi- or tricyclic and are specifically selected from the group consisting of phenyl and naphthyl; and the heteroaryl groups $R^1$, $R^2$, $R^3$, $R^4$, and $R^5$ are in particular mono-, bi- or tricyclic and are specifically selected from the group consisting of 5- or 6-membered heteroaromatic monocyclic rings and 9- or 10-membered heteroaromatic bicyclic rings containing 1, 2, 3 or 4 heteroatoms selected from the group consisting of N, O and S as ring members. Mono- or bicyclic aryl or heteroaryl groups $R^1$, $R^2$, $R^3$, $R^4$, and $R^5$ are are for example phenyl, naphthyl, furanyl, thienyl, pyrrolyl, pyrazolyl, imidazolyl, oxazoyl, isoxazoyl, thiazoyl, isothiazolyl, [1,2,3]triazolyl, [1,2,4]triazolyl, [1,3,4]triazolyl, the oxadiazolyls, the thiadiazolyls, the tetrazolyls, pyridyl, pyrazinyl, pyrimidyl, pyridazinyl, 1,2,4-triazinyl, 1,3,5-triazinyl, indolyl, benzofuranyl, benzothienyl, quinolinyl, isoquinolinyl, quinazalinyl and the like. More particularly, they are for example phenyl, naphthyl, 2-furyl, 3-furyl, 2-thienyl, 3-thienyl, 1-pyrrolyl, 2-pyrrolyl, 3-pyrrolyl, 1-pyrazolyl, 2-pyrazolyl, 3-pyrazolyl, 4-pyrazolyl, 5-pyrazolyl, 1-imidazolyl, 2-imidazolyl, 4-imidazolyl, 5-imidazolyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 3-isothiazolyl, 4-isothiazolyl, 5-isothiazolyl, 1,3,4-triazol-1-yl, 1,3,4-triazol-2-yl, 1,3,4-triazol-3-yl, 1,2,3-triazol-1-yl, 1,2,3-triazol-2-yl, 1,2,3-triazol-4-yl, 1,2,5-oxadiazol-3-yl, 1,2,3-oxadiazol-4-yl, 1,2,3-oxadiazol-5-yl, 1,3,4-oxadiazol-2-yl, 1,2,5-thiadiazol-3-yl, 1,2,3-thiadiazol-4-yl, 1,2,3-thiadiazol-5-yl, 1,3,4-thiadiazol-2-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, 1,2,3,4-tetrazin-1-yl, 1,2,3,4-tetrazin-2-yl, 1,2,3,4-tetrazin-5-yl, indolyl, benzofuranyl, benzothienyl, benzopyrazolyl, benzimidazolyl, benzoxazolyl, benzisoxazolyl, benzothiazolyl, benzisothiazolyl, quinolinyl, isoquinolinyl, quinazalinyl and other heteroaromatic bicyclic rings shown below in the "general definitions".

The aryl and heteroaryl groups $R^1$, $R^2$, $R^3$, $R^4$, and $R^5$ can carry one or more substituents, e.g. 1, 2, 3 or 4, in particular 1, 2 or 3, specifically 1 or 2 substituents. Suitable substituents are listed above in context with aryl and heteroaryl groups $R^1$ and $R^2$ in the Suzuki reaction. In a particular embodiment, the substituents on the aryl and heteroaryl groups $R^1$, $R^2$, $R^3R^4$, and $R^5$ are selected from the group consisting of fluorine, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, phenyl, a 5- or 6-membered heteroaromatic monocyclic ring containing 1, 2, 3 or 4 heteroatoms selected from the group consisting of N, O and S as ring members and a 9- or 10-membered heteroaromatic bicyclic ring containing 1, 2, 3 or 4 heteroatoms selected from the group consisting of N, O and S as ring members, where phenyl and the heteroaromatic rings may carry one or more substituents selected the group consisting of from fluorine, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino. Specifically, the substituents on the aryl and heteroaryl groups $R^1$, $R^2$, $R^3$, $R^4$, and $R^5$ are selected from the group consisting of fluorine, cyano, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl and $C_1$-$C_4$-haloalkoxycarbonyl.

In a more specific embodiment an aromatic or heteroaromatic halogenide $R^2$—$(Z)_n$, where
$R^2$ is a mono- or bicyclic aryl group (i.e. phenyl or naphthyl) or is a 5- or 6-membered heteroaromatic monocyclic ring containing 1, 2, 3 or 4 heteroatoms selected from the group consisting of N, O and S as ring members, where the mono- or bicyclic aryl group and the heteroaromatic monocyclic ring may carry 1, 2 or 3 substituents selected from the group consisting of $C_1$-$C_6$-alkyl, $C_1$-$C_6$-haloalkyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl and $C_1$-$C_4$-haloalkoxycarbonyl, Z is a halogen atom, especially Cl, Br or I, and
n is 1,
is reacted with an amine (derivative) H—N($R^1$)$R^3$, where
$R^1$ is H and
$R^3$ is optionally substituted $C_1$-$C_6$-alkyl, a mono- or bicyclic aryl group (i.e. phenyl or naphthyl), a 5- or 6-membered heteroaromatic monocyclic ring containing 1, 2, 3 or 4 heteroatoms selected from the group consisting of N, O and S as ring members, where the mono- or bicyclic aryl group and the heteroaromatic monocyclic ring may carry 1, 2 or 3 substituents selected from the group consisting of $C_1$-$C_6$-alkyl, $C_1$-$C_6$-haloalkyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl and $C_1$-$C_4$-haloalkoxycarbonyl; —C(O)—$R^4$, —S(O)$_2$—$R^4$, —C(O)—O—$R^4$ or —C(O)—N($R^4$)$R^5$, where the optional substituents on $C_1$-$C_6$-alkyl are selected from the group consisting of a mono- or bicyclic aryl group (i.e. phenyl or naphthyl) and a 5- or 6-membered heteroaromatic monocyclic ring containing 1, 2, 3 or 4 heteroatoms selected from the group consisting of N, O and S as ring members, where the mono- or bicyclic aryl group and the heteroaromatic monocyclic ring may carry 1, 2 or 3 substituents selected from the group consisting of $C_1$-$C_6$-alkyl, $C_1$-$C_6$-haloalkyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl and $C_1$-$C_4$-haloalkoxycarbonyl; and $R^4$ and $R^5$ are independently of each other hydrogen, $C_1$-$C_6$-alkyl, a mono- or bicyclic aryl group (i.e. phenyl or naphthyl) or a 5- or 6-membered heteroaromatic monocyclic ring containing 1, 2, 3 or 4 heteroatoms selected from the group consisting of N, O and S as ring members, where the mono- or bicyclic aryl group and the heteroaromatic monocyclic ring may carry 1, 2 or 3 substituents selected from the group consisting of $C_1$-$C_6$-alkyl, $C_1$-$C_6$-haloalkyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl and $C_1$-$C_4$-haloalkoxycarbonyl; or $R^4$ and $R^5$ form together with the nitrogen atom they are bound to a 3-, 4-, 5-, 6- or 7-membered monocyclic saturated heterocyclic ring, in the presence of a Pd catalyst, specifically of a Pd catalyst with cBRIDP or t-BuXPhos as ligand, and in the presence of a base, specifically of an alkali metal alcoholate, especially an alkali metal tert-butanolate, or a silanolate, especially an alkali metal triisopropylsilanolate.

The reaction is preferably carried out at from 10° C. to 60° C., in particular from 20° C. to 55° C., specifically from 20° C. to 50° C.

The halogenide or sulfonate and the amine (derivative) can be used in a molar ratio of from 10:1 to 1:10, e.g. from 7:1 to 1:7 or from 5:1 to 1:5. In case of di- or polyfunctional halides or sulfonates, the molar ratio relates of course to the number of halide or sulfonate groups in the molecule. If n is 1, $R^2$—$(Z)_n$ and H—$N(R^1)R^3$ are preferably used in a molar ratio of from 3:1 to 1:3, in particular from 2:1 to 1:2. If n is 2, $R^2$—$(Z)_n$ and H—$N(R^1)R^3$ are preferably used in a molar ratio of from 1.5:1 to 1:6, more preferably from 1:1 to 1:4. Specifically, the amine (derivative) H—$N(R^1)R^3$ is used in slight excess, e.g. in a 2-fold or 1.5-fold or 1.2-fold excess with respect to the n groups Z.

The catalyst is used in catalytic, i.e. substoichiometric amounts, e.g. in an amount of from 0.001 to 0.5 mol per mol of that reactant which is not used in excess, in particular 0.002 to 0.3 mol per mol of the reactant not used in excess, specifically 0.003 to 0.2, more specifically 0.005 to 0.1 mol per mol of the reactant not used in excess. If the reactants are used in equimolar ratio, the above amounts of catalyst apply of course to either of the reactants.

The base is generally used in at least equimolar amount and mostly in excess, i.e. in overstoichiometric amounts, with respect to that reactant not used in excess, e.g. in an amount of from 1 to 5 mol per mol of the reactant not used in excess, in particular 1.2 to 3 mol per mol of the reactant not used in excess, specifically 1.3 to 2 mol per mol of the reactant not used in excess. If the reactants are used in equimolar ratio, the above amounts of base apply of course to either of the reactants.

The reaction can be carried out by standard proceedings for Buchwald-Hartwig reactions, e.g. by mixing all reagents, inclusive catalyst or catalyst precursor and ligand(s) and base, water and the cellulose derivative and reacting them at the desired temperature. Alternatively the reagents can be added gradually, especially in the case of a continuous or semicontinuous process.

If the catalyst ligand or any reactant is prone to oxidation by air (such as is the case, for example, for triphenylphosphine, tri(tert-butyl)phosphine, X-Phos, 6,6'-dimethoxy-[1,1'-biphenyl]-2,2'-diyl)bis(bis(3,5-dimethylphenyl)phosphine and several others), the reaction is preferably carried out in an inert atmosphere in order to avoid the presence of oxygen, e.g. under an argon or nitrogen atmosphere. Preferably, moreover, the solvent is used in degassed form. On a laboratory scale this is e.g. obtained by freezing, applying a vacuum and unfreezing under an inert atmosphere or by bubbling a vigorous stream of argon or nitrogen through the solvent or by ultrasonification under an inert atmosphere. On an industrial scale other methods known in the art can be applied.

Workup proceedings will be described below, as they are similar for most reactions.

Au-Catalyzed Cyclodehydratizations of Aminoalcohols

α,β-amino alcohols containing an appropriately positioned alkynyl residue (C—C triple bond) can undergo gold-catalyzed ring closure/dehydration (cyclodehydration). For instance, an alkyne carrying in α-position to the alkyne group an OH group and in β-position a primary or secondary amino function undergoes cyclodehydration to the corresponding pyrrole, as shown in the scheme below; an alkyne carrying in β-position to the alkyne group an OH group and in γ-position a primary or secondary amino function undergoes cyclodehydration to the corresponding dihydropyridine, etc.

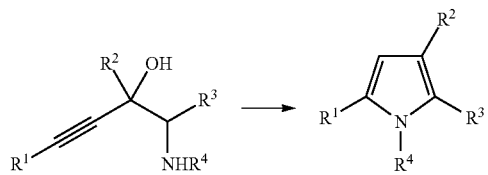

$R^1$, $R^2$, $R^3$ and $R^4$ are independently of each other H, alkyl, cycloalkyl, aryl, heterocyclyl or heteroaryl.

The alkyl, cycloalkyl, aryl, heterocyclyl or heteroaryl groups $R^1$, $R^2$, $R^3$ and $R^4$ can carry one or more substituents. Suitable substituents for alkyl, cycloalkyl, aryl and heteroaryl correspond to those listed above in context with substituents on the alkyl, cycloalkyl, aryl or heteroaryl groups $R^1$ and $R^2$ in the Suzuki coupling. Suitable substituents for heterocyclyl groups correspond to those listed above in context with substituents on the cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling.

In a specific embodiment, $R^2$ and $R^3$ are H, alkyl, cycloalkyl, in particular alkyl, specifically $C_1$-$C_6$-alkyl, and $R^1$ is aryl or heteroaryl, where aryl and heteroaryl may carry one or more substituents. Suitable substituents correspond to those listed above in context with aryl or heteroaryl groups $R^1$ and $R^2$ in the Suzuki coupling.

In a particular embodiment the aryl group $R^1$ is mono-, bi- or tricyclic and is specifically selected from the group consisting of phenyl and naphthyl; and the heteroaryl group $R^1$ is in particular mono-, bi- or tricyclic and is specifically selected from the group consisting of 5- or 6-membered heteroaromatic monocyclic rings and 9- or 10-membered heteroaromatic bicyclic rings containing 1, 2, 3 or 4 heteroatoms selected from the group consisting of N, O and S as ring members. Mono- or bicyclic aryl or heteroaryl groups R are for example phenyl, naphthyl, furanyl, thienyl, pyrrolyl, pyrazolyl, imidazolyl, oxazoyl, isoxazoyl, thiazoyl, isothiazolyl, [1,2,3]triazolyl, [1,2,4]triazolyl, [1,3,4]triazolyl, the oxadiazolyls, the thiadiazolyls, the tetrazolyls, pyridyl, pyrazinyl, pyrimidyl, pyridazinyl, 1,2,4-triazinyl, 1,3,5-triazinyl, indolyl, benzofuranyl, benzothienyl, quinolinyl, isoquinolinyl, quinazalinyl and the like. More particularly, they are for example phenyl, naphthyl, 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 3-isothiazolyl, 4-isothiazolyl, 5-isothiazolyl, 1,3,4-triazol-1-yl, 1,3,4-triazol-2-yl, 1,3,4-triazol-3-yl, 1,2,3-triazol-1-yl, 1,2,3-triazol-2-yl, 1,2,3-triazol-4-yl, 1,3,5-oxadiazol-3-yl, 1,2,3-oxadiazol-4-yl, 1,2,3-oxadiazol-5-yl, 1,3,4-oxadiazol-2-yl, 1,2,5-thiadiazol-3-yl, 1,2,3-thiadiazol-4-yl, 1,2,3-thiadiazol-5-yl, 1,3,4-thiadiazol-2-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, 1,2,3,4-tetrazin-1-yl, 1,2,3,4-tetrazin-2-yl, 1,2,3,4-tetrazin-5-yl, indolyl, benzofuranyl, benzothienyl, benzopyrazolyl, benzimidazolyl, benzoxazolyl, benzisoxazolyl, benzothiazolyl, benzisothiazolyl, quinolinyl, isoquinolinyl, quinazalinyl and other heteroaromatic bicyclic rings shown below in the "general definitions".

The aryl and heteroaryl groups $R^1$ can carry one or more substituents, e.g. 1, 2, 3 or 4, in particular 1, 2 or 3, specifically 1 or 2 substituents. Suitable substituents are listed above in context with aryl and heteroaryl groups $R^1$ and $R^2$ in the Suzuki reaction. In a particular embodiment, the substituents on the aryl and heteroaryl groups $R^1$ are selected from the group consisting of halogen, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino, di-($C_1$-$C_4$-alkyl)amino, phenyl, a 5- or 6-membered heteroaromatic monocyclic ring containing 1, 2, 3 or 4 heteroatoms selected from the group consisting of N, O and S as ring members and a 9- or 10-membered heteroaromatic bicyclic ring containing 1, 2, 3 or 4 heteroatoms selected from the group consisting of N, O and S as ring members, where phenyl and the heteroaromatic rings may carry one or more substituents selected from the group consisting of halogen, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino. Specifically, the substituents on the aryl and heteroaryl groups $R^1$ are selected from the group consisting of halogen, cyano, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino.

Suitable Au catalysts are Au(III) salts and Au complexes. Examples for suitable Au salts are $AuCl_3$, $AuBr_3$ or Au(triflate)$_3$. Suitable complexes are for example $(Ph_3P)AuCl$, [c-$Hex_2$(o-biphenyl)]PAuCl or [t-$Bu_2$(o-biphenyl)]PAuCl.

Ag salts or complexes can be use as co-catalysts. Examples are Ag(I) triflate or $AgNO_3$.

The Au catalyst is used in catalytic, i.e. substoichiometric amounts, e.g. in an amount of from 0.001 to 0.5 mol per mol of aminoalcohol, in particular 0.005 to 0.2 mol per mol of aminoalcohol, specifically 0.005 to 0.1 per mol of aminoalcohol, more specifically 0.01 to 0.05 mol per mol of aminoalcohol.

Also the Ag co-catalyst is used in catalytic, i.e. substoichiometric amounts, e.g. in an amount of from 0.001 to 0.5 mol per mol of aminoalcohol, in particular 0.005 to 0.2 mol per mol of aminoalcohol, specifically 0.005 to 0.1 per mol of aminoalcohol, more specifically 0.01 to 0.05 mol per mol of aminoalcohol.

The reaction is preferably carried out at from 10° C. to 60° C., in particular from 20° C. to 55° C., specifically from 20° C. to 50° C.

The reaction can be carried out, e.g., by mixing all reagents, inclusive catalyst or catalyst precursor and ligand(s), water and the cellulose derivative and reacting them at the desired temperature. Alternatively the reagents can be added gradually, especially in the case of a continuous or semicontinuous process.

If the catalyst ligand or any reactant is prone to oxidation by air, the reaction is preferably carried out in an inert atmosphere in order to avoid the presence of oxygen, e.g. under an argon or nitrogen atmosphere. Preferably, moreover, the solvent is used in degassed form. On a laboratory scale this is e.g. obtained by freezing, applying a vacuum and unfreezing under an inert atmosphere or by bubbling a vigorous stream of argon or nitrogen through the solvent or by ultrasonification under an inert atmosphere. On an industrial scale other methods known in the art can be applied.

Workup proceedings will be described below, as they are similar for most reactions.

c) C—O Coupling Reactions

In a particular embodiment, the transition metal catalyzed reaction is a C—O coupling reaction. Transition metal catalyzed C—O coupling reactions are well known. Examples are Au-catalyzed cyclodehydratizations of alkyne diols, cyclizations of alkynenols, of alkynones or of allenones or the formation of alcohols or ethers via C—O coupling in analogy to the Ullmann biaryl ether synthesis.

Au-Catalyzed Cyclodehydratizations of Diols

α,β-diols containing an appropriately positioned alkynyl residue (C—C triple bond) can undergo gold-catalyzed ring closure/dehydration (cyclodehydration). For instance, an alkyne carrying in α- and β-position to the alkyne group two OH groups undergoes cyclodehydration to the corresponding furane, as shown in the scheme below; an alkyne carrying in β- and γ-position to the alkyne group two OH groups undergoes cyclodehydration to the corresponding pyrane, etc.

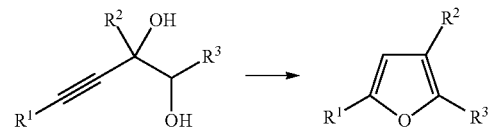

$R^1$, $R^2$ and $R^3$ are independently of each other H, alkyl, cycloalkyl, aryl, heterocyclyl or heteroaryl.

The alkyl, cycloalkyl, aryl, heterocyclyl or heteroaryl groups $R^1$, $R^2$ and $R^3$ can carry one or more substituents. Suitable substituents for alkyl, cycloalkyl, aryl and heteroaryl correspond to those listed above in context with substituents on the alkyl, cycloalkyl, aryl or heteroaryl groups $R^1$ and $R^2$ in the Suzuki coupling. Suitable substituents for heterocyclyl groups correspond to those listed above in context with substituents on the cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling.

In a specific embodiment, $R^2$ and $R^3$ are H, alkyl or cycloalkyl, in particular alkyl, specifically $C_1$-$C_6$-alkyl, and $R^1$ is aryl or heteroaryl, where aryl and heteroaryl may carry one or more substituents. Suitable substituents correspond to those listed above in context with aryl or heteroaryl groups $R^1$ and $R^2$ in the Suzuki coupling.

In a particular embodiment the aryl group $R^1$ is mono-, bi- or tricyclic and is specifically selected from the group consisting of phenyl and naphthyl; and the heteroaryl group $R^1$ is in particular mono-, bi- or tricyclic and is specifically selected from the group consisting of 5- or 6-membered heteroaromatic monocyclic rings and 9- or 10-membered heteroaromatic bicyclic rings containing 1, 2, 3 or 4 heteroatoms selected from the group consisting of N, O and S as ring members. Mono- or bicyclic aryl or heteroaryl groups $R^1$ are for example phenyl, naphthyl, furanyl, thienyl, pyrrolyl, pyrazolyl, imidazolyl, oxazoyl, isoxazoyl, thiazoyl, isothiazolyl, [1,2,3]triazolyl, [1,2,4]triazolyl, [1,3,4]triazolyl, the oxadiazolyls, the thiadiazolyls, the tetrazolyls, pyridyl, pyrazinyl, pyrimidyl, pyridazinyl, 1,2,4-triazinyl, 1,3,5-triazinyl, indolyl, benzofuranyl, benzothienyl, quinolinyl, isoquinolinyl, quinazalinyl and the like. More particularly, they are for example phenyl, naphthyl, 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 3-isothiazolyl, 4-isothiazolyl, 5-isothiazolyl, 1,3,4-triazol-1-yl, 1,3,4-triazol-2-yl, 1,3,4-triazol-3-yl, 1,2,3-triazol-1-yl, 1,2,3-triazol-2-yl, 1,2,3-triazol-4-yl, 1,2,5-oxadiazol-3-yl, 1,2,3-oxadiazol-4-yl, 1,2,3-oxadiazol-5-yl, 1,3,4-oxadiazol-2-yl, 1,2,5-thiadiazol-3-yl, 1,2,3-thiadiazol-4-yl, 1,2,3-thiadiazol-5-yl, 1,3,4-thiadiazol-2-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, 1,2,3,4-tetrazin-1-yl, 1,2,3,4-tetrazin-2-yl, 1,2,3,4-tetrazin-5-yl, indolyl, benzofuranyl, benzothienyl, benzopyrazolyl, benzimidazolyl, benzoxazolyl, benzisoxazolyl, benzothiazolyl, benzisothiazolyl, quinolinyl, isoquinolinyl, quinazalinyl and other heteroaromatic bicyclic rings shown below in the "general definitions".

The aryl and heteroaryl groups $R^1$ can carry one or more substituents, e.g. 1, 2, 3 or 4, in particular 1, 2 or 3, specifically 1 or 2 substituents. Suitable substituents are listed above in context with aryl and heteroaryl groups $R^1$ and $R^2$ in the Suzuki reaction. In a particular embodiment, the substituents on the aryl and heteroaryl groups $R^1$ are selected from the group consisting of halogen, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino, di-($C_1$-$C_4$-alkyl)amino, phenyl, a 5- or 6-membered heteroaromatic monocyclic ring containing 1, 2, 3 or 4 heteroatoms selected from the group consisting of N, O and S as ring members and a 9- or 10-membered heteroaromatic bicyclic ring containing 1, 2, 3 or 4 heteroatoms selected from the group consisting of N, O and S as ring members, where phenyl and the heteroaromatic rings may carry one or more substituents selected from the group consisting of halogen, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino. Specifically, the substituents on the aryl and heteroaryl groups $R^1$ are selected from the group consisting of halogen, cyano, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino.

Suitable Au catalysts are Au(III) salts and Au complexes. Examples for suitable Au salts are $AuCl_3$, $AuBr_3$ or Au(triflate)$_3$. Suitable complexes are for example ($Ph_3P$)AuCl, [c-Hex$_2$(o-biphenyl)]PAuCl or [t-Bu$_2$(o-biphenyl)]PAuCl.

Ag salts or complexes can be use as co-catalysts. Examples are Ag(I) triflate or $AgNO_3$.

The Au catalyst is used in catalytic, i.e. substoichiometric amounts, e.g. in an amount of from 0.001 to 0.5 mol per mol of diol, in particular 0.005 to 0.2 mol per mol of diol, specifically 0.005 to 0.1 per mol of diol, more specifically 0.01 to 0.05 mol per mol of diol.

Also the Ag co-catalyst is used in catalytic, i.e. substoichiometric amounts, e.g. in an amount of from 0.001 to 0.5 mol per mol of diol, in particular 0.005 to 0.2 mol per mol of diol, specifically 0.005 to 0.1 mol per mol of diol, more specifically 0.01 to 0.05 mol per mol of diol.

The reaction is preferably carried out at from 10° C. to 60° C., in particular from 20° C. to 55° C., specifically from 20° C. to 50° C.

The reaction can be carried out, e.g., by mixing all reagents, inclusive catalyst or catalyst precursor and ligand(s), water and the cellulose derivative and reacting them at the desired temperature. Alternatively the reagents can be added gradually, especially in the case of a continuous or semicontinuous process.

If the catalyst ligand or any reactant is prone to oxidation by air, the reaction is preferably carried out in an inert atmosphere in order to avoid the presence of oxygen, e.g. under an argon or nitrogen atmosphere. Preferably, moreover, the solvent is used in degassed form. On a laboratory scale this is e.g. obtained by freezing, applying a vacuum and unfreezing under an inert atmosphere or by bubbling a vigorous stream of argon or nitrogen through the solvent or by ultrasonification under an inert atmosphere. On an industrial scale other methods known in the art can be applied.

Workup proceedings will be described below, as they are similar for most reactions.

Cyclizations of Alkynenols

Alcohols containing an appropriately positioned alkenyl and alkynyl group (C—C triple bond) can undergo transition metal-catalyzed ring closure. For instance, an alkenyne carrying in α-position to the alkene group an OH group undergoes cyclization to the corresponding furane, as shown in the scheme below; an alkenyne carrying in β-position to the alkene group an OH group undergoes cyclization to the corresponding pyrane, etc.

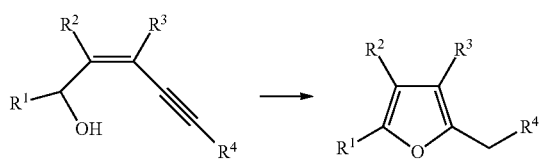

$R^1$, $R^2$, $R^3$ and $R^4$ are independently of each other H, alkyl, cycloalkyl, aryl, heterocyclyl or heteroaryl.

The alkyl, cycloalkyl, heterocyclyl, aryl or heteroaryl groups $R^1$, $R^2$, $R^3$ and $R^4$ can carry one or more substituents. Suitable substituents for alkyl, cycloalkyl, aryl or heteroaryl groups $R^1$, $R^2$, $R^3$ and $R^4$ correspond to those listed above in context with substituents on the alkyl, cycloalkyl, aryl or heteroaryl groups $R^1$ and $R^2$ in the Suzuki coupling. Suitable substituents for heterocyclyl groups $R^1$, $R^2$, $R^3$ and $R^4$ correspond to those listed above in context with substituents on the cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling.

Suitable catalysts are for example Ru, Pd, Ag and Au catalysts, among which Au catalysts generally give the best results.

Suitable Au catalysts are Au(III) salts and Au complexes. Examples for suitable Au salts are $AuCl_3$, $AuBr_3$ or Au(triflate)$_3$. Suitable complexes are for example $(Ph_3P)AuCl$, [c-$Hex_2$(o-biphenyl)]PAuCl or [t-$Bu_2$(o-biphenyl)]PAuCl.

Ag salts or complexes can be use as co-catalysts. Examples are Ag(I) triflate or $AgNO_3$.

The Au catalyst is used in catalytic, i.e. substoichiometric amounts, e.g. in an amount of from 0.001 to 0.5 mol per mol of diol, in particular 0.005 to 0.2 mol per mol of alkenynol, specifically 0.005 to 0.1 per mol of alkenynol, more specifically 0.01 to 0.05 mol per mol of alkenynol.

Also the Ag co-catalyst is used in catalytic, i.e. substoichiometric amounts, e.g. in an amount of from 0.001 to 0.5 mol per mol of alkenynol, in particular 0.005 to 0.2 mol per mol of alkenynol, specifically 0.005 to 0.1 per mol of alkenynol, more specifically 0.01 to 0.05 mol per mol of alkenynol.

The reaction is preferably carried out at from 10° C. to 60° C., in particular from 20° C. to 55° C., specifically from 20° C. to 50° C.

The reaction can be carried out, e.g., by mixing all reagents, inclusive catalyst or catalyst precursor and ligand(s), water and the cellulose derivative and reacting them at the desired temperature. Alternatively the reagents can be added gradually, especially in the case of a continuous or semicontinuous process.

If the catalyst ligand or any reactant is prone to oxidation by air, the reaction is preferably carried out in an inert atmosphere in order to avoid the presence of oxygen, e.g. under an argon or nitrogen atmosphere. Preferably, moreover, the solvent is used in degassed form. On a laboratory scale this is e.g. obtained by freezing, applying a vacuum and unfreezing under an inert atmosphere or by bubbling a vigorous stream of argon or nitrogen through the solvent or by ultrasonification under an inert atmosphere. On an industrial scale other methods known in the art can be applied.

Workup proceedings will be described below, as they are similar for most reactions.

Cyclization of Alkynones

Carbonyl compounds, especially aldehydes or ketones, containing an appropriately positioned alkynyl group (C—C triple bond) can undergo transition metal-catalyzed ring closure. For instance, an alkyne carrying in β-position to the alkyne group a C(O) group undergoes cyclization to the corresponding furane, as shown in the scheme below; an alkyne carrying in γ-position to the alkene group a C(O) group undergoes cyclization to the corresponding pyrane, etc.

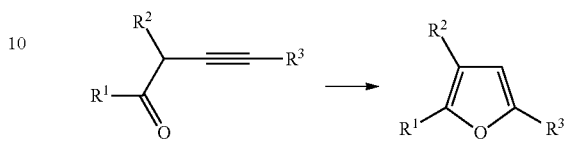

$R^1$, $R^2$ and $R^3$ are independently of each other H, alkyl, cycloalkyl, aryl, heterocyclyl or heteroaryl.

The alkyl, cycloalkyl, heterocyclyl, aryl or heteroaryl groups $R^1$, $R^2$ and $R^3$ can carry one or more substituents. Suitable substituents for alkyl, cycloalkyl, aryl or heteroaryl groups $R^1$, $R^2$ and $R^3$ correspond to those listed above in context with substituents on the alkyl, cycloalkyl, aryl or heteroaryl groups $R^1$ and $R^2$ in the Suzuki coupling. Suitable substituents for heterocyclyl groups $R^1$, $R^2$ and $R^3$ correspond to those listed above in context with substituents on the cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling.

Suitable catalysts are for example Ru, Pd, Ag and Au catalysts, among which Au catalysts generally give the best results.

Suitable Au catalysts are Au(III) salts and Au complexes. Examples for suitable Au salts are $AuCl_3$, $AuBr_3$ or Au(triflate)$_3$. Suitable complexes are for example $(Ph_3P)AuCl$, [c-$Hex_2$(o-biphenyl)]PAuCl or [t-$Bu_2$(o-biphenyl)]PAuCl.

Ag salts or complexes can be use as co-catalysts. Examples are Ag(I) triflate or $AgNO_3$.

The Au catalyst is used in catalytic, i.e. substoichiometric amounts, e.g. in an amount of from 0.001 to 0.5 mol per mol of alkynone, in particular 0.005 to 0.2 mol per mol of alkynone, specifically 0.005 to 0.1 per mol of alkynone, more specifically 0.01 to 0.05 mol per mol of alkynone.

Also the Ag co-catalyst is used in catalytic, i.e. substoichiometric amounts, e.g. in an amount of from 0.001 to 0.5 mol per mol of alkynone, in particular 0.005 to 0.2 mol per mol of alkynone, specifically 0.005 to 0.1 per mol of alkynone, more specifically 0.01 to 0.05 mol per mol of alkynone.

The reaction is preferably carried out at from 10° C. to 60° C., in particular from 20° C. to 55° C., specifically from 20° C. to 50° C.

The reaction can be carried out, e.g., by mixing all reagents, inclusive catalyst or catalyst precursor and ligand(s), water and the cellulose derivative and reacting them at the desired temperature. Alternatively the reagents can be added gradually, especially in the case of a continuous or semicontinuous process.

If the catalyst ligand or any reactant is prone to oxidation by air, the reaction is preferably carried out in an inert atmosphere in order to avoid the presence of oxygen, e.g. under an argon or nitrogen atmosphere. Preferably, moreover, the solvent is used in degassed form. On a laboratory scale this is e.g. obtained by freezing, applying a vacuum and unfreezing under an inert atmosphere or by bubbling a vigorous stream of argon or nitrogen through the solvent or by ultrasonification under an inert atmosphere. On an industrial scale other methods known in the art can be applied.

Workup proceedings will be described below, as they are similar for most reactions.

Cyclization of Allenones

Carbonyl compounds, especially aldehydes or ketones, containing an appropriately positioned allene group can undergo transition metal-catalyzed ring closure. For instance, an allene carrying in α-position to the allene group a C(O) group undergoes cyclization to the corresponding furane, as shown in the scheme below; an allene carrying in β-position to the allene group a C(O) group undergoes cyclization to the corresponding pyrane, etc.

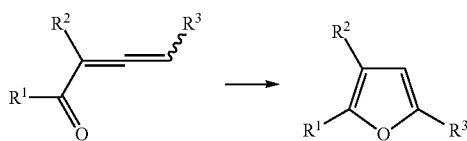

$R^1$, $R^2$ and $R^3$ are independently of each other H, alkyl, cycloalkyl, aryl, heterocyclyl or heteroaryl.

The alkyl, cycloalkyl, heterocyclyl, aryl or heteroaryl groups $R^1$, $R^2$ and $R^3$ can carry one or more substituents. Suitable substituents for alkyl, cycloalkyl, aryl or heteroaryl groups $R^1$, $R^2$ and $R^3$ correspond to those listed above in context with substituents on the alkyl, cycloalkyl, aryl or heteroaryl groups $R^1$ and $R^2$ in the Suzuki coupling. Suitable substituents for heterocyclyl groups $R^1$, $R^2$ and $R^3$ correspond to those listed above in context with substituents on the cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling.

Suitable catalysts are for example Ru, Pd, Ag and Au catalysts, among which Au catalysts generally give the best results.

Suitable Au catalysts are Au(III) salts and Au complexes. Examples for suitable Au salts are $AuCl_3$, $AuBr_3$ or Au(triflate)$_3$. Suitable complexes are for example $(Ph_3P)AuCl$, [c-Hex$_2$(o-biphenyl)]PAuCl or [t-Bu$_2$(o-biphenyl)]PAuCl.

Ag salts or complexes can be use as co-catalysts. Examples are Ag(I) triflate or $AgNO_3$.

The Au catalyst is used in catalytic, i.e. substoichiometric amounts, e.g. in an amount of from 0.001 to 0.5 mol per mol of allenone, in particular 0.005 to 0.2 mol per mol of allenone, specifically 0.005 to 0.1 per mol of allenone, more specifically 0.01 to 0.05 mol per mol of allenone.

Also the Ag co-catalyst is used in catalytic, i.e. substoichiometric amounts, e.g. in an amount of from 0.001 to 0.5 mol per mol of allenone, in particular 0.005 to 0.2 mol per mol of allenone, specifically 0.005 to 0.1 per mol of allenone, more specifically 0.01 to 0.05 mol per mol of allenone.

The reaction is preferably carried out at from 10° C. to 60° C., in particular from 20° C. to 55° C., specifically from 20° C. to 50° C.

The reaction can be carried out, e.g., by mixing all reagents, inclusive catalyst or catalyst precursor and ligand (s), water and the cellulose derivative and reacting them at the desired temperature. Alternatively the reagents can be added gradually, especially in the case of a continuous or semicontinuous process.

If the catalyst ligand or any reactant is prone to oxidation by air, the reaction is preferably carried out in an inert atmosphere in order to avoid the presence of oxygen, e.g. under an argon or nitrogen atmosphere. Preferably, moreover, the solvent is used in degassed form. On a laboratory scale this is e.g. obtained by freezing, applying a vacuum and unfreezing under an inert atmosphere or by bubbling a vigorous stream of argon or nitrogen through the solvent or by ultrasonification under an inert atmosphere. On an industrial scale other methods known in the art can be applied.

Workup proceedings will be described below, as they are similar for most reactions.

Formation of Alcohols or Ethers Via C—O Coupling

The copper-mediated synthesis of biaryl ethers by reaction of an aromatic halide or pseudohalide and a hydroxyaromatic compound to a biaryl ether is known as the Ullmann biaryl ether synthesis or condensation. In the method of the present invention, the use of Cu is however not mandatory; any transition metal catalyst can be used. Mostly a Pd catalyst is used.

Moreover, the oxygen source is not limited to an aromatic hydroxyl compound, but can be any compound with a nucleophilic OH group. Thus, an aromatic or heteroaromatic compound $R^1$—X, where $R^1$ is an aryl or heteroaryl group and X is a halogen atom or a pseudohalide group, such as SCN, and is in particular Cl, Br, I or SCN, is reacted with a metal hydroxide, such as alkali metal hydroxide, e.g. LiOH, NaOH or KOH, or an earth alkaine metal hydroxide, such as $Mg(OH)_2$ or $Ca(OH)_2$, to yield an alcohol $R^1$—OH; or with a hydroxyl compound $R^2$—OH, where $R^2$ is alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl or heteroaryl, to yield an ether $R^1$—O—$R^2$.

In a particular embodiment the aryl group $R^1$ is mono-, bi- or tricyclic and is specifically selected from the group consisting of phenyl and naphthyl; and the heteroaryl group $R^1$ is in particular mono-, bi- or tricyclic and is specifically selected from the group consisting of 5- or 6-membered heteroaromatic monocyclic rings and 9- or 10-membered heteroaromatic bicyclic rings containing 1, 2, 3 or 4 heteroatoms selected from the group consisting of N, O and S as ring members. Mono- or bicyclic aryl or heteroaryl groups $R^1$ are for example phenyl, naphthyl, furanyl, thienyl, pyrrolyl, pyrazolyl, imidazolyl, oxazoyl, isoxazoyl, thiazoyl, isothiazolyl, [1,2,3]triazolyl, [1,2,4]triazolyl, [1,3,4]triazolyl, the oxadiazolyls, the thiadiazolyls, the tetrazolyls, pyridyl, pyrazinyl, pyrimidyl, pyridazinyl, 1,2,4-triazinyl, 1,3,5-triazinyl, indolyl, benzofuranyl, benzothienyl, quinolinyl, isoquinolinyl, quinazalinyl and the like. More particularly, they are for example phenyl, naphthyl, 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 3-isothiazolyl, 4-isothiazolyl, 5-isothiazolyl, 1,3,4-triazol-1-yl, 1,3,4-triazol-2-yl, 1,3,4-triazol-3-yl, 1,2,3-triazol-1-yl, 1,2,3-triazol-2-yl, 1,2,3-triazol-4-yl, 1,2,5-oxadiazol-3-yl, 1,2,3-oxadiazol-4-yl, 1,2,3-oxadiazol-5-yl, 1,3,4-oxadiazol-2-yl, 1,2,5-thiadiazol-3-yl, 1,2,3-thiadiazol-4-yl, 1,2,3-thiadiazol-5-yl, 1,3,4-thiadiazol-2-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, 1,2,3,4-tetrazin-1-yl, 1,2,3,4-tetrazin-2-yl, 1,2,3,4-tetrazin-5-yl, indolyl, benzofuranyl, benzothienyl, benzopyrazolyl, benzimidazolyl, benzoxazolyl, benzisoxazolyl, benzothiazolyl, benzisothiazolyl, quinolinyl, isoquinolinyl, quinazalinyl and other heteroaromatic bicyclic rings shown below in the "general definitions".

The aryl and heteroaryl groups $R^1$ can carry one or more substituents, e.g. 1, 2, 3 or 4, in particular 1, 2 or 3, specifically 1 or 2 substituents. Suitable substituents are listed above in context with aryl and heteroaryl groups $R^1$ and $R^2$ in the Suzuki reaction.

In these substituents, however, all functional groups, especially halogen atoms, pseudohalogen groups and sulfonyloxy groups, have to be less reactive towards the hydroxide or hydroxyl compound than the halogen atom or pseudohalide group on the desired reaction site of the $R^1$—X compound.

In a particular embodiment, the substituents are selected from the group consisting of halogen (provided this is less reactive than X in the C—O coupling reaction), cyano (provided this is less reactive than X in the C—O coupling reaction), nitro, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkythio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, phenyl, a 5- or 6-membered heteroaromatic monocyclic ring containing 1, 2, 3 or 4 heteroatoms selected from N, O and S as ring members and a 9- or 10-membered heteroaromatic bicyclic ring containing 1, 2, 3 or 4 heteroatoms selected from the group consisting of N, O and S as ring members, where phenyl and the heteroaromatic rings may carry one or more substituents selected from the group consisting of fluorine, cyano, nitro, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl and $C_1$-$C_4$-haloalkoxycarbonyl. Specifically, the substituents are selected from the group consisting of $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_6$-alkyl and $C_3$-$C_8$-halocycloalkyl-$C_1$-$C_6$-alkyl.

Very specifically, $R^1$ is selected from the group consisting of phenyl and naphthyl, where phenyl and naphthyl may carry 1, 2 or 3, specifically 1 or 2 substituents as defined above.

The alkyl, alkenyl, alkapolyenyl, alkynyl, mixed alkenyl/alkynyl, alkapolyynyl, cycloalkyl, cycloalkenyl, cycloalkynyl, mixed cycloalkenyl/cycloalkynyl, polycarbocyclyl, heterocyclyl, aryl or heteroaryl groups $R^2$ can carry one or more substituents. Suitable substituents correspond to those listed above in context with substituents on the alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling. Suitable substituents for heterocyclyl groups $R^2$ correspond to those listed above in context with substituents on the cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling.

Suitable Pd catalysts (inclusive ligands) are those mentioned above in context with the Suzuki coupling.

The reaction is preferably carried out at from 10° C. to 60° C., in particular from 20° C. to 55° C., specifically from 20° C. to 50° C.

The halogenide or pseudohalogenide and the OH compound (metal hydroxide or hydroxyl compound) can be used in a molar ratio of from 10:1 to 1:10, e.g. from 7:1 to 1:7 or from 5:1 to 1:5.

The catalyst is used in catalytic, i.e. substoichiometric amounts, e.g. in an amount of from 0.001 to 0.1 mol per mol of that reactant which is not used in excess, in particular 0.005 to 0.07 mol per mol of the reactant not used in excess. If the reactants are used in equimolar ratio, the above amounts of catalyst apply of course to either of the reactants.

The reaction can be carried out by standard proceedings for such reactions, e.g. by mixing all reagents, inclusive catalyst or catalyst precursor and ligand(s), water and the cellulose derivative and reacting them at the desired temperature. Alternatively the reagents can be added gradually, especially in the case of a continuous or semicontinuous process.

If the catalyst ligand or any reactant is prone to oxidation by air (such as is the case, for example, for triphenylphosphine, tri(tert-butyl)phosphine, X-Phos, 6,6'-dimethoxy-[1,1'-biphenyl]-2,2'-diyl)bis(bis(3,5-dimethylphenyl)phosphine and several others), the reaction is preferably carried out in an inert atmosphere in order to avoid the presence of oxygen, e.g. under an argon or nitrogen atmosphere. Preferably, moreover, the solvent is used in degassed form. On a laboratory scale this is e.g. obtained by freezing, applying a vacuum and unfreezing under an inert atmosphere or by bubbling a vigorous stream of argon or nitrogen through the solvent or by ultrasonification under an inert atmosphere. On an industrial scale other methods known in the art can be applied.

Workup proceedings will be described below, as they are similar for most reactions.

d) C—B Coupling Reactions

In a particular embodiment, the transition metal catalyzed reaction is a C—B coupling reaction. Transition metal catalyzed C—B coupling reactions are well known. Examples are the Miyaura boration or borylation.

Miyaura Borylation

The Pd-catalyzed C—B coupling reaction of alkenyl, aryl or heteroaryl halides or sulfonates with tetraalkoxydiboron compounds is called Miyaura borylation. The resulting aryl boronic esters are valuable substrates for Suzuki coupling reactions, Ullmann biaryl ether syntheses and the above described 1,4 additions of organoborane compounds to α,β-olefinically unsaturated carbonyl compounds, such as the Rh-catalyzed 1,4-addition reactions.

Preferably, a halogenide or sulfonate $R^2$—$(Z)_n$, where $R^2$ is an alkenyl, aryl or heteroaryl group, Z is a halogenide or sulfonate group (the sulfonate being in particular a fluorinated alkylsulfonate or tosylate, specifically triflate or nonaflate) and n is 1, 2, 3 or 4, is reacted with a tetraalkoxydiboron $(R^1O)_2B$—$B(OR^1)_2$, where $R^1$ is alkyl or two $R^1$ bound on oxygen atoms bound in turn to the same B atom form together —$C(CH_3)_3$—$C(CH_3)_2$— (so that $B(OR^1)_2$ is the pinacolon ester of boronic acid), in the presence of a transition metal catalyst, in particular of a Pd catalyst, and in general also of a base.

The reaction of the tetraalkoxydiboron $(R^1O)_2B$—$B(OR^1)_2$ with $R^2$—$(Z)_n$ yields a compound $(B(OR^1)_2)_n$—$R^2$. The alkenyl, aryl or heteroaryl halide or sulfonate can contain more than one halide or sulfonate group (when n is 2, 3 or 4), so that multiply coupled compounds can form, especially if the tetraalkoxydiboron compound is used in excess. For instance, a difunctional compound $R^2$—$(Z)_2$ can yield a twofold coupled compound tetraalkoxydiboron $(R^1O)_2B$—$R^2$—$B(OR^1)_2$.

Due to the tolerance of the Miyaura borylation to a wide variety of functional groups, the alkenyl, aryl or heteroaryl groups $R^2$ can carry one or more substituents. Suitable substituents correspond to those listed above in context with substituents on the alkenyl, aryl or heteroaryl groups $R^1$ and $R^2$ in the Suzuki coupling.

In these substituents, however, all functional groups, especially halogen atoms and sulfonyloxy groups, have to be less reactive towards the diboron compound than the halogen atom or sulfonate group on the desired reaction site of the $R^2$—$(Z)_n$ compound.

Suitable Pd catalysts (inclusive ligands) are those mentioned above in context with the Suzuki coupling.

Suitable bases can be inorganic or organic. Examples for suitable are those listed in context with the Suzuki reaction.

Specifically, the present method relates to a Miyaura borylation in which an aromatic or heteroaromatic halogenide $R^2$—$(Z)_n$, where $R^2$ is a mono-, bi- or polycyclic aryl or heteroaryl group, Z is a halogen atom, especially Cl, Br or I, more specifically Br or I, and n is 1, is reacted with a tetraalkoxydiboron, specifically with bis(pinacolato)diboron, in the presence of a Pd catalyst, specifically of bis (tritert-butyl-butylphosphine) palladium(0), and in the presence of a base, specifically of an acetate, specifically sodium or potassium acetate.

In a particular embodiment the aryl group $R^2$ is mono-, bi- or tricyclic and is specifically selected from the group consisting of phenyl and naphthyl; and the heteroaryl group $R^2$ is in particular mono-, bi- or tricyclic and is specifically selected from the group consisting of 5- or 6-membered heteroaromatic monocyclic rings and 9- or 10-membered heteroaromatic bicyclic rings containing 1, 2, 3 or 4 heteroatoms selected from the group consisting of N, O and S as ring members. Mono- or bicyclic aryl or heteroaryl groups $R^2$ are for example phenyl, naphthyl, furanyl, thienyl, pyrrolyl, pyrazolyl, imidazolyl, oxazoyl, isoxazoyl, thiazoyl, isothiazolyl, [1,2,3]triazolyl, [1,2,4]triazolyl, [1,3,4]triazolyl, the oxadiazolyls, the thiadiazolyls, the tetrazolyls, pyridyl, pyrazinyl, pyrimidyl, pyridazinyl, 1,2,4-triazinyl, 1,3,5-triazinyl, indolyl, benzofuranyl, benzothienyl, quinolinyl, isoquinolinyl, quinazalinyl and the like. More particularly, they are for example phenyl, naphthyl, 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 3-isothiazolyl, 4-isothiazolyl, 5-isothiazolyl, 1,3,4-triazol-1-yl, 1,3,4-triazol-2-yl, 1,3,4-triazol-3-yl, 1,2,3-triazol-1-yl, 1,2,3-triazol-2-yl, 1,2,3-triazol-4-yl, 1,2,5-oxadiazol-3-yl, 1,2,3-oxadiazol-4-yl, 1,2,3-oxadiazol-5-yl, 1,3,4-oxadiazol-2-yl, 1,2,5-thiadiazol-3-yl, 1,2,3-thiadiazol-4-yl, 1,2,3-thiadiazol-5-yl, 1,3,4-thiadiazol-2-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, 1,2,3,4-tetrazin-1-yl, 1,2,3,4-tetrazin-2-yl, 1,2,3,4-tetrazin-5-yl, indolyl, benzofuranyl, benzothienyl, benzopyrazolyl, benzimidazolyl, benzoxazolyl, benzisoxazolyl, benzothiazolyl, benzisothiazolyl, quinolinyl, isoquinolinyl, quinazalinyl and other heteroaromatic bicyclic rings shown below in the "general definitions".

The aryl and heteroaryl groups $R^2$ can carry one or more substituents, e.g. 1, 2, 3 or 4, in particular 1, 2 or 3, specifically 1 or 2 substituents. Suitable substituents are listed above in context with aryl and heteroaryl groups $R^1$ and $R^2$ in the Suzuki reaction. In a particular embodiment, the substituents on the aryl and heteroaryl groups $R^2$ are selected from the group consisting of fluorine, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino, di-($C_1$-$C_4$-alkyl)amino, phenyl, a 5- or 6-membered heteroaromatic monocyclic ring containing 1, 2, 3 or 4 heteroatoms selected from the group consisting of N, O and S as ring members and a 9- or 10-membered heteroaromatic bicyclic ring containing 1, 2, 3 or 4 heteroatoms selected from the group consisting of N, O and S as ring members, where phenyl and the heteroaromatic rings may carry one or more substituents selected from the group consisting of fluorine, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino. Specifically, the substituents on the aryl and heteroaryl groups $R^2$ are selected from the group consisting of fluorine, cyano, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino.

The reaction is preferably carried out at from 10° C. to 60° C., in particular from 20° C. to 55° C., specifically from 20° C. to 50° C.

The halogenide or sulfonate and the tetraalkoxydiboron can be used in a molar ratio of from 10:1 to 1:10, e.g. from 7:1 to 1:7 or from 5:1 to 1:5. In case of di- or polyfunctional halides or sulfonates, the molar ratio relates of course to the number of halide or sulfonate groups in the molecule. If n is 1, $R^2$—$(Z)_n$ and the tetraalkoxydiboron are preferably used in a molar ratio of from 2:1 to 1:2, more preferably from 1.5:1 to 1:1.5 and specifically from 1:1 to 1:1.5. If n is 2, $R^2$—$(Z)_n$ and $R^1$—$BY_2$ are preferably used in a molar ratio of from 1:1 to 1:4, more preferably from 1:1.5 to 1:3 and specifically in a molar ratio of from 1:2 to 1:3.

The catalyst is used in catalytic, i.e. substoichiometric amounts, e.g. in an amount of from 0.001 to 0.1 mol per mol of that reactant which is not used in excess, in particular 0.005 to 0.07 mol per mol of the reactant not used in excess, specifically 0.01 to 0.07 mol per mol of the reactant not used in excess. If the reactants are used in equimolar ratio, the above amounts of catalyst apply of course to either of the reactants.

The base is generally used in excess, i.e. in overstoichiometric amounts with respect to that reactant not used in excess, e.g. in an amount of from 1.5 to 5 mol per mol of the reactant not used in excess, in particular 1.5 to 4 mol per mol of the reactant not used in excess, specifically 1.5 to 3 mol per mol of the reactant not used in excess. If the reactants are used in equimolar ratio, the above amounts of base apply of course to either of the reactants.

The reaction can be carried out by standard proceedings for Miyaura borylations, e.g. by mixing all reagents, inclusive catalyst or catalyst precursor and ligand(s) and base, water and the cellulose derivative and reacting them at the desired temperature. Alternatively the reagents can be added gradually, especially in the case of a continuous or semi-continuous process.

If the catalyst ligand or any reactant is prone to oxidation by air (such as is the case, for example, for triphenylphosphine, tri(tert-butyl)phosphine, X-Phos, 6,6'-dimethoxy-[1,1'-biphenyl]-2,2'-diyl)bis(bis(3,5-dimethylphenyl)phosphine and several others), the reaction is preferably carried out in an inert atmosphere in order to avoid the presence of oxygen, e.g. under an argon or nitrogen atmosphere. Preferably, moreover, the solvent is used in degassed form. On a laboratory scale this is e.g. obtained by freezing, applying a vacuum and unfreezing under an inert atmosphere or by bubbling a vigorous stream of argon or nitrogen through the solvent or by ultrasonification under an inert atmosphere. On an industrial scale other methods known in the art can be applied.

Workup proceedings will be described below, as they are similar for most reactions.

e) C-Halogen Coupling

In this reaction a C—H bond is converted into a C-halogen bond by reaction with a halogenating agent in the presence of a transition metal catalyst. In a specific embodiment an aromatic or heteroaromatic compound $R^1$—H, where $R^1$ is aryl or heteroaryl, is reacted with a halogenating agent in the presence of a transition metal catalyst to yield a compound $R^1$—X, where X is a halogen atom, especially Cl, Br or I, very specifically Cl or Br.

Suitable transition metal catalysts are those mentioned above. In particular, an Au or a Pd catalyst is used. Specifically an Au catalyst is used.

Suitable Au catalysts are Au(I) salts and Au complexes.

Suitable Pd catalysts (inclusive ligands) are those mentioned above in context with the Suzuki coupling.

Suitable halogenation reagents are for example the halogens, i.e. $F_2$, $Cl_2$, $Br_2$ or $I_2$, oxalyl chloride, oxalyl bromide, thionyl chloride, thionyl bromide, sulfuryl chloride, sulfuryl bromide, N-bromosuccinimide (NBS), N-chlorosuccinimide (NCS), dichlorodimethylhydantoin, dibromodimethylhydantoin, trichlorisocyanuric acid, chloramine-T, $PCl_5$, $P(O)Cl_3$, sodium hypochlorite, monochloroamine ($NH_2Cl$) and the like. In a specific embodiment NBS or NCS is used.

In a particular embodiment aryl group $R^1$ is mono-, bi- or tricyclic and are specifically selected from the group consisting of phenyl and naphthyl; and heteroaryl group $R^1$ is in particular mono-, bi- or tricyclic and are specifically selected from the group consisting of 5- or 6-membered heteroaromatic monocyclic rings and 9- or 10-membered heteroaromatic bicyclic rings containing 1, 2, 3 or 4 heteroatoms selected from the group consisting of N, O and S as ring members. Mono- or bicyclic aryl or heteroaryl groups $R^1$ are for example phenyl, naphthyl, furanyl, thienyl, pyrrolyl, pyrazolyl, imidazolyl, oxazoyl, isoxazoyl, thiazoyl, isothiazolyl, [1,2,3]triazolyl, [1,2,4]triazolyl, [1,3,4]triazolyl, the oxadiazolyls, the thiadiazolyls, the tetrazolyls, pyridyl, pyrazinyl, pyrimidyl, pyridazinyl, 1,2,4-triazinyl, 1,3,5-triazinyl, indolyl, benzofuranyl, benzothienyl, quinolinyl, isoquinolinyl, quinazalinyl and the like. More particularly, they are for example phenyl, naphthyl, 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 3-isothiazolyl, 4-isothiazolyl, 5-isothiazolyl, 1,3,4-triazol-1-yl, 1,3,4-triazol-2-yl, 1,3,4-triazol-3-yl, 1,2,3-triazol-1-yl, 1,2,3-triazol-2-yl, 1,2,3-triazol-4-yl, 1,2,5-oxadiazol-3-yl, 1,2,3-oxadiazol-4-yl, 1,2,3-oxadiazol-5-yl, 1,3,4-oxadiazol-2-yl, 1,2,5-thiadiazol-3-yl, 1,2,3-thiadiazol-4-yl, 1,2,3-thiadiazol-5-yl, 1,3,4-thiadiazol-2-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, 1,2,3,4-tetrazin-1-yl, 1,2,3,4-tetrazin-2-yl, 1,2,3,4-tetrazin-5-yl, indolyl, benzofuranyl, benzothienyl, benzopyrazolyl, benzimidazolyl, benzoxazolyl, benzisoxazolyl, benzothiazolyl, benzisothiazolyl, quinolinyl, isoquinolinyl, quinazalinyl and other heteroaromatic bicyclic rings shown below in the "general definitions".

The aryl and heteroaryl groups $R^1$ can carry one or more substituents, e.g. 1, 2, 3 or 4, in particular 1, 2 or 3, specifically 1 or 2 substituents. Suitable substituents are listed above in context with aryl and heteroaryl groups $R^1$ and $R^2$ in the Suzuki reaction. In a particular embodiment, the substituents on the aryl and heteroaryl groups $R^1$ are selected from the group consisting of fluorine, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino, di-($C_1$-$C_4$-alkyl)amino, phenyl, a 5- or 6-membered heteroaromatic monocyclic ring containing 1, 2, 3 or 4 heteroatoms selected from the group consisting of N, O and S as ring members and a 9- or 10-membered heteroaromatic bicyclic ring containing 1, 2, 3 or 4 heteroatoms selected from the group consisting of N, O and S as ring members, where phenyl and the heteroaromatic rings may carry one or more substituents selected from the group consisting of fluorine, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino. Specifically, the substituents on the aryl and heteroaryl groups $R^1$ are selected from the group consisting of fluorine, cyano, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$- alkoxycarbonyl, $C_1$-$C_4$-haloalkoxycarbonyl, amino, $C_1$-$C_4$-alkylamino and di-($C_1$-$C_4$-alkyl)amino.

The reaction is preferably carried out at from 10° C. to 60° C., in particular from 20° C. to 55° C., specifically from 20° C. to 50° C.

The (hetero)aromatic compound and the halogenating agent can be used in a molar ratio of from 10:1 to 1:10. More often, however, the halogenating agent is used in at least equimolar amounts, especially if a halogen is used as halogenating agent.

The catalyst is used in catalytic, i.e. substoichiometric amounts, e.g. in an amount of from 0.001 to 0.1 mol per mol of that reactant which is not used in excess, in particular 0.005 to 0.07 mol per mol of the reactant not used in excess. If the reactants are used in equimolar ratio, the above amounts of catalyst apply of course to either of the reactants.

The reaction can be carried out by standard proceedings for halogenations, e.g. by mixing all reagents, inclusive catalyst or catalyst precursor and ligand(s), water and the cellulose derivative and reacting them at the desired temperature. Alternatively the reagents can be added gradually, especially in the case of a continuous or semicontinuous process. If the halogenating agent is gaseous, e.g. fluorine or chlorine, generally all reagents but the gaseous halogen are mixed and the halogen gas is then bubbled through the reaction mixture. If the reaction is carried out at temperatures above or below ambient conditions, the mixture can be brought to the desired temperature before or during the introduction of the halogen gas.

If the catalyst ligand or any reactant is prone to oxidation by air (such as is the case, for example, for triphenylphosphine, tri(tert-butyl)phosphine, X-Phos, 6,6'-dimethoxy-[1,1'-biphenyl]-2,2'-diyl)bis(bis(3,5-dimethylphenyl)phosphine and several others), the reaction is preferably carried out in an inert atmosphere in order to avoid the presence of oxygen, e.g. under an argon or nitrogen atmosphere. Preferably, moreover, the solvent is used in degassed form. On a laboratory scale this is e.g. obtained by freezing, applying a vacuum and unfreezing under an inert atmosphere or by bubbling a vigorous stream of argon or nitrogen through the solvent or by ultrasonification under an inert atmosphere. On an industrial scale other methods known in the art can be applied.

Workup proceedings will be described below, as they are similar for most reactions. If the halogenating agent is used in excess, this is generally neutralized before further workup.

C—C Coupling Reactions not Requiring Transition Metal Catalysis

In another particular embodiment of the invention, the organic reaction is a C—C coupling reaction not requiring transition metal catalysis. Such reactions are well known and often named reactions. Examples are various reactions of carbonyl compounds or nitrile compounds, e.g. with nucleophiles, e.g. with CH acidic compounds, like the Wittig reaction, the Baylis-Hillman reaction, the Aldol addition and condensation, the Knoevenagel condensation, the Michael addition, the Mannich reaction, the Perkin reaction, the Erlenmeyer reaction, the Darzens reaction, the acyloin condensation, Friedel Crafts alkylation and acylation, Grignard reaction etc; further pericyclic reactions like the Diels-Alder reaction, cyclopropanation reactions (without transition metal catalysis in this context) etc. In particular, the C—C coupling reaction not requiring transition metal catalysis is a Wittig reaction, a Diels-Alder reaction or a Baylis-Hillman reaction.

Wittig Reaction

In a particular embodiment, the C—C coupling reaction not requiring transition metal catalysis is a Wittig reaction. The formation of C—C double bonds from carbonyl compounds and phosphoranes (phosphorous ylides) is known as the Wittig reaction. In the below scheme both the phosphorous ylide and ylene mesomeric forms are shown:

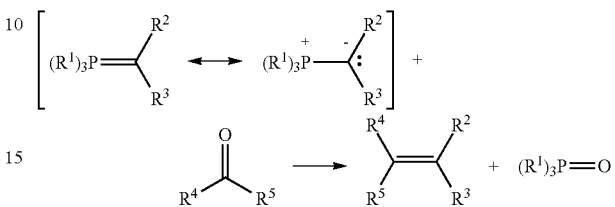

The phosphorous ylide is generally prepared from a triaryl or trialkyl phosphine, mostly triphenyl phosphine, and an alkyl halide followed by deprotonation with a suitable base, such as BuLi, sodium hydride or sodium methanolate.

$R^1$ is in general an aryl group, especially phenyl. $R^2$ and $R^3$ are generally independently of each other hydrogen, alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl, heteroaryl, CN, $C(O)R^{13}$, $C(S)R^{13}$ or $S(O)_2R^{11}$. The alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl and heteroaryl groups $R^1$, $R^2$ and $R^3$ can carry one or more substituents. Suitable substituents for alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl and heteroaryl correspond to those listed above in context with substituents on the alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling. Suitable substituents for heterocyclyl groups correspond to those listed above in context with substituents on the cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling. $R^{11}$ and $R^{13}$ are as defined above in context with the Suzuki coupling.

$R^4$ and $R^5$ are independently of each other hydrogen, alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl or heteroaryl. Alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl, heteroaryl can carry one or more substituents. Suitable substituents for alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl and heteroaryl correspond to those listed above in context with substituents on the alkyl, alkenyl, alkapolyenyl, alkynyl, alkapolyynyl, mixed alkenyl/alkynyl, cycloalkyl, cycloalkynyl, mixed cycloalkenyl/cycloalkynyl, polycarbocyclyl, aryl or heteroaryl groups $R^1$ and $R^2$ in the Suzuki coupling. Suitable substituents for heterocyclyl groups correspond to those listed above in context with substituents on the cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling.

Important variants of the Wittig reaction are

1) Horner-Wittig or Wittig-Horner reaction, in which the phosphorous ylides contain phosphine oxides in place of triarylphosphines or trialkylphosphines;

2) the Horner-Wadsworth-Emmons reaction, in which alkylphosphonicdiethylesters are the phosphorus reagents:

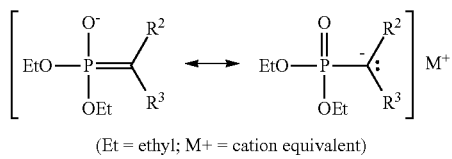

(Et = ethyl; M+ = cation equivalent)

3) the Schlosser modification in which two equivalents of a Li-halide salt are present in the reaction mixture.

In the terms of the present invention the "Wittig reaction" encompasses all these variants.

In the proper Wittig reaction, the ylides can be stabilized, semi-stabilized or nonstabilized. In the stabilized ylides the alkylhalide component has at least one strong electron-withdrawing group (—COOR, C(O)R, S(O)$_2$R, CN etc.) which stabilizes the formal negative charge on the C atom. In the semi-stabilized ylides the alkylhalide component has at least one alkenyl or aryl substituent (i.e. at least one of $R^2$ and $R^3$ is alkenyl or aryl). In the nonstabilized ylides the alkylhalide component has only alkyl substituent(s).

In particular, the C—C coupling reaction not requiring transition metal catalysis is a Wittig reaction in the proper sense. Preferably the ylide used is a stabilized ylide. In particular, one of $R^2$ and $R^3$ is a CN, C(O)$R^{13}$, C(S)$R^{13}$ or S(O)$_2R^{11}$ group and especially a C(O)O$R^{20}$ group, where $R^{11}$, $R^{13}$ and $R^{20}$ are as defined above in context with the Suzuki coupling. In particular, one of $R^2$ and $R^3$ is $C_1$-$C_4$-alkoxycarbonyl. The other radical is in particular hydrogen or $C_1$-$C_4$-alkyl.

In particular, one of $R^4$ and $R^5$ is hydrogen or $C_1$-$C_4$-alkyl and the other is alkyl, alkenyl, alkynyl, cycloalkyl, heterocyclyl, aryl or heteroaryl, where alkyl, alkenyl, alkynyl, cycloalkyl, heterocyclyl, aryl, heteroaryl can carry one or more substituents. Specifically, one of $R^4$ and $R^5$ is hydrogen or $C_1$-$C_4$-alkyl and the other is a mono-, bi- or polycyclic aryl or heteroaryl group which may carry one or more substituents.

In a particular embodiment the aryl group $R^4$ or $R^5$ is mono-, bi- or tricyclic and is specifically selected from the group consisting of phenyl and naphthyl; and the heteroaryl group $R^4$ or $R^5$ is in particular mono-, bi- or tricyclic and is specifically selected from the group consisting of 5- or 6-membered heteroaromatic monocyclic rings and 9- or 10-membered heteroaromatic bicyclic rings containing 1, 2, 3 or 4 heteroatoms selected from the group consisting of N, O and S as ring members. Mono- or bicyclic aryl or heteroaryl groups $R^4$ or $R^5$ are for example phenyl, naphthyl, furanyl, thienyl, pyrrolyl, pyrazolyl, imidazolyl, oxazoyl, isoxazoyl, thiazoyl, isothiazolyl, [1,2,3]triazolyl, [1,2,4]triazolyl, [1,3,4]triazolyl, the oxadiazolyls, the thiadiazolyls, the tetrazolyls, pyridyl, pyrazinyl, pyrimidyl, pyridazinyl, 1,2,4-triazinyl, 1,3,5-triazinyl, indolyl, benzofuranyl, benzothienyl, quinolinyl, isoquinolinyl, quinazalinyl and the like. More particularly, they are for example phenyl, naphthyl, 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 3-isothiazolyl, 4-isothiazolyl, 5-isothiazolyl, 1,3,4-triazol-1-yl, 1,3,4-triazol-2-yl, 1,3,4-triazol-3-yl, 1,2,3-triazol-1-yl, 1,2,3-triazol-2-yl, 1,2,3-triazol-4-yl, 1,2,5-oxadiazol-3-yl, 1,2,3-oxadiazol-4-yl, 1,2,3-oxadiazol-5-yl, 1,3,4-oxadiazol-2-yl, 1,2,5-thiadiazol-3-yl, 1,2,3-thiadiazol-4-yl, 1,2,3-thiadiazol-5-yl, 1,3,4-thiadiazol-2-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, 1,2,3,4-tetrazin-1-yl, 1,2,3,4-tetrazin-2-yl, 1,2,3,4-tetrazin-5-yl, indolyl, benzofuranyl, benzothienyl, benzopyrazolyl, benzimidazolyl, benzoxazolyl, benzisoxazolyl, benzothiazolyl, benzisothiazolyl, quinolinyl, isoquinolinyl, quinazalinyl and other heteroaromatic bicyclic rings shown below in the "general definitions".

The aryl and heteroaryl groups $R^4$ or $R^5$ can carry one or more substituents, e.g. 1, 2, 3 or 4, in particular 1, 2 or 3, specifically 1 or 2 substituents. Suitable substituents are listed above in context with aryl and heteroaryl groups $R^1$ and $R^2$ in the Suzuki reaction. In a particular embodiment, the substituents on the aryl and heteroaryl groups $R^4$ or $R^5$ are selected from the group consisting of halogen, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, amino, $C_1$-$C_4$-alkylamino, di-($C_1$-$C_4$-alkyl)amino, phenyl, a 5- or 6-membered heteroaromatic monocyclic ring containing 1, 2, 3 or 4 heteroatoms selected from the group consisting of N, O and S as ring members and a 9- or 10-membered heteroaromatic bicyclic ring containing 1, 2, 3 or 4 heteroatoms selected from the group consisting of N, O and S as ring members, where phenyl and the heteroaromatic rings may carry one or more substituents selected from the group consisting of fluorine, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonylamino, $C_1$-$C_4$-alkylamino and di-($C_1$-$C_4$-alkyl)amino. Specifically, the substituents on the aryl and heteroaryl groups $R^4$ or $R^5$ are selected from the group consisting of halogen, cyano, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, amino, $C_1$-$C_4$-alkylamino and di-($C_1$-$C_4$-alkyl)amino.

The carbonyl compound and the phosphorous ylide can be used in a molar ratio of from 10:1 to 1:10, e.g. from 7:1 to 1:7 or from 5:1 to 1:5, preferably from 3:1 to 1:3 and in particular from 2:1 to 1:2, e.g. 1.5:1 to 1:1.5.

The reaction is preferably carried out at from 10° C. to 60° C., in particular from 20° C. to 55° C., specifically from 25° C. to 55° C. and very specifically from 40° C. to 50° C.

The reaction can be carried out by standard proceedings for Wittig reactions, e.g. by mixing all reagents, water and the cellulose derivative and reacting them at the desired temperature. Alternatively the reagents can be added gradually, especially in the case of a continuous or semicontinuous process.

Workup proceedings will be described below, as they are similar for most reactions.

Diels-Alder Reaction

In a particular embodiment, the C—C coupling reaction not requiring transition metal catalysis is a Diels-Alder reaction. The [4π+2π] cyclization of a conjugated diene with a dienophile, e.g. an alkene, to a cyclohexene derivative is called Diels-Alder cycloaddition or Diels-Alder reaction.

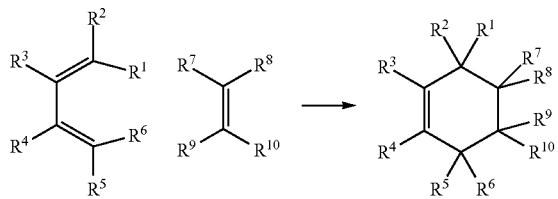

Besides alkenes (as shown in the above reaction scheme), alkynes, benzynes or allenes are also good dienophiles. The diene is usually electron rich and the dienophile is electron poor (this is called "normal electron-demand Diels-Alder reaction"). When the diene is electron poor and the dienophile electron rich, this is called "inverse electron-demand Diels-Alder reaction". If the ring formed contains, apart from carbon ring atoms, one or more heteroatoms as ring member(s), this variant is called "hetero-Diels-Alder reaction". Diels Alder reactions tolerate a wide variety of functional groups. Thus, $R^1$, $R^2$, $R^3$, $R^4$, $R^5$, $R^6$, $R^7$, $R^8$, $R^9$ and $R^{10}$ are independently hydrogen, alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl or heteroaryl, or are one of the substituents listed in context with the Suzuki as suitable radicals on alkyl, alkenyl, alkapolyenyl, alkynyl, alkapolyynyl or mixed alkenyl/alkynyl groups (however except for oxo (=O), =S and =$NR^{12a}$). More precisely, $R^1$, $R^2$, $R^3$, $R^4$, $R^5$, $R^6$, $R^7$, $R^8$, $R^9$ and $R^{10}$, independently of each other, are hydrogen, alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl, or heteroaryl, halogen, cyano, nitro, azido, —SCN, —$SF_5$, $OR^{11}$, $S(O)_mR^{11}$, $NR^{12a}R^{12b}$, C(=O)$R^{13}$, C(=S)$R^{13}$, C(=$NR^{12a}$)$R^{13}$ or —Si($R^{14}$)$_3$; where $R^{11}$, $R^{12a}$, $R^{12b}$, $R^{13}$, $R^{14}$ and $R^{15}$ are independently as defined above in context with the Suzuki reaction.

The alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl, heteroaryl groups can in turn be substituted by one or more substituents. Suitable substituents for alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl and heteroaryl correspond to those listed above in context with substituents on the alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling. Suitable substituents for heterocyclyl groups correspond to those listed above in context with substituents on the cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling. Alternatively, $R^2$ and $R^3$ and/or $R^3$ and $R^4$ and/or $R^4$ and $R^5$ and/or $R^1$ and $R^6$ and/or $R^7$ and $R^9$ can form a mono-, bi- or polycyclic carbocyclic or heterocyclic ring. This ring(s) may in turn be substituted by one or more substituents. Suitable substituents correspond to those listed above in context with substituents on the aryl or heteroaryl groups $R^1$ and $R^2$ in the Suzuki coupling.

$R^1$, $R^2$, $R^3$, $R^4$, $R^5$, $R^6$, $R^7$, $R^8$, $R^9$ and $R^{10}$ are suitably chosen in such a way that the diene is electron rich and the dienophile is electron poor or inversely the diene is electron poor and the dienophile is electron rich. Groups which enhance the electron density on the double bond are for example alkyl groups, cycloalkyl groups, electron-rich heterocyclic rings, ether groups, amino groups, (di)alkyl amino groups. The alkyl, cycloalkyl or heterocyclic groups as well as the carbon atoms in the ether or (di)alkyl amino groups may be substituted as described above, as the electronic influence of optional substituents decreases drastically with the distance to the double bond of the diene or dienophile. Electron-withdrawing groups are for example carbonyl groups (be it in the form of formyl, keto, carbamoyl, carboxyl or ester groups), sulfonyl groups, CN, the nitro group or halogen atoms. Carbon and nitrogen atoms in these groups (i.e. in keto, amido, ester or sulfonyl groups) may be substituted as described above, as the electronic influence of optional substituents decreases drastically with the distance to the double bond of the diene or dienophile.

In a particular embodiment of the present invention, an electron-rich diene and an electron-poor alkene are reacted. Specifically, $R^1$, $R^3$, $R^4$, $R^6$, $R^7$ and $R^9$ are H, $R^7$ and $R^9$ are either both alkyl or one or $R^7$ and $R^9$ is H and the other is alkyl, where alkyl can carry a substituent, where suitable substituents correspond to those listed above in context with substituents on the alkyl groups $R^1$ and $R^2$ in the Suzuki coupling, and is specifically a $OR^{11}$ group; and $R^8$ and $R^{10}$ are either both C(O)$R^{13}$ or one of $R^8$ and $R^{10}$ is H and the other is C(O)$R^{13}$, or $R^8$ and $R^{10}$ form together a bridging group —C(O)-A-C(O)—, where A is an alkylene bridge or O or $NR^{12a}$, where $R^{11}$, $R^{12a}$ and $R^{13}$ areas defined above in context with the Suzuki coupling. Very specifically, $R^8$ and $R^{10}$ form together a bridging group —C(O)—N($R^{12a}$)—C(O)—, where $R^{12a}$ is as defined in context with the Suzuki coupling, and is specifically $C_1$-$C_6$-alkyl. $R^{11}$ is very specifically a $C_1$-$C_6$-alkylcarbonyl group.

The diene and the dienophile can be used in a molar ratio of from 10:1 to 1:10, e.g. from 7:1 to 1:7 or from 5:1 to 1:5, preferably from 3:1 to 1:3 and in particular from 2:1 to 1:2, e.g. 1.5:1 to 1:1.5.

The reaction is preferably carried out at from 10° C. to 60° C., in particular from 20° C. to 55° C., specifically from 25° C. to 55° C. and very specifically from 40° C. to 50° C.

The reaction can be carried out by standard proceedings for Diels-Alder reactions, e.g. by mixing all reagents, water and the cellulose derivative and reacting them at the desired temperature. Alternatively the reagents can be added gradually, especially in the case of a continuous or semicontinuous process.

Workup proceedings will be described below, as they are similar for most reactions.

Baylis-Hillman Reaction

In a particular embodiment, the C—C coupling reaction not requiring transition metal catalysis is a Baylis-Hillman reaction. Classically, in this reaction type, a C—C single bond between the α-position of conjugated carbonyl compounds, e.g. esters or amides, and carbon electrophiles, e.g. aldehydes or activated ketones, in the presence of a suitable nucleophilic catalyst is formed:

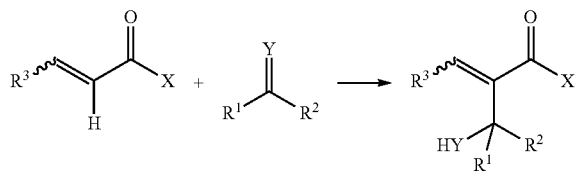

$R^1$, $R^2$ and $R^3$ are independently H, alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl or heteroaryl, or $R^1$ and $R^2$ form together with the carbon atom they are bound to a carbocyclic or heterocyclic ring; X is OR or $N(R)_2$, where R is for example H, alkyl, cycloalkyl, heterocyclyl, aryl or heteroaryl, and Y is O or N substituted with an electron-withdrawing group, such as an arylsulfonyl or an alkoxycarbonyl group. The alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl, heteroaryl groups, as well as the carbocyclic or heterocyclic ring formed by $R^1$ and $R^2$ together with the carbon atom they are bound to, can be substituted by one or more substituents. Suitable substituents for alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl and heteroaryl correspond to those listed above in context with substituents on the alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling. Suitable substituents for heterocyclyl groups and for the carbocyclic or heterocyclic ring formed by $R^1$ and $R^2$ together with the carbon atom they are bound to correspond to those listed above in context with substituents on the cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling.

In these substituents, however, all functional groups have to be less reactive than the desired reaction sites for the desired reaction.

In terms of the present invention, the Baylis-Hillman reaction also encompasses also the reaction of a conjugated nitrile compound with a carbon electrophile, e.g. an aldehydes or an activated ketone, in the presence of a suitable nucleophilic catalyst:

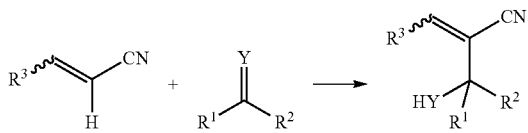

$R^1$, $R^2$, $R^3$ and Y are as defined above.

Nucleophilic catalysts are tertiary amines, e.g. trimethylamine, triethylamine, tripropylamine, diisopropylethylamine, tributylamine, morpholine, DABCO, DBU, DBN or quinuclidine; and tertiary phosphines, e.g. trialkylphosphines, like trimethyl, triethyl-, tripropyl- or tributylphosphine.

In some cases it is advantageous to carry out the reaction in the presence of metal-derived Lews acids, such as $AlCl_3$, $FeCl_3$, $TiCl_4$ and the like.

In a particular embodiment of the present invention, a conjugated nitrile compound, in which in the above scheme $R^3$ is H, alkyl, cycloalkyl, heterocyclyl, aryl or heteroaryl and is specifically H, is reacted with an aldehyde, i.e. in the above scheme Y is O, $R^2$ is H and R is H, alkyl, cycloalkyl, heterocyclyl, aryl or heteroaryl and is specifically aryl, where alkyl, cycloalkyl, heterocyclyl, aryl, heteroaryl groups can be substituted by one or more substituents. Suitable substituents for alkyl, cycloalkyl, aryl and heteroaryl correspond to those listed above in context with substituents on the alkyl, cycloalkyl, aryl or heteroaryl groups $R^1$ and $R^2$ in the Suzuki coupling. Suitable substituents for heterocyclyl groups correspond to those listed above in context with substituents on the cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling.

In these substituents, however, all functional groups have to be less reactive than the desired reaction sites for the desired reaction.

In a particular embodiment the aryl group $R^1$ is mono-, bi- or tricyclic and is specifically selected from the group consisting of phenyl and naphthyl.

The aryl group $R^1$ can carry one or more substituents, e.g. 1, 2, 3 or 4, in particular 1, 2 or 3, specifically 1 or 2 substituents. Suitable substituents are listed above in context with aryl groups $R^1$ and $R^2$ in the Suzuki reaction. In a particular embodiment, the substituents on the aryl group $R^1$ are selected from the group consisting of halogen, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino, di-($C_1$-$C_4$-alkyl)amino, phenyl, a 5- or 6-membered heteroaromatic monocyclic ring containing 1, 2, 3 or 4 heteroatoms selected from the group consisting of N, O and S as ring members and a 9- or 10-membered heteroaromatic bicyclic ring containing 1, 2, 3 or 4 heteroatoms selected from the group consisting of N, O and S as ring members, where phenyl and the heteroaromatic rings may carry one or more substituents selected from the group consisting of fluorine, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino. Specifically, the substituents on the aryl group $R^1$ are selected from the group consisting of halogen, cyano, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino.

The nucleophilic catalyst is in particular a tertiary amine, more particularly a cyclic amine, such as DABCO, DBU, DBN or quinuclidine, and is specifically DABCO.

The conjugated carbonyl or nitrile compound and the carbon electrophile can be used in a molar ratio of from 10:1 to 1:10, e.g. from 7:1 to 1:7 or from 5:1 to 1:5. Specifically, the carbon electrophile is used in excess, e.g. in a 10-fold or 7-fold or 5-fold or 2-fold excess.

The nucleophilic catalyst is generally used in catalytic amounts, i.e. in substoichiometric amounts with respect to that reactant not used in excess, e.g. in an amount of from 0.001 to 0.9 mol per mol of that reactant which is not used in excess, in particular 0.01 to 0.7 mol per mol of the reactant not used in excess, specifically 0.05 to 0.5 mol per mol of the reactant not used in excess. If the reactants are used in equimolar ratio, the above amounts of catalyst apply of course to either of the reactants.

The reaction is preferably carried out at from 10° C. to 60° C., in particular from 20° C. to 55° C., specifically from 20° C. to 50° C. and very specifically from 20° C. to 30° C.

The reaction can be carried out by standard proceedings for Baylis-Hillman reactions, e.g. by mixing all reagents, water and the cellulose derivative and reacting them at the desired temperature. Alternatively the reagents can be added gradually, especially in the case of a continuous or semi-continuous process.

Workup proceedings will be described below, as they are similar for most reactions.

Carboxamide or Sulfonamide Bond Formation not Requiring Transition Metal Catalysis In another particular embodiment of the invention, the organic reaction is a carboxamide or sulfonamide bond formation (not requiring transition metal catalysis).

Carboxamide Bond Formation

For the synthesis of carboxamides, generally a carboxylic acid or a derivative of a carboxylic acid capable of amide formation, for instance an acid halide, acid anhydride or ester, is reacted with a primary or secondary amine.

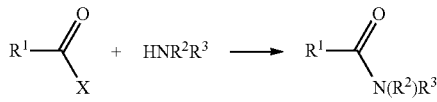

$R^1$, $R^2$ and $R^3$ are independently H, alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl or heteroaryl, or $R^2$ and $R^3$ form together with the nitrogen atom they are bound to a mono-, bi- or polycyclic heterocyclic ring; X is OH, $OR^4$, O—C(O)—$R^{1'}$ or a halogen atom, where $R^4$ is alkyl, alkenyl, alkynyl, cycloalkyl, heterocyclyl, aryl or heteroaryl and $R^{1'}$ is independently defined as $R^1$.

Alternatively, X is another common leaving group, for example thiophenyl or imidazolyl.

The alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl, heteroaryl groups, as well as the the mono- bi- or polycyclic heterocyclic ring formed by $R^2$ and $R^3$ together with the nitrogen atom they are bound to, can be substituted by one or more substituents. Suitable substituents for alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl and heteroaryl correspond to those listed above in context with substituents on the alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling. Suitable substituents for heterocyclyl groups and for the mono- bi- or polycyclic heterocyclic ring formed by $R^2$ and $R^3$ together with the nitrogen atom they are bound to correspond to those listed above in context with substituents on the cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling. If however these groups carry substituents which can compete in the reaction, e.g. further amino groups, it is expedient to protect these groups before the amidation reaction. For example, amino groups can be protected by standard N-protective groups, such as boc, benzyl, F-moc etc. Suitable protective groups are for example described in T. Greene and P. Wuts, Protective Groups in Organic Synthesis (3$^{rd}$ ed.), John Wiley & Sons, NY (1999). Alike, when these groups carry a COY substituent, where Y is as defined as X, Y has to be converted into a group which is less reactive than X versus the amine. For instance, if X is OH, Y has to be converted into an alkoxy group, such as methoxy or ethoxy.

Amidation can be carried out by reacting the carboxylic acid (X=OH) with the amine under heating and removal of reaction water, but is preferably carried out by activation of the carboxylic acid with, e.g. oxalylchloride [(COCl)$_2$] or thionylchloride (SOCl$_2$) to the respective acid chloride (X=Cl), followed by reaction with amine.

Alternatively, amidation is carried out with the carboxylic acid in the presence of a coupling reagent. Suitable coupling reagent (activators) are well known and are for instance selected from the group consisting of carbodiimides, such as EDCI (1-ethyl-3-(3-dimethylaminopropyl)carbodiimide; also abbreviated as EDC), DCC (dicyclohexylcarbodiimide) and DIC (diisopropylcarbodiimide), benzotriazole derivatives, such as HOBt (1-hydroxybenzotriazole), HATU (O-(7-azabenzotriazol-1-yl)-N,N,N',N'-tetramethyluronium hexafluorophosphate), HBTU ((O-benzotriazol-1-yl)-N,N,N',N'-tetramethyluronium hexafluorophosphate) and HCTU (1H-benzotriazolium-1-[bis(dimethylamino)methylene]-5-chloro tetrafluoroborate), phosphonium-derived activators, such as BOP ((benzotriazol-1-yloxy)-tris(dimethylamino) phosphonium hexafluorophosphate), Py-BOP ((benzotriazol-1-yloxy)-tripyrrolidinphosphonium hexafluorophosphate) and Py-BrOP (bromotripyrrolidinphosphonium hexafluorophosphate), and others, such as COMU ((1-cyano-2-ethoxy-2-oxoethylidenaminooxy)dimethylamino-morpholino-carbenium-hexafluorophosphat). The above activators can also be used in combination with each other. Generally, the activator is used in at least equimolar amounts, with respect to that reactant not used in excess. The benzotriazole and phosphonium coupling reagents are generally used in a basic medium.

Suitable esters $R^1$—COOR$^4$ derive expediently from $C_1$-$C_4$-alkanols $R^4$OH in which $R^4$ is $C_1$-$C_4$-alkyl, such as methanol, ethanol, propanol, isopropanol, n-butanol, butan-2-ol, isobutanol and tert-butanol, preference being given to the methyl and ethyl esters ($R^4$=methyl or ethyl). Suitable esters may also derive from $C_2$-$C_6$-polyols such as glycol, glycerol, trimethylolpropane, erythritol, pentaerythritol and sorbitol, preference being given to the glyceryl ester. When polyol esters are used, it is possible to use mixed esters, i.e. esters with different $R^4$ radicals.

Alternatively, the ester $R^1$—COOR$^4$ is a so-called active ester, which is obtained in a formal sense by the reaction of the acid $R^1$—COOH with an active ester-forming alcohol, such as p-nitrophenol, N-hydroxybenzotriazole (HOBt), N-hydroxysuccinimide or OPfp (pentafluorophenol).

The acid anhydride $R^1$—CO—O—OC—$R^{1'}$ is either a symmetric anhydride $R^1$—CO—O—OC—$R^1$ ($R^{1'}$=$R^1$) or an asymmetric anhydride in which —O—OC—$R^{1'}$ is a group which can be displaced easily by the amine HN($R^2$)$R^3$. Suitable acid derivatives with which the carboxylic acid $R^1$—COOH can form suitable mixed anhydrides are, for example, the esters of chloroformic acid, for example isopropyl chloroformate and isobutyl chloroformate, or of chloroacetic acid.

If X is a halogen atom, the reaction is generally carried out in the presence of a base. Suitable bases are those listed above in context with the Suzuki reaction.

In a particular embodiment of the present invention, a carboxylic acid (X=OH) is reacted with a primary or secondary amine in the presence of one or two coupling reagents, specifically of EDCI, HOBt or COMU or a combination thereof.

In a particular embodiment, $R^1$ is alkyl or aryl, where the alkyl or aryl group may be substituted as described above. Specifically, $R^1$ is $C_1$-$C_{10}$-alkyl which may carry a phenyl ring, which may in turn be substituted as described above and in particular by one or more $R^{15}$, or may carry a group C(O)$R^{13}$ or N($R^{12a}$)$R^{12b}$, where $R^{12a}$, $R^{12b}$, $R^{13}$ and $R^{15}$ are as defined in context with the Suzuki reaction; or $R^1$ is phenyl which may be substituted as described above and in particular by one or more $R^{15}$. Specifically $R^{13}$ is $C_1$-$C_4$-alkyl. Specifically $R^{12a}$ and $R^{12b}$ are H, but one of them is replaced by a protective group, such as boc, benzyl or F-moc.

In a particular embodiment, $R^2$ is H and $R^3$ is alky or aryl, where the alkyl or aryl group may be substituted as described above, or $R^2$ and $R^3$ form together with the nitrogen atom they are bound to a mono-, bi- or polycyclic ring, such as piperidine-1-yl, 1-alkyl-piperazin-4-yl, morpholinyl, pyrrolidin-1-yl, pyrrolin-1-yl, pyrrol-1-yl, indolin-1-yl, indol-1-yl etc. Specifically, $R^3$ is $C_1$-$C_{10}$-alkyl which may carry a phenyl ring, which may in turn be substituted as described above and in particular by one or more $R^{15}$, or is C(O)$R^{13}$, or is N($R^{12a}$)$R^{12b}$, where $R^{12a}$, $R^{12b}$, $R^{13}$ and $R^{15}$ are as defined in context with the Suzuki reaction. Specifically $R^{13}$ is $C_1$-$C_6$-alkyl. Specifically $R^{12a}$ and $R^{12b}$ are both $C_1$-$C_{10}$-alkyl or are both H, where however one of the hydrogen atoms is replaced by a protective group, such as boc, benzyl or F-moc.

The acid (derivative) and the amine can be used in a molar ratio of from 10:1 to 1:10, e.g. from 7:1 to 1:7 or from 5:1 to 1:5. In particular, they are used in a molar ratio of from 3:1 to 1:3, more particularly 2:1 to 1:2 and specifically from 1.5:1 to 1:1.5.

If the amidation is carried out in the presence of a coupling agent, this is generally used in at least equimolar amounts, with respect to that reactant not used in excess, e.g. in an amount of from 1 to 5 mol per mol of the reactant not used in excess, in particular 1 to 4 mol per mol of the reactant not used in excess, specifically 1.1 to 3 mol per mol of the reactant not used in excess. If the reactants are used in equimolar ratio, the above amounts of catalyst apply of course to either of the reactants.

The reaction is preferably carried out at from 10° C. to 60° C., in particular from 20° C. to 55° C.

The reaction can be carried out by standard proceedings for carboxamide formation, e.g. by mixing all reagents, water and the cellulose derivative and reacting them at the desired temperature. Alternatively the reagents can be added gradually, especially in the case of a continuous or semi-continuous process.

Workup proceedings will be described below, as they are similar for most reactions.

Sulfonamide Bond Formation

For the synthesis of sulfonamides, generally a sulfonic acid or a derivative of a sulfonic acid capable of amide formation, for instance a sulfonic acid halide, anhydride or ester, is reacted with a primary or secondary amine:

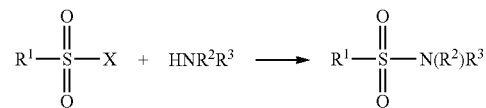

$R^1$, $R^2$, $R^3$ and X are as defined above in context with the carboxamide bond formation, except for $R^1$ here not being H and except of X being in the anhydride alternative O—S(O)$_2$—$R^{1'}$ instead of O—C(O)—$R^{1'}$. The above remarks on how to carry out the reaction, especially the various methods depending on X, apply here, too.

In a particular embodiment of the present invention, a sulfonic acid halide (X=halogen), especially a sulfonic acid chloride (X=Cl), is reacted with a primary or secondary amine in the presence of a base. Suitable bases are those listed above in context with the Suzuki reaction. In particular the base is an alkali metal hydroxide, e.g. LiOH, NaOH or KOH, an alkali metal carbonate, e.g. $Li_2CO_3$, $Na_2CO_3$, $K_2CO_3$ or $Cs_2CO_3$, or a silanolate, e.g. sodium or potassium trimethylsilanolate (($CH_3$)$_3$SiO$^-$) or triisopropylsilanolate (($CH(CH_3)_2$)$_3$SiO$^-$).

In a particular embodiment, $R^1$ is alky or aryl, where the alkyl or aryl group may be substituted as described above. Specifically, $R^1$ is phenyl which may be substituted as described above and in particular by one or more $R^{15}$, where $R^{15}$ is as defined in context with the Suzuki reaction.

In a particular embodiment, $R^2$ is H and $R^3$ is alky or aryl, where the alkyl or aryl group may be substituted as described above, or $R^2$ and $R^3$ form together with the nitrogen atom they are bound to a mono-, bi- or polycyclic ring, such as piperidine-1-yl, 1-alkyl-piperazin-4-yl, morpholinyl, pyrrolidin-1-yl, pyrrolin-1-yl, pyrrol-1-yl, indolin-1-yl, indol-1-yl etc. Specifically, $R^3$ is $C_1$-$C_{10}$-alkyl which may carry a phenyl ring, which may in turn be substituted as described above and in particular by one or more $R^{15}$, or is C(O)$R^{13}$, or is N($R^{12a}$)$R^{12b}$, where $R^{12a}$, $R^{12b}$, $R^{13}$ and $R^{15}$ are as defined in context with the Suzuki reaction; or, specifically, $R^2$ and $R^3$ form together with the nitrogen atom they are bound to a mono-, bi- or polycyclic ring, such as piperidine-1-yl, 1-alkyl-piperazin-4-yl, morpholinyl, pyrrolidin-1-yl, pyrrolin-1-yl, pyrrol-1-yl, indolin-1-yl, indol-1-yl etc. Specifically $R^{13}$ is $C_1$-$C_4$-alkyl. Specifically $R^{12a}$ and $R^{12b}$ are both $C_1$-$C_{10}$-alkyl or are both H, where however one of the hydrogen atoms is replaced by a protective group, such as boc, benzyl or F-moc.

The acid (derivative) and the amine can be used in a molar ratio of from 10:1 to 1:10, e.g. from 7:1 to 1:7 or from 5:1 to 1:5. In particular, they are used in a molar ratio of from 3:1 to 1:3, more particularly 2:1 to 1:2 and specifically from 1.5:1 to 1:1.5.

If the amidation is carried out in the presence of a base, this is generally used in excess, i.e. in overstoichiometric amounts with respect to that reactant not used in excess, e.g. in an amount of from 1.5 to 5 mol per mol of the reactant not used in excess, in particular 1.5 to 4 mol per mol of the reactant not used in excess, specifically 1.5 to 3 mol per mol of the reactant not used in excess. If the reactants are used in equimolar ratio, the above amounts of base apply of course to either of the reactants.

The reaction is preferably carried out at from 10° C. to 60° C., in particular from 20° C. to 55° C., specifically from 20° C. to 50° C. and very specifically from 20° C. to 30° C.

The reaction can be carried out by standard proceedings for sulfonamide formation, e.g. by mixing all reagents, water and the cellulose derivative and reacting them at the desired temperature. Alternatively the reagents can be added gradually, especially in the case of a continuous or semicontinuous process.

Workup proceedings will be described below, as they are similar for most reactions.

In another particular embodiment of the invention, the organic reaction is the introduction of a protective group.

Introduction of Protective Groups

In certain reactions, some functional groups, such as NH, $NH_2$, OH, SH or COOH, have to be protected in order to avoid their (competitive) reaction.

Protection of Primary or Secondary Amino Groups

Protective groups for amino groups are well known. Examples are $C_1$-$C_4$-alkylcarbonyl (e.g. acetyl, tert-butylcarbonyl), $C_1$-$C_4$-haloalkylcarbonyl (e.g. trifluoroacetyl), $C_3$-$C_4$-alkenylcarbonyl (e.g. allylcarbonyl), $C_1$-$C_4$-alkoxycarbonyl (e.g. tert-butyloxycarbonyl=Boc), $C_1$-$C_4$-haloalkoxycarbonyl, $C_3$-$C_4$-alkenyloxycarbonyl (e.g. allyloxycarbonyl=Alloc), fluorenylmethoxycarbonyl (Fmoc), benzyloxycarbonyl (Z or Cbz), $C_1$-$C_4$-alkylaminocarbonyl, di-($C_1$-$C_4$-alkyl)-aminocarbonyl, $C_1$-$C_4$-alkylsulfonyl, $C_1$-$C_4$-haloalkylsulfonyl, benzyl or substituted benzyl (e.g. p-methoxybenzyl (=Mpm) or 2,3-dimethoxybenzyl). Suitable protective groups are for example described in T. Greene and P. Wuts, Protective Groups in Organic Synthesis ($3^{rd}$ ed.), John Wiley & Sons, NY (1999). The (oxy)carbonyl and sulfonyl groups can be principally introduced in accordance with the above-described amidation reactions, especially via reaction of the amine with the respective (oxy)carboxylic chloride, (active) ester or anhydride or with the respective sulfonyl chloride, (Oxy)Carbonyl can moreover be introduced via reaction with the respective succinimidoester. The anhydride is generally a symmetric anhydride. With respect to the terms "active ester" and "symmetric anhydride", reference is made to the above-described amidation reactions. The reagents used for introducing the protective group, such as boc anhydride for introducing boc, are termed in the following "protective group precursors". (Oxy)carbonyl means carbonyl or oxycarbonyl.

Suitable (oxy)carbonylation/sulfonylation reagents (i.e. protective group precursors for introducing (oxy)carbonyl and sulfonyl protective groups) are well known. For example, boc is generally introduced via reaction with boc anhydride. Z is generally also introduced via the respective anhydride. Alkyl carbonyl groups are also often introduced via reaction with the symmetric anhydride, e.g. with acetanhydride or 2,2-dimethylacetanhydride. Benzyl or substituted benzyl is generally introduced via reaction of the amine with (substituted) benzyl chloride or bromide.

If the carbonylation/sulfonylation reagent is an acid chloride or an anhydride, the protection reaction is generally carried out in the presence of a base. Suitable bases are those listed in context with the Suzuki reaction.

In a particular embodiment, a primary or secondary amine $R^1(R^2)NH$ is reacted with an alkylcarbonyl (e.g. acetyl), $C_1$-$C_4$-haloalkylcarbonyl (e.g. trifluoroacetyl), $C_3$-$C_4$-alkenylcarbonyl (e.g. allylcarbonyl), $C_1$-$C_4$-alkoxycarbonyl (e.g. tert-butyloxycarbonyl=Boc), $C_1$-$C_4$-haloalkoxycarbonyl, $C_3$-$C_4$-alkenyloxycarbonyl (e.g. allyloxycarbonyl=Alloc), fluorenylmethoxycarbonyl (Fmoc) or benzyloxycarbonyl (Z or Cbz) chloride, anhydride or succinimidoester. The anhydride is generally a symmetric anhydride. As said, if a chloride or an anhydride is used, the reaction is generally carried out in the presence of a base.

Specifically, a primary or secondary amine $R^1(R^2)NH$ is reacted with boc anhydride.

In another specific embodiment, a primary or secondary amine $R^1(R^2)NH$ is reacted with Z anhydride (dibenzyl dicarbonate).

In another specific embodiment, a primary or secondary amine $R^1(R^2)NH$ is reacted with acetic anhydride.

$R^1$ and $R^2$, independently of each other, are alkyl, alkenyl, alkapolyenyl, alkynyl, alkapolyynyl, mixed alkenyl/alkynyl, cycloalkyl, cycloalkenyl, cycloalkynyl, mixed cycloalkenyl-cycloalkynyl, polycarbocyclyl, heterocyclyl, aryl or heteroaryl, where $R^1$ may additionally be hydrogen; or $R^1$ and $R^2$, together with the nitrogen atom they are bound to, form a mono-, bi- or polycyclic heterocyclic ring, which, apart from the compulsory nitrogen atom, may contain 1, 2 or 3 or 4 further heteroatoms or heteroatom groups selected from the group consisting of N, O, S, NO, SO or $SO_2$ as ring members.

The alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl, heteroaryl groups $R^1$ and $R^2$, as well as the mono-, bi- or polycyclic heterocyclic ring formed by $R^1$ and $R^2$ together with the nitrogen atom they are bound to, can be substituted by one or more substituents. Suitable substituents for the alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl and heteroaryl groups $R^1$ and $R^2$ correspond to those listed above in context with substituents on the alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling. Suitable substituents for heterocyclyl groups $R^1$ and $R^2$ and for the the mono-, bi- or polycyclic heterocyclic ring formed by $R^1$ and $R^2$ together with the nitrogen atom they are bound to correspond to those listed above in context with substituents on the cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling.

In these substituents, however, all functional groups have to be less reactive than the desired reaction site towards the specific protective group precursor.

In a specific embodiment, $R^1$ is hydrogen and $R^2$ is an alkyl, alkenyl, alkynyl, cycloalkyl, polycarbocyclyl, heterocyclyl, aryl or heteroaryl group, where the alkyl, alkenyl, alkynyl, cycloalkyl, polycarbocyclyl, heterocyclyl, aryl or heteroaryl group may carry one or more substituents, where suitable substituents correspond to those listed above in context with substituents on the alkyl, alkenyl, alkynyl, cycloalkyl, polycarbocyclyl, heterocyclyl, aryl and heteroaryl groups $R^1$ and $R^2$ in the Suzuki coupling (suitable substituents for heterocyclyl groups correspond to those listed above in context with substituents on the cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling).

More specifically, $R^1$ is hydrogen and $R^2$ is heterocyclyl, in particular a 3-, 4-, 5-, 6-, 7-, 8-, 9-, 10- or 11-membered monocyclic or bicyclic saturated, partially unsaturated or maximally unsaturated heterocyclic (inclusive heteroaromatic) ring which may carry one or more substituents as defined above. In particular, the heterocyclyl ring $R^2$ is a heteroaryl group. Heteroaryl groups $R^2$ are in particular selected from the group consisting of 5- or 6-membered heteroaromatic monocyclic rings and 9- or 10-membered heteroaromatic bicyclic rings containing 1, 2, 3 or 4 heteroatoms selected from the group consisting of N, O and S as ring members. Mono- or bicyclic heteroaryl groups $R^2$ are for example furanyl, thienyl, pyrrolyl, pyrazolyl, imidazolyl, oxazoyl, isoxazoyl, thiazoyl, isothiazolyl, [1,2,3]triazolyl, [1,2,4]triazolyl, [1,3,4]triazolyl, the oxadiazolyls, the thiadiazolyls, the tetrazolyls, pyridyl, pyrazinyl, pyrimidyl, pyridazinyl, 1,2,4-triazinyl, 1,3,5-triazinyl, indolyl, benzofuranyl, benzothienyl, quinolinyl, isoquinolinyl, quinazalinyl and the like. More particularly, they are for example phenyl, naphthyl, 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 3-isothiazolyl, 4-isothiazolyl, 5-isothiazolyl, 1,3,4-triazol-1-yl, 1,3,4-triazol-2-yl, 1,3,4-triazol-3-yl, 1,2,3-triazol-1-yl, 1,2,3-triazol-2-yl, 1,2,3-triazol-4-yl, 1,2,5-oxadiazol-3-yl, 1,2,3-oxadiazol-4-yl, 1,2,3-oxadiazol-5-yl, 1,3,4-oxadiazol-2-yl, 1,2,5-thiadiazol-3-yl, 1,2,3-thiadiazol-4-yl, 1,2,3-thiadiazol-5-yl, 1,3,4-thiadiazol-2-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyrimidinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, 1,2,3,4-tetrazin-1-yl, 1,2,3,4-tetrazin-2-yl, 1,2,3,4-tetrazin-5-yl, indolyl, benzofuranyl, benzothienyl, benzopyrazolyl, benzimidazolyl, benzoxazolyl, benzisoxazolyl, benzothiazolyl, benzisothiazolyl, quinolinyl, isoquinolinyl, quinazalinyl and other heteroaromatic bicyclic rings shown below in the "general definitions".

Suitable substituents on the heterocyclyl ring $R^2$ are e.g. selected from the group consisting of halogen, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino, di-($C_1$-$C_4$-alkyl)amino, phenyl, a 5- or 6-membered heteroaromatic monocyclic ring containing 1, 2, 3 or 4 heteroatoms selected from the group consisting of N, O and S as ring members and a 9- or 10-membered heteroaromatic bicyclic ring containing 1, 2, 3 or 4 heteroatoms selected from the group consisting of N, O and S as ring members, where phenyl and the heteroaromatic rings may carry one or more substituents selected from the group consisting of fluorine, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino. Specifically, the substituents on the heterocyclyl ring $R^2$ are selected from the group consisting of halogen, cyano, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino. In case of amino and $C_1$-$C_4$-alkylamino substituents, these may also react with the protective agent.

In another specific embodiment, $R^1$ is hydrogen and $R^2$ is aryl, specifically phenyl, which may carry one or more substituents as defined above. Suitable substituents on the aryl group $R^2$ are e.g. selected from the group consisting of halogen, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkyl substituted by a radical selected from the group consisting of CN, OH, SH, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino, di-($C_1$-$C_4$-alkyl)amino, phenyl, a 5- or 6-membered heteroaromatic monocyclic ring containing 1, 2, 3 or 4 heteroatoms selected from the group consisting of N, O and S as ring members and a 9- or 10-membered heteroaromatic bicyclic ring containing 1, 2, 3 or 4 heteroatoms selected from the group consisting of N, O and S as ring members, where phenyl and the heteroaromatic rings may carry one or more substituents selected from the group consisting of fluorine, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino; $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino, di-($C_1$-$C_4$-alkyl)amino, phenyl, a 5- or 6-membered heteroaromatic monocyclic ring containing 1, 2, 3 or 4 heteroatoms selected from the group consisting of N, O and S as ring members and a 9- or 10-membered heteroaromatic bicyclic ring containing 1, 2, 3 or 4 heteroatoms selected from the group consisting of N, O and S as ring members, where phenyl and the heteroaromatic rings may carry one or more substituents selected from the group consisting of fluorine, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino. Specifically, the substituents on the aryl group $R^2$ are selected from the group consisting of halogen, cyano, $C_1$-$C_6$-alkyl, $C_1$-$C_6$-haloalkyl, $C_1$-$C_4$-alkyl substituted by a radical selected from the group consisting of CN, OH, $C_1$-$C_6$-alkylsulfonyl, $C_1$-$C_6$-haloalkylsulfonyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino, di-($C_1$-$C_4$-alkyl)amino and phenyl; $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino, di-($C_1$-$C_4$-alkyl)amino, phenyl, a 5- or 6-membered heteroaromatic monocyclic ring containing 1, 2, 3 or 4 heteroatoms selected from the group consisting of N, O and S as ring members and a 9- or 10-membered heteroaromatic bicyclic ring containing 1, 2, 3 or 4 heteroatoms selected from the group consisting of N, O and S as ring members, where phenyl and the heteroaromatic rings may carry one or more substituents selected from the group consisting of fluorine, cyano, nitro, OH, SH, $C_1$-$C_6$-alkyl, $C_1$-$C_6$-haloalkyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino. Very specifically, the substituents on the aryl group $R^2$ are selected from the group consisting of halogen, cyano, $C_1$-$C_6$-alkyl, $C_1$-$C_6$-haloalkyl, $C_1$-$C_4$-alkyl substituted by a radical selected from the group consisting of CN, OH, $C_1$-$C_6$-alkylsulfonyl, $C_1$-$C_6$-haloalkylsulfonyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, and phenyl; $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, phenyl, a 5- or 6-membered heteroaromatic monocyclic ring containing 1, 2, 3 or 4 heteroatoms selected from the group consisting of N, O and S as ring members and a 9- or 10-membered heteroaromatic bicyclic ring containing 1, 2, 3 or 4 heteroatoms selected from the group consisting of N, O and S as ring members, where phenyl and the heteroaromatic rings may carry one or more substituents selected from the group consisting of fluorine, cyano, nitro, OH, SH, $C_1$-$C_6$-alkyl, $C_1$-$C_6$-haloalkyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_4$-alkylcarbonyl, $C_1$-$C_4$-haloalkylcarbonyl, $C_1$-$C_4$-alkoxycarbonyl and $C_1$-$C_4$-haloalkoxycarbonyl.

In another specific embodiment, $R^1$ is hydrogen and $R^2$ is polycarbocyclyl which may carry one or more substituents as defined above; preferably a 9- to 10-membered condensed saturated or partially unsaturated carbocyclic ring system, in particular selected from indanyl, tetrahydronaphthyl, hexahydronaphthyl, octahydronaphthyl and decahydronaphthyl, which may carry one or more substituents as defined above. In indanyl and tetrahydronaphthyl the attachment point to N is on the nonaromatic ring moiety. Suitable substituents on the polycarbocyclyl ring $R^2$ are e.g. selected from the group consisting of halogen, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkyl substituted by a radical selected from the group consisting of CN, OH, SH, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino, di-($C_1$-$C_4$-alkyl)amino, phenyl, a 5- or 6-membered heteroaromatic monocyclic ring containing 1, 2, 3 or 4 heteroatoms selected from the group consisting of N, O and S as ring members and a 9- or 10-membered heteroaromatic bicyclic ring containing 1, 2, 3 or 4 heteroatoms selected from the group consisting of N, O and S as ring members, where phenyl and the heteroaromatic rings may carry one or more substituents selected from the group consisting of fluorine, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkythio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino, di-($C_1$-$C_4$-alkyl)amino, phenyl, a 5- or 6-membered heteroaromatic monocyclic ring containing 1, 2, 3 or 4 heteroatoms selected from the group consisting of N, O and S as ring members and a 9- or 10-membered heteroaromatic bicyclic ring containing 1, 2, 3 or 4 heteroatoms selected from the group consisting of N, O and S as ring members, where phenyl and the heteroaromatic rings may carry one or more substituents selected from the group consisting of fluorine, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino.

In another specific embodiment, $R^1$ and $R^2$, together with the nitrogen atom they are bound to, form a mono-, bi- or polycyclic heterocyclic ring, which, apart from the compulsory nitrogen atom, may contain 1, 2 or 3 or 4 further heteroatoms or heteroatom groups selected from the group consisting of N, O, S, NO, SO or $SO_2$ as ring members. Very specifically, $R^1$ and $R^2$, together with the nitrogen atom they are bound to, form a mono- or bicyclic heterocyclic ring, specifically a 3-, 4-, 5-, 6-, 7-, 8-, 9-, 10- or 11-membered mono- or bicyclicsaturated, partially zunsaturated or maximally unsaturated heterocyclic ring, which, apart from the compulsory nitrogen atom, may contain 1 or 2 further heteroatoms or heteroatom groups selected from the group consisting of N, O, S, NO, SO or $SO_2$ as ring members.

The amine and the protective group precursor can be used in a molar ratio of from 10:1 to 1:10, e.g. from 7:1 to 1:7 or from 5:1 to 1:5. In particular, they are used in a molar ratio of from 3:1 to 1:3, more particularly 2:1 to 1:2 and specifically from 1.5:1 to 1:1.5.

If the reaction is carried out in the presence of a base, this is generally used in excess, i.e. in overstoichiometric amounts with respect to that reactant not used in excess, e.g. in an amount of from 1.1 to 5 mol per mol of the reactant not used in excess, in particular 1.1 to 4 mol per mol of the reactant not used in excess, specifically 1.1 to 3 mol per mol of the reactant not used in excess. If the reactants are used in equimolar ratio, the above amounts of base apply of course to either of the reactants.

The reaction is preferably carried out at from 10° C. to 60° C., in particular from 20° C. to 55° C., specifically from 20° C. to 50° C. and very specifically from 20° C. to 30° C.

The reaction can be carried out by standard proceedings for introducing the respective protective group, e.g. by mixing all reagents, water and the cellulose derivative and reacting them at the desired temperature. Alternatively the reagents can be added gradually, especially in the case of a continuous or semicontinuous process.

Workup proceedings will be described below, as they are similar for most reactions.

Deprotection Reaction

In another particular embodiment of the invention, the organic reaction is a deprotection reaction, i.e. the removal of a protective group. The specific deprotection conditions depend on the protective group to be removed and are known in the art. They are described, for example, in T. Greene and P. Wuts, Protective Groups in Organic Synthesis (3$^{rd}$ ed.), John Wiley & Sons, NY (1999).

Deprotection of Protected Primary or Secondary Amines

Suitable and preferred protective groups and suitable and preferred amines are described above. Conditions for deprotecting primary or secondary amines depend on the specific protective group and the susceptibility of the amine to undergo undesired reactions during deprotection. Generally they involve a hydrolysis or a hydrogenolysis. For instance, boc is removed via hydrolysis under acidic conditions using e.g. HCl, trifluoroacetic acid or toluenesulfonic acid. Other oxycarbonyl protective groups, such as Fmoc, can be removed via basic hydrolysis, e.g. with NaOH or an organic base, such as piperidine or pyridine. Cbz can be removed via hydrogenolysis, mostly catalyzed with Pd or Pt, or using $Na/NH_3$, or with trimethylsilyl iodide, or via reaction with strong acids, e.g. HBr/acetic acid. Alloc is generally removed metal-catalyzed with Ni or Pt. Carbonyl protective groups, e.g. acetyl, are removed via acidic or basic hydrolysis. Generally, this requires harsher conditions, such as heating to reflux. Benzyl is generally removed via hydrogenolysis, mostly catalyzed with Pd or Pt.

In another particular embodiment of the invention, the organic reaction is a nucleophilic substitution reaction.

Nucleophilic Substitution Reactions

Nucleophilic substitution is a fundamental class of reactions in which an electron-rich nucleophile selectively bonds with or attacks the positive or partially positive charge of an atom or a group of atoms to replace a leaving group; the positive or partially positive atom being termed electrophile: Nu: +R-LG→R-Nu+LG:

"Nu" is the nucleophile; ":" is an electron pair; "LG" is a leaving group and "R" is a hydrocarbyl radical, e.g. an aliphatic, cycloaliphatic, aromatic, hetercyclic or heteroaromatic radical.

The electron pair (:) from the nucleophile (Nu) attacks the substrate (R-LG) forming a new bond, while the leaving group (LG) departs with an electron pair. The principal product in this case is R-Nu. The nucleophile may be electrically neutral or negatively charged, whereas the substrate is typically neutral or positively charged.

Advantageously, the leaving group forms an anion of low energy or an uncharged molecule or can be removed by an energetically advantageous process. Therefore, the leaving group is frequently a halide, a sulfonate or a diazonium group.

Nucleophilic substitution reactions form one of the largest classes of organic reactions and are therefore often treated in subclasses depending on the functional group formed, on the product formed or on the substrate used. For instance, many carbonyl reactions are nucleophilic substitutions, e.g. ester bond formations, trans esterifications, hydrolyses, amide bond formation or carbonyl halide formation; ether and thioether bond formation, amine bond formation etc. The method of the invention can be applied to all types of nucleophilic substitutions, but given the vastness of this reaction type, only some representative examples are discussed in more detail.

One subclass of nucleophilic substitution is nucleophilic aromatic substitution. Thus, in particular embodiment of the invention, the organic reaction, to be more precise the nucleophilic substitution reaction, is a nucleophilic aromatic substitution reaction.

Nucleophilic Aromatic Substitution Reactions

Nucleophilic aromatic substitution is a substitution reaction in which a nucleophile displaces a good leaving group on an aromatic or a heteroaromatic ring. Due to the system of conjugated double bonds, aromatic compounds (especially carboaromatic compounds and electron-rich heteroaromatic compounds) are Lewis bases and thus the exchange of substituents by nucleophilic reagents is distinctly more difficult than electrophilic substitutions. It is essential that the leaving group forms an anion of low energy or an uncharged molecule or can be removed by an energetically advantageous process. Therefore, the leaving group is mostly a halide, a sulfonic acid group or a diazonium group in non-activated (hetero)aromatic compounds. Nucleophilic aromatic substitution on carboaromatic rings (phenyl, naphthyl etc.) is eased if the aromatic ring is activated, i.e. contains substituents with a -M effect in ortho and/or para position to the carbon atom carrying the leaving group. Substituents with a -M effect are for example the diazonium, nitroso, nitro, cyano, formyl, or acetyl group. In this case, also less favoured leaving groups can react; e.g. even hydrogen atoms can be replaced. Electron-poor heteroaromatic rings, like the 6-membered heteroaromatic compounds (pyridine, pyridazine, pyrimidine, pyrazine, the triazines) or quinoline, also undergo readily nucleophilic substitution, even with poor leaving groups, like the hydrogen atom.

Suitable nucleophiles are in particular Lewis bases, like water, alcohols, thiols or primary or secondary amines.

The reaction is often carried out in the presence of a base, especially if the leaving group is a halide and the nucleophile is water, an alcohol, a thiol or a primary or secondary amine.

In a particular embodiment of the present invention a mono-, bi- or polycyclic aromatic or heteroaromatic halide $R^1$—X is reacted with an alcohol $R^2$—OH, a thiol $R^2$—SH, a primary amine $R^3NH_2$ or a secondary amine $R^3(R^4)NH$. $R^1$ is a mono-, bi- or polycyclic aryl or heteroaryl group; X is a halide, especially F or Cl, and $R^2$, $R^3$ and $R^4$ are independently of each other an alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl or heteroaryl group. The alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl, heteroaryl groups $R^1$, $R^2$, $R^3$ and $R^4$ can be substituted by one or more substituents. Suitable substituents correspond to those listed above in context with substituents on the alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling. Suitable substituents for heterocyclyl groups $R^1$, $R^2$, $R^3$ and $R^4$ correspond to those listed above in context with substituents on the cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling.

In these substituents, however, all functional groups have to be less reactive than the desired reaction sites for the desired reaction (i.e. less reactive than X in $R^1$—X towards $R^2$—OH, $R^2$—SH, $R^3NH_2$ or $R^3(R^4)NH$; less reactive than OH, SH, $NH_2$ or NH in $R^2$—OH, $R^2$—SH, $R^3NH_2$ and $R^3(R^4)NH$, respectively, towards $R^1$—X).

In a particular embodiment the aryl group $R^1$ is mono-, bi- or tricyclic and is specifically selected from the group consisting of phenyl and naphthyl; and the heteroaryl group $R^1$ is in particular mono-, bi- or tricyclic and is specifically selected from the group consisting of 5- or 6-membered heteroaromatic monocyclic rings and 9- or 10-membered heteroaromatic bicyclic rings containing 1, 2, 3 or 4 heteroatoms selected from the group consisting of N, O and S as ring members. Mono- or bicyclic aryl or heteroaryl groups $R^1$ are for example phenyl, naphthyl, furanyl, thienyl, pyrrolyl, pyrazolyl, imidazolyl, oxazoyl, isoxazoyl, thiazoyl, isothiazolyl, [1,2,3]triazolyl, [1,2,4]triazolyl, [1,3,4]triazolyl, the oxadiazolyls, the thiadiazolyls, the tetrazolyls, pyridyl, pyrazinyl, pyrimidyl, pyridazinyl, 1,2,4-triazinyl, 1,3,5-triazinyl, indolyl, benzofuranyl, benzothienyl, quinolinyl, isoquinolinyl, quinazalinyl and the like. More particularly, they are for example phenyl, naphthyl, 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 3-isothiazolyl, 4-isothiazolyl, 5-isothiazolyl, 1,3,4-triazol-1-yl, 1,3,4-triazol-2-yl, 1,3,4-triazol-3-yl, 1,2,3-triazol-1-yl, 1,2,3-triazol-2-yl, 1,2,3-triazol-4-yl, 1,2,5-oxadiazol-3-yl, 1,2,3-oxadiazol-4-yl, 1,2,3-oxadiazol-5-yl, 1,3,4-oxadiazol-2-yl, 1,2,5-thiadiazol-3-yl, 1,2,3-thiadiazol-4-yl, 1,2,3-thiadiazol-5-yl, 1,3,4-thiadiazol-2-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, 1,2,3,4-tetrazin-1-yl, 1,2,3,4-tetrazin-2-yl, 1,2,3,4-tetrazin-5-yl, indolyl, benzofuranyl, benzothienyl, benzopyrazolyl, benzimidazolyl, benzoxazolyl, benzisoxazolyl, benzothiazolyl, benzisothiazolyl, quinolinyl, isoquinolinyl, quinazalinyl, chromanyl bound via the 5-, 6-, 7- or 8-position and other heteroaromatic bicyclic rings shown below in the "general definitions".

The aryl and heteroaryl groups $R^1$ can carry one or more substituents, e.g. 1, 2, 3 or 4, in particular 1, 2 or 3, specifically 1 or 2 substituents. Suitable substituents are listed above in context with aryl and heteroaryl groups $R^1$ and $R^2$ in the Suzuki reaction. In a particular embodiment, the substituents on the aryl and heteroaryl groups $R^1$ are selected from the group consisting of halogen, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_1$-$C_6$-haloalkynyl, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino, di-($C_1$-$C_4$-alkyl)amino, where the alkyl groups in alkylamino and dialkylamino can in turn be substituted by one or more substituents selected from the group consisting of CN, OH, SH, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino, di-($C_1$-$C_4$-alkyl)amino, phenyl, a 5- or 6-membered heteroaromatic monocyclic ring containing 1, 2, 3 or 4 heteroatoms selected from the group consisting of N, O and S as ring members and a 9- or 10-membered heteroaromatic bicyclic ring containing 1, 2, 3 or 4 heteroatoms selected from the group consisting of N, O and S as ring members, where phenyl and the heteroaromatic rings may carry one or more substituents selected from the group consisting of fluorine, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino; phenyl, a 5- or 6-membered heteroaromatic monocyclic ring containing 1, 2, 3 or 4 heteroatoms selected from the group consisting of N, O and S as ring members and a 9- or 10-membered heteroaromatic bicyclic ring containing 1, 2, 3 or 4 heteroatoms selected from the group consisting of N, O and S as ring members, where phenyl and the heteroaromatic rings may carry one or more substituents selected from the group consisting of halogen, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino. Specifically, the substituents on the aryl and heteroaryl groups $R^1$ are selected from the group consisting of halogen, cyano, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl and $C_1$-$C_4$-haloalkoxycarbonyl. Especially in the case of the carboaromatis, e.g. the above-listed phenyl, naphthyl, anthracenyl and phenanthrenyl groups, it is expedient for these to carry a substituent with -M effect in ortho- and/or para-position to X, e.g. a nitro group. Analogously, electron-rich heterocyclic rings, like the 5-membered heteroaromatic rings, especially pyrrole, carry advantageously a -M substituent.

Especially, the mono-, bi- or polycyclic aryl or heteroaryl groups $R^1$ are selected from the group consisting of phenyl carrying in ortho- and/or para-position to X a substituent with -M effect, specifically a nitro group, from the 6-membered heteroaromatic groups, i.e. from pyridyl, pyrazinyl, pyrimidyl, pyridazinyl, 1,2,4-triazinyl and 1,3,5-triazinyl, and from quinolinyl. Specifically, the mono-, bi- or polycyclic aryl or heteroaryl groups $R^1$ are selected from the group consisting of phenyl carrying in ortho- and/or para-position to X a substituent with -M effect, specifically a nitro group; pyridyl and pyrimidyl. The 6-membered heteroaromatic groups and quinolinyl may carry one or more substituents, e.g. those described above, for example those mentioned as $R^{15}$ in the Suzuki reaction.

In particular, $R^2$, $R^3$ and $R^4$ are independently of each other an alkyl or aryl group, where the alkyl group may carry an aryl group, where the aryl groups may carry one or more substituents, e.g. those described above, for example those mentioned as $R^{15}$ in the Suzuki reaction. Specifically, $R^2$ is an aryl group, in particular phenyl or naphthyl, which may carry one or more substituents, e.g. those described above, for example those mentioned as $R^{15}$ in the Suzuki reaction. Specifically, $R^4$ is hydrogen and $R^3$ is $C_1$-$C_4$-alkyl, where alkyl may carry one or more aryl substituents, specifically one phenyl substituent, where the aryl substituents may in turn carry one or more substituents, e.g. those described above, for example those mentioned as $R^{15}$ in the Suzuki reaction, specifically CN, $C_1$-$C_4$-alkyl, $C_1$-$C_4$-haloalkyl, $C_1$-$C_4$-alkoxy or $C_1$-$C_4$-alkoxy.

The reaction is often carried out in the presence of a base, especially if the leaving group is a halide and the nucleophile is water, an alcohol, a thiol or a primary or secondary amine. Suitable bases are those listed above in context with the Suzuki reaction.

The reaction is preferably carried out at from 10° C. to 60° C., in particular from 20° C. to 55° C., specifically from 20° C. to 50° C. and very specifically from 20° C. to 30° C.

The (hetero)aromatic compound to be substituted and the nucleophile can be used in a molar ratio of from 10:1 to 1:10, e.g. from 7:1 to 1:7 or from 5:1 to 1:5. Preferably they are used in a molar ratio of from 3:1 to 1:3, in particular 2:1 to 1:2 and specifically 1.5:1 to 1:1.5.

The base is generally used in at least equimolar amount, with respect to that reactant not used in excess, e.g. in an amount of from 1 to 5 mol per mol of the reactant not used in excess, in particular 1 to 3 mol per mol of the reactant not used in excess, specifically 1 to 2 mol per mol of the reactant not used in excess. If the reactants are used in equimolar ratio, the above amounts of base apply of course to either of the reactants.

The reaction can be carried out by standard proceedings for nucleophilic aromatic substitutions, e.g. by mixing all reagents, inclusive base, water and the cellulose derivative, and reacting them at the desired temperature. Alternatively the reagents can be added gradually, especially in the case of a continuous or semicontinuous process.

Workup proceedings will be described below, as they are similar for most reactions.

In another particular embodiment of the present invention a mono-, bi- or polycyclic aromatic or heteroaromatic alcohol $R^1$—OH, thiol $R^1$—SH, primary amine $R^1NH_2$ or a secondary amine $R^1(R^4)NH$ is reacted with a halide $R^2$—X, resulting in a ether $R^1$—O—$R^2$, thioether $R^1$—S—$R^2$, secondary amine $R^1$—N(H)—$R^2$ or tertiary amine $R^1$—N($R^4$)—$R^2$. $R^1$, $R^2$ and $R^4$ are as defined above. The reaction conditions are also as described above in context with the reaction of an aromatic or heteroaromatic halide $R^1$—X with an alcohol $R^2$—OH, thiol $R^2$—SH, primary amine $R^3NH_2$ or a secondary amine $R^3(R^4)NH$.

Another subclass of nucleophilic substitution is ether bond formation. Thus, in particular embodiment of the invention, the organic reaction, to be more precise the nucleophilic substitution reaction, is an etherification reaction.

Ether Bond Formation

In this reaction class, generally a hydroxyl compound $R^1$—OH is reacted with a compound $R^2$-LG, wherein LG is leaving group, such as a halide, a hydroxyl group, a sulfonate group or, especially in aromatic or heteroaromatic groups $R^2$, a diazonium group. $R^1$ and $R^2$ can be any aliphatic, cycloaliphatic, heterocyclic, aromatic or heteroaromatic group. If one of $R^1$ and $R^2$ or both are aromatic or heteroaromatic, reference is made to the above remarks made in context with nucleophilic aromatic substitution.

$R^1$ and $R^2$ are preferably independently alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl or heteroaryl. The alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl, heteroaryl groups can be substituted by one or more substituents. Suitable substituents for alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl and heteroaryl correspond to those listed above in context with substituents on the alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling. Suitable substituents for heterocyclyl groups correspond to those listed above in context with substituents on the cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling.

In these substituents, however, all functional groups have to be less reactive than the desired reaction sites for the desired reaction.

In a particular embodiment $R^1$ is aryl or hetaryl, where preferably, the aryl group $R^1$ is mono-, bi- or tricyclic and is specifically selected from the group consisting of phenyl and naphthyl; and the heteroaryl group $R^1$ is in particular mono-, bi- or tricyclic and is specifically selected from the group consisting of 5- or 6-membered heteroaromatic monocyclic rings and 9- or 10-membered heteroaromatic bicyclic rings containing 1, 2, 3 or 4 heteroatoms selected from the group consisting of N, O and S as ring members. Mono- or bicyclic aryl or heteroaryl groups $R^1$ are for example phenyl, naphthyl, furanyl, thienyl, pyrrolyl, pyrazolyl, imidazolyl, oxazoyl, isoxazoyl, thiazoyl, isothiazolyl, [1,2,3]triazolyl, [1,2,4]triazolyl, [1,3,4]triazolyl, the oxadiazolyls, the thiadiazolyls, the tetrazolyls, pyridyl, pyrazinyl, pyrimidyl, pyridazinyl, 1,2,4-triazinyl, 1,3,5-triazinyl, indolyl, benzofuranyl, benzothienyl, quinolinyl, isoquinolinyl, quinazalinyl and the like. More particularly, they are for example phenyl, naphthyl, 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 3-isothiazolyl, 4-isothiazolyl, 5-isothiazolyl, 1,3,4-triazol-1-yl, 1,3,4-triazol-2-yl, 1,3,4-triazol-3-yl, 1,2,3-triazol-1-yl, 1,2,3-triazol-2-yl, 1,2,3-triazol-4-yl, 1,2,5-oxadiazol-3-yl, 1,2,3-oxadiazol-4-yl, 1,2,3-oxadiazol-5-yl, 1,3,4-oxadiazol-2-yl, 1,2,5-thiadiazol-3-yl, 1,2,3-thiadiazol-4-yl, 1,2,3-thiadiazol-5-yl, 1,3,4-thiadiazol-2-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, 1,2,3,4-tetrazin-1-yl, 1,2,3,4-tetrazin-2-yl, 1,2,3,4-tetrazin-5-yl, indolyl, benzofuranyl, benzothienyl, benzopyrazolyl, benzimidazolyl, benzoxazolyl, benzisoxazolyl, benzothiazolyl, benzisothiazolyl, quinolinyl, isoquinolinyl, quinazalinyl, chromanyl bound via the 5-, 6-, 7- or 8-position and other heteroaromatic bicyclic rings shown below in the "general definitions". Specifically, $R^1$ is chromanyl bound via the 5-, 6-, 7- or 8-position.

The aryl and heteroaryl groups $R^1$ can carry one or more substituents, e.g. 1, 2, 3 or 4, in particular 1, 2 or 3, specifically 1 or 2 substituents. Suitable substituents are listed above in context with aryl and heteroaryl groups $R^1$ and $R^2$ in the Suzuki reaction. In a particular embodiment, the substituents on the aryl and heteroaryl groups $R^1$ are selected from the group consisting of halogen, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, (protected) amino, (protected) $C_1$-$C_4$-alkylamino, di-($C_1$-$C_4$-alkyl)amino, where the alkyl groups in alkylamino and dialkylamino can in turn be substituted by one or more substituents selected from the group consisting of CN, OH, SH, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino, di-($C_1$-$C_4$-alkyl)amino, phenyl, a 5- or 6-membered heteroaromatic monocyclic ring containing 1, 2, 3 or 4 heteroatoms selected from the group consisting of N, O and S as ring members and a 9- or 10-membered heteroaromatic bicyclic ring containing 1, 2, 3 or 4 heteroatoms selected from the group consisting of N, O and S as ring members, where phenyl and the heteroaromatic rings may carry one or more substituents selected from the group consisting of fluorine, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_1$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino;

phenyl, a 5- or 6-membered heteroaromatic monocyclic ring containing 1, 2, 3 or 4 heteroatoms selected from the group consisting of N, O and S as ring members and a 9- or 10-membered heteroaromatic bicyclic ring containing 1, 2, 3 or 4 heteroatoms selected from the group consisting of N, O and S as ring members, where phenyl and the heteroaromatic rings may carry one or more substituents selected from the group consisting of halogen, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, (protected) amino, (protected) $C_1$-$C_4$-alkylamino and di-($C_1$-$C_4$-alkyl)amino. Specifically, the substituents on the aryl and heteroaryl groups $R^1$ are selected from the group consisting of halogen, cyano, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkythio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, protected amino, (protected) $C_1$-$C_4$-alkylamino and di-($C_1$-$C_4$-alkyl)amino. Very specifically, the substituents on the aryl and heteroaryl groups $R^1$ are selected from the group consisting of protected amino, (protected) $C_1$-$C_4$-alkylamino and di-($C_1$-$C_4$-alkyl)amino.

In particular, $R^4$ is $C_1$-$C_4$-alkyl, where alkyl may carry one or more aryl substituents, specifically one phenyl substituent, where the aryl substituents may in turn carry one or more substituents, e.g. those described above, for example those mentioned as $R^{15}$ in the Suzuki reaction, specifically F, Cl, CN, $C_1$-$C_4$-alkyl, $C_1$-$C_4$-haloalkyl, $C_1$-$C_4$-alkoxy or $C_1$-$C_4$-alkoxy.

Another subclass of nucleophilic substitution is ester bond formation (esterification) and the reverse reaction (ester hydrolysis). Thus, in particular embodiment of the invention, the organic reaction, to be more precise the nucleophilic substitution reaction, is an esterification reaction or an ester hydrolysis.

Esterifications and Ester Hydrolysis

For the synthesis of carboxylic esters, generally a carboxylic acid or a derivative of a carboxylic acid capable of ester bond formation, for instance an acid halide or acid anhydride, is reacted with a hydroxyl compound:

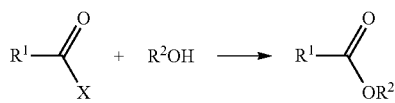

In an ester hydrolysis the inverse reaction takes place: An ester is reacted (formally) with water to the respective carboxylic acid:

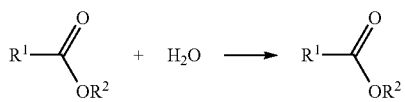

$R^1$ and $R^2$ are independently alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl or heteroaryl, where $R^1$ can also be H; X is OH, $OR^4$, O—C(O)—$R^{1'}$ or a halogen atom, where $R^4$ is alkyl, alkenyl, alkynyl, cycloalkyl, heterocyclyl, aryl or heteroaryl and $R^{1'}$ is independently defined as $R^1$. Alternatively, X is another common leaving group, for example thiophenyl or imidazolyl.

The alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl, heteroaryl groups can be substituted by one or more substituents. Suitable substituents for alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl and heteroaryl correspond to those listed above in context with substituents on the alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling. Suitable substituents for heterocyclyl groups correspond to those listed above in context with substituents on the cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling. If however these groups carry substituents which can compete in the esterification reaction, e.g. further OH groups, it is expedient to protect these groups before the esterification reaction. For example, OH groups can be protected by standard O-protective groups, such as silyl groups. Suitable protective groups are for example described in T. Greene and P. Wuts, Protective Groups in Organic Synthesis ($3^{rd}$ ed.), John Wiley & Sons, NY (1999). Alike, when these groups carry a COY substituent, where Y is as defined as X, Y has to be converted into a group which is less reactive than X versus the hydroxy compound in the esterification reaction or versus water in the hydrolysis. For instance, if X is OH, Y has to be converted into an alkoxy group, such as methoxy or ethoxy.

Esterification can be carried out by reacting the carboxylic acid (X=OH) with the hydroxy compound under heating and removal of reaction water, but is preferably carried out by activation of the carboxylic acid with, e.g. oxalylchloride [$(COCl)_2$] or thionylchloride ($SOCl_2$) to the respective acid chloride (X=Cl), followed by reaction with the hydroxy compound.

Alternatively, the ester $R^1$—$COOR^4$ is a so-called active ester, which is obtained in a formal sense by the reaction of the acid $R^1$—COOH with an active ester-forming alcohol, such as p-nitrophenol, N-hydroxybenzotriazole (HOBt), N-hydroxysuccinimide or OPfp (pentafluorophenol).

The acid anhydride $R^1$—CO—O—OC—$R^{1'}$ is either a symmetric anhydride $R^1$—CO—O—OC—$R^1$ ($R^{1'}$=$R^1$) or an asymmetric anhydride in which —O—OC—$R^{1'}$ is a group which can be displaced easily by the hydroxy compound. Suitable acid derivatives with which the carboxylic acid $R^1$—COOH can form suitable mixed anhydrides are, for example, the esters of chloroformic acid, for example isopropyl chloroformate and isobutyl chloroformate, or of chloroacetic acid.

If X is a halogen atom, the reaction is generally carried out in the presence of a base. Suitable bases are those listed above in context with the Suzuki reaction.

In ester hydrolysis, generally a base is used and elevated temperature is applied, e.g. from 30 to 70° C. or from 40 to 60° C. or from 45 to 60° C. Suitable bases are those listed above in context with the Suzuki reaction, especially the inorganic bases, specifically alkali metal hydroxides, such as NaOH or KOH.

In a particular embodiment, $R^1$ is heterocyclyl which may be substituted as described above. Specifically, $R^1$ is a saturated 3-, 4-, 5-, 6- or 7-membered heterocyclic ring containing 1, 2 or 3 heteroatoms or heteroatom groups selected from N, O, S, NO, SO and $SO_2$ as ring members, where the heterocyclic ring may be substituted as described above. Specifically, the heterocyclic ring may carry one or more substituents selected from alkyl, cycloalkyl, polycarbocyclyl, aryl and hetaryl which may in turn be substituted. Very specifically, the heterocyclic ring may carry one or more substituents selected from $C_1$-$C_4$-alkyl, $C_3$-$C_8$-cycloalkyl and a bicyclic carbocyclic ring containing 8, 9 or 10 carbon atoms as ring members, such as indanyl, indenyl, dihydronaphthyl, terahydronaphthyl, hexahydronaphthyl, octahydronaphthyl or decalin.

In the esterification, the acid (derivative) and the hydroxy compound can be used in a molar ratio of from 10:1 to 1:10, e.g. from 7:1 to 1:7 or from 5:1 to 1:5. In particular, they are used in a molar ratio of from 3:1 to 1:3, more particularly 2:1 to 1:2 and specifically from 1.5:1 to 1:1.5.

In the hydrolysis reaction, water is generally used in excess.

The esterification reaction is preferably carried out at from 10° C. to 60° C., in particular from 20° C. to 55° C.

Hydrolysis is preferably carried at at elevated temperature, e.g. from 30 to 70° C. or in particular from 40 to 60° C. or specifically from 45 to 60° C.

The esterification reaction can be carried out by standard proceedings for ester bond formation, e.g. by mixing all reagents, water and the cellulose derivative and reacting them at the desired temperature. Alternatively the reagents can be added gradually, especially in the case of a continuous or semicontinuous process.

The hydrolysis reaction can be carried out by standard proceedings for ester bond hydrolysis.

Workup proceedings will be described below, as they are similar for most reactions.

Another class of nucleophilic substitution is amine bond formation in which an amine is reacted with a compound carrying a leaving group.

Amination

In this context, "amination" refers only to nucleophilic substitution of a leaving group by an amino group. Suitable amines are primary and secondary amines, and also ammonia can be used. Reaction conditions and suitable reactants correspond analogously to those listed above in context with etherification reactions. Thus, generally an amino compound $NHR^3R^4$ is reacted with a compound $R^2$-LG, wherein LG is leaving group, such as a halide, a hydroxyl group or a sulfonate group. $R^3$ and $R^4$, independently of each other, can be H or any aliphatic, cycloaliphatic, heterocyclic, aromatic or heteroaromatic group. If one of $R^3$, $R^4$ and $R^2$ or two thereof or all three are aromatic or heteroaromatic, reference is made to the above remarks made in context with nucleophilic aromatic substitution.

Preferably, $R^3$ is H and $R^4$ and $R^2$ are preferably independently alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl or heteroaryl. The alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl, heteroaryl groups can be substituted by one or more substituents. Suitable substituents for alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl and heteroaryl correspond to those listed above in context with substituents on the alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling. Suitable substituents for heterocyclyl groups correspond to those listed above in context with substituents on the cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling.

In these substituents, however, all functional groups have to be less reactive than the desired reaction sites for the desired reaction, unless a second reaction site is desired, like in the below-described ring formation (ammonia or a primary amine reacts at two reaction sites of $R^2$, thus giving a ring).

Specifically, $R^3$ is H and $R^4$ is polycarbocyclyl which may be substituted as described above. More specifically, $R^1$ is a 9- to 10-membered condensed saturated or partially unsaturated carbocyclic ring system, in particular selected from indanyl, tetrahydronaphthyl, hexahydronaphthyl, octahydronaphthyl and decahydronaphthyl which may carry one or more substituents as defined above. In indanyl and tetrahydronaphthyl the attachment point to N is on the nonaromatic ring moiety. Suitable substituents are e.g. selected from the group consisting of halogen, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkyl substituted by a radical selected from the group consisting of CN, OH, SH, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino, di-($C_1$-$C_4$-alkyl)amino, phenyl, a 5- or 6-membered heteroaromatic monocyclic ring containing 1, 2, 3 or 4 heteroatoms selected from the group consisting of N, O and S as ring members and a 9- or 10-membered heteroaromatic bicyclic ring containing 1, 2, 3 or 4 heteroatoms selected from the group consisting of N, O and S as ring members, where phenyl and the heteroaromatic rings may carry one or more substituents selected from the group consisting of fluorine, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino;

$C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino, di-($C_1$-$C_4$-alkyl)amino, phenyl, a 5- or 6-membered heteroaromatic monocyclic ring containing 1, 2, 3 or 4 heteroatoms selected from the group consisting of N, O and S as ring members and a 9- or 10-membered heteroaromatic bicyclic ring containing 1, 2, 3 or 4 heteroatoms selected from the group consisting of N, O and S as ring members, where phenyl and the heteroaromatic rings may carry one or more substituents selected from the group consisting of fluorine, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino.

$R^2$ is specifically alkyl, in particular $C_1$-$C_{10}$-alkyl which, apart from one or more groups LG, may carry other substituents. Suitable substituents are those listed above as in context with substituents on the alkyl groups $R^1$ and $R^2$ in the Suzuki coupling. In particular, the substituents are selected from the group consisting of halogen, cyano, nitro, OH, SH, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino, di-($C_1$-$C_4$-alkyl)amino, phenyl, a 5- or 6-membered heteroaromatic monocyclic ring containing 1, 2, 3 or 4 heteroatoms selected from the group consisting of N, O and S as ring members and a 9- or 10-membered heteroaromatic bicyclic ring containing 1, 2, 3 or 4 heteroatoms selected from the group consisting of N, O and S as ring members, where phenyl and the heteroaromatic rings may carry one or more substituents selected from the group consisting of fluorine, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino. Specifically, the substituents are selected from the group consisting of $C_1$-$C_4$-alkylcarbonyl, $C_1$-$C_4$-haloalkylcarbonyl, $C_1$-$C_4$-alkoxycarbonyl and $C_1$-$C_4$-haloalkoxycarbonyl, and very specifically from $C_1$-$C_4$-alkoxycarbonyl and $C_1$-$C_4$-haloalkoxycarbonyl.

The reaction product of the amination depends on the substituents $R^3$ and $R^4$ and on the molar ratio of the reactants. Thus, if neither $R^3$ nor $R^4$ is H, the reaction product will generally be a tertiary amine $R^2$—$N(R^3)R^4$. If $R^3$ is H and $R^4$ is not H and $R^2$-LG is used in excess, the reaction product might be a secondary amine $R^2$—$N(H)R^4$ or a tertiary amine $(R^2)_2NR^4$ or a mixture thereof. If ammonia is used and $R^2$-LG is used in excess, the reaction product might be a primary amine $NH_2R^2$, a secondary amine $NH(R^2)_2$ or a tertiary amine $(R^2)_3N$ or a mixture thereof.

The reaction product of the amination depends moreover on the nature of $R^2$: $R^2$ may carry more than one leaving group LG, e.g. two. If ammonia or a primary amine is used, this may result in the formation of a heterocyclic ring containing the nitrogen atom deriving from ammonia or the primary amine as heteroatom ring member, especially if ammonia or the amine is not used in excess. This ring formation is favoured if the two leaving groups are bound at such a distance from each other that a 4-, 5-, 6- or 7-membered ring can form. Ring formation is also favoured by a higher dilution of the reactants in the reaction medium.

Amination is generally carried out in the presence of a base. Suitable bases are those listed above in context with the Suzuki reaction, where especially inorganic bases, specifically alkali metal hydroxides, such as NaOH or KOH, are used. In case an organic base is used, this is of course not a primary or secondary amine. The base is generally used in at least equimolar amounts, with respect to that reactant not used in excess, e.g. in an amount of from 1 to 10 mol per mol of the reactant not used in excess, in particular 1.5 to 8 mol per mol of the reactant not used in excess, specifically 2 to 7 mol per mol of the reactant not used in excess. If the reactants are used in equimolar ratio, the above amounts of base apply of course to either of the reactants.

Amination is preferably carried out at from 10° C. to 70° C., more preferably from 20° C. to 70° C., in particular from 30 to 70° C., more particularly from 40 to 60° C. and specifically from 45 to 60° C.

The reaction can be carried out by standard proceedings for amination reactions via nucleophilic substitution, e.g. by mixing all reagents, inclusive base, water and the cellulose derivative, and reacting them at the desired temperature. Alternatively the reagents can be added gradually, especially in the case of a continuous or semicontinuous process.

Workup proceedings will be described below, as they are similar for most reactions.

The organic reaction can also take another form of amination than an amination via nucleophilic substitution. For instance, the amination may be a Michael addition of an N nucleophile.

Michael Addition, Especially of N Nucleophiles

In another particular embodiment of the invention, the organic reaction is a Michael addition, especially of N nucleophiles. In general terms, Michael reaction or Michael addition is the nucleophilic addition of a carbanion or another nucleophile to an α,β-unsaturated carbonyl compound. It belongs to the larger class of conjugate additions. In case of N nucleophiles, the reaction can be depicted as follows:

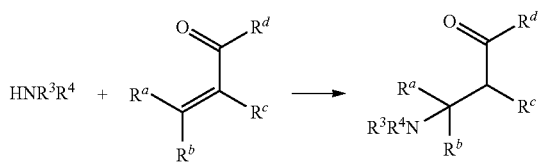

$R^3$ and $R^4$ are as defined above in context with aminations as nucleophilic substitution. $R^a$, $R^b$ and $R^c$ are independently of each other selected from the group consisting of hydrogen, alkyl, alkenyl, alkapolyenyl, alkynyl, alkapolynyl, mixed alkenyl/alkynyl, cycloalkyl, cycloalkenyl, cycloalkynyl, mixed cycloalkenyl/cycloalkynyl, polycarbocyclyl, heterocyclyl, aryl, heteroaryl, or are one of the substituents listed in context with the Suzuki reaction as suitable radicals on alkyl, alkenyl, alkapoyenyl, alkynyl, alkapolyynyl or mixed alkenyl/alkynyl groups (however except for oxo (=O), =S, and =$NR^{12a}$). More precisely, $R^a$, $R^b$ and $R^c$ are independently of each other selected from the group consisting of hydrogen, alkyl, alkenyl, alkapolyenyl, alkynyl, alkapolynyl, mixed alkenyl/alkynyl, cycloalkyl, cycloalkenyl, cycloalkynyl, mixed cycloalkenyl/cycloalkynyl, polycarbocyclyl, heterocyclyl, aryl, heteroaryl, halogen, cyano, nitro, azido, —SCN, —$SF_5$, $OR^{11}$, $S(O)_m R^{11}$, $NR^{12a}R^{12b}$, C(=O)$R^{13}$, C(=S)$R^{13}$, C(=$NR^{12a}$)$R^{13}$ or —Si($R^{14}$)$_3$; where $R^{11}$, $R^{12a}$, $R^{12b}$, $R^{13}$, $R^{14}$ and $R^{15}$ are independently as defined above in context with the Suzuki reaction. The alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl, heteroaryl groups can be substituted by one or more substituents. Suitable substituents for alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl and heteroaryl correspond to those listed above in context with substituents on the alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling. Suitable substituents for heterocyclyl groups correspond to those listed above in context with substituents on the cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling.

In particular at least two of $R^a$, $R^b$ and $R^c$ is hydrogen and the other is alkyl, in particular $C_1$-$C_4$-alkyl, which may be substituted. In particular, the alkyl substituents are selected from the group consisting of halogen, cyano, nitro, OH, SH, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino, di-($C_1$-$C_4$-alkyl)amino, phenyl, a 5- or 6-membered heteroaromatic monocyclic ring containing 1, 2, 3 or 4 heteroatoms selected from the group consisting of N, O and S as ring members and a 9- or 10-membered heteroaromatic bicyclic ring containing 1, 2, 3 or 4 heteroatoms selected from the group consisting of N, O and S as ring members, where phenyl and the heteroaromatic rings may carry one or more substituents selected from the group consisting of fluorine, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino. Specifically, the substituents are selected from the group consisting of OH, $C_1$-$C_6$-alkoxy and $C_1$-$C_6$-haloalkoxy.

$R^d$ is selected from the group consisting of hydrogen, alkyl, alkenyl, alkapolyenyl, alkynyl, alkapolynyl, mixed alkenyl/alkynyl, cycloalkyl, cycloalkenyl, cycloalkynyl, mixed cycloalkenyl/cycloalkynyl, polycarbocyclyl, heterocyclyl, aryl, heteroaryl, $OR^{11}$, $SR^{11}$ or $NR^{12a}R^{12b}$; where $R^{11}$, $R^{12a}$ and $R^{12b}$ are independently as defined above in context with the Suzuki reaction. The alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl, heteroaryl groups can be substituted by one or more substituents. Suitable substituents for alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl and heteroaryl correspond to those listed above in context with substituents on the alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling. Suitable substituents for heterocyclyl groups correspond to those listed above in context with substituents on the cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling.

In particular, $R^d$ is selected from the group consisting of OH, $C_1$-$C_6$-alkoxy and $C_1$-$C_6$-haloalkoxy.

The amine and the α,β-unsaturated carbonyl compound can be used in a molar ratio of from 10:1 to 1:10, e.g. from 5:1 to 1:5 or from 3:1 to 1:3 or, preferably, from 2:1 to 1:2.

The reaction is generally carried out in the presence of a base. Suitable bases are those listed above in context with the Suzuki reaction. In case an organic base is used, this is of course not a primary or secondary amine. The base is generally used in at least equimolar amounts, with respect to that reactant not used in excess, e.g. in an amount of from 1 to 10 mol per mol of the reactant not used in excess, in particular 1.5 to 8 mol per mol of the reactant not used in excess, specifically 2 to 7 mol per mol of the reactant not used in excess. If the reactants are used in equimolar ratio, the above amounts of base apply of course to either of the reactants.

The reaction is preferably carried out at from 10° C. to 60° C., more preferably from 20° C. to 50° C., in particular from 20 to 40° C., more particularly from 20 to 30° C.

The reaction can be carried out by standard proceedings for Michael additions, e.g. by mixing all reagents, inclusive base, water and the cellulose derivative, and reacting them at the desired temperature. Alternatively the reagents can be added gradually, especially in the case of a continuous or semicontinuous process.

Workup proceedings will be described below, as they are similar for most reactions.

Reductions and Oxidations

In another particular embodiment of the invention, the organic reaction is a reduction or an oxidation reaction, preferably a reduction reaction.

Reduction is the gain of electrons or a decrease in oxidation state by a molecule, atom, or ion. Oxidation, inversely, is the loss of electrons or an increase in oxidation state by a molecule, atom, or ion. Reduction reactions as well as oxidation reactions are of course always redox reactions, as the reduction agent used in the former case is necessarily oxidized, and the oxidation agent in the latter case is necessarily reduced. Redox reactions are however termed "reduction reactions" when the product of value is obtained by reducing the respective starting compound and are analogously termed "oxidation reactions" when the product of value is obtained by oxidizing the respective starting compound.

Reduction Reactions

Reduction reactions are very widespread. Some interesting reduction reactions are for example the reduction of nitro to amino groups, the reduction (hydrogenation) of olefins to alkanes, the reduction of esters to ketones, aldehydes or alcohols, the reduction of ketones or aldehydes to alcohols, the reduction of carbonyl compounds to amines (reductive amination) or the reduction of nitrile groups to amino groups. The present invention relates in particular to the reduction of nitro compounds to the corresponding amino compounds, to the reduction of C—C double bonds to C—C single bonds and to reductive aminations.

Reduction of Nitro Compounds

Nitro compounds can be reduced to the corresponding amino compounds by various reducing agents, the most widely used methods being the reduction with base metals, usually in acidic solution; and catalytic hydrogenation. Also suitable are metal hydrides, such as lithium or sodium hydride, complex hydrides, such as sodium boron hydride ($NaBH_4$), lithium triethylborohydride (superhydride; $LiBH(CH_2CH_3)_2$), lithium tri-sec-butyl(hydrido)borate (L-selectride; $LiBH(CH(CH_3)CH_2CH_3)_2$), lithium aluminum hydride (LAH; $LiAlH_4$) or diisobutlyaluminum hydride (DIBAL-H; $((CH_3)_2CHCH_2)_2AlH$), or boranes, e.g. diborane.

Base metals which can act as reducing agents are principally all those with a suitable redox potential and a reactivity which is controllable in aqueous medium. Despite of their redox potential, alkali metals are thus not very well suited. Examples of suitable base metals are earth alkaline metals, especially magnesium or calcium, aluminum, iron, copper, cobalt, nickel, zinc, titanium or chromium.

In view of their suitable redox potential, controllable reactivity, versatility under various reaction conditions and price, zinc and iron are among the most wide-spread reducing agents. Generally they are used in an acidic reaction medium, e.g. in diluted aqueous HCl or in ammonium chloride solution.

Thus, in a particular embodiment, the present invention relates to a method for reducing nitro compounds with Zn or Fe, optionally in acidic solution, such as aqueous HCl or ammonium chloride solution. In a specific embodiment, the present invention relates to a method for reducing nitro compounds with Zn, optionally in acidic solution, such as aqueous HCl or ammonium chloride solution. HCl or ammonium chloride are generally used in such concentration/amount that the pH of the reaction medium is from 1 to 6.

The base metal is generally used in finely divided form, e.g. in form of small granules, powder or dust, and in particular of powder or dust. As a rule, the less reactive the metal, the finer divided its use form in order to achieve a sufficient conversion rate. Accordingly, Zn and Fe are preferably used in form of powder or dust.

For reduction by catalytic hydrogenation, the catalysts may generally be all prior art catalysts which catalyze the hydrogenation of nitro compounds to the corresponding amino compounds. The catalysts may be used either in heterogeneous phase or as homogeneous catalysts. The hydrogenation catalysts preferably comprise at least one metal of group VIII and also VIIa.

Suitable metals of group VIII are selected from the group consisting of ruthenium, cobalt, rhodium, nickel, palladium und platinum. A suitable metal of group VIIa is rhenium.

The metals may also be used in the form of mixtures. Metals of group VIII may also comprise small amounts of further metals, for example metals of group VIIa, in particular rhenium, or metals of group Ib, i.e. copper, silver or gold. Particularly suitable metals of group VIII are ruthenium, nickel, palladium and platinum. The catalyst especially comprises palladium as the catalytically active species.

When a heterogeneous catalyst is used, it is suitably present in finely divided form. The finely divided form is achieved, for example, as follows:

a) Black catalyst: shortly before use as a catalyst, the metal is deposited reductively from the solution of one of its salts.

b) Adams catalyst: the metal oxides, in particular the oxides of platinum and palladium, are reduced in situ by the hydrogen used for the hydrogenation.

c) Skeletal or Raney catalyst: the catalyst is prepared as a "metal sponge" from a binary alloy of the metal (in particular nickel or cobalt) with aluminum or silicon by leaching out one partner with acid or alkali. Residues of the original alloy partner often act synergistically.

d) Supported catalyst: black catalysts can also be precipitated on the surface of a support substance. Suitable supports and support materials are described below.

The support material is generally used in the form of a fine powder. The supports may consist of metallic or nonmetallic, porous or nonporous material. Suitable metallic materials are, for example, highly alloyed stainless steels. Suitable nonmetallic materials are, for example, mineral materials, for example natural and synthetic minerals, glasses or ceramics, plastics, for example synthetic or natural polymers, or a combination of the two. Preferred support materials are carbon, in particular activated carbon, silicon dioxide, in particular amorphous silicon dioxide, alumina, and also the sulfates and carbonates of the alkaline earth metals, calcium carbonate, calcium sulfate, magnesium carbonate, magnesium sulfate, barium carbonate and barium sulfate.

The catalyst may be applied to the support by customary processes, for example by impregnating, wetting or spraying the support with a solution which comprises the catalyst or a suitable precursor thereof.

It is also possible to use homogeneous hydrogenation catalysts, such as, for example, the Wilkinson catalyst and derivatives thereof, or BINAP-ruthenium complexes, e.g. $Ru(OAc)_2$—(S)-BINAP. However, disadvantages of use of homogeneous catalysts are their preparation costs and also the fact that they generally cannot be regenerated. Therefore, preference is given to using heterogeneous hydrogenation catalysts.

The catalytic metal is in particular used in supported form or as metal sponge. Examples of supported catalysts are palladium, nickel or ruthenium on carbon, in particular activated carbon, silicon dioxide, in particular on amorphous silicon dioxide, barium carbonate, calcium carbonate, magnesium carbonate or alumina.

The metallic catalysts may also be used in the form of their oxides, in particular palladium oxide, platinum oxide or nickel oxide, which are then reduced under the hydrogenation conditions to the corresponding metals.

A suitable metal sponge is for example Raney nickel.

The catalyst and the form in which this is used is selected in accordance with the type of nitro compound to be reduced. For instance, if the nitro compound contains further functional groups which may principally also be hydrogenated, such as C—C double bonds, aromatic rings, carbonyl, carboxyl or cyano groups, the catalyst and the reaction conditions are chosen to be as selective as possible for the nitro group. Suitable conditions and catalysts are known to those skilled in the art and can be determined by simple preliminary tests.

In a particular embodiment of the present invention, the nitro compound is an aromatic or heteroaromatic nitro compound $R^1$—$N_2$, where $R^1$ is a mono-, bi- or polycyclic aryl or heteroaryl group.

In a particular embodiment the aryl group $R^1$ is mono-, bi- or tricyclic and is specifically selected from the group consisting of phenyl and naphthyl; and the heteroaryl group $R^1$ is in particular mono-, bi- or tricyclic and is specifically selected from the group consisting of 5- or 6-membered heteroaromatic monocyclic rings and 9- or 10-membered heteroaromatic bicyclic rings containing 1, 2, 3 or 4 heteroatoms selected from the group consisting of N, O and S as ring members. Mono- or bicyclic aryl or heteroaryl groups $R^1$ are for example phenyl, naphthyl, furanyl, thienyl, pyrrolyl, pyrazolyl, imidazolyl, oxazoyl, isoxazoyl, thiazoyl, isothiazolyl, [1,2,3]triazolyl, [1,2,4]triazolyl, [1,3,4]triazolyl, the oxadiazolyls, the thiadiazolyls, the tetrazolyls, pyridyl, pyrazinyl, pyrimidyl, pyridazinyl, 1,2,4-triazinyl, 1,3,5-triazinyl, indolyl, benzofuranyl, benzothienyl, quinolinyl, isoquinolinyl, quinazalinyl and the like. More particularly, they are for example phenyl, naphthyl, 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 3-isothiazolyl, 4-isothiazolyl, 5-isothiazolyl, 1,3,4-triazol-1-yl, 1,3,4-triazol-2-yl, 1,3,4-triazol-3-yl, 1,2,3-triazol-1-yl, 1,2,3-triazol-2-yl, 1,2,3-triazol-4-yl, 1,2,5-oxadiazol-3-yl, 1,2,3-oxadiazol-4-yl, 1,2,3-oxadiazol-5-yl, 1,3,4-oxadiazol-2-yl, 1,2,5-thiadiazol-3-yl, 1,2,3-thiadiazol-4-yl, 1,2,3-thiadiazol-5-yl, 1,3,4-thiadiazol-2-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, 1,2,3,4-tetrazin-1-yl, 1,2,3,4-tetrazin-2-yl, 1,2,3,4-tetrazin-5-yl, indolyl, benzofuranyl, benzothienyl, benzopyrazolyl, benzimidazolyl, benzoxazolyl, benzisoxazolyl, benzothiazolyl, benzisothiazolyl, quinolinyl, isoquinolinyl, quinazalinyl and other heteroaromatic bicyclic rings shown below in the "general definitions". Specifically, $R^1$ is phenyl.

The aryl and heteroaryl groups $R^1$ can carry one or more substituents, e.g. 1, 2, 3 or 4, in particular 1, 2 or 3, specifically 1 or 2 substituents. Suitable substituents are listed above in context with aryl and heteroaryl groups $R^1$ and $R^2$ in the Suzuki reaction. In a particular embodiment, the substituents on the aryl and heteroaryl groups $R^1$ are selected from the group consisting of halogen, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl. $C_1$-$C_4$-alkoxycarbonyl, $C_1$-$C_4$-haloalkoxycarbonyl, amino, $C_1$-$C_4$-alkylamino, di-($C_1$-$C_4$-alkyl)amino, aminocarbonyl, $C_1$-$C_4$-alkylaminocarbonyl, di-($C_1$-$C_4$-alkyl)aminocarbonyl, phenyl, a 5- or 6-membered heteroaromatic monocyclic ring containing 1, 2, 3 or 4 heteroatoms selected from the group consisting of N, O and S as ring members and a 9- or 10-membered heteroaromatic bicyclic ring containing 1, 2, 3 or 4 heteroatoms selected from the group consisting of N, O and S as ring members, where phenyl and the heteroaromatic rings may carry one or more substituents selected from the group consisting of halogen, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino. The alkyl groups in $C_1$-$C_4$-alkylamino, di-($C_1$-$C_4$-alkyl)amino, $C_1$-$C_4$-alkylaminocarbonyl and di-($C_1$-$C_4$-alkyl)aminocarbonyl may in turn carry one or more substituents selected from the group consisting of halogen, cyano, OH, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino. Specifically, the substituents on the aryl and heteroaryl groups $R^1$ are selected from the group consisting of halogen, cyano, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-halocycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino, di-($C_1$-$C_4$-alkyl)amino, aminocarbonyl, $C_1$-$C_4$-alkylaminocarbonyl and di-($C_1$-$C_4$-alkyl)aminocarbonyl, where the alkyl groups in $C_1$-$C_4$-alkylamino, di-($C_1$-$C_4$-alkyl)amino, $C_1$-$C_4$-alkylaminocarbonyl and di-($C_1$-$C_4$-alkyl)aminocarbonyl may in turn carry one or more substituents selected from the group consisting of amino, $C_1$-$C_4$-alkylamino and di-($C_1$-$C_4$-alkyl)amino. Specifically, the substituents on the aryl and heteroaryl groups $R^1$ are selected from the group consisting of halogen, $C_1$-$C_6$-alkoxy, $C_1$-$C_6$-haloalkoxy, aminocarbonyl, $C_1$-$C_4$-alkylaminocarbonyl and di-($C_1$-$C_4$-alkyl)aminocarbonyl, where the alkyl groups in $C_1$-$C_4$-alkylaminocarbonyl and di-($C_1$-$C_4$-alkyl)aminocarbonyl may in turn carry one or more substituents selected from the group consisting of amino, $C_1$-$C_4$-alkylamino and di-($C_1$-$C_4$-alkyl)amino.

Preferably however, the aryl or heteroaryl groups do not carry any groups prone to hydrogenation under the applied reaction conditions, such as alkenyl, alkynyl, cycloalkenyl, cycloalkynyl, cyano, $C(O)R^{13}$, $C(S)R^{13}$ or $C(=NR^{12a})R^{13}$ groups.

For such aromatic or heteroaromatic nitro compounds $R^1$—$NO_2$, the hydrogenation catalyst is in particular palladium on carbon.

The amount of catalyst to be used depends on factors including the particular catalytically active metal and its use form, and may be determined in the individual case by those skilled in the art. When noble metal catalysts are used which comprise, for example, platinum or palladium, the amount can be smaller by a factor of 10 as compared to the amount of for example, nickel- or cobalt-containing hydrogenation catalysts. In case of Pd or Pt, for example, the catalyst is used in catalytic, i.e. substoichiometric amounts, e.g. in an amount of from 0.001 to 0.2 mol per mol of nitro compound, in particular 0.005 to 0.1 mol per mol of nitro compound, specifically 0.01 to 0.1 mol per mol of nitro compound. The amount of catalyst specified relates to the amount of active metal, i.e. to the catalytically active component of the catalyst.

The reduction (with a base metal as well as via hydrogenation) is preferably carried out at from 10° C. to 60° C., in particular from 20° C. to 55° C., specifically from 20° C. to 50° C. and very specifically from 20° C. to 30° C.

The reaction pressure of the hydrogenation reaction is preferably in the range of from 1 to 250 bar, in particular from 1 to 50 bar and more particularly from 1 to 5 bar. In case that the nitro compound contains groups which can also be hydrogenated, especially aromatic or heteroaromatic rings, it is expedient to work at lower pressure in order to avoid hydrogenation of such groups. In this case, the reaction pressure of the hydrogenation reaction is preferably in the range from 1 to 5 bar, more preferably 1 to 2 bar and in particular 1 to 1.5 bar.

Reduction of C—C Double Bonds

C—C double bonds are generally reduced by hydrogenation. The above remarks to the hydrogenation of nitro compounds apply here analogously, except, however, for metal hydrides, complex hydrides and boranes, which are not suitable here.

Here, too, the catalyst and the form in which this is used is selected in accordance with the type of olefinically unsaturated compound to be reduced. For instance, if the olefinically unsaturated compound contains further functional groups which may principally also be hydrogenated, such as aromatic rings, carbonyl, carboxyl or cyano groups, the catalyst and the reaction conditions are chosen to be as selective as possible for the C—C double bond. Suitable conditions and catalysts are known to those skilled in the art and can be determined by simple preliminary tests.

The compound with C—C double bonds to be hydrogenated is preferably an olefinically unsaturated compound, i.e. a compound which contains at least one C—C double bond which is not part of an aromatic or heteroaromatic system. Preferably it is a compound of formula $(R^1)(R^2)C=C(R^3)(R^4)$, where $R^1$, $R^2$, $R^3$, and $R^4$, independently of each other, are hydrogen, alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl, heterocyclyl or are one of the substituents listed in context with the Suzuki as suitable radicals on alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl or polycarbocyclyl groups (however except for oxo (=O), =S and =$NR^{12a}$). More precisely, $R^1$, $R^2$, $R^3$, and $R^4$, independently of each other, are hydrogen, alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl, heterocyclyl, halogen, cyano, nitro, azido, —SCN, —SF$_5$, OR$^{11}$, S(O)$_m$R$^{11}$, NR$^{12a}$R$^{12b}$, C(=O)R$^{13}$, C(=S)R$^{13}$, C(=NR$^{12a}$)R$^{13}$ or —Si(R$^{14}$)$_3$; where R$^{11}$, R$^{12a}$, R$^{12b}$, R$^{13}$, R$^{14}$ and R$^{15}$ are independently as defined above in context with the Suzuki reaction.

The alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl, heteroaryl groups R$^1$, R$^2$, R$^3$ and R$^4$ can be substituted by one or more substituents. Suitable substituents for alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl and heteroaryl correspond to those listed above in context with substituents on the alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl or heteroaryl groups R$^1$ and R$^2$ in the Suzuki coupling. Suitable substituents for heterocyclyl groups correspond to those listed above in context with substituents on the cycloalkyl, cycloalkenyl, cycloalkynyl, mixed cycloalkenyl/cycloalkynyl, polycarbocyclyl, aryl or heteroaryl groups R$^1$ and R$^2$ in the Suzuki coupling. Alternatively, R$^1$ and R$^3$, together with the carbon atoms they are bound to, form a carbocyclic or heterocyclic, non aromatic ring, where the ring may be substituted; suitable substituents corresponding to those listed above in context with substituents on the cycloalkyl, cycloalkenyl, cycloalkynyl, mixed cycloalkenyl/cycloalkynyl, polycarbocyclyl, aryl or heteroaryl groups R$^1$ and R$^2$ in the Suzuki coupling.

In particular, R$^1$, R$^2$, R$^3$, and R$^4$, independently of each other, are hydrogen, alkyl, cycloalkyl, heterocyclyl, aryl, heteroaryl or C(=O)R$^{13}$, where R$^{13}$ is as defined above in context with the Suzuki reaction and is in particular C$_1$-C$_4$-alkyl, C$_1$-C$_4$-haloalkyl, C$_1$-C$_4$-alkoxy or C$_1$-C$_4$-haloalkoxy. Specifically, R$^1$, R$^2$, R$^3$, and R$^4$, independently of each other, are hydrogen, alkyl, aryl, heteroaryl or C(=O)R$^{13}$, where R$^{13}$ is as defined above in context with the Suzuki reaction and is in particular C$_1$-C$_4$-alkyl.

If one or more of R$^1$, R$^2$, R$^3$, and R$^4$ are aryl, heteroaryl or C(=O)R$^{13}$, it is expedient to carry out the hydrogenation either under low hydrogen pressure, as said above.

In a specific embodiment, the olefinically unsaturated compound is a Michael-type compound, i.e. a compound carrying an electron withdrawing group bound to the C—C double bond, especially a C(O) group, such as C(O)R$^3$. Preferably, one of R$^1$, R$^2$, R$^3$, and R$^4$, is C(=O)R$^{13}$, where R$^{13}$ is as defined above in context with the Suzuki reaction and is in particular C$_1$-C$_4$-alkyl, C$_1$-C$_4$-haloalkyl, C$_1$-C$_4$-alkoxy or C$_1$-C$_4$-haloalkoxy; and the others, independently of each other, are hydrogen, alkyl, cycloalkyl, heterocyclyl, aryl or heteroaryl. As said, the alkyl, cycloalkyl, heterocyclyl, aryl, heteroaryl groups R$^1$, R$^2$, R$^3$ and R$^4$ can be substituted by one or more substituents. Suitable substituents for alkyl, cycloalkyl, aryl and heteroaryl correspond to those listed above in context with substituents on the alkyl, cycloalkyl, aryl or heteroaryl groups R$^1$ and R$^2$ in the Suzuki coupling. Suitable substituents for heterocyclyl groups correspond to those listed above in context with substituents on the cycloalkyl, cycloalkenyl, cycloalkynyl, mixed cycloalkenyl/cycloalkynyl, polycarbocyclyl, aryl or heteroaryl groups R$^1$ and R$^2$ in the Suzuki coupling.

In a particular embodiment the reduction agent is ligated CuH. This is generally prepared in situ by reacting a Cu salt, generally a Cu(II) salt, e.g. Cu(II) acetate, with a hydride source in the presence of a suitable ligand.

Suitable ligands are those mentioned in context with the Suzuki coupling as Pd or Ni ligands. A specific ligand in this case is 6,6'-dimethoxy-[1,1'-biphenyl]-2,2'-diyl)bis(bis(3,5-dimethylphenyl)phosphine.

Suitable hydride sources are for example silanes, such as polymethylhydrosiloxane (PMHS; a ca. 29mer), phenylsilane or diethoxymethylsilane (DEMS). Among these, PMHS is preferred.

If a non-racemic ligand is used and R$^1$ and R$^2$ are different from each other and are not H and/or R$^3$ and R$^4$ are different from each other and are not H, the reduction can proceed stereoselectively and yield essentially just one stereoisomer.

Suitable non-racemic ligands are for example [(4R)-(4,4'-bis-1,3-benzodioxole)-5,5'-diyl]bis[bis(3,5-di-tert-butyl-4-methoxyphenyl)phosphine] ((R)-DTBM-SEGPHOS®), (R)- or (S)-3,5-Xyl-MeO-BIPHEP, (R,S)- or (S,R)-PPF-P(t-Bu)$_2$, or the Josiphos ligands.

The metal is generally used in catalytic, i.e. substoichiometric amounts, e.g. in an amount of from 0.001 to 0.2 mol per mol of nitro compound, in particular 0.005 to 0.1 mol per mol of nitro compound, specifically 0.01 to 0.05 mol per mol of olefinically unsaturated compound.

The silane is generally used in excess with respect to the compound to be reduced. "Excess" in this case relates to the amount of hydrogen atoms present in the siloxane molecule, divided by two (as two hydrogen atoms are necessary for the hydrogenation of the double bond), and thus, in case of polymeric silanes, such as PMHS, depends on the polymerization degree. Generally it used in such an amount that it can theoretically release 3 to 100 mol of hydrogen atoms per mol of compound with C—C double bonds, in particular 3 to 50 mol of hydrogen atoms per mol of compound with C—C double bonds, more particularly 4 to 20 mol of hydrogen atoms per mol of compound with C—C double bonds, specifically 6 to 15 mol of hydrogen atoms per mol of compound with C—C double bonds.

The reduction is preferably carried out at from 10° C. to 60° C., in particular from 20° C. to 55° C., specifically from 20° C. to 50° C. and very specifically from 20° C. to 30° C.

If the catalyst ligand or any reactant is prone to oxidation by air (such as is the case, for example, for triphenylphosphine, tri(tert-butyl)phosphine, X-Phos, 6,6'-dimethoxy-[1,1'-biphenyl]-2,2'-diyl)bis(bis(3,5-dimethylphenyl)phosphine and several others), the reaction is preferably carried out in an inert atmosphere in order to avoid the presence of oxygen, e.g. under an argon or nitrogen atmosphere. Preferably, moreover, the solvent is used in degassed form. On a laboratory scale this is e.g. obtained by freezing, applying a vacuum and unfreezing under an inert atmosphere or by bubbling a vigorous stream of argon or nitrogen through the solvent or by ultrasonification under an inert atmosphere. On an industrial scale other methods known in the art can be applied.

Workup proceedings will be described below, as they are similar for most reactions.

Reductive Amination

In reductive aminations a carbonyl group is converted into an amino group via an intermediate imine. The carbonyl group is most commonly a ketone or an aldehyde. Generally, the amine first reacts with the carbonyl group to form a hemiaminal species, which subsequently loses one molecule of water in a reversible manner by alkylimino-de-oxobisubstitution, to form the imine. This intermediate imine can then be reduced with a suitable reducing agent to give an amine:

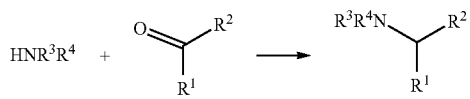

As the reaction is often carried out as a one pot reaction without intermediate isolation of the imine, the reduction agent and the reaction conditions are in this case expediently such that the reduction agent does not react with the carbonyl compound before the imine is formed. Suitable reduction agents are complex boron hydrides, such as sodium boron hydride (NaBH$_4$), sodium cyanoborohydride (NaBH$_3$CN), sodium triacetoxyborohydride (NaBH(OCOCH$_3$)$_3$), lithium triethylborohydride (superhydride; LiBH(CH$_2$CH$_3$)$_2$), or lithium tri-sec-butyl(hydrido)borate (L-selectride; LiBH(CH(CH$_3$)CH$_2$CH$_3$)$_2$), or boranes, e.g. diborane or borane complexes, such as borane-2-picoline complex. A specifically suitable reduction agent is the borane-2-picoline complex. Also suitable is formic acid. In this case, the reductive amination is a Leuckert-Wallach reaction.

$R^3$ and $R^4$ are as defined above in context with aminations as nucleophilic substitution. $R^1$ and $R^2$ are independently of each other selected from the group consisting of hydrogen, alkyl, alkenyl, alkapolyenyl, alkynyl, alkapolynyl, mixed alkenyl/alkynyl, cycloalkyl, cycloalkenyl, cycloalkynyl, mixed cycloalkenyl/cycloalkynyl, polycarbocyclyl, heterocyclyl, aryl, heteroaryl, or are one of the substituents listed in context with the Suzuki reaction as suitable radicals on alkyl, alkenyl, alkapoyenyl, alkynyl, alkapolyynyl or mixed alkenyl/alkynyl groups (however except for oxo (=O), =S, and =NR$^{12a}$). More precisely, $R^1$ and $R^2$ are independently of each other selected from the group consisting of hydrogen, alkyl, alkenyl, alkapolyenyl, alkynyl, alkapolynyl, mixed alkenyl/alkynyl, cycloalkyl, cycloalkenyl, cycloalkynyl, mixed cycloalkenyl/cycloalkynyl, polycarbocyclyl, heterocyclyl, aryl, heteroaryl, halogen, cyano, nitro, azido, —SCN, —SF$_5$, OR$^{11}$, S(O)$_m$R$^{11}$, NR$^{12a}$R$^{12b}$, C(=O)R$^{13}$, C(=S)R$^{13}$, C(=NR$^{12a}$)R$^{13}$ or —Si(R$^{14}$)$_3$; where R$^{11}$, R$^{12a}$, R$^{12b}$, R$^{13}$, R$^{14}$ and R$^{15}$ are independently as defined above in context with the Suzuki reaction. The alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl, heteroaryl groups can be substituted by one or more substituents. Suitable substituents for alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl and heteroaryl correspond to those listed above in context with substituents on the alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling. Suitable substituents for heterocyclyl groups correspond to those listed above in context with substituents on the cycloalkyl, cycloalkenyl, cycloalkynyl, mixed cycloalkenyl/cycloalkynyl, polycarbocyclyl, aryl or heteroaryl groups $R^1$ and $R^2$ in the Suzuki coupling.

In particular, $R^3$ is H and $R^4$ is aryl, where aryl may be substituted as described above. Specifically, $R^4$ is phenyl which may be substituted. In particular, the aryl or phenyl substituents are selected from the group consisting of halogen, cyano, nitro, OH, SH, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino, di-($C_1$-$C_4$-alkyl)amino, phenyl, a 5- or 6-membered heteroaromatic monocyclic ring containing 1, 2, 3 or 4 heteroatoms selected from the group consisting of N, O and S as ring members and a 9- or 10-membered heteroaromatic bicyclic ring containing 1, 2, 3 or 4 heteroatoms selected from the group consisting of N, O and S as ring members, where phenyl and the heteroaromatic rings may carry one or more substituents selected from the group consisting of fluorine, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_4$-alkoxycarbonyl, $C_1$-$C_4$-haloalkoxycarbonyl, amino, $C_1$-$C_4$-alkylamino and di-($C_1$-$C_4$-alkyl)amino. Specifically, the substituents are selected from the group consisting of OH, $C_1$-$C_6$-alkoxy and $C_1$-$C_6$-haloalkoxy.

In particular, $R^1$ is H or $C_1$-$C_4$-alkyl and $R^2$ is aryl, where aryl may be substituted as described above. Specifically, $R^2$ is phenyl which may be substituted. In particular, the aryl or phenyl substituents are selected from the group consisting of halogen, cyano, nitro, OH, SH, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, amino, $C_1$-$C_4$-alkylamino, di-($C_1$-$C_4$-alkyl)amino, phenyl, a 5- or 6-membered heteroaromatic monocyclic ring containing 1, 2, 3 or 4 heteroatoms selected from the group consisting of N, O and S as ring members and a 9- or 10-membered heteroaromatic bicyclic ring containing 1, 2, 3 or 4 heteroatoms selected from the group consisting of N, O and S as ring members, where phenyl and the heteroaromatic rings may carry one or more substituents selected from the group consisting of fluorine, cyano, nitro, OH, SH, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, formyl, $C_1$-$C_4$-alkylcarbonyl, $C_1$-$C_4$-haloalkylcarbonyl, $C_1$-$C_4$-alkoxycarbonyl and $C_1$-$C_4$-haloalkoxycarbonyl.

The amine and the carbonyl compound can be used in a molar ratio of from 5:1 to 1:5, e.g. from 3:1 to 1:3, or from 2:1 to 1:2 or, preferably, from 1.5:1 to 1:1.5.

The reduction agent is generally used in at least equimolar amounts, with respect to that reactant not used in excess, e.g. in an amount of from 1 to 3 mol per mol of the reactant not used in excess, in particular 1 to 2 mol per mol of the reactant not used in excess, specifically 1.1 to 1.5 mol per mol of the reactant not used in excess. If the reactants are used in equimolar ratio, the above amounts of base apply of course to either of the reactants.

The reaction may be carried out in the presence of an acid. Suitable acids are inorganic acids, such as HCl or phosphoric acid, and organic acids, such as acetic acid, trifluoroacetic acid, toluenesulfonic acid or diphenyl phosphate. The acid is generally used in substoichiometric mounts, relative to the reactant not used in excess, such as 1 to 50 mol %, in particular 5 to 20 mol %, relative to 1 mol of that reactant not used in excess.

The reaction is preferably carried out at from 10° C. to 60° C., more preferably from 20° C. to 50° C., in particular from 20 to 40° C., more particularly from 20 to 30° C.

The reaction can be carried out by standard proceedings for reductive aminations, e.g. by mixing all reagents, inclusive the reduction agent, water and the cellulose derivative, and reacting them at the desired temperature. Alternatively the reagents can be added gradually, especially in the case of a continuous or semicontinuous process.

Workup proceedings will be described below, as they are similar for most reactions.

Although the above reactions have all been depicted as a reaction between at least two different molecules, they can of course also be carried out as intramolecular reactions if the reactant contains the suitable functional groups in a suitable position to each other. Examples are especially intramolecular cyclizations. For instance, a compound containing both an acid and an amino group in a suitable distance to each other can react in an intramolecular amidation reaction to give a lactam. Suitable dilution is however required for intramolecular reactions if these are not favoured for other reasons over the respective intermolecular reaction.

The method of the present invention is also suitable for a suit or cascade of reaction steps, which may occur either spontaneously or by addition of further reagents after completion of one step. For instance, in reactions with Michael-type reactants, like the above-described (Rh-catalyzed) 1,4-additions or the hydrogenation of such compounds, the carboxyl, ester, amide etc. group may react spontaneously in a subsequent reaction, especially if the Michael-type reactant contains functional groups in suitable position which can give a further reaction with this carboxyl, ester, amide etc. group. For instance, if the Michael-type reactant contains an ester group and also an amine group in suitable position, a lactam can form after or before or during the 1,4-addition or the hydrogenation reaction. Another example is the protection of a functional group in a compound containing more than one functional group, e.g. protection of a primary or secondary amino group, of an OH or SH group, reaction of the other functional group(s) in as desired and deprotection of the protected group and if desired further reaction of the deprotected functional group. This suit of reactions can be carried out as a one pot reaction.

The organic reactions can be carried out in the presence of a surfactant (of course different from the cellulose derivative used according to the present invention).

Suitable surfactants are surface-active compounds, such as anionic, cationic, nonionic and amphoteric surfactants, block polymers, polyelectrolytes, and mixtures thereof.

Anionic surfactants are for example alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Nonionic surfactants are for example alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Cationic surfactants are for example quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

In a particular embodiment, the surfactant is a polyoxyethanyl-α-tocopheryl succinate derivative. Suitable surfactants of this type are for example the above-described TPGS-750-M, TPGS-1000 and PTS-600:

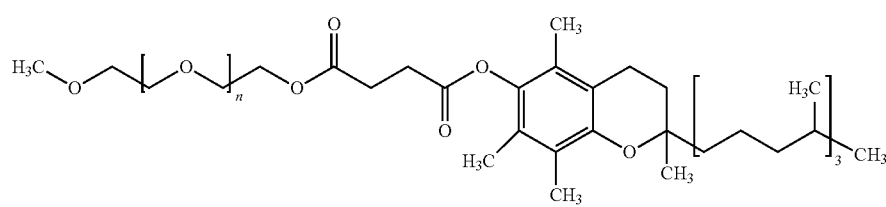

TPGS-750-M n = 17

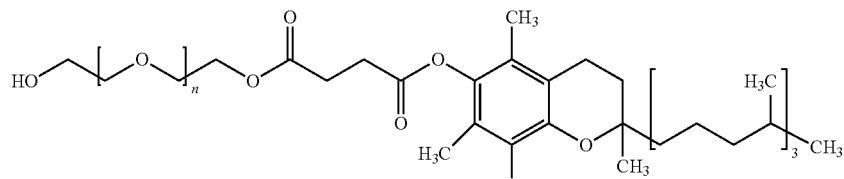

TPGS-1000 n = ca. 23

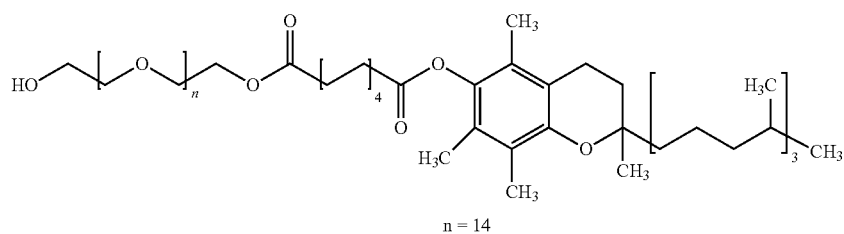

PTS-600 n = 14

Among these, TPGS-750-M is particularly suitable. The polyoxyethanyl-α-tocopheryl succinate derivative surfactants are generally used in an amount of from 0.01 to 15% by weight, in particular 0.05 to 10% by weight, more particularly 0.1 to 7% by weight, specifically 0.2 to 5% by weight, more specifically 1 to 5% by weight, based on the weight of water (water being the only solvent or making up at least 90% by weight of the solvent, in particular at least 97% by weight of the solvent, the percentages being based on the total weight of the solvent).

Specifically however, no surfactant (different from the cellulose derivative used according to the invention) is used.

One advantage of the method of the present invention is the facile workup. The cellulose derivative can be removed in a very simple way: after completion of the reaction, the resulting reaction mixture can be extracted with an organic solvent which has a sufficiently low miscibility with water and a good solubility for the desired product and reactants, if the conversion was not complete. Suitable organic solvents are for instance alkyl carboxylates, such as ethylacetate, open-chained ethers, such as diethyl ether or methyl-tert-butyl ether, halogenated alkanes, such as dichloromethane, chloroform or dichloroethane, alkanes, such as pentane, hexane, heptane or technical mixtures like petroleum ether, cycloalkanes, like cyclohexane or cycloheptane, or aromatic solvents, like toluene and the xylenes. In most cases, ethylacetate or a open-chained ethers, such as diethyl ether or methyl-tert-butyl ether, is the most useful solvent for extraction.

While the desired product and any unreacted reactants move to the organic phase, the cellulose derivative remains in the aqueous phase. If desired, this aqueous phase can be reused, if necessary after a purification step.

Cellulose derivatives with a viscosity of above 10 mPa·s can be removed by salting them out, i.e. by causing their precipitation by addition of a salt. For this purpose, an inorganic salt, e.g. in form of an aqueous solution, is added to the reaction mixture after completion of the reaction, suitably together with an organic solvent as described above. Alternatively, the organic solvent is added first and then the inorganic salt (solution). Principally, the organic solvent may also be added after the inorganic salt (solution). This proceeding is however less suited, as the products might precipitate together with the cellulose derivative. The risk of co-precipitation is somewhat reduced for water-miscible products, as compared to products with low or now miscibility with water, but still existent. Suitable salts are for example sodium sulfate, potassium sulfate, magnesium sulfate, ammonium sulfate, sodium phosphate, potassium phosphate, sodium hydrogenphosphate, potassium hydrogenphosphate, sodium chloride and the like, among which preference is given to salts with large anions, such as the sulfates, phosphates and hydrogenphosphates. In particular, sodium sulfate is used. The addition of the inorganic salt causes the cellulose derivative to precipitate, which can then be removed by standard procedures, such as sedimentation, decantation, filtration or centrifugation, while the product moves to the organic phase. If desired, the aqueous phase can be extracted once or several times with an organic solvent to remove any residual organic products from the water phase.

Another method for causing precipitation of certain cellulose derivative is heating, e.g. to at least 80° C.

If desired, the precipitated cellulose derivative can be reactivated and reused in the method of the invention. Reactivation is for example achieved by cooling, if precipitation was caused by heating, or by washing with water to remove the salt with which the cellulose derivative was salted out.

Thus, in a preferred embodiment of the present invention, after completion of the organic reaction the cellulose derivative is precipitated by heating or by adding an inorganic salt, preferably by adding an inorganic salt, where the inorganic salt is selected from the group consisting of sodium sulfate, potassium sulfate, magnesium sulfate, ammonium sulfate, sodium phosphate, potassium phosphate, sodium hydrogenphosphate, potassium hydrogenphosphate and sodium chloride, and is in particular sodium sulfate; where precipitation of the cellulose derivative can be carried out before or after removing the reaction product and, if present, unreacted starting compounds, and where the precipitated cellulose derivative, after a reactivation step, can be reused in the method as claimed in any of the preceding claims.

If the organic reaction was carried out in the presence of a heterogenous catalyst, the isolated precipitate (of the precipitated cellulose derivative) often contains the catalyst in essentially quantitative amounts. Thus, not only the cellulose derivative can be recycled, but also the heterogenous catalyst.

If the product is initially obtained as a salt, e.g. because it is a Lewis base, e.g. an amine, and the reaction medium is acidic, the reaction mixture is expediently first neutralized or made alkaline before the organic solvent is added for extraction, as otherwise the product would remain in the aqueous phase. Inversely, if the product is a salt because it is an acid and the reaction medium is basic, the reaction mixture is expediently first neutralized or made acidic before the organic solvent is added for extraction, as otherwise the product would remain in the aqueous phase.

If a silyl compound is used in the reaction, as is the case, for example, in the CuH reduction of olefinic double bonds with silanes as hydride source, it is expedient to quench this silyl compound, e.g. by addition of $NH_4F$.

After separation from the cellulose derivative, the reaction product can be isolated and, if required, purified by standard procedures, such as chromatographic methods, distillation, sublimation, crystallization etc.

The method of the invention allows carrying out virtually all organic reactions so far carried out in organic solvents. This is surprising in cases in which one or more of the reagents or products are not or only scarcely water soluble/miscible. This is even more surprising in cases in which one or more of the reagents or products are hydrolytically labile or in which water is produced, such as in esterifications or in the above-described cyclodehydratizations, as one would expect in the latter case that the reaction would proceed extremely slowly, if at all.

Yields and purities are satisfactory to very good, and, surprisingly, in many cases better than in organic solvents. The reaction times are generally short, especially if higher reaction temperatures, e.g. around 50° C., are applied. In some cases, they are even extremely short, such as just some 15 minutes or even just 10 or 5 or 2 minutes (for a mmol scale).

The cellulose derivatives are significantly less expensive than TPGS-750-M and the other polyoxyethanyl-α-tocopheryl derivatives described above and readily available. Moreover, they can be easily separated from the reaction mixtures. If desired, they can be reused in the method of the invention, if necessary after a reactivation step.

General Definitions

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine.

Pseudohalogens are polyatomic analogues of halogens, whose chemistry, resembling that of the true halogens, allows them to substitute for halogens in several classes of chemical compounds. Examples for pseudohalogen groups, in terms of the present invention also named pseudohalogenide groups, pseudohalogenides, pseudohalide groups or or pseudohalides, are —CN, —$N_3$, —OCN, —NCO, —CNO, —SCN, —NCS or —SeCN.

If the term "alkyl" as used herein and in the alkyl moieties of alkoxy, alkylthio, alkylsulfinyl, alkylsulfonyl, alkylcarbonyl and the like is used without prefix ($C_n$-$C_m$), it indicates saturated straight-chain or branched aliphatic hydrocarbon radicals having in general 1 to 30 ("$C_1$-$C_{30}$-alkyl") carbon atoms, preferably 1 to 20 ("$C_1$-$C_{20}$-alkyl") carbon atoms, in particular 1 to 10 ("$C_1$-$C_{30}$-alkyl") carbon atoms, specifically 1 to 6 ("$C_1$-$C_6$-alkyl") or 1 to 4 ("$C_1$-$C_4$-alkyl") carbon atoms. "$C_1$-$C_2$-Alkyl" is a saturated aliphatic hydrocarbon radical having 1 or 2 carbon atoms. "$C_1$-$C_3$-alkyl" is a saturated straight-chain or branched aliphatic hydrocarbon radical having 1 to 3 carbon atoms. "$C_1$-$C_4$-Alkyl" is a saturated straight-chain or branched aliphatic hydrocarbon radical having 1 to 4 carbon atoms. "$C_1$-$C_6$-Alkyl" is a saturated straight-chain or branched aliphatic hydrocarbon radical having 1 to 6 carbon atoms. "$C_1$-$C_8$-Alkyl" is a saturated straight-chain or branched aliphatic hydrocarbon radical having 1 to 8 carbon atoms; etc. $C_1$-$C_2$-Alkyl is methyl or ethyl. Examples for $C_1$-$C_3$-alkyl are, in addition to those mentioned for $C_1$-$C_2$-alkyl, propyl and isopropyl. Examples for $C_1$-$C_4$-alkyl are, in addition to those mentioned for $C_1$-$C_3$-alkyl, butyl, 1-methylpropyl (sec-butyl), 2-methylpropyl (isobutyl) or 1,1-dimethylethyl (tert-butyl). Examples for $C_1$-$C_6$-alkyl are, in addition to those mentioned for $C_1$-$C_4$-alkyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl. Examples for $C_1$-$C_8$-alkyl are, in addition to those mentioned for $C_1$-$C_6$-alkyl, heptyl, octyl, 2-ethylhexyl and positional isomers thereof. Examples for $C_1$-$C_{10}$-alkyl are, in addition to those mentioned for $C_1$-$C_6$-alkyl, nonyl, decyl and positional isomers thereof. Examples for $C_1$-$C_{20}$-alkyl are, in addition to those mentioned for $C_1$-$C_{10}$-alkyl, n-undecyl, n-dodecyl, n-tridecyl, n-tetradecyl, n-hexadecyl, n-heptadecyl, n-octadecyl, n-nonadecyl, n-eicosyl and position isomers thereof. Examples for $C_1$-$C_{30}$-alkyl are, in addition to those mentioned for $C_1$-$C_{20}$-alkyl, n-henicosyl, n-docosyl, n-tricosyl, n-tetracosyl, n-pentacosyl, n-hexacosyl, n-octacosyl, n-nonacosyl, n-triacontyl and position isomers thereof.

If the term "haloalkyl" as used herein, which is also expressed as "alkyl which is partially or fully halogenated", and in the alkyl moieties of haloalkoxy, haloalkylthio, haloalkylsulfinyl, haloalkylsulfonyl, haloalkylcarbonyl and the like is used without prefix ($C_n$-$C_m$), it indicates saturated straight-chain or branched aliphatic hydrocarbon radicals having in general 1 to 30 ("$C_1$-$C_{30}$-haloalkyl") carbon atoms, preferably 1 to 20 ("$C_1$-$C_{20}$-haloalkyl") carbon atoms, in particular 1 to 10 ("$C_1$-$C_{10}$-haloalkyl") carbon atoms, specifically 1 to 6 ("$C_1$-$C_6$-haloalkyl") or 1 to 4 ("$C_1$-$C_4$-haloalkyl") carbon atoms, where some or all of the hydrogen atoms in these groups are replaced by halogen atoms as mentioned above, in particular fluorine, chlorine and/or bromine.

"Halomethyl" or "halogenated methyl" or "$C_1$-haloalkyl" is methyl in which 1, 2 or 3 of the hydrogen atoms are replaced by halogen atoms as mentioned above, in particular fluorine, chlorine and/or bromine. "$C_1$-$C_2$-Haloalkyl" refers to alkyl groups having 1 or 2 carbon atoms (as mentioned above), where some or all of the hydrogen atoms in these groups are replaced by halogen atoms as mentioned above, in particular fluorine, chlorine and/or bromine. "$C_1$-$C_3$-Haloalkyl" refers to straight-chain or branched alkyl groups having 1 to 3 carbon atoms (as mentioned above), where some or all of the hydrogen atoms in these groups are replaced by halogen atoms as mentioned above, in particular fluorine, chlorine and/or bromine. "$C_1$-$C_4$-Haloalkyl" refers to straight-chain or branched alkyl groups having 1 to 4 carbon atoms (as mentioned above), where some or all of the hydrogen atoms in these groups are replaced by halogen atoms as mentioned above, in particular fluorine, chlorine and/or bromine. "$C_1$-$C_6$-Haloalkyl" refers to straight-chain or branched alkyl groups having 1 to 6 carbon atoms (as mentioned above), where some or all of the hydrogen atoms in these groups are replaced by halogen atoms as mentioned above, in particular fluorine, chlorine and/or bromine. "$C_1$-$C_8$-Haloalkyl" refers to straight-chain or branched alkyl groups having 1 to 8 carbon atoms (as mentioned above), where some or all of the hydrogen atoms in these groups are replaced by halogen atoms as mentioned above, in particular fluorine, chlorine and/or bromine. "$C_1$-$C_{10}$-Haloalkyl" refers to straight-chain or branched alkyl groups having 1 to 10 carbon atoms (as mentioned above), where some or all of the hydrogen atoms in these groups are replaced by halogen atoms as mentioned above, in particular fluorine, chlorine and/or bromine; etc. Examples for halomethyl are bromomethyl, chloromethyl, fluoromethyl, dichloromethyl, trichloromethyl, difluoromethyl, trifluoromethyl, chlorofluoromethyl, dichlorofluoromethyl, chlorodifluoromethyl and the like. Examples for $C_1$-$C_2$-haloalkyl are chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl. Examples for $C_1$-$C_3$-haloalkyl are, in addition to those mentioned for $C_1$-$C_2$-haloalkyl, 1-fluoropropyl, 2-fluoropropyl, 3-fluoropropyl, 1,1-difluoropropyl, 2,2-difluoropropyl, 1,2-difluoropropyl, 3,3-difluoropropyl, 3,3,3-trifluoropropyl, heptafluoropropyl, 1,1,1-trifluoroprop-2-yl, 3-chloropropyl and the like. Examples for $C_1$-$C_4$-haloalkyl are, in addition to those mentioned for $C_1$-$C_3$-haloalkyl, 4-chlorobutyl and the like.

If the term "fluorinated alkyl" is used without prefix ($C_n$-$C_m$), it indicates saturated straight-chain or branched aliphatic hydrocarbon radicals having in general 1 to 30 ("fluorinated $C_1$-$C_{30}$-alkyl") carbon atoms, preferably 1 to 20 ("fluorinated $C_1$-$C_{20}$-alkyl") carbon atoms, in particular 1 to 10 ("fluorinated $C_1$-$C_{10}$-alkyl") carbon atoms, specifically 1 to 6 ("fluorinated $C_1$-$C_6$-alkyl") or 1 to 4 ("fluorinated $C_1$-$C_4$-alkyl") carbon atoms, where some or all of the hydrogen atoms in these groups are replaced by fluorine atoms. "Fluorinated methyl" is methyl in which 1, 2 or 3 of the hydrogen atoms are replaced by fluorine atoms. "Fluorinated $C_1$-$C_2$-alkyl" refers to alkyl groups having 1 or 2 carbon atoms (as mentioned above), where some or all of the hydrogen atoms in these groups are replaced by fluorine atoms. "Fluorinated $C_1$-$C_3$-alkyl" refers to straight-chain or branched alkyl groups having 1 to 3 carbon atoms (as mentioned above), where some or all of the hydrogen atoms in these groups are replaced by fluorine atoms. "Fluorinated $C_1$-$C_4$-alkyl" refers to straight-chain or branched alkyl groups having 1 to 4 carbon atoms (as mentioned above), where some or all of the hydrogen atoms in these groups are replaced by fluorine atoms. "Fluorinated $C_1$-$C_6$-alkyl" refers to straight-chain or branched alkyl groups having 1 to 6 carbon atoms (as mentioned above), where some or all of the hydrogen atoms in these groups are replaced by fluorine atoms. "Fluorinated $C_1$-$C_8$-alkyl" refers to straight-chain or branched alkyl groups having 1 to 8 carbon atoms (as mentioned above), where some or all of the hydrogen atoms in these groups are replaced by fluorine atoms. "Fluorinated $C_1$-$C_{10}$-alkyl" refers to straight-chain or branched alkyl groups having 1 to 10 carbon atoms (as mentioned above), where some or all of the hydrogen atoms in these groups are replaced by fluorine atoms; etc. Examples for fluorinated methyl are fluoromethyl, difluoromethyl and trifluoromethyl. Examples for fluorinated $C_1$-$C_2$-alkyl are fluoromethyl, difluoromethyl, trifluoromethyl, 1-fluoroethyl, 2-fluoroethyl, 2,2-difluoroethyl, 2,2,2-trifluoroethyl, or pentafluoroethyl. Examples for fluorinated $C_1$-$C_3$-alkyl are, in addition to those mentioned for fluorinated $C_1$-$C_2$-alkyl, 1-fluoropropyl, 2-fluoropropyl, 3-fluoropropyl, 1,1-difluoropropyl, 2,2-difluoropropyl, 1,2-difluoropropyl, 3,3-difluoropropyl, 3,3,3-trifluoropropyl, heptafluoropropyl, 1,1,1-trifluoroprop-2-yl, heptafluoropropyl, and the like. Examples for fluorinated $C_1$-$C_4$-alkyl are, in addition to those mentioned for fluorinated $C_1$-$C_3$-alkyl, 4-fluorobutyl, the nonafluorobutyls, the heptadecafluorooctyls and the like.

In perfluorinated alkyl, all hydrogen atoms are replaced by fluorine atoms. Examples are trifluoromethyl, pentafluoroethyl, heptafluoropropyl, the nonafluorobutyls, the heptadecafluorooctyls and the like.

If the term "hydroxyalkyl" is used without prefix ($C_n$-$C_m$), it indicates saturated straight-chain or branched aliphatic hydrocarbon radicals having in general 1 to 30 ("$C_1$-$C_{30}$-hydroxyalkyl") carbon atoms, preferably 1 to 20 ("$C_1$-$C_{20}$-hydroxyalkyl") carbon atoms, in particular 1 to 10 ("$C_1$-$C_{10}$-hydroxyalkyl") carbon atoms, specifically 2 to 6 ("$C_2$-$C_6$-hydroxyalkyl") or 2 to 4 ("$C_2$-$C_4$-hydroxyalkyl") or 2 to 3 ("$C_2$-$C_3$-hydroxyalkyl") carbon atoms, where one hydrogen atom in these groups is replaced by a hydroxyl group. $C_2$-$C_3$-Hydroxyalkyl is for example 1-hydroxyethyl, 2-hydroxyethyl, 1-hydroxyprop-1-yl, 1-hydroxyprop-2-yl, 2-hydroxyprop-1-yl, 2-hydroxyprop-2-yl or 3-hydroxyprop-1-yl, and in particular 2-hydroxyethyl or 2-hydroxyprop-1-yl. Examples for $C_2$-$C_4$-hydroxyalkyl are, in addition to those listed for $C_2$-$C_3$-hydroxyalkyl, 1-hydroxybut-1-yl, 1-hydroxybut-2-yl, 1-hydroxybut-3-yl, 2-hydroxybut-1-yl, 2-hydroxybut-2-yl, 2-hydroxybut-3-yl, 3-hydroxybut-1-yl, 4-hydroxybut-1-yl, 1-hydroxy-2-methyl-propy-1-yl, 2-hydroxy-2-methyl-propy-1-yl, 3-hydroxy-2-methyl-propy-1-yl and 2-(hydroxymethyl)-2-methyl-eth-1-yl, and in particular 2-hydroxyethyl, 2-hydroxyprop-1-yl or 4-hydroxybut-1-yl.

If the term "alkenyl" as used herein and in the alkyl moieties of alkenyloxy, alkenylthio, alkenylsulfinyl, alkenylsulfonyl, alkenylcarbonyl and the like is used without prefix ($C_n$-$C_m$), it indicates monounsaturated (i.e. containing one C—C double bond) straight-chain or branched aliphatic hydrocarbon radicals having in general 2 to 30 ("$C_2$-$C_{30}$-alkenyl") carbon atoms, preferably 2 to 20 ("$C_2$-$C_{20}$-alkenyl") carbon atoms, in particular 2 to 10 ("$C_2$-$C_{10}$-alkenyl") carbon atoms, specifically 2 to 6 ("$C_2$-$C_6$-alkenyl") or 2 to 4 ("$C_2$-$C_4$-alkenyl") carbon atoms, where the C—C double bond can be in any position. "$C_2$-$C_3$-alkenyl" refers to monounsaturated straight-chain or branched aliphatic hydrocarbon radicals having 2 to 3 carbon atoms and a C—C double bond in any position. "$C_2$-$C_4$-alkenyl" refers to monounsaturated straight-chain or branched aliphatic hydrocarbon radicals having 2 to 4 carbon atoms and a C—C double bond in any position. "$C_2$-$C_6$-alkenyl" refers to monounsaturated straight-chain or branched aliphatic hydrocarbon radicals having 2 to 6 carbon atoms and a C—C double bond in any position. "$C_2$-$C_8$-alkenyl" refers to monounsaturated straight-chain or branched aliphatic hydrocarbon radicals having 2 to 8 carbon atoms and a C—C double bond in any position. "$C_2$-$C_{10}$-alkenyl" refers to monounsaturated straight-chain or branched aliphatic hydrocarbon radicals having 2 to 10 carbon atoms and a C—C double bond in any position. Examples for $C_2$-$C_3$-alkenyl are ethenyl, 1-propenyl, 2-propenyl or 1-methylethenyl. Examples for $C_2$-$C_4$-alkenyl are ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl. Examples for $C_2$-$C_6$-alkenyl are ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl and the like. Examples for $C_2$-$C_{10}$-alkenyl are, in addition to the examples mentioned for $C_2$-$C_6$-alkenyl, 1-heptenyl, 2-heptenyl, 3-heptenyl, 1-octenyl, 2-octenyl, 3-octenyl, 4-octenyl, 1-nonenyl, 2-nonenyl, 3-nonenyl, 4-nonenyl, 1-decenyl, 2-decenyl, 3-decenyl, 4-decenyl, 5-decenyl and the positional isomers thereof.

If the terminal C—C double bond is in a terminal position, i.e. if the radical contains a C=$CH_2$ group, the alkenyl group is also termed a vinyl group.

If the term "haloalkenyl" as used herein, which is also expressed as "alkenyl which is partially or fully halogenated", and in the alkenyl moieties of haloalkenyloxy, haloalkenylthio, haloalkenylsulfinyl, haloalkenylsulfonyl, haloalkenylcarbonyl and the like is used without prefix ($C_n$-$C_m$), it indicates monounsaturated straight-chain or branched aliphatic hydrocarbon radicals having in general 2 to 30 ("$C_2$-$C_{30}$-haloalkenyl") carbon atoms, preferably 2 to 20 ("$C_2$-$C_{20}$-haloalkenyl") carbon atoms, in particular 2 to 10 ("$C_2$-$C_{10}$-haloalkenyl") carbon atoms, specifically 2 to 6 ("$C_2$-$C_6$-haloalkenyl") or 2 to 4 ("$C_2$-$C_4$-haloalkenyl") carbon atoms, where some or all of the hydrogen atoms in these groups are replaced by halogen atoms as mentioned above, in particular fluorine, chlorine and bromine, and where the C—C double bond can be in any position. "$C_2$-$C_3$-Haloalkenyl" refers to monounsaturated straight-chain or branched aliphatic hydrocarbon radicals having 2 to 3 carbon atoms and a C—C double bond in any position (as mentioned above), where some or all of the hydrogen atoms in these groups are replaced by halogen atoms as mentioned above, in particular fluorine, chlorine and/or bromine. "$C_2$-$C_4$-Haloalkenyl" refers to monounsaturated straight-chain or branched aliphatic hydrocarbon radicals having 2 to 4 carbon atoms and a C—C double bond in any position (as mentioned above), where some or all of the hydrogen atoms in these groups are replaced by halogen atoms as mentioned above, in particular fluorine, chlorine and/or bromine. "$C_2$-$C_6$-Haloalkenyl" refers to monounsaturated straight-chain or branched aliphatic hydrocarbon radicals having 2 to 6 carbon atoms and a double bond in any position (as mentioned above), where some or all of the hydrogen atoms in these groups are replaced by halogen atoms as mentioned above, in particular fluorine, chlorine and/or bromine. "$C_2$-$C_8$-Haloalkenyl" refers to monounsaturated straight-chain or branched aliphatic hydrocarbon radicals having 2 to 8 carbon atoms and a double bond in any position (as mentioned above), where some or all of the hydrogen atoms in these groups are replaced by halogen atoms as mentioned above, in particular fluorine, chlorine and/or bromine. "$C_2$-$C_{10}$-Haloalkenyl" refers to monounsaturated straight-chain or branched aliphatic hydrocarbon radicals having 2 to 10 carbon atoms and a double bond in any position (as mentioned above), where some or all of the hydrogen atoms in these groups are replaced by halogen atoms as mentioned above, in particular fluorine, chlorine and/or bromine; etc. Examples are chlorovinyl, chloroallyl and the like.

If the term "alkapolyenyl" is used without prefix ($C_n$-$C_m$), it indicates straight-chain or branched aliphatic hydrocarbon radicals having in general 4 to 30 ("$C_4$-$C_{30}$-alkapolyenyl") carbon atoms, preferably 4 to 20 ("$C_4$-$C_{20}$-alkapolyenyl") carbon atoms, in particular 4 to 10 ("$C_4$-$C_{10}$-alkapolyenyl") carbon atoms, and two or more conjugated or isolated, but non-cumulated C—C double bonds. Examples are buta-1,3-dien-1-yl, buta-1,3-dien-2-yl, penta-1,3-dien-1-yl, penta-1,3-dien-2-yl, penta-1,3-dien-3-yl, penta-1,3-dien-4-yl, penta-1,3-dien-5-yl, penta-1,4-dien-1-yl, penta-1,4-dien-2-yl, penta-1,4-dien-3-yl, and the like.

If the term "haloalkapolyenyl" is used without prefix ($C_n$-$C_m$), it indicates straight-chain or branched aliphatic hydrocarbon radicals having in general 4 to 30 ("$C_4$-$C_{30}$-haloalkapolyenyl") carbon atoms, preferably 4 to 20 ("$C_4$-$C_{20}$-haloalkapolyenyl") carbon atoms, in particular 4 to 10 ("$C_4$-$C_{10}$-haloalkapolyenyl") carbon atoms, and two or more conjugated or isolated, but non-cumulated C—C double bonds, as defined above, where some or all of the hydrogen atoms in these groups are replaced by halogen atoms as mentioned above, in particular fluorine, chlorine and bromine.

If the term "alkynyl" as used herein and in the alkynyl moieties of alkynyloxy, alkynylthio, alkynylsulfinyl, alkynylsulfonyl, alkynylcarbonyl and the like is used without prefix ($C_n$-$C_m$), it indicates straight-chain or branched aliphatic hydrocarbon radicals having in general 2 to 30 ("$C_2$-$C_{30}$-alkynyl") carbon atoms, preferably 2 to 20 ("$C_2$-$C_{20}$-alkynyl") carbon atoms, in particular 2 to 10 ("$C_2$-$C_{10}$-alkynyl") carbon atoms, specifically 2 to 6 ("$C_2$-$C_6$-alkynyl") or 2 to 4 ("$C_2$-$C_4$-alkynyl") carbon atoms, and one triple bond in any position. "$C_2$-$C_3$-Alkynyl" indicates straight-chain or branched hydrocarbon radicals having 2 to 3 carbon atoms and one triple bond in any position. "$C_2$-$C_4$-Alkynyl" indicates straight-chain or branched hydrocarbon radicals having 2 to 4 carbon atoms and one triple bond in any position. "$C_2$-$C_6$-Alkynyl" indicates straight-chain or branched hydrocarbon radicals having 2 to 6 carbon atoms and one triple bond in any position. "$C_2$-$C_8$-Alkynyl" indicates straight-chain or branched hydrocarbon radicals having 2 to 8 carbon atoms and one triple bond in any position. "$C_2$-$C_{10}$-Alkynyl" indicates straight-chain or branched hydrocarbon radicals having 2 to 10 carbon atoms and one triple bond in any position; etc. Examples for $C_2$-$C_3$-alkynyl are ethynyl, 1-propynyl or 2-propynyl. Examples for $C_2$-$C_4$-alkynyl are ethynyl, 1-propynyl, 2-propynyl, 1-butynyl, 2-butynyl, 3-butynyl, 1-methyl-2-propynyl and the like. Examples for $C_2$-$C_6$-alkynyl are ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl and the like.

If the term "alkyne" as used herein is used without prefix ($C_n$-$C_m$), it indicates a straight-chain or branched aliphatic hydrocarbon having in general 2 to 30 ("$C_2$-$C_{30}$-alkyne") carbon atoms, preferably 2 to 20 ("$C_2$-$C_{20}$-alkyne") carbon atoms, in particular 2 to 10 ("$C_2$-$C_{10}$-alkyne") carbon atoms, specifically 2 to 6 ("$C_2$-$C_6$-alkyne") or 2 to 4 ("$C_2$-$C_4$-alkyne") carbon atoms, and one triple bond in any position. "$C_2$-$C_3$-Alkyne" indicates a straight-chain or branched hydrocarbon having 2 or 3 carbon atoms and one triple bond. "$C_2$-$C_4$-Alkyne" indicates a straight-chain or branched hydrocarbon having 2 to 4 carbon atoms and one triple bond in any position. "$C_2$-$C_6$-Alkyne" indicates a straight-chain or branched hydrocarbon having 2 to 6 carbon atoms and one triple bond in any position. "$C_2$-$C_8$-Alkyne" indicates a straight-chain or branched hydrocarbon having 2 to 8 carbon atoms and one triple bond in any position. "$C_2$-$C_{10}$-Alkyne" indicates a straight-chain or branched hydrocarbon having 2 to 10 carbon atoms and one triple bond in any position; etc. Examples for $C_2$-$C_3$-alkyne are ethyne and propyne. Examples for $C_2$-$C_4$-alkyne are ethyne, propyne, but-1-yne and but-2-yne. Examples for $C_2$-$C_6$-alkynyl are ethyne, propyne, but-1-yne, but-2-yne, pent-1-yne, pent-2-yne, 3-methyl-but-1-yne, hex-1-yne, hex-2-yne, hex-3-yne, 4-methyl-pent-1-yne, 4-methyl-pent-2-yne, 3-methyl-pent-1-yne, 3,3-dimethyl-but-1-yne, and the like.

In a terminal alkyne the C—C triple bond is in a terminal position; i.e. the alkyne contains a C≡CH group.

If the term "haloalkynyl" as used herein, which is also expressed as "alkynyl which is partially or fully halogenated", and in the alkynyl moieties of haloalkynyloxy, haloalkynylthio, haloalkynylsulfinyl, haloalkynylsulfonyl, haloalkynylcarbonyl and the like is used without prefix ($C_n$-$C_m$), it indicates straight-chain or branched aliphatic hydrocarbon radicals having in general 2 to 30 ("$C_2$-$C_{30}$-haloalkynyl") carbon atoms, preferably 2 to 20 ("$C_2$-$C_{20}$-haloalkynyl") carbon atoms, in particular 2 to 10 ("$C_2$-$C_{10}$-haloalkynyl") carbon atoms, specifically 2 to 6 ("$C_2$-$C_6$-haloalkynyl") or 2 to 4 ("$C_2$-$C_4$-haloalkynyl") carbon atoms, and one triple bond in any position, where some or all of the hydrogen atoms in these groups are replaced by halogen atoms as mentioned above, in particular fluorine, chlorine and bromine. "$C_2$-$C_3$-Haloalkynyl" indicates straight-chain or branched hydrocarbon radicals having 2 to 3 carbon atoms and one triple bond in any position, where some or all of the hydrogen atoms in these groups are replaced by halogen atoms as mentioned above, in particular fluorine, chlorine and bromine. "$C_2$-$C_4$-Haloalkynyl" indicates straight-chain or branched hydrocarbon radicals having 2 to 4 carbon atoms and one triple bond in any position, where some or all of the hydrogen atoms in these groups are replaced by halogen atoms as mentioned above, in particular fluorine, chlorine and bromine. "$C_2$-$C_6$-Haloalkynyl" indicates straight-chain or branched hydrocarbon radicals having 2 to 6 carbon atoms and one triple bond in any position, where some or all of the hydrogen atoms in these groups are replaced by halogen atoms as mentioned above, in particular fluorine, chlorine and bromine. "$C_2$-$C_8$-Haloalkynyl" indicates straight-chain or branched hydrocarbon radicals having 2 to 8 carbon atoms and one triple bond in any position, where some or all of the hydrogen atoms in these groups are replaced by halogen atoms as mentioned above, in particular fluorine, chlorine and bromine. "$C_2$-$C_{10}$-Haloalkynyl" indicates straight-chain or branched hydrocarbon radicals having 2 to 10 carbon atoms and one triple bond in any position, where some or all of the hydrogen atoms in these groups are replaced by halogen atoms as mentioned above, in particular fluorine, chlorine and bromine; etc.

If the term "alkapolyynyl" is used without prefix ($C_n$-$C_m$), it indicates straight-chain or branched aliphatic hydrocarbon radicals having in general 4 to 30 ("$C_4$-$C_{30}$-alkapolyynyl") carbon atoms, preferably 4 to 20 ("$C_4$-$C_{20}$-alkapolyynyl") carbon atoms, in particular 4 to 10 ("$C_4$-$C_{10}$-alkypolyenyl") carbon atoms, and two or more C—C triple bonds. Examples are buta-1,3-diyn-1-yl, penta-1,3-diyn-1-yl, penta-2,4-diyn-1-yl, penta-1,4-diyn-1-yl, penta-1,4-diyn-3-yl, and the like.

If the term "haloalkapolyynyl" is used without prefix ($C_n$-$C_m$), it indicates straight-chain or branched aliphatic hydrocarbon radicals having in general 4 to 30 ("$C_4$-$C_{30}$-haloalkapolyynyl") carbon atoms, preferably 4 to 20 ("$C_4$-$C_2$-haloalkapolyynyl") carbon atoms, in particular 4 to 10 ("$C_4$-$C_{10}$-haloalkapolyynyl") carbon atoms, and two or C—C double triple, as defined above, where some or all of the hydrogen atoms in these groups are replaced by halogen atoms as mentioned above, in particular fluorine, chlorine and bromine.

"Mixed alkenyl/alkynyl" indicates straight-chain or branched aliphatic hydrocarbon radicals having at least one C—C double bond and at least one C—C triple bond. If the term "mixed alkenyl/alkynyl" is used without prefix ($C_n$-$C_m$), it indicates straight-chain or branched hydrocarbon radicals having in general 4 to 30 ("$C_4$-$C_{30}$-mixed alkenyl/alkynyl") carbon atoms, preferably 4 to 20 ("$C_4$-$C_{20}$-mixed alkenyl/alkynyl") carbon atoms, in particular 4 to 10 ("$C_4$-$C_{10}$-mixed alkenyl/alkynyl") carbon atoms, and at least one C—C double bond and at least one C—C triple bond.

If the term "mixed haloalkenyl/alkynyl" is used without prefix ($C_n$-$C_m$), it indicates straight-chain or branched aliphatic hydrocarbon radicals having in general 4 to 30 ("$C_4$-$C_{30}$-mixed haloalkenyl/alkynyl") carbon atoms, preferably 4 to 20 ("$C_4$-$C_{20}$-mixed haloalkenyl/alkynyl") carbon atoms, in particular 4 to 10 ("$C_4$-$C_{10}$-mixed haloalkenyl/alkynyl") carbon atoms, and at least one C—C double bond and at least one C—C triple bond, where some or all of the hydrogen atoms in these groups are replaced by halogen atoms as mentioned above, in particular fluorine, chlorine and bromine.

If the term "cycloalkyl" is used without prefix ($C_n$-$C_m$), it indicates monocyclic saturated hydrocarbon radicals having in general 3 to 20 ("$C_3$-$C_{20}$-cycloalkyl"), in particular 3 to 10 ("$C_3$-$C_{10}$-cycloalkyl"), specifically 3 to 8 ("$C_3$-$C_8$-cycloalkyl") or more specifically 3 to 6 ("$C_3$-$C_6$-cycloalkyl") carbon atoms (and of course no heteroatoms) as ring members; i.e. all ring members are carbon atoms. Examples of cycloalkyl having 3 to 4 carbon atoms comprise cyclopropyl and cyclobutyl. Examples of cycloalkyl having 3 to 5 carbon atoms comprise cyclopropyl, cyclobutyl and cyclopentyl. Examples of cycloalkyl having 3 to 6 carbon atoms comprise cyclopropyl, cyclobutyl, cyclopentyl and cyclohexyl. Examples of cycloalkyl having 3 to 8 carbon atoms comprise cyclopropyl, cyclobutyl, cyclopentyl, cyclohexyl, cycloheptyl and cyclooctyl. Examples of cycloalkyl having 3 to 10 carbon atoms comprise cyclopropyl, cyclobutyl, cyclopentyl, cyclohexyl, cycloheptyl, cyclooctyl, cyclononyl and cyclodecyl.

If the term "halocycloalkyl", which is also expressed as "cycloalkyl which is partially or fully halogenated", is used without prefix ($C_n$-$C_m$), it indicates monocyclic saturated hydrocarbon radicals having in general 3 to 20 ("$C_3$-$C_{20}$-halocycloalkyl"), in particular 3 to 10 ("$C_3$-$C_{10}$-halocycloalkyl"), specifically 3 to 8 ("$C_3$-$C_8$-halocycloalkyl") or more specifically 3 to 6 ("$C_3$-$C_6$-halocycloalkyl") carbon atoms (as mentioned above), in which some or all of the hydrogen atoms are replaced by halogen atoms as mentioned above, in particular fluorine, chlorine and bromine.

If the term "polycarbocyclyl" is used without prefix ($C_n$-$C_m$), it indicates bi- or polycyclic saturated or unsaturated hydrocarbon radicals having in general 4 to 20 ("$C_4$-$C_{20}$-polycarbocyclyl"), in particular 6 to 20 ("$C_6$-$C_{20}$-polycarbocyclyl") carbon atoms (and of course no heteroatoms) as ring members; i.e. all ring members are carbon atoms. The bi- and polycyclic radicals can be condensed, bridged or spiro-bound rings. Unsaturated polycarbocyclyl contains one or more C—C double and/or triple bonds in the ring and are not throughout aromatic. Examples of bicyclic condensed saturated radicals having 6 to 10 carbon atoms comprise bicyclo[3.1.0]hexyl, bicyclo[3.2.0]heptyl, bicyclo [3.3.0]octyl (1,2,3,3a,4,5,6,6a-octahydropentalenyl), bicyclo[4.2.0]octyl, bicyclo[4.3.0]nonyl (2,3,3a,4,5,6,7,7a-octahydro-1H-indene), bicyclo[4.4.0]decyl (decalinyl) and the like. Examples of bridged bicyclic condensed saturated radicals having 7 to 10 carbon atoms comprise bicyclo [2.2.1]heptyl, bicyclo[3.1.1]heptyl, bicyclo[2.2.2]octyl, bicyclo[3.2.1]octyl and the like. Examples of bicyclic spiro-bound saturated radicals are spiro[2.2]pentyl, spiro[2.4] heptyl, spiro[4.4]nonyl, spiro[4.5]decyl, spiro[5.5]undecyl and the like. Examples for saturated polycyclic radicals comprise 2,3,4,4a,4b,5,6,7,8,8a,9,9a-dodecahydro-1H-fluorenyl, 1,2,3,4,4a,5,6,7,8,8a,9,9a,10,10a-tetradecahydroanthracenyl, 1,2,3,4,4a,4b,5,6,7,8,8a,9,10,10a-tetradecahydrophenanthrenyl, 2,3,3a,4,5,6,6a,7,8,9,9a,9b-dodecahydro-1H-phenalenyl, adamantly and the like. Examples for bicyclic condensed unsaturated radicals are 1,2,3,4,4a,5,8, 8a-octahydronaphthalenyl, 1,2,3,4,4a,5,6,8a-octahydronaphthalenyl, 1,2,3,4,4a,5,6,7-octahydronaphthalenyl, 1,2,3,4,5,6,7,8-octahydronaphthalenyl, 1,2,3,4,5,8-hexahydronaphthalenyl, 1,4,4a,5,8,8a-hexahydronaphthalenyl, indanyl, indenyl, the hexahydroindenyls, such as 2,3,3a,4, 7,7a-hexahydro-1H-indenyl or 2,3,3a,4,5,7a-hexahydro-1H-indenyl, the tetrahydroindenyls, such as 2,3,3a,7a-tetrahydro-1H-indenyl or 2,3,4,7-tetrahydro-1H-indenyl, and the like. Examples for tricyclic condensed unsaturated radicals are fluorenyl, the dihydrofluorenyl, the tetrahydrofluorenyl, the hexahydrofluorenyls and the decahydrofluorenyls.

Some partially unsaturated polycarbocyclyl rings may be considered as aryl groups in the terms of the present invention if the moiety taking part in the reaction in question is aromatic. Examples are indanyl, indenyl and fluorenyl: If the reaction takes place on the 6-membered aromatic moiety of these fused systems or on a functional group bound to the 6-membered aromatic moiety of these fused systems, the indanyl, indenyl or fluorenyl radical is considered as an aryl ring (see also below definition of aryl). If the reaction is to take place on the 5-membered non-aromatic moiety or on a functional group bound to the 5-membered non-aromatic moiety, indanyl, indenyl and fluorenyl are considered as a polycarbocyclyl ring. Another example is 1,2,3,4-tetrahydronaphthyl: If the reaction takes place on the aromatic moiety of this fused system or on a functional group bound to the 6-membered aromatic moiety, the radical is considered as an aryl ring. If it takes place on the non-aromatic moiety or on a functional group bound thereto, this radical is considered as a polycarbocyclyl ring.

If the term "halopolycarbocyclyl" is used without prefix ($C_n$-$C_m$), it indicates bi- or polycyclic saturated or unsaturated hydrocarbon radicals having in general 4 to 20 ("$C_4$-$C_{20}$-halopolycarbocyclyl"), in particular 6 to 20 ("$C_6$-$C_{20}$-halopolycarbocyclyl") carbon atoms, as defined above, in which some or all of the hydrogen atoms are replaced by halogen atoms as mentioned above, in particular fluorine, chlorine and bromine. The bi- and polycyclic radicals can be condensed, bridged or spiro-bound rings.

If the term "cycloalkenyl" is used without prefix ($C_n$-$C_m$), it indicates monocyclic partially unsaturated, non-aromatic hydrocarbon radicals having in general 3 to 20 ("$C_3$-$C_{20}$-cycloalkenyl"), in particular 3 to 10 ("$C_3$-$C_{10}$-cycloalkenyl"), specifically 3 to 8 ("$C_3$-$C_8$-cycloalkenyl") or more specifically 5 to 7 ("$C_5$-$C_7$-cycloalkenyl") carbon atoms (and of course no heteroatoms) as ring members; i.e. all ring members are carbon atoms; and one or more non-cumulative, preferably one, C—C double bonds in the ring. Examples for $C_5$-$C_6$-cycloalkenyl are cyclopent-1-en-1-yl, cyclopent-1-en-3-yl, cyclopent-1-en-4-yl, cyclopenta-1,3-dien-1-yl, cyclopenta-1,3-dien-2-yl, cyclopenta-1,3-dien-5-yl, cyclohex-1-en-1-yl, cyclohex-1-en-3-yl, cyclohex-1-en-4-yl, cyclohexa-1,3-dien-1-yl, cyclohexa-1,3-dien-2-yl, cyclohexa-1,3-dien-5-yl, cyclohexa-1,4-dien-1-yl and cyclohexa-1,4-dien-3-yl. Examples of $C_5$-$C_7$-cycloalkenyl are, in addition to those mentioned above for $C_5$-$C_6$-cycloalkenyl, cyclohept-1-en-1-yl, cyclohept-1-en-3-yl, cyclohept-1-en-4-yl, cyclohept-1-en-5-yl, cyclohepta-1,3-dien-1-yl, cyclohepta-1,3-dien-2-yl, cyclohepta-1,3-dien-5-yl, cyclohepta-1,3-dien-6-yl, cyclohepta-1,4-dien-1-yl, cyclohepta-1,4-dien-2-yl, cyclohepta-1,4-dien-3-yl and cyclohepta-1,4-dien-6-yl. Examples of $C_3$-$C_8$-cycloalkenyl are, in addition to those mentioned above for $C_5$-$C_7$-cycloalkenyl, cycloprop-1-en-1-yl, cycloprop-1-en-3-yl, cyclobut-1-en-1-yl, cyclobut-1-en-3-yl, cyclooct-1-en-1-yl, cyclooct-1-en-3-yl, cyclooct-1-en-4-yl, cyclooct-1-en-5-yl, cycloocta-1,3-dien-1-yl, cycloocta-1,3-dien-2-yl, cycloocta-1,3-dien-5-yl, cycloocta-1,3-dien-6-yl, cycloocta-1,4-dien-1-yl, cycloocta-1,4-dien-2-yl, cycloocta-1,4-dien-3-yl, cycloocta-1,4-dien-6-yl, cycloocta-1,4-dien-7-yl, cycloocta-1,5-dien-1-yl, and cycloocta-1,5-dien-3-yl.

If the term "halocycloalkenyl", which is also expressed as "cycloalkenyl which is partially or fully halogenated", is used without prefix ($C_n$-$C_m$), it indicates monocyclic partially unsaturated, non-aromatic hydrocarbon hydrocarbon radicals having in general 3 to 20 ("$C_3$-$C_{20}$-halocycloalkenyl"), in particular 3 to 10 ("$C_3$-$C_{10}$-halocycloalkenyl"), specifically 3 to 8 ("$C_3$-$C_8$-halocycloalkenyl") or more specifically 3 to 6 ("$C_3$-$C_6$-halocycloalkenyl") carbon atoms (as mentioned above) and one or more non-cumulative, preferably one, C—C double bonds in the ring, where some or all of the hydrogen atoms are replaced by halogen atoms as mentioned above, in particular fluorine, chlorine and bromine.

If the term "cycloalkynyl" is used without prefix ($C_n$-$C_m$), it indicates monocyclic hydrocarbon radicals having in general 8 to 20 ("$C_8$-$C_{20}$-cycloalkynyl"), in particular 8 to 16 ("$C_8$-$C_{16}$-cycloalkynyl"), specifically 8 to 14 ("$C_8$-$C_{14}$-cycloalkynyl") carbon atoms (and of course no heteroatoms) as ring members; i.e. all ring members are carbon atoms; and one or more, preferably one, C—C triple bonds in the ring. Examples are cyclooctynyl, cyclodecynyl, cyclododecynyl, cyclotetradecynyl, cyclohexadecynyl and the like.

If the term "halocycloalkynyl", which is also expressed as "cycloalkynyl which is partially or fully halogenated", is used without prefix ($C_n$-$C_m$), it indicates monocyclic hydrocarbon radicals having in general 8 to 20 ("$C_8$-$C_{20}$-cycloalkynyl"), in particular 8 to 10 ("$C_8$-$C_{16}$-cycloalkynyl"), specifically 8 to 14 ("$C_8$-$C_{14}$-cycloalkynyl") carbon atoms and one or more, preferably one, C—C triple bonds in the ring, where some or all of the hydrogen atoms are replaced by halogen atoms as mentioned above, in particular fluorine, chlorine and bromine.

"Mixed cycloalkenyl/cycloalkynyl" relates to monocyclic hydrocarbon radicals comprising at least one C—C double bond and at least one C—C triple bond in the ring. If used without prefix prefix ($C_n$-$C_m$), it indicates monocyclic hydrocarbon radicals having in general 8 to 20 ("$C_8$-$C_{20}$-mixed cycloalkenyl/cycloalkynyl"), in particular 8 to 16 ("$C_8$-$C_{16}$-mixed cycloalkenyl/cycloalkynyl"), specifically 8 to 14 ("$C_8$-$C_{14}$-mixed cycloalkenyl/cycloalkynyl") carbon atoms (and of course no heteroatoms) as ring members; i.e. all ring members are carbon atoms.

If used without prefix prefix ($C_n$-$C_m$), the term "mixed haloycloalkenyl/cycloalkynyl" indicates monocyclic hydrocarbon radicals having in general 8 to 20 ("$C_8$-$C_{20}$-mixed cycloalkenyl/cycloalkynyl"), in particular 8 to 16 ("$C_8$-$C_{16}$-mixed cycloalkenyl/cycloalkynyl"), specifically 8 to 14 ("$C_8$-$C_{14}$-mixed cycloalkenyl/cycloalkynyl") carbon atoms and at least one C—C double bond and at least one C—C triple bond in the ring, as defined above, where some or all of the hydrogen atoms are replaced by halogen atoms as mentioned above, in particular fluorine, chlorine and bromine.

If the term "cycloalkyl-alkyl" is used without prefix ($C_n$-$C_m$), it indicates a cycloalkyl group as defined above, in particular a $C_3$-$C_8$-cycloalkyl group, specifically a $C_3$-$C_6$-cycloalkyl group as defined above which is bound to the remainder of the molecule via an alkyl group as defined above, in particular a $C_1$-$C_4$-alkyl group. The term "cycloalkyl-$C_1$-$C_4$-alkyl" refers to a cycloalkyl group as defined above, in particular a $C_3$-$C_8$-cycloalkyl group ("$C_3$-$C_8$-cycloalkyl-$C_1$-$C_4$-alkyl"), specifically a $C_3$-$C_6$-cycloalkyl group ("$C_3$-$C_8$-cycloalkyl-$C_1$-$C_4$-alkyl") as defined above, which is bound to the remainder of the molecule via a $C_1$-$C_4$-alkyl group, as defined above. Examples for $C_3$-$C_4$-cycloalkyl-$C_1$-$C_4$-alkyl are cyclopropylmethyl, cyclopropylethyl, cyclopropylpropyl, cyclobutylmethyl, cyclobutylethyl and cyclobutylpropyl, Examples for $C_3$-$C_6$-cycloalkyl-$C_1$-$C_4$-alkyl are, in addition to those mentioned for $C_3$-$C_4$-cycloalkyl-$C_1$-$C_4$-alkyl, cyclopentylmethyl, cyclopentylethyl, cyclopentylpropyl, cyclohexylmethyl, cyclohexylethyl and cyclohexylpropyl. Examples for $C_3$-$C_8$-cycloalkyl-$C_1$-$C_4$-alkyl are, in addition to those mentioned for $C_3$-$C_6$-cycloalkyl-$C_1$-$C_4$-alkyl, cycloheptylmethyl, cycloheptylethyl, cyclooctylmethyl and the like.

If the term "halocycloalkyl-alkyl" is used without prefix ($C_n$-$C_m$), it indicates a halocycloalkyl group as defined above, in particular a $C_3$-$C_8$-halocycloalkyl group, specifically a $C_3$-$C_6$-halocycloalkyl group as defined above, which is bound to the remainder of the molecule via an alkyl group as defined above, in particular a $C_1$-$C_4$-alkyl group. The term "halocycloalkyl-$C_1$-$C_4$-alkyl" refers to halocycloalkyl group as defined above, in particular a $C_3$-$C_8$-halocycloalkyl group as defined above, which is bound to the remainder of the molecule via a $C_1$-$C_4$-alkyl group, as defined above.

"Alkoxy" is an alkyl group, as defined above, attached via an oxygen atom to the remainder of the molecule; generally a $C_1$-$C_{30}$-alkyl group ("$C_1$-$C_{30}$-alkoxy"), preferably a $C_1$-$C_2$-alkyl group ("$C_1$-$C_{20}$-alkoxy"), in particular a $C_1$-$C_{10}$-alkyl group ("$C_1$-$C_{10}$-alkoxy"), specifically a $C_1$-$C_6$-alkyl group ("$C_1$-$C_6$-alkoxy") or a $C_1$-$C_4$-alkyl group ("$C_1$-$C_4$-aloxy") attached via an oxygen atom to the remainder of the molecule. "$C_1$-$C_2$-Alkoxy" is a $C_1$-$C_2$-alkyl group, as defined above, attached via an oxygen atom. "$C_1$-$C_3$-Alkoxy" is a $C_1$-$C_3$-alkyl group, as defined above, attached via an oxygen atom. $C_1$-$C_2$-Alkoxy is methoxy or ethoxy. $C_1$-$C_3$-Alkoxy is additionally, for example, n-propoxy and 1-methylethoxy (isopropoxy). $C_1$-$C_4$-Alkoxy is additionally, for example, butoxy, 1-methylpropoxy (sec-butoxy), 2-methylpropoxy (isobutoxy) or 1,1-dimethylethoxy (tert-butoxy). $C_1$-$C_6$-Alkoxy is additionally, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy. $C_5$-$C_8$-Alkoxy is additionally, for example, heptyloxy, octyloxy, 2-ethylhexyloxy and positional isomers thereof. $C_1$-$C_{10}$-Alkoxy is additionally, for example, nonyloxy, decyloxy and positional isomers thereof.

"Haloalkoxy" is a haloalkyl group, as defined above, attached via an oxygen atom to the remainder of the molecule; generally a $C_1$-$C_{30}$-haloalkyl group ("$C_1$-$C_{30}$-haloalkoxy"), preferably a $C_1$-$C_{20}$-haloalkyl group ("$C_1$-$C_{20}$-haloalkoxy"), in particular a $C_1$-$C_{10}$-haloalkyl group ("$C_1$-$C_{10}$-haloalkoxy"), specifically a $C_1$-$C_6$-haloalkyl group ("$C_1$-$C_6$-haloalkoxy") or a $C_1$-$C_4$-haloalkyl group ("$C_1$-$C_4$-haloaloxy") attached via an oxygen atom to the remainder of the molecule. The term "$C_1$-$C_2$-haloalkoxy" is a $C_1$-$C_2$-haloalkyl group, as defined above, attached via an oxygen atom. The term "$C_1$-$C_3$-haloalkoxy" is a $C_1$-$C_3$-haloalkyl group, as defined above, attached via an oxygen atom. $C_1$-$C_2$-Haloalkoxy is, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or $OC_2F_5$. $C_1$-$C_3$-Haloalkoxy is additionally, for example, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy or 1-($CH_2Br$)-2-bromoethoxy. $C_1$-$C_4$-Haloalkoxy is additionally, for example, 4-fluorobutoxy, 4-chlorobutoxy, 4-bromobutoxy or nonafluorobutoxy. $C_1$-$C_6$-Haloalkoxy is additionally, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy or dodecafluorohexoxy.

The term "alkoxy-alkyl" as used herein, refers to a straight-chain or branched alkyl group, as defined above, where one hydrogen atom is replaced by an alkoxy group, as defined above, generally to a $C_1$-$C_{30}$-alkyl group where one hydrogen atom is replaced by a $C_1$-$C_{30}$-alkoxy group ("$C_1$-$C_{30}$-alkoxy-$C_1$-$C_{30}$-alkyl"), preferably to a $C_1$-$C_{20}$-alkyl group where one hydrogen atom is replaced by a $C_1$-$C_{20}$-alkoxy group ("$C_1$-$C_{20}$-alkoxy-$C_1$-$C_{20}$-alkyl"), in particular to a $C_1$-$C_{10}$-alkyl group where one hydrogen atom is replaced by a $C_1$-$C_{10}$-alkoxy group ("$C_1$-$C_{10}$-alkoxy-$C_1$-$C_{10}$-alkyl"), specifically to a $C_1$-$C_6$-alkyl group where one hydrogen atom is replaced by a $C_1$-$C_6$-alkoxy group ("$C_1$-$C_6$-alkoxy-$C_1$-$C_6$-alkyl"), more specifically to a $C_1$-$C_4$-alkyl group where one hydrogen atom is replaced by a $C_1$-$C_4$-alkoxy group ("$C_1$-$C_4$-alkoxy-$C_1$-$C_4$-alkyl"). The term "$C_1$-$C_3$-alkoxy-$C_1$-$C_3$-alkyl" as used herein, refers to a straight-chain or branched alkyl group having 1 to 3 carbon atoms, as defined above, where one hydrogen atom is replaced by a $C_1$-$C_3$-alkoxy group, as defined above. Examples are methoxymethyl, ethoxymethyl, propoxymethyl, isopropoxymethyl, n-butoxymethyl, sec-butoxymethyl, isobutoxymethyl, tert-butoxymethyl, 1-methoxyethyl, 1-ethoxyethyl, 1-propoxyethyl, 1-isopropoxyethyl, 1-n-butoxyethyl, 1-sec-butoxyethyl, 1-isobutoxyethyl, 1-tert-butoxyethyl, 2-methoxyethyl, 2-ethoxyethyl, 2-propoxyethyl, 2-isopropoxyethyl, 2-n-butoxyethyl, 2-sec-butoxyethyl, 2-isobutoxyethyl, 2-tert-butoxyethyl, 1-methoxypropyl, 1-ethoxypropyl, 1-propoxypropyl, 1-isopropoxypropyl, 1-n-butoxypropyl, 1-sec-butoxypropyl, 1-isobutoxypropyl, 1-tert-butoxypropyl, 2-methoxypropyl, 2-ethoxypropyl, 2-propoxypropyl, 2-isopropoxypropyl, 2-n-butoxypropyl, 2-sec-butoxypropyl, 2-isobutoxypropyl, 2-tert-butoxypropyl, 3-methoxypropyl, 3-ethoxypropyl, 3-propoxypropyl, 3-isopropoxypropyl, 3-n-butoxypropyl, 3-sec-butoxypropyl, 3-isobutoxypropyl, 3-tert-butoxypropyl and the like.

The term "haloalkoxy-alkyl" as used herein, refers to a straight-chain or branched alkyl group, as defined above, where one hydrogen atom is replaced by an alkoxy group, as defined above, and wherein at least one, e.g. 1, 2, 3, 4 or all of the remaining hydrogen atoms (either in the alkoxy moiety or in the alkyl moiety or in both) are replaced by halogen atoms, in particular by fluorine, chlorine or bromine; generally to a $C_1$-$C_{30}$-alkyl group where one hydrogen atom is replaced by a $C_1$-$C_{30}$-alkoxy group ("$C_1$-$C_{30}$-alkoxy-$C_1$-$C_{30}$-alkyl"), preferably to a $C_1$-$C_{20}$-alkyl group where one hydrogen atom is replaced by a $C_1$-$C_{20}$-alkoxy group ("$C_1$-$C_{20}$-alkoxy-$C_1$-$C_{20}$-alkyl"), in particular to a $C_1$-$C_{10}$-alkyl group where one hydrogen atom is replaced by a $C_1$-$C_{10}$-alkoxy group ("$C_1$-$C_{10}$-alkoxy-$C_1$-$C_{10}$-alkyl"), specifically to a $C_1$-$C_6$-alkyl group where one hydrogen atom is replaced by a $C_1$-$C_6$-alkoxy group ("$C_1$-$C_6$-alkoxy-$C_1$-$C_6$-alkyl"), more specifically to a $C_1$-$C_4$-alkyl group where one hydrogen atom is replaced by a $C_1$-$C_4$-alkoxy group ("$C_1$-$C_4$-alkoxy-$C_1$-$C_4$-alkyl"), and wherein at least one, e.g. 1, 2, 3, 4 or all of the remaining hydrogen atoms (either in the alkoxy moiety or in the alkyl moiety or in both) are replaced by halogen atoms, in particular by fluorine, chlorine or bromine. Examples are difluoromethoxymethyl ($CHF_2OCH_2$), trifluoromethoxymethyl, 1-difluoromethoxyethyl, 1-trifluoromethoxyethyl, 2-difluoromethoxyethyl, 2-trifluoromethoxyethyl, difluoro-methoxy-methyl ($CH_3OCF_2$), 1,1-difluoro-2-methoxyethyl, 2,2-difluoro-2-methoxyethyl and the like.

"Alkylthio" is an alkyl group, as defined above, attached via a sulfur atom to the remainder of the molecule; generally a $C_1$-$C_{30}$-alkyl group ("$C_1$-$C_{30}$-alkylthio"), preferably a $C_1$-$C_{20}$-alkyl group ("$C_1$-$C_{20}$-alkylthio"), in particular a $C_1$-$C_{10}$-alkyl group ("$C_1$-$C_{10}$-alkylthio"), specifically a $C_1$-$C_6$-alkyl group ("$C_1$-$C_6$-alkylthio") or a $C_1$-$C_4$-alkyl group ("$C_1$-$C_4$-alkylthio") attached via a sulfur atom to the remainder of the molecule. The term "$C_1$-$C_2$-alkylthio" is a $C_1$-$C_2$-alkyl group, as defined above, attached via a sulfur atom. The term "$C_1$-$C_3$-alkylthio" is a $C_1$-$C_3$-alkyl group, as defined above, attached via a sulfur atom. $C_1$-$C_2$-Alkylthio is methylthio or ethylthio. $C_1$-$C_3$-Alkylthio is additionally, for example, n-propylthio or 1-methylethylthio (isopropylthio). $C_1$-$C_4$-Alkylthio is additionally, for example, butylthio, 1-methylpropylthio (sec-butylthio), 2-methylpropylthio (isobutylthio) or 1,1-dimethylethylthio (tert-butylthio). $C_1$-$C_6$-Alkylthio is additionally, for example, pentylthio, 1-methylbutylthio, 2-methylbutylthio, 3-methylbutylthio, 1,1-dimethylpropylthio, 1,2-dimethylpropylthio, 2,2-dimethylpropylthio, 1-ethylpropylthio, hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio. $C_1$-$C_8$-Alkylthio is additionally, for example, heptylthio, octylthio, 2-ethylhexylthio and positional isomers thereof. $C_1$-$C_{10}$-Alkylthio is additionally, for example, nonylthio, decylthio and positional isomers thereof.

"Haloalkylthio" is a haloalkyl group, as defined above, attached via a sulfur atom to the remainder of the molecule; generally a $C_1$-$C_{30}$-haloalkyl group ("$C_1$-$C_{30}$-haloalkylthio"), preferably a $C_1$-$C_{20}$-haloalkyl group ("$C_1$-$C_{20}$-haloalkylthio"), in particular a $C_1$-$C_{10}$-haloalkyl group ("$C_1$-$C_{10}$-haloalkylthio"), specifically a $C_1$-$C_6$-haloalkyl group ("$C_1$-$C_6$-haloalkylthio") or a $C_1$-$C_4$-haloalkyl group ("$C_1$-$C_4$-haloalkylthio") attached via a sulfur atom to the remainder of the molecule. The term "$C_1$-$C_2$-haloalkylthio" is a $C_1$-$C_2$-haloalkyl group, as defined above, attached via a sulfur atom. The term "$C_1$-$C_3$-haloalkylthio" is a $C_1$-$C_3$-haloalkyl group, as defined above, attached via a sulfur atom. $C_1$-$C_2$-Haloalkylthio is, for example, $SCH_2F$, $SCHF_2$, $SCF_3$, $SCH_2Cl$, $SCHCl_2$, $SCCl_3$, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or $SC_2F_5$. $C_1$-$C_3$-Haloalkylthio is additionally, for example, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, $SCH_2$—$C_2F_5$, $SCF_2$—$C_2F_5$, 1-($CH_2F$)-2-fluoroethylthio, 1-($CH_2Cl$)-2-chloroethylthio or 1-($CH_2Br$)-2-bromoethylthio. $C_1$-$C_4$-Haloalkylthio is additionally, for example, 4-fluorobutylthio, 4-chlorobutylthio, 4-bromobutylthio or nonafluorobutylthio. $C_1$-$C_6$-Haloalkylthio is additionally, for example, 5-fluoropentylthio, 5-chloropentylthio, 5-brompentylthio, 5-iodopentylthio, undecafluoropentylthio, 6-fluorohexylthio, 6-chlorohexylthio, 6-bromohexylthio, 6-iodohexylthio or dodecafluorohexylthio.

"Alkylsulfinyl" is an alkyl group, as defined above, attached via a sulfinyl [S(O)] group to the remainder of the molecule; generally a $C_1$-$C_{30}$-alkyl group ("$C_1$-$C_{30}$-alkylsulfinyl"), preferably a $C_1$-$C_{20}$-alkyl group ("$C_1$-$C_{20}$-alkylsulfinyl"), in particular a $C_1$-$C_{10}$-alkyl group ("$C_1$-$C_{10}$-alkylsulfinyl"), specifically a $C_1$-$C_6$-alkyl group ("$C_1$-$C_6$-alkylsulfinyl") or a $C_1$-$C_4$-alkyl group ("$C_1$-$C_4$-alkylsulfinyl") attached via a sulfinyl [S(O)] group to the remainder of the molecule. The term "$C_1$-$C_2$-alkylsulfinyl" is a $C_1$-$C_2$-alkyl group, as defined above, attached via a sulfinyl [S(O)] group. The term "$C_1$-$C_3$-alkylsulfinyl" is a $C_1$-$C_3$-alkyl group, as defined above, attached via a sulfinyl [S(O)] group. $C_1$-$C_2$-Alkylsulfinyl is methylsulfinyl or ethylsulfinyl. $C_1$-$C_4$-Alkylsulfinyl is additionally, for example, n-propylsulfinyl, 1-methylethylsulfinyl (isopropylsulfinyl), butylsulfinyl, 1-methylpropylsulfinyl (sec-butylsulfinyl), 2-methylpropylsulfinyl (isobutylsulfinyl) or 1,1-dimethylethylsulfinyl (tert-butylsulfinyl). $C_1$-$C_6$-Alkylsulfinyl is additionally, for example, pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl. $C_1$-$C_8$-Alkylsulfinyl is additionally, for example, heptylsulfinyl, octylsulfinyl, 2-ethylhexylsulfinyl and positional isomers thereof. $C_1$-$C_{10}$-Alkylsulfinyl is additionally, for example, nonylsulfinyl, decylsulfinyl and positional isomers thereof.

"Haloalkylsulfinyl" is a haloalkyl group, as defined above, attached via a sulfinyl [S(O)] group to the remainder of the molecule; generally a $C_1$-$C_{30}$-haloalkyl group ("$C_1$-$C_{30}$-haloalkylsulfinyl"), preferably a $C_1$-$C_{20}$-haloalkyl group ("$C_1$-$C_{20}$-haloalkylsulfinyl"), in particular a $C_1$-$C_{10}$-haloalkyl group ("$C_1$-$C_{10}$-haloalkylsulfinyl"), specifically a $C_1$-$C_6$-haloalkyl group ("$C_1$-$C_6$-haloalkylsulfinyl") or a $C_1$-$C_4$-haloalkyl group ("$C_1$-$C_4$-haloalkylsulfinyl") attached via a sulfinyl [S(O)] group to the remainder of the molecule. The term "$C_1$-$C_2$-haloalkylsulfinyl" is a $C_1$-$C_2$-haloalkyl group, as defined above, attached via a sulfinyl [S(O)] group. The term "$C_1$-$C_3$-haloalkylsulfinyl" is a $C_1$-$C_3$-haloalkyl group, as defined above, attached via a sulfinyl [S(O)] group. $C_1$-$C_2$-Haloalkylsulfinyl is, for example, S(O)CH$_2$F, S(O)CHF$_2$, S(O)CF$_3$, S(O)CH$_2$Cl, S(O)CHCl$_2$, S(O)CCl$_3$, chlorofluoromethylsulfinyl, dichlorofluoromethylsulfinyl, chlorodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2-chloro-2-fluoroethylsulfinyl, 2-chloro-2,2-difluoroethylsulfinyl, 2,2-dichloro-2-fluoroethylsulfinyl, 2,2,2-trichloroethylsulfinyl or S(O)C$_2$F$_5$. $C_1$-$C_4$-Haloalkylsulfinyl is additionally, for example, 2-fluoropropylsulfinyl, 3-fluoropropylsulfinyl, 2,2-difluoropropylsulfinyl, 2,3-difluoropropylsulfinyl, 2-chloropropylsulfinyl, 3-chloropropylsulfinyl, 2,3-dichloropropylsulfinyl, 2-bromopropylsulfinyl, 3-bromopropylsulfinyl, 3,3,3-trifluoropropylsulfinyl, 3,3,3-trichloropropylsulfinyl, S(O)CH$_2$—C$_2$F$_5$, S(O)CF$_2$—C$_2$F$_5$, 1-(CH$_2$F)-2-fluoroethylsulfinyl, 1-(CH$_2$Cl)-2-chloroethylsulfinyl, 1-(CH$_2$Br)-2-bromoethylsulfinyl, 4-fluorobutylsulfinyl, 4-chlorobutylsulfinyl, 4-bromobutylsulfinyl or nonafluorobutylsulfinyl. $C_1$-$C_6$-Haloalkylsulfinyl is additionally, for example, 5-fluoropentylsulfinyl, 5-chloropentylsulfinyl, 5-brompentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl or dodecafluorohexylsulfinyl.

"Alkylsulfonyl" is an alkyl group, as defined above, attached via a sulfonyl [S(O)$_2$] group to the remainder of the molecule; generally a $C_1$-$C_{30}$-alkyl group ("$C_1$-$C_{30}$-alkylsulfonyl"), preferably a $C_1$-$C_{20}$-alkyl group ("$C_1$-$C_{20}$-alkylsulfonyl"), in particular a $C_1$-$C_{10}$-alkyl group ("$C_1$-$C_{10}$-alkylsulfonyl"), specifically a $C_1$-$C_6$-alkyl group ("$C_1$-$C_6$-alkylsulfonyl") or a $C_1$-$C_4$-alkyl group ("$C_1$-$C_4$-alkylsulfonyl") attached via a sulfonyl [S(O)$_2$] group to the remainder of the molecule. The term "$C_1$-$C_2$-alkylsulfonyl" is a $C_1$-$C_2$-alkyl group, as defined above, attached via a sulfonyl [S(O)$_2$] group. The term "$C_1$-$C_3$-alkylsulfonyl" is a $C_1$-$C_3$-alkyl group, as defined above, attached via a sulfonyl [S(O)$_2$] group. $C_1$-$C_2$-Alkylsulfonyl is methylsulfonyl or ethylsulfonyl. $C_1$-$C_3$-Alkylsulfonyl is additionally, for example, n-propylsulfonyl or 1-methylethylsulfonyl (isopropylsulfonyl). $C_1$-$C_4$-Alkylsulfonyl is additionally, for example, butylsulfonyl, 1-methylpropylsulfonyl (sec-butylsulfonyl), 2-methylpropylsulfonyl (isobutylsulfonyl) or 1,1-dimethylethylsulfonyl (tert-butylsulfonyl). $C_1$-$C_6$-Alkylsulfonyl is additionally, for example, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl. $C_1$-$C_8$-Alkylsulfonyl is additionally, for example, heptylsulfonyl, octylsulfonyl, 2-ethylhexylsulfonyl and positional isomers thereof. $C_1$-$C_{10}$-Alkylsulfonyl is additionally, for example, nonylsulfonyl, decylsulfonyl and positional isomers thereof.

"Haloalkylsulfonyl" is a haloalkyl group, as defined above, attached via a sulfonyl [S(O)$_2$] group to the remainder of the molecule; generally a $C_1$-$C_{30}$-haloalkyl group ("$C_1$-$C_{30}$-haloalkylsulfonyl"), preferably a $C_1$-$C_{20}$-haloalkyl group ("$C_1$-$C_{20}$-haloalkylsulfonyl"), in particular a $C_1$-$C_{10}$-haloalkyl group ("$C_1$-$C_{10}$-haloalkylsulfonyl"), specifically a $C_1$-$C_6$-haloalkyl group ("$C_1$-$C_6$-haloalkylsulfonyl") or a $C_1$-$C_4$-haloalkyl group ("$C_1$-$C_4$-haloalkylsulfonyl") attached via a sulfonyl [S(O)$_2$] group to the remainder of the molecule. The term "$C_1$-$C_2$-haloalkylsulfonyl" is a $C_1$-$C_2$-haloalkyl group, as defined above, attached via a sulfonyl [S(O)$_2$] group. The term "$C_1$-$C_3$-haloalkylsulfonyl" is a $C_1$-$C_3$-haloalkyl group, as defined above, attached via a sulfonyl [S(O)$_2$] group. $C_1$-$C_2$-Haloalkylsulfonyl is, for example, S(O)CH$_2$F, S(O)$_2$CHF$_2$, S(OCF$_3$, S(O)$_2$CH$_2$Cl, S(O)$_2$CHCl$_2$, S(O)$_2$CCl$_3$, chlorofluoromethylsulfonyl, dichlorofluoromethylsulfonyl, chlorodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl or S(O)$_2$C$_2$F$_5$. $C_1$-$C_3$-Haloalkylsulfonyl is additionally, for example, 2-fluoropropylsulfonyl, 3-fluoropropylsulfonyl, 2,2-difluoropropylsulfonyl, 2,3-difluoropropylsulfonyl, 2-chloropropylsulfonyl, 3-chloropropylsulfonyl, 2,3-dichloropropylsulfonyl, 2-bromopropylsulfonyl, 3-bromopropylsulfonyl, 3,3,3-trifluoropropylsulfonyl, 3,3,3-trichloropropylsulfonyl, S(O)$_2$CH$_2$—C$_2$F$_5$, S(O)$_2$CF$_2$—C$_2$F$_5$, 1-(CH$_2$F)-2-fluoroethylsulfonyl, 1-(CH$_2$Cl)-2-chloroethylsulfonyl or 1-(CH$_2$Br)-2-bromoethylsulfonyl. $C_1$-$C_4$-Haloalkylsulfonyl is additionally, for example, 4-fluorobutylsulfonyl, 4-chlorobutylsulfonyl, 4-bromobutylsulfonyl or nonafluorobutylsulfonyl. $C_1$-$C_4$-Haloalkylsulfonyl is additionally, for example, 5-fluoropentylsulfonyl, 5-chloropentylsulfonyl, 5-brompentylsulfonyl, 5-iodopentylsulfonyl, undecafluoropentylsulfonyl, 6-fluorohexylsulfonyl, 6-chlorohexylsulfonyl, 6-bromohexylsulfonyl, 6-iodohexylsulfonyl or dodecafluorohexylsulfonyl.

The substituent "oxo" replaces a CH$_2$ group by a C(=O) group.

Alike, the substituent "=S" replaces a CH$_2$ group by a C(=S) group.

Alike, the substituent "=NR$^{12a}$" replaces a CH$_2$ group by a C(=NR$^{12a}$) group.

"Alkylcarbonyl" is an alkyl group, as defined above, attached via a carbonyl [C(=O)] group to the remainder of the molecule; generally a C$_1$-C$_{30}$-alkyl group ("C$_1$-C$_{30}$-alkylcarbonyl"), preferably a C$_1$-C$_{20}$-alkyl group ("C$_1$-C$_{20}$-alkylcarbonyl"), in particular a C$_1$-C$_{10}$-alkyl group ("C$_1$-C$_{10}$-alkylcarbonyl"), specifically a C$_1$-C$_6$-alkyl group ("C$_1$-C$_6$-alkylcarbonyl") or a C$_1$-C$_4$-alkyl group ("C$_1$-C$_4$-alkylcarbonyl") attached via a carbonyl [C(=O)] group to the remainder of the molecule. Examples are acetyl (methylcarbonyl), propionyl (ethylcarbonyl), propylcarbonyl, isopropylcarbonyl, n-butylcarbonyl and the like.

"Haloalkylcarbonyl" is a haloalkyl group, as defined above, attached via a carbonyl [C(=O)] group to the remainder of the molecule; generally a C$_1$-C$_{30}$-haloalkyl group ("C$_1$-C$_{30}$-haloalkylcarbonyl"), preferably a C$_1$-C$_{20}$-haloalkyl group ("C$_1$-C$_{20}$-haloalkylcarbonyl"), in particular a C$_1$-C$_{10}$-haloalkyl group ("C$_1$-C$_{10}$-haloalkylcarbonyl"), specifically a C$_1$-C$_6$-haloalkyl group ("C$_1$-C$_6$-haloalkylcarbonyl") or a C$_1$-C$_4$-haloalkyl group ("C$_1$-C$_4$-haloalkylcarbonyl") attached via a carbonyl [C(=O)] group to the remainder of the molecule. Examples are trifluoromethylcarbonyl, 2,2,2-trifluoroethylcarbonyl and the like.

"Alkoxycarbonyl" is an alkoxy group, as defined above, attached via a carbonyl [C(=O)] group to the remainder of the molecule; generally a C$_1$-C$_3$-alkoxy group ("C$_1$-C$_{30}$-alkoxycarbonyl"), preferably a C$_1$-C$_{20}$-alkoxy group ("C$_1$-C$_{20}$-alkoxycarbonyl"), in particular a C$_1$-C$_{10}$-alkoxy group ("C$_1$-C$_{10}$-alkoxycarbonyl"), specifically a C$_1$-C$_6$-alkoxy group ("C$_1$-C$_6$-alkoxycarbonyl") or a C$_1$-C$_4$-alkoxy group ("C$_1$-C$_4$-alkoxycarbonyl") attached via a carbonyl [C(=O)] group to the remainder of the molecule. Examples are methoxycarbonyl, ethoxycarbonyl, propoxycarbonyl, isopropoxycarbonyl, n-butoxycarbonyl and the like.

"Haloalkoxycarbonyl" is a haloalkoxy group, as defined above, attached via a carbonyl [C(=O)] group to the remainder of the molecule; generally a C$_1$-C$_{30}$-haloalkoxy group ("C$_1$-C$_{30}$-haloalkoxycarbonyl"), preferably a C$_1$-C$_{20}$-haloalkoxy group ("C$_1$-C$_{20}$-haloalkoxycarbonyl"), in particular a C$_1$-C$_{10}$-haloalkoxy group ("C$_1$-C$_{10}$-haloalkoxycarbonyl"), specifically a C$_1$-C$_6$-haloalkoxy group ("C$_1$-C$_6$-haloalkoxycarbonyl") or a C$_1$-C$_4$-haloalkoxy group ("C$_1$-C$_4$-haloalkoxycarbonyl") attached via a carbonyl [C(=O)] group to the remainder of the molecule. Examples are trifluoromethoxycarbonyl, 2,2,2-trifluoroethoxycarbonyl and the like.

The term "aminocarbonyl" is a group —C(=O)—NH$_2$.

The term "alkylaminocarbonyl" is a group —C(=O)—N(H)-alkyl, where alkyl is as defined above and is in general a C$_1$-C$_{30}$-alkyl group ("C$_1$-C$_{30}$-alkylaminocarbonyl"), preferably a C$_1$-C$_{20}$-alkyl group ("C$_1$-C$_{20}$-alkylaminocarbonyl"), in particular a C$_1$-C$_{10}$-alkyl group ("C$_1$-C$_{10}$-alkylaminocarbonyl"), specifically a C$_1$-C$_6$-alkyl group ("C$_1$-C$_6$-alkylaminocarbonyl") or a C$_1$-C$_4$-alkyl group ("C$_1$-C$_4$-alkylaminocarbonyl"). Examples are methylaminocarbonyl, ethylaminocarbonyl, propylaminocarbonyl, isopropylaminocarbonyl, butylaminocarbonyl and the like.

The term "di(alkyl)aminocarbonyl" is a group —C(=O)—N(alkyl)$_2$, where each alkyl is independently as defined above and is independently in general a C$_1$-C$_6$-alkyl group ("di-(C$_1$-C$_{30}$-alkyl)aminocarbonyl"), preferably a C$_1$-C$_{20}$-alkyl group ("di-(C$_1$-C$_{20}$-alkyl)aminocarbonyl"), in particular a C$_1$-C$_{10}$-alkyl group ("di-(C$_1$-C$_{10}$-alkyl)aminocarbonyl"), specifically a C$_1$-C$_6$-alkyl group ("di-(C$_1$-C$_6$-alkyl)aminocarbonyl"), or a C$_1$-C$_4$-alkyl group ("di-(C$_1$-C$_4$-alkyl)aminocarbonyl"). Examples are dimethylaminocarbonyl, diethylaminocarbonyl, ethylmethylaminocarbonyl, dipropylaminocarbonyl, diisopropylaminocarbonyl, methylpropylaminocarbonyl, methylisopropylaminocarbonyl, ethylpropylaminocarbonyl, ethylisopropylaminocarbonyl, dibutylaminocarbonyl and the like.

Aryl is a mono-, bi- or polycyclic carbocyclic (i.e. without heteroatoms as ring members) aromatic radical. One example for a monocyclic aromatic radical is phenyl. In bicyclic aryl rings two aromatic rings are condensed, i.e. they share two vicinal C atoms as ring members. One example for a bicyclic aromatic radical is naphthyl. In polycyclic aryl rings, three or more rings are condensed. Examples for polycyclic aryl radicals are phenanthrenyl, anthracenyl, tetracenyl, 1H-benzo[a]phenalenyl, pyrenyl and the like. In the terms of the present invention "aryl" encompasses however also bi- or polycyclic radicals in which not all rings are aromatic, as long as at least one ring is; especially if the reactive site is on the aromatic ring (or on a functional group bound thereto). Examples are indanyl, indenyl, tetralinyl, 6,7,8,9-tetrahydro-5H-benzo[7]annulenyl, fluorenyl, 9,10-dihydroanthracenyl, 9,10-dihydrophenanthrenyl, 1H-benzo[a]phenalenyl and the like, and also ring systems in which not all rings are condensed, but for example spiro-bound or bridged, such as benzonorbornyl. In particular, the aryl group has 6 to 30, more particularly 6 to 20, specifically 6 to 10 carbon atoms as ring members.

Rings termed as heterocyclic rings or heterocyclyl or heteroaromatic rings or heteroaryl or hetaryl contain one or more heteroatoms as ring members, i.e. atoms different from carbon. In the terms of the present invention, these heteroatoms are N, O and S, where N and S can also be present as heteroatom groups, namely as NO, SO or SO$_2$. Thus, in the terms of the present invention, rings termed as heterocyclic rings or heterocyclyl or heteroaromatic rings or heteroaryl or hetaryl contain one or more heteroatoms and/or heteroatom groups selected from the group consisting of N, O, S, NO, SO and SO$_2$ as ring members.

In the terms of the present invention a heterocyclic ring or heterocyclyl is a saturated, partially unsaturated or maximally unsaturated, but not aromatic heteromono-, bi- or polycyclic ring (if the ring is aromatic, it is termed heteroaromatic ring or heteroaryl or hetaryl) containing one ore more, in particular 1, 2, 3 or 4 heteroatoms or heteroatom groups independently selected from the group consisting of N, O, S, NO, SO and SO$_2$ as ring members.

Unsaturated rings contain at least one C—C and/or C—N and/or N—N double bond(s). Maximally unsaturated rings contain as many conjugated C—C and/or C—N and/or N—N double bonds as allowed by the ring size. Maximally unsaturated 5- or 6-membered heteromonocyclic rings are generally aromatic (and thus not enclosed in the present term "heterocyclic ring" or "heterocyclyl". Exceptions are maximally unsaturated 6-membered rings containing O, S, SO and/or SO$_2$ as ring members, such as pyran and thiopyran, which are not aromatic). Partially unsaturated rings contain less than the maximum number of C—C and/or C—N and/or N—N double bond(s) allowed by the ring size.

Although they do not contain as many conjugated double bonds as principally allowed by the ring size, some partially unsaturated heterobi- or polycyclic rings may be considered as heteroaromatic in the terms of the present invention if the moiety taking part in the reaction in question is aromatic. One example is indoline: If the reaction takes place on the 6-membered aromatic moiety of this fused system, the indoline is considered as a heteroaromatic ring. See also below examples for partially unsaturated heterobicyclic rings. If the reaction is to take place on the 5-membered non-aromatic moiety, indoline is considered as a heterocyclyl ring.

The heterocyclic and heteroaromatic ring may be attached to the remainder of the molecule via a carbon ring member or via a nitrogen ring member. As a matter of course, the heterocyclic and heteroaromatic ring contains at least one carbon ring atom. If the ring contains more than one O ring atom, these are not adjacent.

Heterocyclic rings are in particular 3 to 30-membered, more particularly 3 to 20-membered, specifically 3- to 12-membered or 3- to 11-membered.

Heteromonocyclic rings are in particular 3- to 8-membered. The term "3-, 4-, 5-, 6-, 7- or 8-membered heterocyclic ring containing 1, 2, 3 or 4 heteroatoms or heteroatom groups independently selected from the group consisting of N, O, S, NO, SO and $SO_2$ groups as ring members" denotes a 3-, 4-, 5-, 6-, 7- or 8-membered saturated, partially unsaturated or maximum unsaturated (but not aromatic) heteromonocyclic ring containing 1, 2, 3 or 4 (preferably 1, 2 or 3) heteroatoms or heteroatom groups selected from the group consisting of N, O, S, SO and $SO_2$ as ring members.

Examples of a 3-, 4-, 5-, 6-, 7- or 8-membered saturated heteromonocyclic ring include: Oxiran-2-yl, thiiran-2-yl, aziridin-1-yl, aziridin-2-yl, oxetan-2-yl, oxetan-3-yl, thietan-2-yl, thietan-3-yl, 1-oxothietan-2-yl, 1-oxothietan-3-yl, 1,1-dioxothietan-2-yl, 1,1-dioxothietan-3-yl, azetidin-1-yl, azetidin-2-yl, azetidin-3-yl, tetrahydrofuran-2-yl, tetrahydrofuran-3-yl, tetrahydrothien-2-yl, tetrahydrothien-3-yl, 1-oxotetrahydrothien-2-yl, 1,1-dioxotetrahydrothien-2-yl, 1-oxotetrahydrothien-3-yl, 1,1-dioxotetrahydrothien-3-yl, pyrrolidin-1-yl, pyrrolidin-2-yl, pyrrolidin-3-yl, pyrazolidin-1-yl, pyrazolidin-3-yl, pyrazolidin-4-yl, pyrazolidin-5-yl, imidazolidin-1-yl, imidazolidin-2-yl, imidazolidin-4-yl, oxazolidin-2-yl, oxazolidin-3-yl, oxazolidin-4-yl, oxazolidin-5-yl, isoxazolidin-2-yl, isoxazolidin-3-yl, isoxazolidin-4-yl, isoxazolidin-5-yl, thiazolidin-2-yl, thiazolidin-3-yl, thiazolidin-4-yl, thiazolidin-5-yl, isothiazolidin-2-yl, isothiazolidin-3-yl, isothiazolidin-4-yl, isothiazolidin-5-yl, 1,2,4-oxadiazolidin-2-yl, 1,2,4-oxadiazolidin-3-yl, 1,2,4-oxadiazolidin-4-yl, 1,2,4-oxadiazolidin-5-yl, 1,2,4-thiadiazolidin-2-yl, 1,2,4-thiadiazolidin-3-yl, 1,2,4-thiadiazolidin-4-yl, 1,2,4-thiadiazolidin-5-yl, 1,2,4-triazolidin-1-yl, 1,2,4-triazolidin-3-yl, 1,2,4-triazolidin-4-yl, 1,3,4-oxadiazolidin-2-yl, 1,3,4-oxadiazolidin-3-yl, 1,3,4-thiadiazolidin-2-yl, 1,3,4-thiadiazolidin-3-yl, 1,3,4-triazolidin-1-yl, 1,3,4-triazolidin-2-yl, 1,3,4-triazolidin-3-yl, tetrahydropyran-2-yl, tetrahydropyran-3-yl, tetrahydropyran-4-yl, 1,3-dioxan-2-yl, 1,3-dioxan-4-yl, 1,3-dioxan-5-yl, 1,4-dioxan-2-yl, piperidin-1-yl, piperidin-2-yl, piperidin-3-yl, piperidin-4-yl, hexahydropyridazin-1-yl, hexahydropyridazin-3-yl, hexahydropyridazin-4-yl, hexahydropyrimidin-1-yl, hexahydropyrimidin-2-yl, hexahydropyrimidin-4-yl, hexahydropyrimidin-5-yl, piperazin-1-yl, piperazin-2-yl, 1,3,5-hexahydrotriazin-1-yl, 1,3,5-hexahydrotriazin-2-yl, 1,2,4-hexahydrotriazin-1-yl, 1,2,4-hexahydrotriazin-2-yl, 1,2,4-hexahydrotriazin-3-yl, 1,2,4-hexahydrotriazin-4-yl, 1,2,4-hexahydrotriazin-5-yl, 1,2,4-hexahydrotriazin-6-yl, morpholin-2-yl, morpholin-3-yl, morpholin-4-yl, thiomorpholin-2-yl, thiomorpholin-3-yl, thiomorpholin-4-yl, 1-oxothiomorpholin-2-yl, 1-oxothiomorpholin-3-yl, 1-oxothiomorpholin-4-yl, 1,1-dioxothiomorpholin-2-yl, 1,1-dioxothiomorpholin-3-yl, 1,1-dioxothiomorpholin-4-yl, azepan-1-, -2-, -3- or -4-yl, oxepan-2-, -3-, -4- or -5-yl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl, oxocane, thiocane, azocanyl, [1,3]diazocanyl, [1,4]diazocanyl, [1,5]diazocanyl, [1,5]oxazocanyl and the like.

Examples of a 3-, 4-, 5-, 6-, 7- or 8-membered partially unsaturated heteromonocyclic ring include: 2,3-dihydrofuran-2-yl, 2,3-dihydrofuran-3-yl, 2,4-dihydrofuran-2-yl, 2,4-dihydrofuran-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7-tetrahydro[1H]azepin-1-, -2-, -3-, -4-, -5-, -6- or -7-yl, 2,3,6,7-tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7-tetrahydro[1H]oxepin-2-, -3-, -4-, -5-, -6- or -7-yl, 2,3,6,7-tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl, tetrahydro-1,4-dioxepinyl, 1,2,3,4,5,6-hexahydroazocine, 2,3,4,5,6,7-hexahydroazocine, 1,2,3,4,5,8-hexahydroazocine, 1,2,3,4,7,8-hexahydroazocine, 1,2,3,4,5,6-hexahydro-[1,5]diazocine, 1,2,3,4,7,8-hexahydro-[1,5]diazocine and the like.

Examples of a 3-, 4-, 5-, 6-, 7- or 8-membered maximally unsaturated (but not aromatic) heteromonocyclic ring are pyran-2-yl, pyran-3-yl, pyran-4-yl, thiopryan-2-yl, thiopryan-3-yl, thiopryan-4-yl, 1-oxothiopryan-2-yl, 1-oxothiopryan-3-yl, 1-oxothiopryan-4-yl, 1,1-dioxothiopryan-2-yl, 1,1-dioxothiopryan-3-yl, 1,1-dioxothiopryan-4-yl, 2H-oxazin-2-yl, 2H-oxazin-3-yl, 2H-oxazin-4-yl, 2H-oxazin-5-yl, 2H-oxazin-6-yl, 4H-oxazin-3-yl, 4H-oxazin-4-yl, 4H-oxazin-5-yl, 4H-oxazin-6-yl, 6H-oxazin-3-yl, 6H-oxazin-4-yl, 7H-oxazin-5-yl, 8H-oxazin-6-yl, 2H-1,3-oxazin-2-yl, 2H-1,3-oxazin-4-yl, 2H-1,3-oxazin-5-yl, 2H-1,3-oxazin-6-yl, 4H-1,3-oxazin-2-yl, 4H-1,3-oxazin-4-yl, 4H-1,3-oxazin-5-yl, 4H-1,3-oxazin-6-yl, 6H-1,3-oxazin-2-yl, 6H-1,3-oxazin-4-yl, 6H-1,3-oxazin-5-yl, 6H-1,3-oxazin-6-yl, 2H-1,4-oxazin-2-yl, 2H-1,4-oxazin-3-yl, 2H-1,4-oxazin-5-yl, 2H-1,4-oxazin-6-yl, 4H-1,4-oxazin-2-yl, 4H-1,4-oxazin-3-yl, 4H-1,4-oxazin-4-yl, 4H-1,4-oxazin-5-yl, 4H-1,4-oxazin-6-yl, 6H-1,4-oxazin-2-yl, 6H-1,4-oxazin-3-yl, 6H-1,4-oxazin-5-yl, 6H-1,4-oxazin-6-yl, 1,4-dioxine-2-yl, 1,4-oxathiin-2-yl, 1H-azepine, 1H-[1,3]-diazepine, 1H-[1,4]-diazepine, [1,3]diazocine, [1,5]diazocine, [1,5]diazocine and the like.

Heteroaromatic monocyclic rings are in particular 5- or 6-membered.

Examples for 5- or 6-membered monocyclic heteroaromatic rings are 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 3-isothiazolyl, 4-isothiazolyl, 5-isothiazolyl, 1,3,4-triazol-1-yl, 1,3,4-triazol-2-yl, 1,3,4-triazol-3-yl, 1,2,3-triazol-1-yl, 1,2,3-triazol-2-yl, 1,2,3-triazol-4-yl, 1,2,5-oxadiazol-3-yl, 1,2,3-oxadiazol-4-yl, 1,2,3-oxadiazol-5-yl, 1,3,4-oxadiazol-2-yl, 1,2,5-thiadiazol-3-yl, 1,2,3-thiadiazol-4-yl, 1,2,3-thiadiazol-5-yl, 1,3,4-thiadiazol-2-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, 1,2,3,4-tetrazin-1-yl, 1,2,3,4-tetrazin-2-yl, 1,2,3,4-tetrazin-5-yl and the like.

In the present invention, the "heterobicyclic rings" or "heterobicyclyl" contain two rings which have at least one ring atom in common. At least one of the two rings contains a heteroatom or heteroatom group selected from the group consisting of N, O, S, NO, SO and SO$_2$ as ring member. The term comprises condensed (fused) ring systems, in which the two rings have two neighboring ring atoms in common, as well as spiro systems, in which the rings have only one ring atom in common, and bridged systems with at least three ring atoms in common. In terms of the present invention, the heterobicyclic rings do not include throughout aromatic bicyclic ring systems; these are termed heteroaromatic bicyclic rings or bicycyclic het(ero)aryl or heterobiaryl. If in a condensed system one ring is aromatic and the other is not and if the reaction in question is to take place on the aromatic moiety of the bicyclic system, these rings are considered to belong to heteroaromatic rings (het(ero)aryl), although the system is not completely aromatic. The heterobicyclic rings are preferably 7-, 8-, 9-, 10- or 11-membered. The heteroaromatic bicyclic rings are preferably 9-, 10- or 11-membered. Throughout heteroaromatic heterobicyclic rings are 9- or 10-membered.

Examples for fused systems:

Examples for a 7-, 8-, 9-, 10- or 11-membered saturated heterobicyclic ring containing 1, 2 or 3 (or 4) heteroatoms or heteroatom groups selected from the group consisting of N, O, S, NO, SO and SO$_2$, as ring members are:

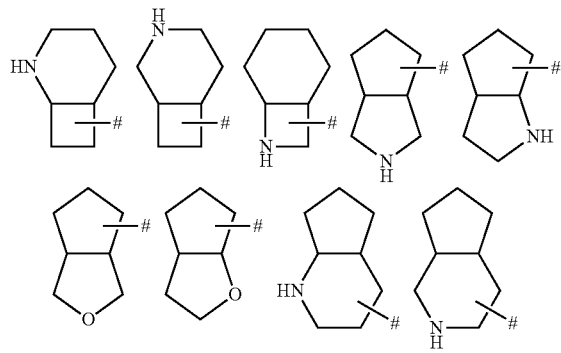

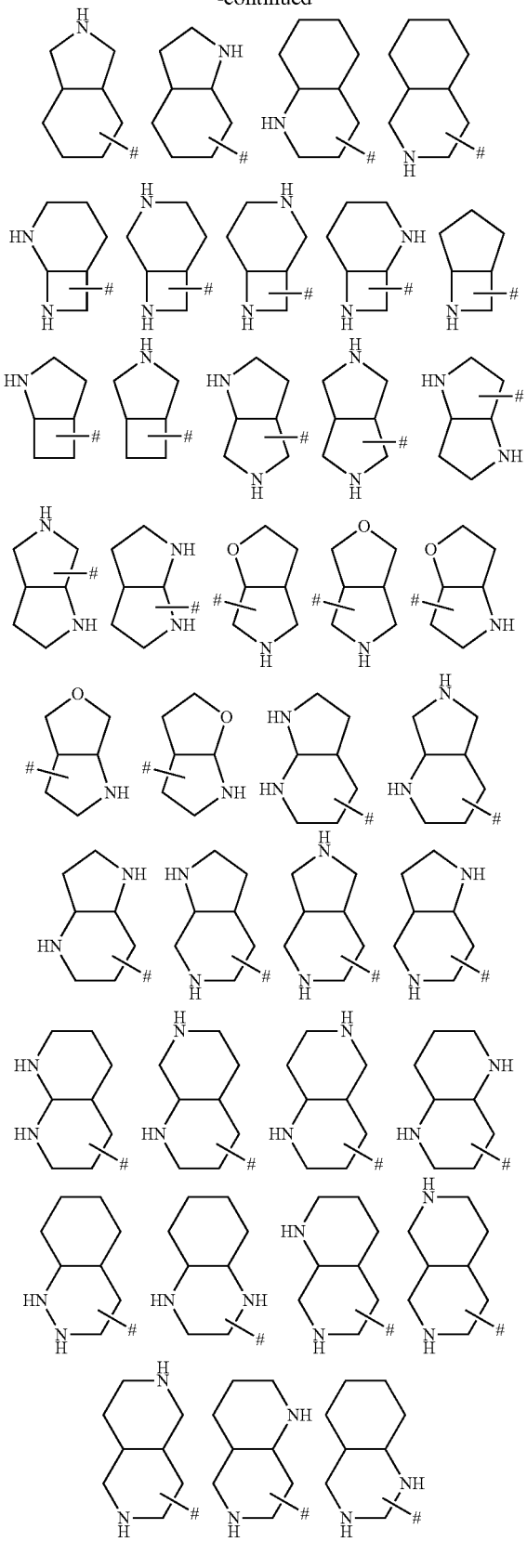

Examples for a 7-, 8-, 9-, 10- or 11-membered saturated heterobicyclic ring containing 1, 2 or 3 (or 4) heteroatoms or heteroatom groups selected from the group consisting of N, O, S, NO, SO and SO$_2$, as ring members are:

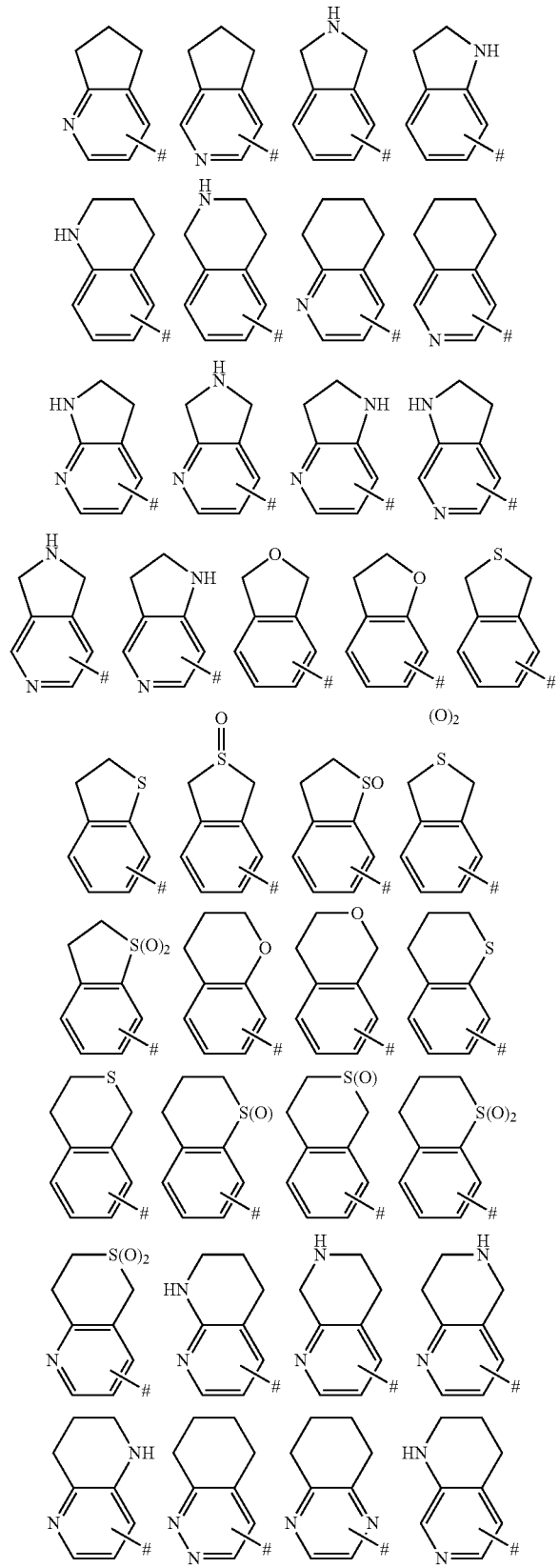
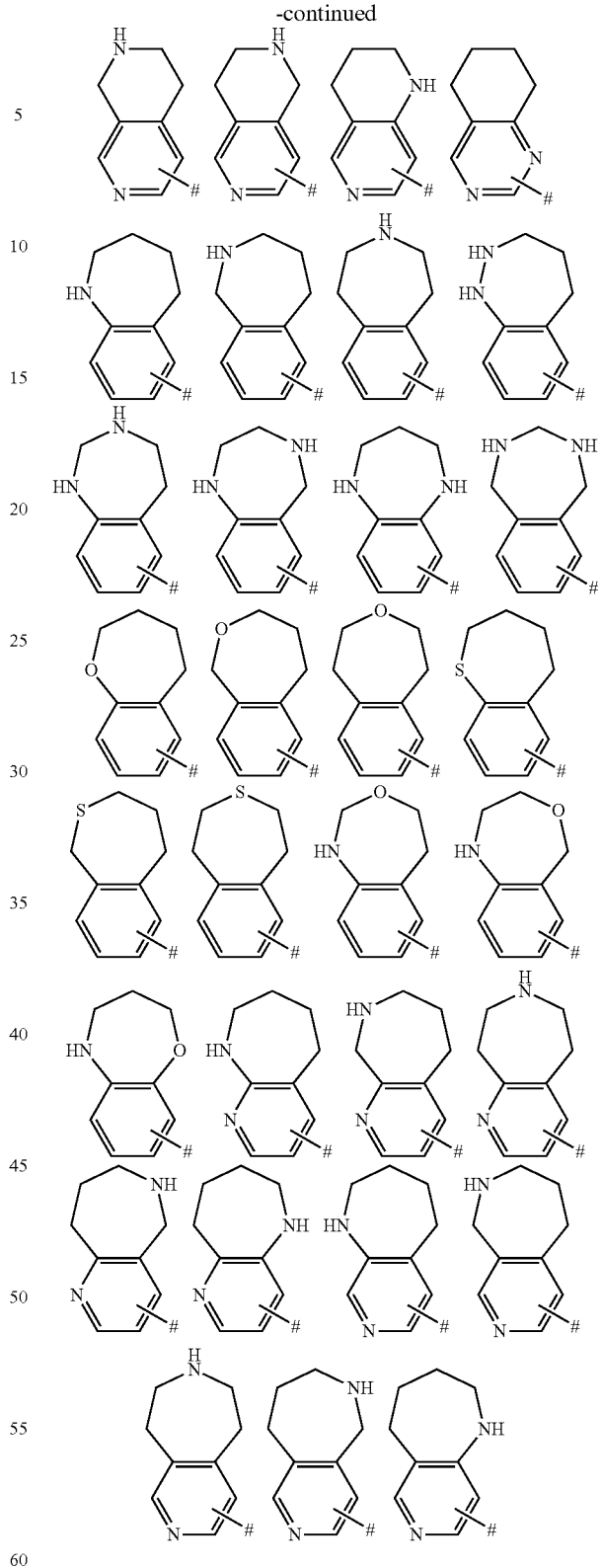

In the above examples, one ring is aromatic. If the reaction in question is to take place on the aromatic moiety of the bicyclic system (or on a functional group bound thereto), these rings are considered to belong to heteroaromatic rings (het(ero)aryl), although the system is not completely heteroaromatic.

Examples for a 7-, 8-, 9-, 10- or 11-membered maximally unsaturated (but not throughout heteroaromatic) heterobicyclic ring containing 1, 2 or 3 (or 4) heteroatoms or heteroatom groups selected from the group consisting of N, O, S, NO, SO and SO$_2$, as ring members are:

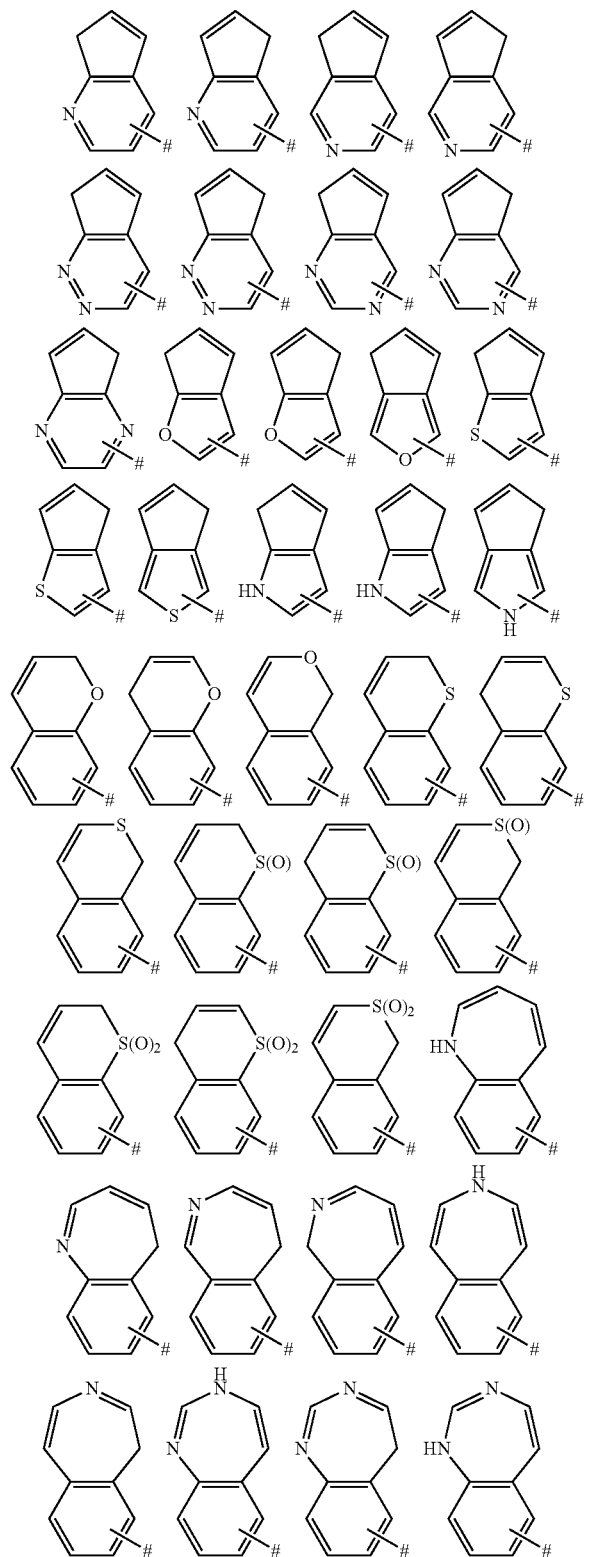

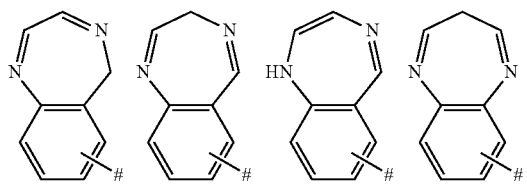

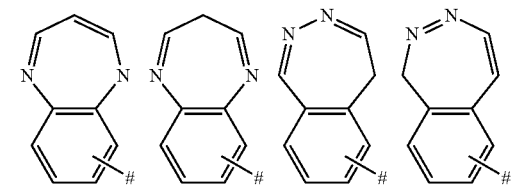

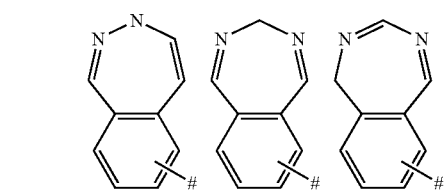

In the above examples, one ring is (hetero)aromatic. If the reaction in question is to take place on the (hetero)aromatic moiety of the bicyclic system (or on a functional group bound thereto), these rings are considered to belong to heteroaromatic rings (het(ero)aryl), although the system is not completely heteroaromatic.

Examples for a 9- or 10-membered maximally unsaturated, throughout heteroaromatic heterobicyclic ring containing 1, 2 or 3 (or 4) heteroatoms or heteroatom groups selected from the group consisting of N, O, S, NO, SO and SO$_2$, as ring members are:

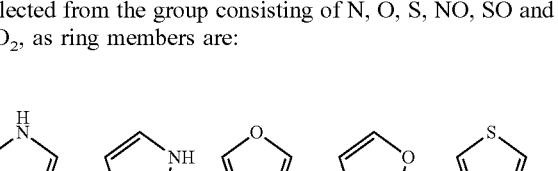

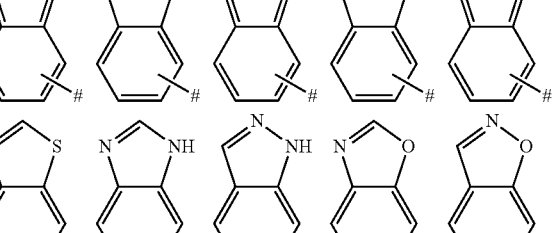

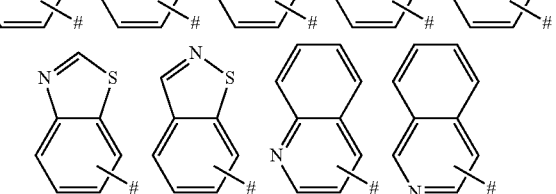

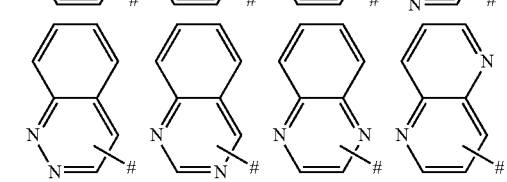

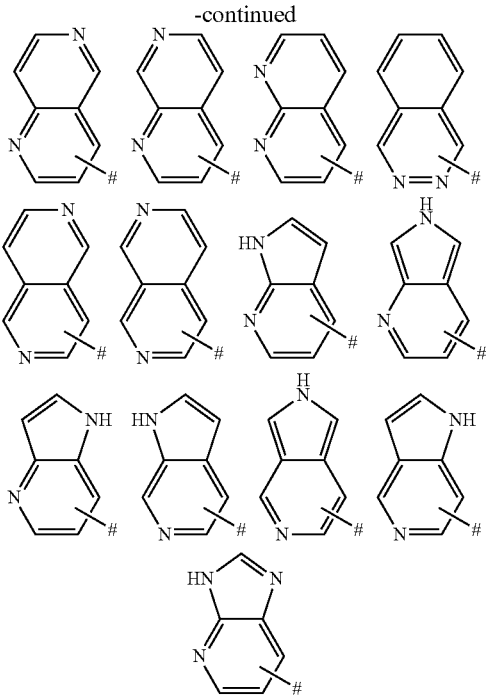

Examples for spiro-bound 7-, 8-, 9-, 10- or 11-membered heterobicyclic rings containing 1, 2 or 3 (or 4) heteroatoms or heteroatom groups selected from the group consisting of N, O, S, NO, SO and SO$_2$, as ring members are

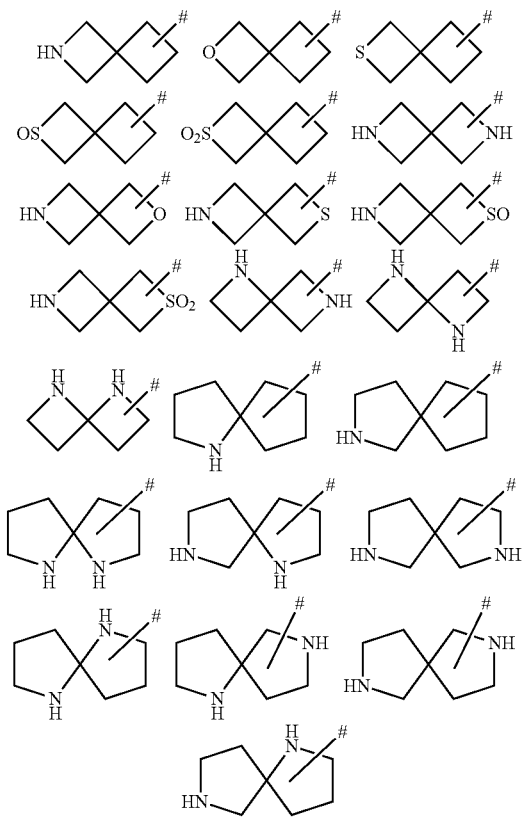

Examples for bridged 7-, 8-, 9-, 10- or 1-membered heterobicyclic rings containing 1, 2 or 3 (or 4) heteroatoms or heteroatom groups selected from the group consisting of N, O, S, NO, SO and SO$_2$, as ring members are

and the like.

In the above structures # denotes the attachment point to the remainder of the molecule. The attachment point is not restricted to the ring on which this is shown, but can be on either of the two rings, and may be on a carbon or on a nitrogen ring atom. If the rings carry one or more substituents, these may be bound to carbon and/or to nitrogen ring atoms.

Polycyclic heterocyclic rings (polyheterocyclyl) contain three or more rings, each of which having at least one ring atom in common with at least one of the other rings of the polycyclic system. The rings can be condensed, spiro-bound or bridged; mixed systems (e.g. one ring is spiro-bound to a condensed system, or a bridged system is condensed with another ring) are also possible. Throughout aromatic rings are not encompassed in the polycyclic heterocyclic ring (polyheterocyclyl); these are termed polycyclic heteroaromatic rings or heteropolyaryls.

If in a polycyclic system one ring is aromatic and (one of) the other(s) is/are not and if the reaction in question is to take place on the aromatic moiety of the polycyclic system (or on a functional group bound thereto), these rings are considered to belong to heteroaromatic rings (het(ero)aryl), although the system is not completely aromatic.

Aryloxy, heterocyclyloxy and heteroaryloxy (also expressed as O-aryl, O-heterocyclyl and O-heteroaryl) are aryl, heterocyclyl and heteroaryl, respectively, as defined above, bound via an oxygen atom to the remainder of the molecule. Examples are phenoxy or pyridyloxy.

If two radicals bound on the same nitrogen and, together with this nitrogen atom, form a mono-, bi- or polycyclic heterocyclic ring (e.g.: in the Buchwald Hartwig reaction: R$^1$ and R$^3$, together with the nitrogen atom they are bound to, may form a mono-, bi- or polycyclic heterocyclic ring, or R$^4$ and R$^5$, together with the nitrogen atom they are bound to, may form a mono-, bi- or polycyclic heterocyclic ring; or in the carboxamide or sulfonamide bond formation not requiring transition metal catalysis R$^2$ and R$^3$, together with the nitrogen atom they are bound to, may form a mono-, bi- or polycyclic heterocyclic ring; or in the protection of primary or secondary amino groups R$^1$ and R$^2$, together with the nitrogen atom they are bound to, may form a mono-, bi- or polycyclic heterocyclic ring) this ring, apart from the compulsory nitrogen atom, may contain 1, 2 or 3 or 4 further heteroatoms or heteroatom groups selected from the group consisting of N, O, S, NO, SO or SO$_2$ as ring members. The ring may be saturated, partially unsaturated or maximally unsaturated, including heteroaromatic. Monocyclic rings are in particular 3- to 8-membered. Bicyclic rings are in particular 7- to 20-membered, specifically 7- to 11-membered.

Examples of such monocyclic saturated heterocyclic rings are aziridin-1-yl, azetidin-1-yl, pyrrolidin-1-yl, pyrazolidin-1-yl, imidazolidin-1-yl, oxazolidin-3-yl, isoxazolidin-2-yl, thiazolidin-3-yl, isothiazolidin-2-yl, 1,2,4-oxadiazolidin-2-yl, 1,2,4-oxadiazolidin-4-yl, 1,2,4-thiadiazolidin-2-yl, 1,2,4- thiadiazolidin-4-yl, 1,2,4-triazolidin-1-yl, 1,2,4-triazolidin-4-yl, 1,3,4-oxadiazolidin-3-yl, 1,3,4-thiadiazolidin-3-yl, 1,3,4-triazolidin-1-yl, 1,3,4-triazolidin-3-yl, piperidin-1-yl, hexahydropyridazin-1-yl, hexahydropyrimidin-1-yl, 1 piperazin-1-yl, 1 1,3,5-hexahydrotriazin-1-yl, 1 1,2,4-hexahydrotriazin-1-yl, 1,2,4-hexahydrotriazin-2-yl, 1,2,4-hexahydrotriazin-4-yl, morpholin-4-ylthiomorpholin-4-yl, 1-oxothiomorpholin-4-yl, 1,1-dioxothiomorpholin-4-yl, azepan-1-yl, hexahydro-1,3-diazepin-1-yl, hexahydro-1,4-diazepin-1-yl, hexahydro-1,3-oxazepin-3-yl, hexahydro-1,4-oxazepin-4-yl, azocan-1-yl, [1,3]diazocan-1-yl, [1,4]diazocan-1-yl, [1,5]diazocan-1-yl, [1,5]oxazocan-1-yl and the like.

Examples of such monocyclic partially unsaturated heterocyclic rings include: 2,3-dihydro-1H-pyrrol-1-yl, 2,5-dihydro-1H-pyrrol-1-yl, 2,3-dihydro-1H-pyrazol-1-yl, 4,5-dihydro-1H-pyrazol-1-yl, 2,3-dihydro-1H-imidazol-1-yl, 2,5-dihydro-1H-imidazol-1-yl, 4,5-dihydro-1H-imidazol-1-yl, 2,3-dihydrooxazol-3-yl, 2,3-dihydroisoxazol-2-yl, 2,5-dihydroisoxazol-2-yl, 2,3-dihydrothiazol-3-yl, 2,3-dihydroisothiazol-2-yl, 2,5-dihydroisothiazol-2-yl, 1,2-dihydropyridin-1-yl, 1,4-dihydropyridin-1-yl, 1,2,3,4-tetrahydropyridin-1-yl, 1,2,3,6-tetrahydropyridin-1-yl, 1,2,3,4-tetrahydropyridazin-1-yl, 1,2,3,4-tetrahydropyridazin-2-yl, 1,2,3,6-tetrahydropyridazin-1-yl, 1,2-dihydropyridazin-1-yl, 1,4-dihydropyridazin-1-yl, 1,6-dihydropyridazin-1-yl, 1,2-dihydropyrimidin-1-yl, 1,4-dihydropyrimidin-1-yl, 1,2,3,4-tetrahydropyrimidin-1-yl, 1,2,3,4-tetrahydropyrimidin-3-yl, 1,2,5,6-tetrahydropyrimidin-1-yl, 1,4,5,6-tetrahydropyrimidin-1-yl, 1,2-dihydropyrazin-1-yl, 1,4-dihydropyrazin-1-yl, 1,2,3,4-tetrahydropyrazin-1-yl, 1,2,3,6-tetrahydropyrazin-1-yl, 1,2-dihydro-1,3,5-triazin-1-yl, 1,4-dihydro-1,3,5-triazin-1-yl, 1,2,3,4-tetrahydro-1,3,5-triazin-1-yl, 1,2,3,4-tetrahydro-1,3,5-triazin-3-yl, 2,3,4,5-tetrahydro-1H-azepin-1-yl, 2,3,4,7-tetrahydro-1H-azepin-1-yl, 2,3,6,7-tetrahydro-1H-azepin-1-yl, 2,3-dihydro-1H-azepin-1-yl, 2,5-dihydro-1H-azepin-1-yl, 4,5-dihydro-1H-azepin-1-yl, Examples of such monocyclic maximally unsaturated heterocyclic, inclusive heteroaromatic, rings include 1-pyrrolyl, 1-pyrazolyl, 1-imidazolyl, 1,3,4-triazol-1-yl, 1,3,4-triazol-3-yl, 1,2,3-triazol-1-yl, 1,2,3-triazol-2-yl, 1H-azepin-1-yl and the like.

Examples of such bicyclic heterocyclic rings are the above-depicted 7-, 8-, 9-, 10- or 11-membered saturated, partially unsaturated or maximally unsaturated fused, spirobound or bridged heterobicyclic rings which contain at least one secondary nitrogen atom (NH) as ring member and in which the attachment point to the remainder of the molecule (#) is on this secondary nitrogen ring atom.

In the Baylis-Hillman reaction, $R^1$ and $R^2$ may form together with the carbon atom they are bound to a carbocyclic or heterocyclic ring. This ring may be saturated or partially unsaturated, monocyclic, bicyclic or polycyclic. If this ring is heterocyclic, it contains 1, 2 or 3 or 4 heteroatoms or heteroatom groups selected from the group consisting of N, O, S, NO, SO or $SO_2$ as ring members.

For instance, $R^1$ and $R^2$ may form together —(CH$_2$)$_3$—, —(CH$_2$)$_4$—, —(CH$_2$)$_5$—, —(CH$_2$)$_6$—, —CH=CH—, —CH=CH—CH$_2$—, —CH=CH—CH=CH—, —CH$_2$—CH=CH—CH$_2$—, —CH=CH—CH$_2$—CH=CH—, —CH$_2$—O—CH$_2$—CH$_2$—, —CH$_2$—N(R)—CH$_2$—CH$_2$—, —CH$_2$—CH$_2$—O—CH$_2$—CH$_2$—, —CH$_2$—CH$_2$—N(R)—CH$_2$—CH$_2$—, and the like.

Sulfonates as leaving groups (as used, for example, in most of the above-described transition-metal catalyzed C—C coupling reactions, like the Suzuki, Sonogashira, Heck reactions etc.) are in general fluorinated alkyl sulfonates, in particular fluorinated $C_1$-$C_{10}$-alkylsulfonates, more particularly perfluorinated $C_1$-$C_{10}$-alkylsulfonates, or aryl sulfonates, such as tosylate (p-toluene sulfonate). In particular they are triflate (trifluoromethane sulfonate), nonaflate (nonafluorobutyl sulfonate), heptadecafluorooctyl sulfonate or tosylate.

A metal equivalent M (as present for example in the boron compound $R^1$—$BF_3M$) is a metal cation equivalent of formula $(M^{n+})_{1/n}$, where M is a metal, in particular an alkali metal, such as Li, Na or K, an earth alkaline metal, such as Mg or Ca, Al or a transition metal, such as Fe, Ni, Cu etc.

An acyl group in a group R—C(=O)—, where R is alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl or heteroaryl group, as defined above, where this group may carry one or more substituents, as defined above.

The invention will be further illustrated by the following, non-limiting examples.

EXAMPLES

Abbreviations r.t. room temperature (20 to 25° C.)
TLC thin layer chromatography
LCMS liquid chromatography mass spectrometry
t-Bu, $^t$Bu tert-butyl
O-t-Bu, O$^t$Bu tert-butanolate
KO-t-Bu, KO$^t$Bu potassium tert-butanolate
NaO-t-Bu, NaO$^t$Bu sodium tert-butanolate
OAc acetate
KOAc potassium acetate
EtOAc ethylacetate
OTf triflate
dtbpf 1,1'-bis(di-tert-butylphosphino)ferrocene
mida, MIDA N-methyliminodiacetic acid (see above)
Fmoc fluorenylmethoxycarbonyl
Val-OH L-valine
Fmoc-Val-OH N-(9-fluorenylmethoxycarbonyl)-L-valine
$B_2pin_2$ bis(pinacolato)diboron In order to have reproducible conditions and exclude any (positive or negative) influence from the water used (e.g. from traces of metal or metal ions which may be present in common distilled water), Milli-Q® water was used. This Millipore Corporation trademark relates to 'ultrapure' water of "Type 1", as defined by various authorities (e.g. ISO 3696). The purification processes involve successive steps of filtration and deionization to achieve a purity expediently characterised in terms of resistivity (typically 18 MΩ·cm at 25° C.). In the present case it was obtained with an EMD Millipore Milli-Q™ Advantage A10 water purification system from EMD Millipore Z00Q0V0US. This water is termed in the following "Millipore water". But the reactions of the present invention can of course also be carried out with "normal" distilled water as used in any laboratory or industry or also just with tap water.

Preliminary Remarks

The viscosities of the cellulose derivatives given in the below examples are the values given by the respective suppliers of a 2% by weight solution at 20° C. They coincide well with the values obtained with the methods described above (for 1-70 mPa·s: Malvern Instruments Viscosizer 200 and an uncoated glass capillary; 25° C.; for >70-4000 mPa·s: falling-sphere viscosimeter; 25° C.; for >4000 mPa·s: single-cylinder type spindle viscosimeter; 20° C.

Following cellulosic products were used:

| Product | Commercial product name | Supplier | Viscosity given by supplier [mPa·s or cps] | Determined viscosity [mPa·s or cps] |
|---|---|---|---|---|
| HPMC | Mantrocel E5 2910 | Parmentier | 4-6 | 3.9 |
| HPMC | Hydroxypropyl methyl cellulose 40-60 | Sigma-Aldrich | 40-60 | |
| HPMC | Hydroxypropyl methyl cellulose 40-60 | Alfa Aesar | 40-60 | 42.8 |
| HPMC | Hydroxypropyl methyl cellulose 80-120 | Sigma-Aldrich | 80-120 | 77.3 |
| HPMC | Hydroxypropyl methyl cellulose 2600-5600 | Sigma-Aldrich | 2600-5600 | |
| HPMC | Methocel E4M Premium EP | Colorcon GmbH | 3000-5600 | |
| HPMC | Mantrocel K4M | Parmentier GmbH | 4100 | 3263 |
| MC | Methyl cellulose M6385 | Sigma-Aldrich | 25 | |
| MC | Methyl cellulose M7140 | Sigma-Aldrich | 15 | |
| MC | Methyl cellulose AB211131 | ABCR | 1600 | |
| HEC | Hydroxyethylcellulose | Sigma-Aldrich | 80-125 | |
| HEC | Hydroxyethylcellulose | Sigma-Aldrich | 145 | |
| HPC | Hydroxypropylcellulose AB137066 | ABCR | 3-5 | |
| HPC | Hydroxypropylcellulose 191884 | Sigma-Aldrich | 75-150* | |
| HECE | Polyquaternium 10 | Sigma-Aldrich | 400 | |
| MH | Tylose MH300 | Sigma-Aldrich | 150-450 | |

*determined at 25° C.; 5% in H$_2$O
HPMC hydroxypropylmethylcellulose
MC methylcellulose
HEC hydroxyethylcellulose
HPC hydroxypropylcellulose
HECE Polyquaternium-10; hydroxyethylcellulose ethoxylate (quaternized hydroxyethyl cellulose)
Tylose MH300 methyl-2-hydroxyethylcellulose

I. General Procedure for the Preparation of the Aqueous Oligosaccharide Solutions (Per 100 ml)

66 ml of Millipore water was heated to 70° C. under stirring in a reaction flask. The appropriate amount of an oligosaccharide was added. Subsequently 34 ml of Millipore water was added and the reaction mixture was allowed to cool to room temperature under stirring. The solution was purged with Argon for 30 minutes.

A. Procedure for the Preparation of 2% HPMC (40-60 cps=mPa·s) in Water (Per 100 ml):
66 ml of Millipore water was heated to 70° C. under stirring in a reaction flask. 2 g of HPMC (40-60 cps) were added. The reaction mixture formed a cloudy solution. Subsequently 34 ml of Millipore water was added and the reaction mixture was allowed to cool to room temperature under stirring to form a clear solution. The solution was purged with Argon for 30 minutes.

B. Procedure for the Preparation of 5% HPMC (40-60 cps) in Water (Per 100 ml):
66 ml of Millipore water was heated to 70° C. under stirring in a reaction flask. 5 g of HPMC (40-60 cps) were added. The reaction mixture formed a cloudy solution. Subsequently 34 ml of Millipore water was added and the reaction mixture was allowed to cool to room temperature under stirring to form a clear solution. The solution was purged with Argon for 30 minutes.

C. Procedure for the Preparation of 3% HPMC (40-60 cps) in Water (Per 100 ml):
66 ml of Millipore water was heated to 70° C. under stirring in a reaction flask. 3 g of HPMC (40-60 cps) were added. The reaction mixture formed a cloudy solution. Subsequently 34 ml of Millipore water was added and the reaction mixture was allowed to cool to room temperature under stirring to form a clear solution. The solution was purged with Argon for 30 minutes.

D. Procedure for the Preparation of 1% HPMC (40-60 cps) in Water (Per 100 ml):
66 ml of Millipore water was heated to 70° C. under stirring in a reaction flask. 1 g of HPMC (40-60 cps) were added. The reaction mixture formed a cloudy solution. Subsequently 34 ml of Millipore water was added and the reaction mixture was allowed to cool to room temperature under stirring to form a clear solution. The solution was purged with Argon for 30 minutes.

E. Procedure for the Preparation of 0.5% HPMC (40-60 cps) in Water (Per 100 ml):
66 ml of Millipore water was heated to 70° C. under stirring in a reaction flask. 500 mg of HPMC (40-60 cps) were added. The reaction mixture formed a cloudy solution. Subsequently 34 ml of Millipore water was added and the reaction mixture was allowed to cool to room temperature under stirring to form a clear solution. The solution was purged with Argon for 30 minutes.

Other oligosaccharides were prepared analogously.

II. Preparation Examples $^1$H-NMR: The signals are characterized by chemical shift (ppm) vs. tetramethylsilane, by their multiplicity and by their integral (relative number of hydrogen atoms given). The following abbreviations are used to characterize the multiplicity of the signals: m=multiplett, q=quartett, t=triplett, d=doublet, s=singlett, dd=doublet of doublets, dt=doublet of tripletts, dq=doublet of quartetts, ddd=doublet of doublets of doublets, td=triplett of doublets, tdd=triplett of doublets of doublets; tt=triplett of tripletts, br or=broad (e.g. s$_{br}$ or bs=broad singlett).

1. Buchwald-Hartwig Reactions

General Procedure for Buchwald-Hartwig Aminations I

[(π-allyl)PdCl]$_2$ catalyst (0.005 eq), a phosphine ligand (0.020 eq) and a base (1.50 eq) were added under an Argon atmosphere into a 5.0 mL microwave vial containing a magnetic stir bar and Teflon-lined septum. HPMC in water solution (40-60 cps, 3 ml of 2 wt % in degassed Millipore water) was added under a positive flow of argon, followed by the addition of the amine (1.20 eq) and subsequently of the aryl bromide (1.0 eq) (however, any liquid components were always added after the solvent). The reaction mixture was stirred at 1200 rpm for the indicated time at the indicated temperature. To the reaction mixture were added ethyl acetate and saturated aqueous sodium sulfate solution. The organic phase was separated from the solid. The solid was washed three times with ethyl acetate. The combined ethyl acetate phases were dried in vacuo and the residue was further purified by flash chromatography on silica gel.

General Procedure for Buchwald-Hartwig Aminations II

An amine (1.2 eq), an aryl bromide (1.0 eq), [(π-allyl)PdCl]$_2$ catalyst (0.005 eq), a phosphine ligand (0.020 eq) and a base (1.50 eq) were added under an Argon atmosphere into a 5.0 mL microwave vial containing a magnetic stir bar and Teflon-lined septum. HPMC in water solution (40-60 cps, 3 ml of 2 wt % in degassed Millipore water) was added under a positive flow of argon (however, any liquid components were always added after the solvent). The reaction mixture was stirred at 1200 rpm for the indicated time at the indicated temperature. To the reaction mixture were added ethyl acetate and saturated aqueous sodium sulfate solution. The organic phase was separated from the solid. The solid was washed three times with ethyl acetate. The combined ethyl acetate phases were dried in vacuo and the residue was further purified by flash chromatography on silica gel (0-30% ethyl acetate/heptane).

1.1 Preparation of N-(p-tolyl)naphthalen-2-amine According to the General Procedure I

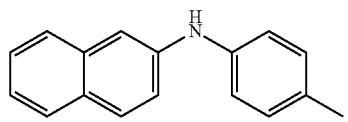 [SMILES: Cc1ccc(Nc2ccc3ccccc3c2)cc1]

Following the general procedure I using [(π-allyl)PdCl]$_2$ catalyst (1.8 mg, 0.005 mmol), di-tert-butyl(1-methyl-2,2-diphenylcyclopropyl)phosphine (cBRIDP) ligand (7.0 mg, 0.020 mmol), KO-t-Bu (168 mg, 1.50 mmol), a HPMC-solution (40-60 cps, 3 ml of 2 wt % in degassed Millipore water), p-toluidine (129 mg, 1.20 mmol) and naphthyl bromide (211 mg, 1.0 mmol). The reaction mixture was stirred at 1200 rpm for 4 h at room temperature LC-MS indicated however that the reaction was already completed after 2 h. To the reaction mixture were added 20 ml of ethyl acetate and 3 ml of saturated aqueous sodium sulfate solution. The organic phase was separated from the solid. The solid was washed three times with ethyl acetate. The combined ethyl acetate phases were dried in vacuo and the residue was further purified by flash chromatography on silica gel (0-30% ethyl acetate/heptane). The desired product was obtained as an off-white solid (211 mg, 88% yield).

ESI-MS: m/z (%): 234.20 (100, [M+H]$^+$).

$^1$H NMR (600 MHz, CDCl$_3$): δ [ppm]: 7.70 (m, 2H), 7.60 (m, 1H), 7.40 (m, 2H), 7.30 (m, 1H), 7.20 (m, 1H), 7.15 (m, 2H), 7.10 (m, 2H), 5.80 (s$_{br}$, 1H), 2.30 (s, 3H).

1.2 Preparation of N-(p-tolyl)naphthalen-2-amine According to the General Procedure II

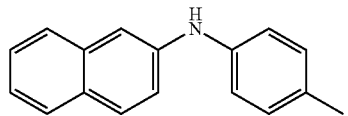 [SMILES: Cc1ccc(Nc2ccc3ccccc3c2)cc1]

Following the general procedure II using p-toluidine (129 mg, 1.20 mmol), naphthyl bromide (211 mg, 1.0 mmol), [(π-allyl)PdCl]$_2$ catalyst (1.8 mg, 0.005 mmol), di-tert-butyl (1-methyl-2,2-diphenylcyclopropyl)phosphine (cBRIDP) ligand (7.0 mg, 0.020 mmol), KO-t-Bu (168 mg, 1.50 mmol) and a HPMC-solution (40-60 cps, 3 ml of 2 wt % in degassed Millipore water) were stirred at 1200 rpm for 15 min. at 50° C. To the reaction mixture were added 20 ml of ethyl acetate and 3 ml of saturated aqueous sodium sulfate solution. The organic phase was separated from the solid. The solid was washed three times with ethyl acetate. The combined ethyl acetate phases were dried in vacuo and the residue was further purified by flash chromatography on silica gel (0-30% ethyl acetate/heptane). The desired product was obtained as an off-white solid (224 mg, 90% yield, 94% purity).

ESI-MS: m/z (%): 234.20 (100, [M+H]$^+$).

$^1$H NMR (600 MHz, CDCl$_3$): δ [ppm]: 7.70 (m, 2H), 7.60 (m, 1H), 7.35 (m, 2H), 7.25 (m, 1H), 7.20 (m, 1H), 7.15 (m, 2H), 7.10 (m, 2H), 5.85 (s$_{br}$, 1H), 2.35 (s, 3H).

1.3 Preparation of 4-methoxy-N-(p-tolyl)aniline According to General Procedure II

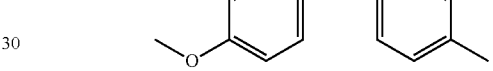

1.3.1) According to the general procedure II, p-toluidine (129 mg, 1.20 mmol), 1-bromo-4-methoxybenzene (189 mg, 1.0 mmol), [(π-allyl)PdCl]$_2$ catalyst (1.8 mg, 0.005 mmol), di-tert-butyl(1-methyl-2,2-diphenylcyclopropyl)phosphine (cBRIDP) ligand (7.0 mg, 0.020 mmol), KO-t-Bu (168 mg, 1.50 mmol) and a HPMC-solution (40-60 cps, 3 ml of 2 wt % in degassed Millipore water) were stirred at 1200 rpm overnight at room temperature. To the reaction mixture were added 20 ml of ethyl acetate and 3 ml of saturated aqueous sodium sulfate solution. The organic phase was separated from the solid. The solid was washed three times with ethyl acetate. The combined ethyl acetate phases were dried in vacuo and the residue was further purified by flash chromatography on silica gel (0-100% ethyl acetate/cyclohexane). The desired product was obtained as an off-white solid (213 mg, 100% yield).

1.3.2) According to the general procedure II, p-toluidine (129 mg, 1.20 mmol), 1-bromo-4-methoxybenzene (189 mg, 1.0 mmol), [(π-allyl)PdCl]$_2$ catalyst (1.8 mg, 0.005 mmol), di-tert-butyl(1-methyl-2,2-diphenylcyclopropyl)phosphine (cBRIDP) ligand (7.0 mg, 0.020 mmol, KO-t-Bu (168 mg, 1.50 mmol) and HPMC-solution (40-60 cps, 3 ml of 2 wt % in degassed Millipore water) were stirred at 1200 rpm for 1 h at 50° C. To the reaction mixture were added 20 ml of ethyl acetate and 3 ml of saturated aqueous sodium sulfate solution. The organic phase was separated from the solid. The solid was washed three times with ethyl acetate. The combined ethyl acetate phases were dried in vacuo and the residue was further purified by flash chromatography on silica gel (0-100% ethyl acetate/cyclohexane). The desired product was obtained as an off-white solid (209 mg, 98% yield).

1.3.3) According to the general procedure II, p-toluidine (129 mg, 1.20 mmol), 1-bromo-4-methoxybenzene (189 mg, 1.0 mmol), [(π-allyl)PdCl]$_2$ catalyst (1.8 mg, 0.005 mmol), di-tert-butyl(1-methyl-2,2-diphenylcyclopropyl)phosphine (cBRIDP) ligand (7.0 mg, 0.020 mmol), KO-t-Bu (168 mg, 1.50 mmol) and a HPMC-solution (4-6 cps, 3 ml of 2 wt % in degassed Millipore water) were stirred at 1200 rpm for 40 min at 50° C. To the reaction mixture were added 20 ml of ethyl acetate and 3 ml of saturated aqueous sodium sulfate solution. The organic phase was separated from the solid. The solid was washed three times with ethyl acetate. The combined ethyl acetate phases were dried in vacuo and the residue was further purified by flash chromatography on silica gel (0-100% ethyl acetate/cyclohexane). The desired product was obtained as an off-white solid (204 mg, 96% yield).

1.3.4) According to the general procedure II, p-toluidine (129 mg, 1.20 mmol), 1-bromo-4-methoxybenzene (189 mg, 1.0 mmol), [(π-allyl)PdCl]$_2$ catalyst (1.8 mg, 0.005 mmol), di-tert-butyl(1-methyl-2,2-diphenylcyclopropyl)phosphine (cBRIDP) ligand (7.0 mg, 0.020 mmol), KO-t-Bu (168 mg, 1.50 mmol) and a HPMC-solution (4-6 cps, 0.35 ml of 2 wt % in degassed Millipore water) were stirred at 1200 rpm for 9 min at 50° C. To the reaction mixture were added 20 ml of ethyl acetate and 3 ml of saturated aqueous sodium sulfate solution. The organic phase was separated from the solid. The solid was washed three times with ethyl acetate. The combined ethyl acetate phases were dried in vacuo and the residue was further purified by flash chromatography on silica gel (0-100% ethyl acetate/cyclohexane). The desired product was obtained as an off-white solid (183 mg, 86% yield).

ESI-MS: m/z (%): 214.20 (100, [M+H]$^+$).
$^1$H NMR (600 MHz, d$^6$-DMSO): δ [ppm]: 7.68 (s, 1H), 7.01-6.95 (m, 4H), 6.87-6.80 (m, 4H), 3.70 (s, 3H), 2.19 (s, 3H).

1.4 Preparation of 4-methoxy-N-(m-tolyl)benzamide

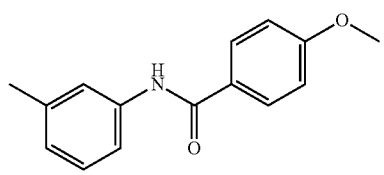

1.4.1) According to the general procedure II, 4-methoxybenzamide (181 mg, 1.20 mmol), 3-bromo-toluene (171 mg, 0.98 mmol), [(π-allyl)PdCl]$_2$ catalyst (5.6 mg, 0.011 mmol), di-tert-butyl(2',4',6'-triisopropyl-[1,1'-biphenyl]-2-yl)phosphine (tBuXPhos) ligand (18.3 mg, 0.043 mmol), NaO-t-Bu (141 mg, 1.50 mmol) and a HPMC-solution (40-60 cps, 3 ml of 2 wt % in degassed Millipore water) were stirred at 1200 rpm for 5 h at room temperature. To the reaction mixture were added 20 ml of ethyl acetate and 3 ml of saturated aqueous sodium sulfate solution. The organic phase was separated from the solid. The solid was washed three times with ethyl acetate. The combined ethyl acetate phases were dried in vacuo and the residue was further purified by flash chromatography on silica gel (0-100% ethyl acetate/cyclohexane). The desired product was obtained as an off-white solid (209 mg, 89% yield).

1.4.2) According to the general procedure II, 4-methoxybenzamide (181 mg, 1.20 mmol), 3-bromo-toluene (171 mg, 0.98 mmol), [(π-allyl)PdCl]$_2$ catalyst (5.6 mg, 0.011 mmol), di-tert-butyl(2',4',6'-triisopropyl-[1,1'-biphenyl]-2-yl)phosphine (tBuXPhos) ligand (18.3 mg, 0.043 mmol), NaO-t-Bu (141 mg, 1.50 mmol) and a HPMC-solution (40-60 cps, 3 ml of 2 wt % in degassed Millipore water) were stirred at 1200 rpm for 30 min at 50° C. To the reaction mixture were added 20 ml of ethyl acetate and 3 ml of saturated aqueous sodium sulfate solution. The organic phase was separated from the solid. The solid was washed three times with ethyl acetate. The combined ethyl acetate phases were dried in vacuo and the residue was further purified by flash chromatography on silica gel (0-100% ethyl acetate/cyclohexane). The desired product was obtained as an off-white solid (230 mg, 97% yield).

1.4.3) According to the general procedure II, 4-methoxybenzamide (181 mg, 1.20 mmol), 3-bromo-toluene (171 mg, 0.98 mmol), [(π-allyl)PdCl]$_2$ catalyst (5.6 mg, 0.011 mmol), di-tert-butyl(2',4',6'-triisopropyl-[1,1'-biphenyl]-2-yl)phosphine (tBuXPhos) ligand (18.3 mg, 0.043 mmol), NaO-t-Bu (141 mg, 1.50 mmol) and a HPMC-solution (4-6 cps, 2 wt % in 0.35 ml degassed Millipore water) were stirred at 1200 rpm for 30 min at 50° C. To the reaction mixture were added 20 ml of ethyl acetate and 3 ml of saturated aqueous sodium sulfate solution. The organic phase was separated from the solid. The solid was washed three times with ethyl acetate. The combined ethyl acetate phases were dried in vacuo and the residue was further purified by flash chromatography on silica gel (0-100% ethyl acetate/cyclohexane). The desired product was obtained as an off-white solid (221 mg, 89% yield, 95% purity).

ESI-MS: m/z (%): 242.20 (100, [M+H]$^+$).
$^1$H NMR (600 MHz, d$_6$-DMSO): δ [ppm]: 10.01 (s, 1H), 7.99-7.92 (m, 2H), 7.61 (d, J=1.8 Hz, 1H), 7.59-7.53 (m, 1H), 7.22 (t, J=7.8 Hz, 1H), 7.09-7.03 (m, 2H), 6.90 (d, J=7.5 Hz, 1H), 3.84 (s, 3H), 2.30 (s, 3H).

1.5 Preparation of ethyl-4-((tert-butoxycarbonyl)amino)benzoate

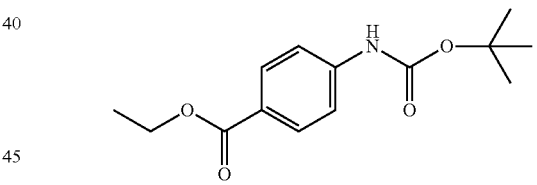

1.5.1) According to the general procedure I, tert-butyl carbamate (176 mg, 1.50 mmol), ethyl 4-bromobenzoate (229 mg, 1.00 mmol), [(π-allyl)PdCl]$_2$ catalyst (1.8 mg, 0.005 mmol), di-tert-butyl(1-methyl-2,2-diphenylcyclopropyl)phosphine (cBRIDP) ligand (7.1 mg, 0.020 mmol), NaO-t-Bu (144 mg, 1.50 mmol) and a HPMC-solution (40-60 cps, 3 ml of 2 wt % in degassed Millipore water) were stirred at 1200 rpm for 1 h at room temperature. To the reaction mixture were added 20 ml of ethyl acetate and 3 ml of saturated aqueous sodium sulfate solution. The organic phase was separated from the solid. The solid was washed three times with ethyl acetate. The combined ethyl acetate phases were dried in vacuo and the residue was further purified by flash chromatography on silica gel (0-100% ethyl acetate/cyclohexane). The desired product was obtained as an off-white solid (220 mg, 79% yield).

1.5.2) According to the general procedure I, tert-butyl carbamate (176 mg, 1.50 mmol), ethyl 4-bromobenzoate (229 mg, 1.00 mmol), [(π-allyl)PdCl]$_2$ catalyst (1.8 mg, 0.005 mmol), di-tert-butyl(1-methyl-2,2-diphenylcyclopropyl)phosphine (cBRIDP) ligand (7.1 mg, 0.020 mmol), NaO-t-Bu (144 mg, 1.50 mmol) and a HPMC-solution (40-60 cps, 3 ml of 2 wt % in degassed Millipore water) were stirred at 1200 rpm for 15 min at 50° C. To the reaction mixture were added 20 ml of ethyl acetate and 3 ml of saturated aqueous sodium sulfate solution. The organic phase was separated from the solid. The solid was washed three times with ethyl acetate. The combined ethyl acetate phases were dried in vacuo and the residue was further purified by flash chromatography on silica gel (0-100% ethyl acetate/cyclohexane). The desired product was obtained as an off-white solid (225 mg, 85% yield).

1.5.3) According to the general procedure I, tert-butyl carbamate (176 mg, 1.50 mmol), ethyl 4-bromobenzoate (229 mg, 1.00 mmol), [(π-allyl)PdCl]$_2$ catalyst (1.8 mg, 0.005 mmol), di-tert-butyl(1-methyl-2,2-diphenylcyclopropyl)phosphine (cBRIDP) ligand (7.1 mg, 0.020 mmol), NaO-t-Bu (144 mg, 1.50 mmol) and a HPMC-solution (4-6 cps, 0.35 ml of 2 wt % in degassed Millipore water) were stirred at 1200 rpm for 4 min at 50° C. To the reaction mixture were added 20 ml of ethyl acetate and 3 ml of saturated aqueous sodium sulfate solution. The organic phase was separated from the solid. The solid was washed three times with ethyl acetate. The combined ethyl acetate phases were dried in vacuo and the residue was further purified by flash chromatography on silica gel (0-100% ethyl acetate/cyclohexane). The desired product was obtained as an off-white solid (275 mg, 98% yield).

ESI-MS: m/z (%): 210.20 (100, [M+H-t-Bu]$^+$), 266.25 (75, [M+H]$^+$).

$^1$H NMR (600 MHz, CDCl$_3$): δ [ppm]: 8.00 (m, 2H), 7.45 (m, 2H), 6.65 (s$_{br}$, 1H), 4.35 (m, 2H), 1.50 (s, 9H), 1.40 (m, 3H).

1.6 Preparation of tert-butyl pyrimidin-5-ylcarbamate

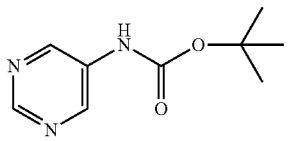

According to the general procedure I, tert-butyl carbamate (176 mg, 1.50 mmol), 5-bromopyrimidine (164 mg, 1.00 mmol), [Pd(1-phenylallyl)Cl]$_2$ catalyst (10.4 mg, 0.02 mmol), di-tert-butyl(2',4',6'-triisopropyl-[1,1'-biphenyl]-2-yl)phosphine (tBuXPhos) ligand (17.0 mg, 0.04 mmol), potassium hydroxide (84 mg, 1.50 mmol), triisopropylsilanol (267 mg, 1.50 mmol) and a HPMC-solution (4-6 cps, 0.333 ml of 2 wt % in degassed Millipore water) were stirred at 1200 rpm for 45 min at 50° C. To the reaction mixture was added bulk sorbents (diatomaceous earth; mean particle size: 150-850 µm; pore size/porosity; 60 A; Telos® NM from Kinesis Bulk Media). The solid was then added on top of a silica gel chromatography cartridge and was further purified by flash chromatography on silica gel (0-40% ethyl dichloromethane/methanol). The desired product was obtained as an off-white solid (191 mg, 83% yield, 85% purity).

APCI-MS: m/z (%): 196.20 (100, [M+H]$^+$).

$^1$H NMR (600 MHz, CDCl$_3$): δ [ppm]: 8.95 (s, 1H), 8.85 (s, 2H), 6.50 (s$_{br}$, 1H), 1.55 (s, 9H).

1.7 Preparation of 6-methyl-N-(3-phenylpropyl)pyridine-2-amine

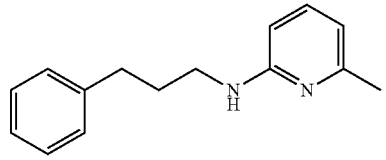 [SMILES: Cc1cccc(NCCCc2ccccc2)n1]

1.7.1) According to the general procedure II, 3-phenylpropylamine (162 mg, 1.20 mmol), 2-chloro-6-methylpyridine (128 mg, 1.00 mmol), [(π-allyl)PdCl]$_2$ catalyst (5.7 mg, 0.011 mmol), di-tert-butyl(2',4',6'-triisopropyl-[1,1'-biphenyl]-2-yl)phosphine (t-BuXPhos) ligand (18.8 mg, 0.044 mmol) NaO-t-Bu (145 mg, 1.50 mmol) and a HPMC-solution (40-60 cps, 1 ml of 2 wt % in degassed Millipore water) were stirred at 1200 rpm for 5 h at room temperature. To the reaction mixture were added 20 ml of ethyl acetate and 3 ml of saturated aqueous sodium sulfate solution. The organic phase was separated from the solid. The solid was washed three times with ethyl acetate. The combined ethyl acetate phases were dried in vacuo and the residue was further purified by flash chromatography on silica gel (0-100% ethyl acetate/cyclohexane). The desired product was obtained as an off-white solid (150 mg, 66% yield).

1.7.2) According to the general procedure II, 3-phenylpropylamine (162 mg, 1.20 mmol), 2-chloro-6-methylpyridine (128 mg, 1.00 mmol), [(π-allyl)PdCl]$_2$ catalyst (5.7 mg, 0.011 mmol), di-tert-butyl(2',4',6'-triisopropyl-[1,1'-biphenyl]-2-yl)phosphine (t-BuXPhos) ligand (18.8 mg, 0.044 mmol), NaO-t-Bu (145 mg, 1.50 mmol) and a HPMC-solution (40-60 cps, 1 ml of 2 wt % in degassed Millipore water) were stirred at 1200 rpm for 3 h at 50° C. To the reaction mixture were added 20 ml of ethyl acetate and 3 ml of saturated aqueous sodium sulfate solution. The organic phase was separated from the solid. The solid was washed three times with ethyl acetate. The combined ethyl acetate phases were dried in vacuo and the residue was further purified by flash chromatography on silica gel (0-100% ethyl acetate/cyclohexane). The desired product was obtained as an off-white solid (183 mg, 81% yield).

ESI-MS: m/z (%): 227.20 (100, [M+H]$^+$).

$^1$H NMR (600 MHz, d$_6$-DMSO): δ [ppm]: 7.31-7.24 (m, 2H), 7.27-7.19 (m, 3H), 7.21-7.14 (m, 1H), 6.38 (t, J=5.5 Hz, 1H), 6.30 (d, J=7.1 Hz, 1H), 6.22 (d, J=8.3 Hz, 1H), 3.23-3.16 (m, 2H), 2.68-2.61 (m, 2H), 2.23 (s, 3H), 1.81 (tt, J=7.5, 6.4 Hz, 2H).

General Procedure for Buchwald-Hartwig Reactions Using Sulfonamides

To allylpalladium chloride dimer (0.02 equiv.), di-tert-butyl(1-methyl-2,2-diphenylcyclopropyl)phosphine (0.04 equiv.), NaO$^t$Bu (1.5 equiv.) and the sulfonamide (1.2 equiv.) under an argon atmosphere was added 2 wt % solution of HPMC (40-60 cps) in Millipore water and the arylbromide (1.0 equiv.). The reaction was stirred under an argon atmosphere for the indicated time at the indicated temperature. The mixture was diluted with EtOAc (3 mL) and then with a sat. solution of Na$_2$SO$_4$ (3 mL). After Extraction with EtOAc (1×15 mL), the mixture was brought to pH 3 by using a 5% solution of citric acid in water (3 mL)

and extracted again using EtOAc (2×15 mL). The clean product was obtained after flash chromatography on silica gel.

1.8 Preparation of ethyl 4-(methylsulfonamido)benzoate

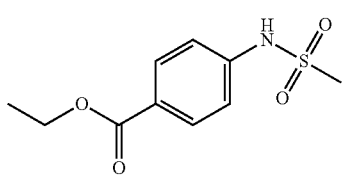 [SMILES: CCOC(=O)c1ccc(NS(C)(=O)=O)cc1]

1.8.1) Following the general procedure using ethyl 4-bromobenzoate (229 mg, 1.00 mmol, 1.0 equiv.), methanesulfonamide (114 mg, 1.20 mmol, 1.2 equiv.), allylpalladium chloride dimer (7.3 mg, 0.02 mmol, 0.02 equiv.), di-tert-butyl(1-methyl-2,2-diphenylcyclopropyl)phosphine (14 mg, 0.04 mmol, 0.04 equiv.), NaO$^t$Bu (144 mg, 1.50 mmol, 1.5 equiv.) and a HPMC solution (40-60 cps, 1 ml of 2 wt % in degassed Millipore water) the reaction was allowed to stir vigorously under an argon atmosphere for 6 h at 50° C., 20 h at room temperature, 6 h at 50° C. and again for 20 h at room temperature. After column chromatography (0-50% EtOAc/heptane), the product was obtained (158 mg, 0.65 mmol, 65%).

1.8.2) Following the general procedure using ethyl 4-bromobenzoate (229 mg, 1.00 mmol, 1.0 equiv.), methanesulfonamide (114 mg, 1.20 mmol, 1.2 equiv.), allylpalladium chloride dimer (7.3 mg, 0.02 mmol, 0.02 equiv.), di-tert-butyl(1-methyl-2,2-diphenylcyclopropyl)phosphine (14 mg, 0.04 mmol, 0.04 equiv.), NaO$^t$Bu (144 mg, 1.50 mmol, 1.5 equiv.) and a HPMC-solution (40-60 cps, 0.333 ml of 2 wt % in degassed Millipore water) the reaction was allowed to stir vigorously under an argon atmosphere for 6 h at 50° C., 20 h at room temperature, 6 h at 50° C. and again for 20 h at room temperature. After column chromatography (0-50% EtOAc/heptane), the product was obtained (158 mg, 0.65 mmol, 65%).

ESI-MS: m/z (%): 244.0 (100, [M+H]$^+$).

$^1$H NMR (600 MHz, CDCl$_3$): δ [ppm]: 8.10-7.97 (m, 2H), 7.25-7.21 (m, 2H), 6.61 (s$_{br}$, 1H), 4.37 (q, J=7.1 Hz, 2H), 3.09 (s, 3H), 1.39 (t, J=7.1 Hz, 3H).

General Procedure for Buchwald-Hartwig Reactions Using Urea Derivatives

To allylpalladium chloride dimer (0.02 equiv.), di-tert-butyl(1-methyl-2,2-diphenylcyclopropyl)phosphine (0.04 equiv.), KOH (1.5 equiv.) and the urea derivative (1.2 equiv.) under an argon atmosphere was added a 2 wt % solution of HPMC in Millipore water, the arylbromide (1.0 equiv.) and finally TIPS-OH (1.2 equiv.). The reaction was stirred under an argon atmosphere for the indicated time at the indicated temperature. The mixture was diluted with EtOAc (3 mL) and then with a sat. solution of Na$_2$SO$_4$ (3 mL). After Extraction with EtOAc (up to 9×5 mL), the crude product was purified by flash chromatography on silica gel.

1.9 Preparation of ethyl 4-(piperidine-1-carboxamido)benzoate

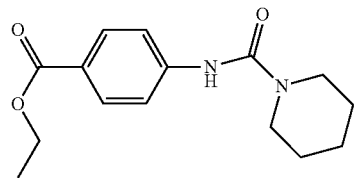 [SMILES: CCOC(=O)c1ccc(NC(=O)N2CCCCC2)cc1]

1.9.1) Following the general procedure using ethyl 4-bromobenzoate (229 mg, 1.00 mmol, 1.0 equiv.), piperidine-1-carboxamide (159 mg, 1.20 mmol, 1.2 equiv.), allylpalladium chloride dimer (7.2 mg, 0.02 mmol, 0.02 equiv.), di-tert-butyl(1-methyl-2,2-diphenylcyclopropyl)phosphine (14 mg, 0.04 mmol, 0.04 equiv.), KOH (82 mg, 1.50 mmol, 1.5 equiv.), triisopropylsilanol (261 mg, 1.50 mmol, 1.5 equiv.) and a 2 wt % solution of HPMC (40-60 cps) in Millipore water (2.0 mL) the reaction was allowed to stir vigorously under an argon atmosphere for 2.5 h at 50° C. After column chromatography (0-50% EtOAc/heptane), the product was obtained (249 mg, 0.88 mmol, 89%).

1.9.2) Following the general procedure using ethyl 4-bromobenzoate (229 mg, 1.00 mmol, 1.0 equiv.), piperidine-1-carboxamide (159 mg, 1.20 mmol, 1.2 equiv.), allylpalladium chloride dimer (7.2 mg, 0.02 mmol, 0.02 equiv.), di-tert-butyl(1-methyl-2,2-diphenylcyclopropyl)phosphine (14 mg, 0.04 mmol, 0.04 equiv.), KOH (82 mg, 1.50 mmol, 1.5 equiv.), triisopropylsilanol (261 mg, 1.50 mmol, 1.5 equiv.) and a 2 wt % solution of HPMC (4-6 cps) in Millipore water (0.33 mL) the reaction was allowed to stir vigorously under an argon atmosphere for 40 min at 50° C. After column chromatography (0-50% EtOAc/heptane), the product was obtained (276 mg, 0.95 mmol, 97%).

ESI-MS: m/z (%): 277.1 (100, [M+H]$^+$).

$^1$H NMR (600 MHz, CDCl$_3$): δ [ppm]: 8.00-7.94 (m, 2H), 7.47-7.42 (m, 2H), 6.53 (s$_{br}$, 1H), 4.35 (q, J=7.1 Hz, 2H), 3.50-3.44 (m, 4H), 1.70-1.60 (m, 6H), 1.38 (t, J=7.1 Hz, 3H).

1.10 Preparation of N-(p-tolyl)naphthalen-2-amine Using HPMC in Various Concentrations

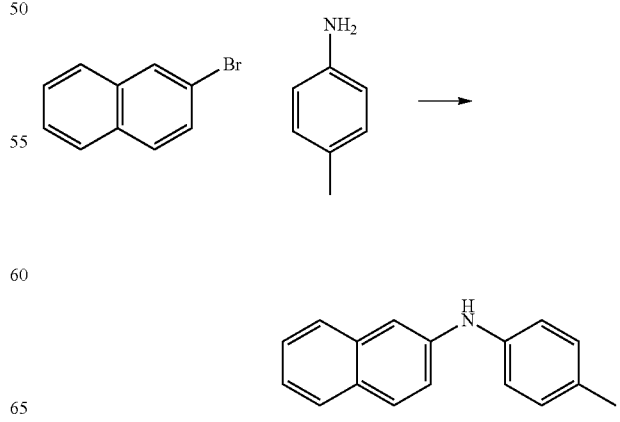

[(π-allyl)PdCl]₂ catalyst (1.8 mg, 0.005 mmol), di-tert-butyl(1-methyl-2,2-diphenyl-cyclopropyl)phosphine (cBRIDP) ligand (7.0 mg, 0.020 mmol) and KO-t-Bu as base (168 mg, 1.50 mmol) were added under an Argon atmosphere into a 5.0 mL microwave vial containing a magnetic stir bar and Teflon-lined septum. As solvent an HPMC (40-60 cps)-water solution (specifications & volume see table below) was added under a positive flow of Argon, followed by the addition of p-toluidine (129 mg, 1.20 mmol) and subsequently naphthyl bromide (211 mg, 1.0 mmol). The reaction mixture was stirred at 1200 rpm for the indicated time (see table below) at 50° C. To the reaction mixture were added ethyl acetate and 3 ml of saturated aqueous sodium sulfate solution. The organic phase was separated from the solid. The solid was extracted three times with ethyl acetate. The combined ethyl acetate phases were dried in vacuo and the residue was further purified by flash chromatography on silica gel (0-30% ethyl acetate/heptane). The desired product was obtained as an off-white solid.

| Ex. No. | Amount HPMC | Viscosity solvent | Volume solvent | Molarity reaction[1] | Reaction time | Yield[2] |
|---|---|---|---|---|---|---|
| 1.10.1 | 0.2 wt % | 1.02 cps | 3.00 mL | 0.33M | 30 min | 87% |
| 1.10.2 | 0.2 wt % | 1.02 cps | 0.35 mL | 2.86M | 90 sec | 92% |
| 1.10.3 | 2.0 wt % | 42.88 cps | 3.00 mL | 0.33M | 15 min | 90% |
| 1.10.4 | 2.0 wt % | 42.88 cps | 0.35 mL | 2.86M | 90 sec | 98% |

[1] mol naphthyl bromide per 1l of solvent
[2] realtive to naphthyl bromide

The same reaction as in 1.10.3 and 1.10.4 was carried out at room temperature. The results are compiled in the following table:

| Ex. No. | Amount HPMC | Viscosity solvent | Volume solvent | Molarity reaction[1] | Reaction time | Yield[2] |
|---|---|---|---|---|---|---|
| 1.10.5 | 2.0 wt % | 42.88 cps | 3.00 mL | 0.33M | 3 h | 91% |
| 1.10.6 | 2.0 wt % | 42.88 cps | 0.35 mL | 2.86M | 5 min | 97% |

[1] mol naphthyl bromide per 1l of solvent
[2] realtive to naphthyl bromide

1.11 Preparation of N-(p-tolyl)naphthalen-2-amine Using HPMCs of Various Viscosities and Other Cellulose Derivatives

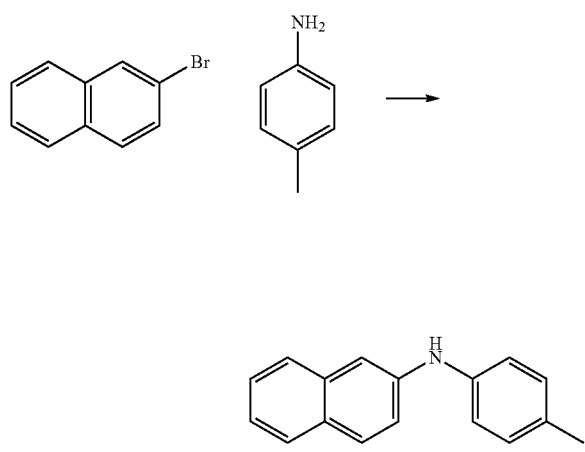

[(π-allyl)PdCl]₂ catalyst (1.8 mg, 0.005 mmol), di-tert-butyl(1-methyl-2,2-diphenylcyclopropyl)phosphine (cBRIDP) ligand (7.0 mg, 0.020 mmol) and KO-t-Bu as base (168 mg, 1.50 mmol) were added under an argon atmosphere into a 5.0 mL microwave vial containing a magnetic stir bar and Teflon-lined septum. A 2 wt % solution of cellulose derivative in Millipore water (molarity of the reaction: 0.3 M, specifications of the cellulose derivative: see table below) was added under a positive flow of Argon, followed by the addition of p-toluidine (129 mg, 1.20 mmol) and subsequently naphthyl bromide (211 mg, 1.0 mmol). The reaction mixture was stirred at 1200 rpm until full conversion (followed by LCMS, see table below) at 50° C. To the reaction mixture were added ethyl acetate and 3 ml of saturated aqueous sodium sulfate solution. The organic phase was separated from the solid. The solid was washed three times with ethyl acetate. The combined ethyl acetate phases were dried in vacuo and the residue was further purified by flash chromatography on silica gel (0-30% ethyl acetate/heptane). The desired product was obtained as an off-white solid.

| Ex. No. | Cellulose derivative | Temperature | Reaction time | Yield |
|---|---|---|---|---|
| 1.11.1 | HPMC (4.8-7.2 cps) | RT | 3 h | 90% |
| 1.11.2 | HPMC (80-120 cps) | RT | 72 h | 89% |
| 1.11.3 | HPMC (2600-5600 cps) | RT | 6.5 h | 92% |
| 1.11.4 | HPMC (3000-5600 cps) | RT | 3 h | 93% |
| 1.11.5 | HPMC (4100 cps) | RT | 1 h | 89% |
| 1.11.6 | MC (25 cps) | RT | 4 h | 94% |
| 1.11.7 | HPMC (4-6 cps) | 50° C. | 15 min | 89% |
| 1.11.8 | HPMC (40-60 cps) | 50° C. | 15 min | 90% |
| 1.11.9 | MC (15 cps) | 50° C. | 15 min | 92% |
| 1.11.10 | MC (1600 cps) | 50° C. | 5 min | 88% |
| 1.11.11 | HEC (80-125 cps) | 50° C. | 20 min | 89% |
| 1.11.12 | HEC (145 cps) | 50° C. | 6 min | 95% |
| 1.11.13 | HECE (Polyquat. 10) | 50° C. | 12 min | 94% |
| 1.11.14 | HPC (3-5 cps) | 50° C. | 15 min | 92% |
| 1.11.15 | HPC (75-150 cps) | 50° C. | 20 min | 84% |
| 1.11.16 | Tylose MH300 | 50° C. | 25 min | 94% |

HPMC hydroxypropylmethylcellulose
MC methylcellulose
HEC hydroxyethylcellulose
HPC hydroxypropylcellulose
HECE Polyquaternium-10; hydroxyethylcellulose ethoxylate (quaternized hydroxyethyl cellulose)
Tylose MH300 methyl-2-hydroxyethylcellulose The same reaction as in 1.11.7 was carried out, using however only 0.35 ml of the 2 wt % solution of HPMC (4-6) in Millipore water (molarity of the reaction: 2.86 M). The result is compiled below:

| Ex. No. | Cellulose derivative | Temperature | Reaction time | Yield |
|---|---|---|---|---|
| 1.11.17 | HPMC (4-6 cps) | 50° C. | 90 sec | 90% |

2. Suzuki Reactions

General Procedure for Suzuki Reactions Using Boronic Acids

A 5 mL microwave vial was charged with the aryl halide (1.0 equiv.), the boronic acid (1.0-2.10 equiv.) and $PdCl_2$(dtbpf) (0.02 equiv.). After the addition of HPMC-solution (40-60 cps, 2 wt % in Millipore water, 3.0 mL) and triethylamine (3.0 equiv.) the reaction mixture was vigorously stirred (1200 rpm) at the defined temperature until LCMS or TLC showed full conversion of the aryl halide. The mixture was diluted with EtOAc (5 mL) followed by the addition of a saturated aqueous solution of sodium sulfate (4 mL). After 5 min of stirring (200 rpm) the precipitated solids were filtered off and washed with EtOAc (3×15 mL)). After extraction, the organic layer was dried over sodium sulfate. The crude product was purified by flash chromatography on silica gel.

2.1 Preparation of 3-(thiophen-3-yl)quinoline

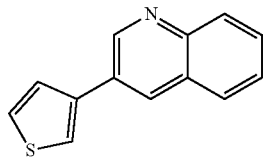 [SMILES: c1ccc2ncc(-c3ccsc3)cc2c1]

2.1.1) Following the general procedure using 3-bromoquinoline (208 mg, 1.00 mmol, 1.0 equiv.), thiophene-3-boronic acid (256 mg, 2.00 mmol, 2.00 equiv.), $PdCl_2$(dtbpf) (13.0 mg, 0.02 mmol, 0.02 equiv.) and triethylamine (304 mg, 3.00 mmol, 3.0 equiv.) the reaction was allowed to stir for 1 h at room temperature. After column chromatography on silica gel (0-30% ethyl acetate-cyclohexane) the product was obtained as a white solid (199 mg, 0.94 mmol, 94%).

2.1.2) Following the general procedure using 3-bromoquinoline (219 mg, 1.05 mmol, 1.0 equiv.), thiophene-3-boronic acid (269 mg, 2.11 mmol, 2.00 equiv.), $PdCl_2$(dtbpf) (13.7 mg, 0.02 mmol, 0.021 equiv.) and triethylamine (320 mg, 3.16 mmol, 3.0 equiv.) the reaction was allowed to stir for 10 min at 50° C. After column chromatography on silica gel (0-30% ethyl acetate-cyclohexane) the product was obtained as a white solid (209 mg, 0.99 mmol, 94%).

ESI-MS: m/z (%): 212.1 (100, [M+H]$^+$).

$^1$H NMR (600 MHz, $CDCl_3$): δ [ppm]: 9.20 (d, J=2.3 Hz, 1H), 8.28 (d, J=2.3, 1H), 8.19-8.04 (m, 1H), 7.90-7.77 (m, 1H), 7.73-7.68 (m, 1H), 7.67-7.64 (m, 1H), 7.59-7.54 (m, 1H), 7.54-7.51 (m, 1H), 7.50-7.47 (m, 1H).

2.2 Preparation of 4,6-bis(4-(trifluoromethyl)phenyl)pyrimidine

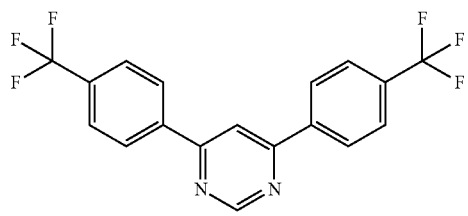 [SMILES: FC(F)(F)c1ccc(-c2cc(-c3ccc(C(F)(F)F)cc3)ncn2)cc1]

Following the general procedure using 4,6-dichloropyrimidine (149 mg, 1.00 mmol, 1.0 equiv.), 4-(trifluoromethyl)phenylboronic acid (399 mg, 2.10 mmol, 2.10 equiv.), $PdCl_2$(dtbpf) (13.0 mg, 0.02 mmol, 0.02 equiv.) and triethylamine (304 mg, 3.00 mmol, 3.0 equiv.) the reaction was allowed to stir for 1 h at 50° C. After column chromatography on silica gel (0-30% ethyl acetate-cyclohexane) the product was obtained as a white solid (345 mg, 0.94 mmol, 94%).

ESI-MS: m/z (%): 369.2 (100, [M+H]$^+$).

$^1$H NMR (600 MHz, $CDCl_3$): δ [ppm]: 9.36 (s, 1H), 8.26 (d, J=8.2 Hz, 4H), 8.13 (s, 1H), 7.79 (d, J=8.4 Hz, 4H).

General Procedure for Suzuki Reactions Using Boronic Acid Mida Esters

A 5 mL microwave vial was charged with the boronic acid mida ester (1.0 equiv.), the aryl halide (1.0 equiv.) and $PdCl_2$(dtbpf) (0.02 equiv.). After the addition of HPMC-solution (40-60 cps, 2 wt % in Millipore water, 1.5 mL) and triethylamine (152 mg, 1.50 mmol, 3.0 equiv.) the reaction mixture was vigorously stirred (1200 rpm) at room temperature until LCMS or TLC showed full conversion of the aryl halide. The mixture was diluted with EtOAc (3 mL) followed by the addition of a saturated aqueous solution of sodium sulfate (4 mL). After 5-15 min of stirring (200 rpm) the mixture was filtered through a plug of silica which was then washed with EtOAc (3×15 mL). After extraction, the organic layer was dried over sodium sulfate. The solvent was removed to obtain the product.

2.3 Preparation of 5-(benzofuran-2-yl)pyrimidine

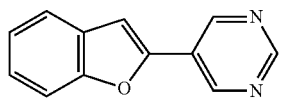 [SMILES: c1ccc2oc(-c3cncnc3)cc2c1]

Following the general procedure using 2-benzofuranylboronic acid mida ester (137 mg, 0.50 mmol, 1.0 equiv.), 5-bromopyrimidine (79 mg, 0.50 mmol, 1.0 equiv.), $PdCl_2$(dtbpf) (6.5 mg, 0.01 mmol, 0.02 equiv.) and triethylamine (152 mg, 1.50 mmol, 3.0 equiv.) the reaction was allowed to stir for 6 h at room temperature. The product was obtained as a white solid (88 mg, 0.45 mmol, 90%).

ESI-MS: m/z (%): 197.3 (100, [M+H]$^+$).

$^1$H NMR (600 MHz, $CDCl_3$): δ [ppm]: 9.25-9.12 (m, 3H), 7.67-7.63 (m, 1H), 7.60-7.56 (m, 1H), 7.40-7.35 (m, 1H), 7.32-7.28 (m, 1H), 7.22 (s, 1H).

2.4 Preparation of 4-(benzofuran-3-yl)aniline

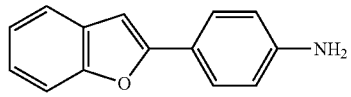 [SMILES: Nc1ccc(-c2cc3ccccc3o2)cc1]

Following the general procedure using 2-benzofuranylboronic acid mida ester (137 mg, 0.50 mmol, 1.0 equiv.), 4-bromoaniline (86 mg, 0.50 mmol, 1.0 equiv.), PdCl$_2$(dtbpf) (6.5 mg, 0.01 mmol, 0.02 equiv.) and triethylamine (152 mg, 1.50 mmol, 3.0 equiv.) the reaction was allowed to stir for 14 h at room temperature. The product was obtained as a yellow solid (101 mg, 0.48 mmol, 96%).

ESI-MS: m/z (%): 210.2 (100, [M+H]$^+$).

$^1$H NMR (600 MHz, CDCl$_3$): δ [ppm]: 7.72-7.64 (m, 2H), 7.57-7.45 (m, 2H), 7.25-7.14 (m, 2H), 6.87-6.79 (m, 1H), 6.79-6.71 (m, 2H), 3.84 (s, 2H).

3. Sonogashira Reactions

General Procedure for Sonogashira Reactions

Under an argon atmosphere, an aryl halide (1.00 mmol), bis(acetonitrile)palladium(II) dichloride (0.01 mmol) and dicyclohexyl(2',4',6'-triisopropyl-[1,1'biphenyl]-2-yl)phosphine (0.013 mmol) were weighed into a 5 mL microwave vial containing a magnetic stir bar and Teflon-lined septum. Aqueous oligosaccharide solution (3 ml of 2 wt % HPMC, 40-60 cps, in degassed Millipore water) and subsequently an alkyne (1.00 mmol) and a base (2.00 mmol) were added. The mixture was stirred vigorously at room temperature for the indicated time. To the reaction mixture was added ethyl acetate and saturated aqueous sodium sulfate solution. The solids were filtered off and the aqueous phase was extracted 4× with ethyl acetate. The combined organic extracts were combined and concentrated in vacuo. The crude product was purified by flash chromatography on silica gel.

3.1 Preparation of 2-methoxy-4-(phenylethynyl)benzonitrile

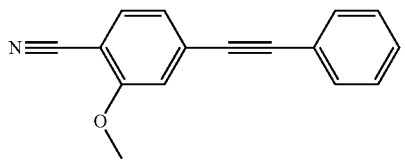 [SMILES: COc1cc(C#Cc2ccccc2)ccc1C#N]

3.1.1) Following the general procedure using 4-bromo-2-methoxybenzonitrile (212 mg, 1.00 mmol), triethylamine (0.28 ml, 2.00 mmol) and phenylacetylene (110 μg, 1.00 mmol) the reaction was allowed to stir overnight at room temperature. After column chromatography (0-35% ethyl acetate-cyclohexane), the product was obtained as a clear oil (186 mg, 80%; 91% purity).

3.1.2) Following the general procedure using 4-bromo-2-methoxybenzonitrile (212 mg, 1.00 mmol), cesium carbonate (652 mg, 2.00 mmol) and phenylacetylene (110 μg, 1.00 mmol) the reaction was allowed to stir overnight at room temperature. After column chromatography (0-35% ethyl acetate-cyclohexane), the product was obtained as a clear oil (210 mg, 90%, 79% purity).

ESI-MS: m/z (%): 234.10 (100, [M+H]$^+$).

$^1$H NMR (600 MHz, d$_6$-DMSO): δ [ppm]: 7.79 (d, J=7.9 Hz, 1H), 7.65-7.58 (m, 2H), 7.52-7.44 (m, 3H), 7.43 (d, J=1.3 Hz, 1H), 7.27 (dd, J=7.9, 1.4 Hz, 1H), 3.97 (s, 3H).

4. Heck Couplings

General Procedure for Heck Couplings

Under an argon atmosphere, Pd(t-Bu$_3$)P$_2$ (5.1 mg, 0.010 mmol) and an aryl halide (0.50 mmol) were weighed into a 5 mL microwave vial containing a magnetic stir bar and Teflon-lined septum. An acrylate (1.00 mmol) followed by the aqueous oligosaccharide solution (1.5 ml of 2 wt % HPMC, 40-60 cps, in degassed Millipore water) were added. Triethylamine (0.21 ml, 1.50 mmol) was then added via syringe. The mixture was stirred vigorously for the indicated time at the indicated temperature. To the reaction mixture was added ethyl acetate (4 ml) and subsequently a saturated aqueous sodium sulfate solution (1.5 ml). The solids were filtered off and the solid was washed 3× with ethyl acetate. The aqueous phase was extracted once with ethyl acetate. The organic extracts were combined and concentrated in vacuo. The crude product was purified by flash chromatography on silica gel.

4.1 Preparation of (E)-t-butyl 3-(4-methoxyphenyl)acrylate

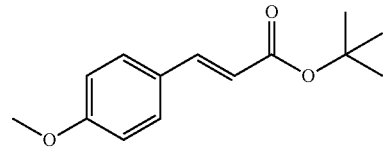 [SMILES: COc1ccc(/C=C/C(=O)OC(C)(C)C)cc1]

4.1.1) Following the general procedure using 1-iodo-4-methoxybenzene (117 mg, 0.50 mmol) and t-butyl acrylate (128 mg, 1.00 mmol) the reaction was allowed to stir for 4 h at room temperature. After column chromatography (0-30% ethyl acetate-heptane), the product was obtained as a clear oil (80 mg, 65%).

4.1.2) Following the general procedure using 1-iodo-4-methoxybenzene (117 mg, 0.50 mmol) and t-butyl acrylate (128 mg, 1.00 mmol) the reaction was allowed to stir for 1 h at 50° C. After column chromatography (0-30% ethyl acetate-heptane), the product was obtained as a clear oil (98 mg, 81%).

ESI-MS: m/z (%): 179.10 (100, [M+H-t-Bu]$^+$).

$^1$H NMR (600 MHz, CDCl$_3$): δ [ppm]: 7.55 (d, J=16.1 Hz, 1H), 7.45 (d, J=8.6 Hz, 2H), 6.90 (d, J=8.8 Hz, 2H), 6.25 (d, J=16.1 Hz, 1H), 3.85 (s, 3H), 1.55 (s, 9H).

4.2 Preparation of t-butyl Cinnamate

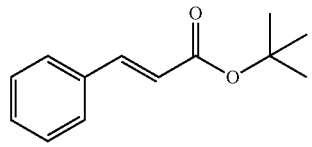

4.2.1) Following the general procedure using bromobenzene (79 mg, 0.50 mmol) and t-butyl acrylate (128 mg, 1.00 mmol) the reaction was allowed to stir for 72 h at room temperature. After column chromatography (0-30% ethyl acetate-heptane), the product was obtained as a pale oil (80 mg, 40%).

4.2.2) Following the general procedure using bromobenzene (79 mg, 0.50 mmol) and t-butyl acrylate (128 mg, 1.00 mmol) the reaction was allowed to stir for 4 h at 50° C. (the conversion was however already completed after 3 h, as indicated by LC-MS). After column chromatography (0-30% ethyl acetate-heptane), the product was obtained as a clear oil (93 mg, 88%).

ESI-MS: m/z (%): 149.10 (100, [M+H-t-Bu]$^+$).

$^1$H NMR (600 MHz, CDCl$_3$): a [ppm]: 7.60 (d, J=16.1 Hz, 1H), 7.55 (m, 2H), 7.35 (m, 3H), 6.35 (d, J=16.1 Hz, 1H), 1.55 (s, 9H).

5. C—H-Activation Reactions

General Procedure for C—H-Activation Reactions

Urea (1.0 equiv.), aryl halide (2.0 equiv.), AgOAc (2.0 equiv.), and Pd(OAc)$_2$ (0.1 equiv.) were sequentially added in air to a microwave reaction tube equipped with a stir bar and a septum. HPMC solution (4-6 cps) in Millipore water (0.25M, 2 wt %), and 48 wt % HBF$_4$ solution (5 equiv.) were added by syringe and vigorously stirred at room temperature for 72 h (1200 rpm). EtOAc (3 mL) was added and the mixture was stirred for 15 min at room temperature. A sat. aq. sol. of Na$_2$SO$_4$ (3 mL) was added and the mixture was stirred for an additional 15 min. The layers were separated and the aqueous layer was extracted with EtOAc (3×10 mL). The organic layers were combined and washed with water and brine and then dried over Na$_2$SO$_4$. Concentration of the organic layer afforded the crude material. The clean product was obtained after flash chromatography on silica gel.

5.1 Preparation of 3-(4'-methoxy-[1,1'-biphenyl]-2-yl)-1,1-dimethylurea

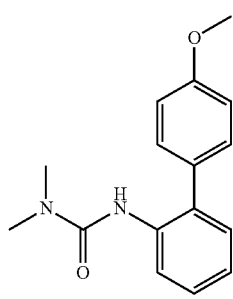 [SMILES: COc1ccc(-c2ccccc2NC(=O)N(C)C)cc1]

Following the general procedure using 1,1-Dimethyl-3-phenylurea (100 mg, 0.61 mmol, 1.0 equiv.), 4-iodoanisole (285 mg, 1.22 mmol, 2.0 equiv.), AgOAc (203 mg, 1.22 mmol, 2.0 equiv.), Pd(OAc)$_2$ (14 mg, 0.06 mmol, 0.1 equiv.), HPMC solution (2.4 mL, 2 wt %), and 48 wt % HBF$_4$ solution (0.38 mL, 3.04 mmol, 5 equiv.) the reaction was allowed to stir for 72 h at room temperature. After chromatography on silica gel (25-50% EtOAc/Hept) the pure product was obtained as an orange solid (114 mg, 0.42 mmol, 69%, 76% brsm).

APCI-MS: m/z (%): 271.2 (100, [M+H]$^+$).

$^1$H NMR (600 MHz, CDCl$_3$): δ [ppm]: 8.17 (d, J=8.3 Hz, 1H), 7.39-7.28 (m, 3H), 7.17 (dd, J=7.6, 1.6 Hz, 1H), 7.05 (td, J=7.6, 1.2 Hz, 1H), 7.04-6.93 (m, 2H), 6.52 (s, 1H), 3.86 (s, 3H), 2.82 (s, 6H).

6. Stile Couplings

General Procedure for Stille Couplings

To Pd(P$^t$Bu$_3$)$_2$ (0.02 equiv.), 1,4-diazabicyclo[2.2.2]octane (3.0 equiv.) and NaCl (1.0 equiv.) under an argon atmosphere was given a 2 wt % solution of HPMC (4-6 cps) in Millipore water (0.5 M), followed by the aryl halide (1.0 equiv.) and the stannyl reagent (1.1 equiv.). The mixture was stirred vigorously under an argon atmosphere at the indicated temperature for the indicated time. The reaction was quenched with trimethylamine (0.5 mL) and diluted with EtOAc (1 mL). After the addition of a saturated Na$_2$SO$_4$-solution (1 mL) the mixture was extracted with EtOAc (2×10 mL). The clean product was obtained after flash chromatography on silica gel.

6.1 Preparation of (Z)-2-(2-ethoxyvinyl)-1,3-dimethylbenzene

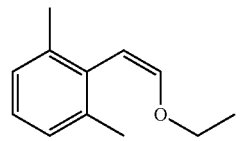

6.1.1) Following the general procedure using 2-bromo-m-xylene (92 mg, 0.5 mmol, 1.0 equiv), (Z)-1-ethoxy-2-(tributylstannyl)ethene (197 mg, 0.55 mml, 1.1 equiv), Pd(P$^t$Bu$_3$)$_2$ (5.0 mg, 0.01 mmol, 0.02 equiv.), 1,4-diazabicyclo[2.2.2]octane (167 mg, 1.5 mmol, 3.0 equiv.) and NaCl (29 mg, 0.5 mmol, 1.0 equiv.) the reaction was allowed to stir vigorously under an argon atmosphere for 48 h at room temperature. After column chromatography (EtOAc/hexanes), the product was obtained (68 mg, 0.38 mmol, 78%)

6.1.2) Following the general procedure using 2-bromo-m-xylene (92 mg, 0.5 mmol, 1.0 equiv), (Z)-1-ethoxy-2-(tributylstannyl)ethene (197 mg, 0.55 mmol, 1.1 equiv), Pd(P$^t$Bu$_3$)$_2$ (5.0 mg, 0.01 mmol, 0.02 equiv.), 1,4-diazabicyclo[2.2.2]octane (167 mg, 1.5 mmol, 3.0 equiv.) and NaCl (29 mg, 0.5 mmol, 1.0 equiv.) the reaction was allowed to stir vigorously (1200 rpm) under an argon atmosphere for 2 h at 50° C. and then for 24 h at room temperature. After column chromatography (EtOAc/hexanes), the product was obtained (45 mg, 0.26 mmol, 52%)

ESI-MS: m/z (%): 177.2 (100, [M+H]$^+$).

$^1$H NMR (600 MHz, CDCl$_3$): δ [ppm]: 7.10-6.98 (m, 3H), 6.20 (d, J=6.9 Hz, 1H), 5.20 (d. J=6.9 Hz, 1H), 3.86 (q, J=7.1 Hz, 2H), 2.27 (s, 6H), 1.24 (t, J=7.1 Hz, 3H).

7. Cross Metathesis

General Procedure for Cross Metathesis

Under an argon atmosphere, Grubbs second-generation catalyst (3.4 mg, 0.004 mmol) was weighed into a 5 mL microwave vial containing a magnetic stir bar and Teflon-lined septum. The alkene (0.50 mmol) and acrylate (1.00 mmol) were added sequentially into the vial, followed by addition of the aqueous oligosaccharide solution (2 ml of 2 wt % HPMC, 40-60 cps, in degassed Millipore water). The mixture was stirred vigorously at room temperature for the indicated time. To the reaction mixture was added ethyl acetate and saturated aqueous sodium sulfate solution. The solids were filtered off and the aqueous phase was extracted 3× with ethyl acetate. The combined organic extracts were combined and concentrated in vacuo. The crude product was purified by flash chromatography on silica gel.

7.1 Preparation of (E)-tert-butyl 4-(4-methoxyphenyl)but-2-enoate

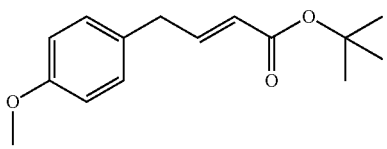 [SMILES: COc1ccc(C/C=C/C(=O)OC(C)(C)C)cc1]

7.1.1) Following the general procedure using 4-allylanisole (74 mg, 0.50 mmol) and tert-butyl acrylate (128 mg, 1.00 mmol) the reaction was allowed to stir overnight at room temperature. After column chromatography (0-10% ethyl acetate-dichloromethane), the product was obtained as a clear oil (73 mg, 59%).

7.1.2) Following the general procedure using 4-allylanisole (74 mg, 0.50 mmol), tert-butyl acrylate (128 mg, 1.00 mmol) and additionally citric acid (9.6 mg, 0.005 mmol) was added and the reaction was allowed to stir overnight at room temperature. After column chromatography (0-20% ethyl acetate-dichloromethane), the product was obtained as a clear oil (96 mg, 77%).

ESI-MS: m/z (%): 193.10 (100, [M+H-$^t$Bu]$^+$).

$^1$H NMR (600 MHz, CDCl$_3$): δ [ppm]: 7.11-7.07 (m, 2H), 7.00-6.94 (m, 1H), 6.87-6.83 (m, 2H), 5.73-5.68 (m, 1H), 3.80 (s, 3H), 3.45-3.41 (m, 2H), 1.46 (s, 9H).

8. Rh-Catalyzed 1,4-Additions

General Procedure for Rh-Catalyzed 1,4-Additions

Under an argon atmosphere, an aryl boronic acid (1.84 mmol), potassium carbonate (254 mg, 1.84 mmol) and hydroxyl(cyclooctadiene)rhodium(I)dimer (21 mg, 0.046 mmol) were weighed into a 5 mL microwave vial containing a magnetic stir bar, Teflon-lined septum and the aqueous oligosaccharide solution (3 ml of 2 wt % HPMC, 40-60 cps, in degassed Millipore water). To the reaction mixture was added an α,β-unsaturated ethyl ester (0.92 mmol) and stirred vigorously at the indicated temperature for the indicated time. To the reaction mixture was added saturated aqueous sodium sulfate solution and ethyl acetate. The aqueous phase was extracted 4× with ethyl acetate. The combined organic extracts were combined and concentrated in vacuo. The crude product was purified by flash chromatography on silica gel.

8.1 Preparation of 4-methyl-3,4-dihydroquinolin-2(1H)-one

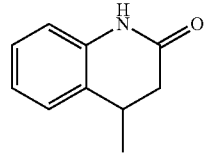

Following the general procedure using (2-aminophenyl)boronic acid (252 mg, 1.84 mmol) and (E-)ethyl but-2-enoate (105 mg, 0.92 mmol) the reaction was allowed to stir for 5 h at 50° C. After column chromatography (0-30% ethyl acetate-cyclohexane), the product was obtained (147 mg, 99%).

ESI-MS: m/z (%): 162.20 (100, [M+H]$^+$).

$^1$H NMR (600 MHz, d$_6$-DMSO): δ [ppm]: 10.09 (s, 1H), 7.19 (ddd, J=7.5, 1.5, 0.8 Hz, 1H), 7.13 (td, J=7.6, 1.5 Hz, 1H), 6.94 (td, J=7.5, 1.2 Hz, 1H), 6.85 (dd, J=7.9, 1.2 Hz, 1H), 3.04 (q, J=6.9 Hz, 1H), 2.58 (dd, J=15.9, 5.9 Hz, 1H), 2.23 (dd, J=15.9, 7.0 Hz, 1H), 1.17 (d, J=7.0 Hz, 3H).

9. Gold-Catalyzed Cyclizations

General Procedure for Gold-Catalyzed Cyclizations

Under an argon atmosphere the diol (1.0 equiv.) was dissolved in a 2 wt % solution of HPMC (4-6 cps) in Millipore water (0.8 mL). After the addition of gold(III) bromide (0.025 equiv.) and silver triflate (0.025 equiv.) the mixture was stirred under an argon atmosphere at room temperature (1200 rpm) for 4 h. The mixture was diluted with EtOAc (3 mL) and filtered through a pad of silica which was washed with EtOAc (3×10 ml). The clean product was obtained after flash chromatography on silica gel.

9.1 Preparation of 2,3-dimethyl-5-phenylfuran

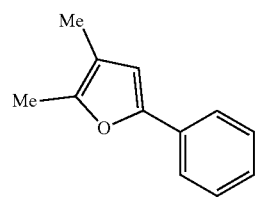 [SMILES: Cc1cc(-c2ccccc2)oc1C]

Following the general procedure using 3-methyl-5-phenylpent-4-yne-2,3-diol (76 mg, 0.40 mmol, 1.0 equiv.), AuBr$_3$ (4.4 mg, 0.01 mmol, 0.025 equiv.) and AgOTf (2.6 mg, 0.01 mmol, 0.025 equiv.) the reaction was allowed to stir for 4 h at room temperature under an argon atmosphere. After column chromatography (cyclohexane), the product was obtained as a pale orange oil (49 mg, 0.29 mmol, 71%).

ESI-MS: m/z (%): 173.3 (100, [M+H]$^+$).

$^1$H NMR (600 MHz, CDCl$_3$): δ [ppm]: 7.63-7.56 (m, 2H), 7.37-7.28 (m, 2H), 7.23-7.14 (m, 1H), 6.43 (s, 1H), 2.26 (s, 3H), 1.97 (s, 3H).

10. Miyaura Borylations

General Procedure for Miyaura Borylations

To Pd(P$^t$Bu$_3$)$_2$ (0.03 equiv.), B$_2$pin$_2$ (1.1 equiv.) and KOAc (3.0 equiv) under an argon atmosphere was given a 2 wt % solution of HPMC (4-6 cps) in Millipore water (1.0 mL). After 10 min of vigorous stirring, the aryl bromide (1.0 equiv.) was added, followed by an additional amount of a 2 wt % solution of HPMC (4-6 cps) in Millipore water (1.0 mL). The mixture was stirred vigorously under an argon atmosphere for the indicated time at the indicated temperature. The reaction was diluted with a saturated $Na_2SO_4$-solution (2 mL), stirred for 3 min and then extracted with EtOAc (3×10 mL). The clean product was obtained after flash chromatography on silica gel.

10.1 Preparation of 2-(4-methoxyphenyl)-4,4,5,5-tetramethyl-1,3,2-dioxaborolane

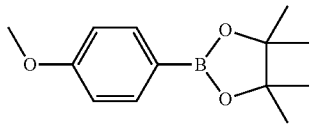

Following the general procedure using 4-bromoanisole (94 mg, 0.5 mmol, 1.0 equiv.), bis(pinacolato)diboron (140 mg, 0.55 mmol, 1.1 equiv.), bis(tri-tert-butylphosphine)palladium(0) (7.7 mg, 0.015 mmol, 0.03 equiv.) and KOAc (147 mg, 1.5 mmol, 3.0 equiv.) the reaction was allowed to stir vigorously for 2 h at room temperature. After column chromatography (EtOAc/hexanes), the product was obtained (94 mg, 0.40 mmol, 80%).

ESI-MS: m/z (%): 235.1 (100, [M+H]$^+$).
$^1$H NMR (600 MHz, $CDCl_3$): δ [ppm]: 7.77-7.73 (m, 2H), 6.91-6.87 (m, 2H), 3.82 (s, 3H), 1.33 (s, 12H).

10.2 Preparation of 2-(2,6-dimethylphenyl)-4,4,5,5-tetramethyl-1,3,2-dioxaborolane

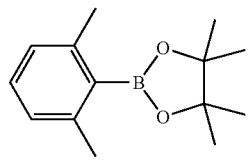 [SMILES: Cc1cccc(C)c1B1OC(C)(C)C(C)(C)O1]

Following the general procedure using 2-bromo-m-xylene (93 mg, 0.5 mmol, 1.0 equiv.), bis(pinacolato)diboron (140 mg, 0.55 mmol, 1.1 equiv.), bis(tri-tert-butylphosphine)palladium(0) (15 mg, 0.03 mmol, 0.06 equiv.) and KOAc (147 mg, 1.5 mmol, 3.0 equiv.) the reaction was allowed to stir vigorously (1200 rpm) for 7 h at 50° C. and then for 24 h at room temperature. After column chromatography (EtOAc/hexanes), the product was obtained (85 mg, 0.37 mmol, 73%).

ESI-MS: m/z (%): 233.1 (100, [M+H]$^+$).
$^1$H NMR (600 MHz, $CDCl_3$): δ [ppm]: 7.15-7.08 (m, 1H), 6.97-6.89 (m, 2H), 2.39 (s, 6H), 1.39 (s, 12H).

11. Wittig Reactions

General Procedure for Wittig Reactions

A 5 mL microwave vial was charged with the carbonyl compound (1.0 equiv.) and the Wittig reagent (1.5 equiv.). After the addition of HPMC-solution (40-60 cps, 2 wt % in Millipore water, 2.0 mL) the reaction mixture was vigorously stirred (1200 rpm) at the indicated temperature until LCMS or TLC showed full conversion of the carbonyl compound. The mixture was diluted with EtOAc (3 mL) followed by the addition of a saturated aqueous solution of sodium sulfate (4 mL). After 5-15 min of stirring (200 rpm) the mixture was filtered through a plug of silica which was then washed with EtOAc (3×15 mL). The combined organic layers were dried over sodium sulfate. The crude product was purified by flash chromatography on silica gel.

11.1 Preparation of (E)-methyl 3-(4-methoxyphenyl)acrylate

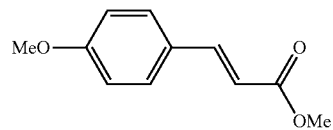

Following the general procedure using 4-methoxybenzaldehyde (68 mg, 0.50 mmol, 1.0 equiv.) and methyl (triphenylphosphoranylidene)acetate (251 mg, 0.75 mmol, 1.5 equiv.) the reaction was allowed to stir for 30 min at 50° C. After column chromatography on silica gel (5-30% ethyl acetate-cyclohexane) the product was obtained as a white solid (90 mg, 0.47 mmol, 94%). (E/Z=14/1)

ESI-MS: m/z (%): 193.2 (80, [M+H]$^+$).
$^1$H NMR (600 MHz, $CDCl_3$) (of the E configurated product): δ [ppm]: 7.66 (d, J=16.0 Hz, 1H), 7.54-7.42 (m, 2H), 6.97-6.86 (m, 2H), 6.32 (d, J=16.0 Hz, 1H), 3.84 (s, 3H), 3.80 (s, 3H).

12. Diels-Alder Reactions

General Procedure for Diels-Alder Reactions

A 5 mL microwave vial was charged with the dienophile (1.0 equiv.) and the diene (1.0-1.5 equiv.). After the addition of HPMC-solution (40-60 cps, 2 wt % in Millipore water, 1.0 mL) the reaction mixture was vigorously stirred (1200 rpm) at the indicated temperature until LCMS or TLC showed full conversion of the dienophile. The mixture was diluted with EtOAc (3 mL) followed by the addition of a saturated aqueous solution of sodium sulfate (4 mL). After 5-15 min of stirring (200 rpm) the mixture was filtered through a plug of silica which was then washed with EtOAc (3×15 mL). After phase separation, the organic layer was dried over sodium sulfate. The clean product was obtained after flash chromatography on silica gel.

12.1 Preparation of (7-methyl-1,3-dioxo-2-propyl-2,3,3a,4,7,7a-hexahydro-1H-iso-indol-4-yl)methyl Acetate

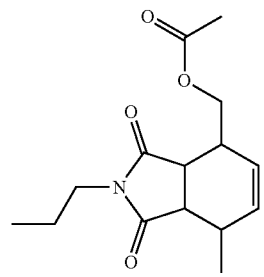 [SMILES: CCCN1C(=O)C2C(C)C=CC(COC(C)=O)C2C1=O]

Following the general procedure using 1-propyl-1H-pyrrole-2,5-dione (139 mg, 1.00 mmol, 1.0 equiv.) and (2E,4E)-hexa-2,4-dien-1-yl acetate (154 mg, 1.10 mmol, 1.1 equiv.) the reaction was allowed to stir for 4 h at 50° C. After column chromatography on silica gel (0-30% ethyl acetate-cyclohexane) the product was obtained as a colourless oil (201 mg, 0.72 mmol, 72%)

ESI-MS: m/z (%): 280.3 (80, [M+H]$^+$), 581.3 (100, [2M+H]$^+$).

$^1$H NMR (600 MHz, CDCl$_3$): 5.82-5.69 (m, 2H), 4.74-4.60 (m, 1H), 4.55-4.46 (m, 1H), 3.44-3.32 (m, 2H), 3.28-3.18 (m, 1H), 3.09-2.99 (m, 1H), 2.68-2.55 (m, 1H), 2.49-2.38 (m, 1H), 2.09 (s, 3H), 1.54-1.47 (m, 2H), 1.45 (d, J=7.4 Hz, 3H), 0.83 (t, J=7.5 Hz, 3H).

13. Baylis-Hillman Reactions

General Procedure for Baylis-Hillman Reactions

To the aldehyde (1.0 equiv.) in a 2 wt % solution of HPMC (4-6 cps) in Millipore water (0.3 M) was given the alkene (7.0 equiv.) and 1,4-diazabicyclo[2.2.2]octane (0.2 equiv.). The mixture was stirred in a spetum-closed 5 mL-microwave vial for the indicated time at room temperature. The mixture was diluted with EtOAc (3 mL) and then with a sat. solution of Na$_2$SO$_4$ (3 mL). After stirring for 3 min the mixture was filtered through a pad of silica which was washed with EtOAc (3×15 mL). The clean product was obtained after flash chromatography on silica gel.

13.1 Preparation of 2-((4-chlorophenyl)(hydroxy)methyl)acrylonitrile

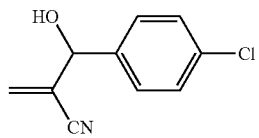

Following the general procedure using 4-chlorobenzaldehyde (141 mg, 1.0 mmol, 1.0 equiv.), acrylonitrile (371 mg, 7.0 mmol, 7.0 equiv.) and 1,4-diazabicyclo[2.2.2]octane (22 mg, 0.2 mmol, 0.2 equiv.) the reaction was allowed to stir for 23 h at room temperature. After column chromatography (ethyl acetate/cyclohexane), the product was obtained as a white solid (148 mg, 0.76 mmol, 76%).

APCI-MS: m/z (%): 194.0 (100, [M+H]$^+$).

$^1$H NMR (600 MHz, CDCl$_3$): δ [ppm]: 7.38-7.32 (m, 2H), 7.32-7.27 (m, 2H), 6.13-6.04 (m, 1H), 6.04-5.96 (m, 1H), 5.24 (s, 1H), 3.07 (s$_{br}$, 1H).

14. Amide Bond Formations

General Procedure for Amide Bond Formations Using 1-hydroxybenzotriazol (HOBT) and 1-ethyl-3-(3-dimethylaminopropyl)carbodiimid Hydrochloride (EDC Hydrochloride)

Under an argon atmosphere, an acid (1.00 mmol) was weighed into a 5 mL microwave vial containing a magnetic stir bar and a Teflon-lined septum. Subsequently EDC hydrochloride (240 mg, 1.25 mmol), HOBT (184 mg, 1.20 mmol) and an aqueous oligosaccharide solution (3 ml of 2 wt % HPMC, 40-60 cps, in degassed Millipore water) were added and the reaction mixture was stirred vigorously at the indicated temperature. After 2 min an amine (1.10 mmol) was added and stirring was continued for the indicated time. The reaction mixture was adjusted to an alkaline pH by adding 1 ml of a 2N aqueous sodium hydroxide solution and extracted 4× with ethyl acetate. The combined organic extracts were dried with magnesium sulfate and after filtration concentrated in vacuo. The crude product was purified by flash chromatography on silica gel.

14.1 Preparation of N-(2-(diethylamino)ethyl)-4-nitrobenzamide

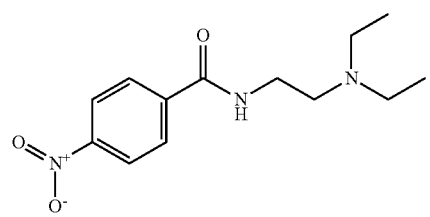 [SMILES: CCN(CC)CCNC(=O)c1ccc([N+](=O)[O-])cc1]

Following the general procedure using 4-nitrobenzoic acid (167 mg, 1.00 mmol) and N,N-diethylethylenediamine (128 mg, 1.10 mmol) the reaction was allowed to stir for 20 min at room temperature (the conversion was however already completed after 2 min, as indicated by LC-MS). After column chromatography (0-10% methanol-dichloromethane), the product was obtained (220 mg, 83%).

ESI-MS: m/z (%): 266.20 (100, [M+H]$^+$).

$^1$H NMR (600 MHz, CDCl$_3$): δ [ppm]: 8.31-8.24 (m, 2H), 8.02-7.97 (m, 2H), 3.63-3.57 (m, 2H), 2.83 (s, 2H), 2.73 (d, J=12.3 Hz, 4H), 1.17-1.10 (m, 6H).

General Procedure for Amide Bond Formations Using (1-cyano-2-ethoxy-2-oxoethyliden-aminooxy) dimethylamino-morpholino-carbenium-hexafluorophosphat (COMU)

Under an argon atmosphere, an acid (1.10 mmol) was weighed into a 5 mL microwave vial containing a magnetic stir bar and a Teflon-lined septum. The aqueous oligosaccharide solution (2 wt % HPMC, 40-60 cps, in degassed Millipore water) was added, followed by 2,6-dimethylpyridine (332 mg, 3.1 mmol), and the reaction mixture was vigorously stirred at room temperature for 5 min. An amine (1.00 mmol) followed by 1-cyano-2-ethoxy-2-oxoethylidenaminooxy)dimethylamino-morpholino-carbenium-hexafluorophosphat (COMU) (471 mg, 1.10 mmol) were added to the reaction mixture and stirring was continued for the indicated time at the indicated temperature. The reaction mixture was diluted with ethyl acetate and saturated aqueous sodium sulfate solution. The solids were filtered and washed 4× with ethyl acetate. The combined organic extracts were treated 3× with aqueous 1 N hydrochloride solution and subsequently 4× with saturated aqueous sodium carbonate solution. The organic phase was dried with magnesium sulfate, filtered and concentrated in vacuo. The crude product was purified by flash chromatography on silica gel.

14.2 Preparation of (R)-ethyl 2-(((S)-2-((((9H-fluoren-9-yl)methoxy)carbonyl)amino)-3-methylbutanoyl)oxy-4-methylpentanoate

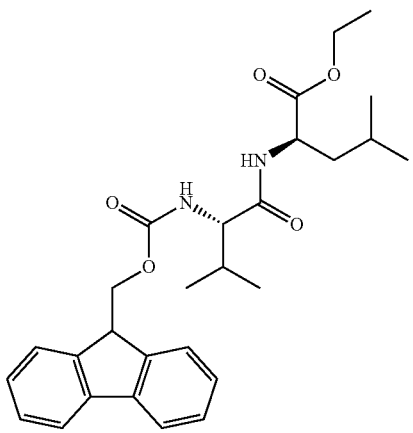 [SMILES: CCOC(=O)[C@@H](CC(C)C)NC(=O)[C@@H](NC(=O)OCC1c2ccccc2-c2ccccc21)C(C)C]

Following the general procedure using Fmoc-Val-OH (373 mg, 1.10 mmol), L-Leucine ethyl ester hydrochloride (196 mg, 1.00 mmol) and 1-cyano-2-ethoxy-2-oxoethylidenaminooxy)dimethylamino-morpholino-carbenium-hexafluorophosphat (COMU) (471 mg, 1.10 mmol) in 1.25 ml of aqueous oligosaccharide solution (2 wt % HPMC, 40-60 cps, in degassed Millipore water), the reaction was allowed to stir overnight at room temperature. After column chromatography (0-10% methanol-dichloromethane), the product was obtained (430 mg, 89%).

ESI-MS: m/z (%): 481.20 (100, [M+H]$^+$).

$^1$H NMR (600 MHz, CDCl$_3$): δ [ppm]: 7.77 (dq, J=7.7, 1.2 Hz, 2H), 7.60 (d, J=7.5 Hz, 2H), 7.40 (tdd, J=7.4, 2.2, 1.0 Hz, 2H), 7.32 (tdd, J=7.5, 2.4, 1.1 Hz, 2H), 6.06 (d, J=8.2 Hz, 1H), 5.40 (d, J=9.0 Hz, 1H), 4.64-4.57 (m, 1H), 4.42 (dd, J=10.6, 7.4 Hz, 1H), 4.36 (dd, J=10.6, 7.1 Hz, 1H), 4.26-4.15 (m, 3H), 4.00 (dd, J=8.9, 6.3 Hz, 1H), 2.13 (dt, J=13.4, 6.7 Hz, 1H), 1.65 (s, 2H), 1.55 (s, 1H), 1.28 (t, J=7.2 Hz, 3H), 1.01-0.90 (m, 12H).

14.3 Preparation of N-3,4-dimethoxyphenethyl)-2-phenylacetamide

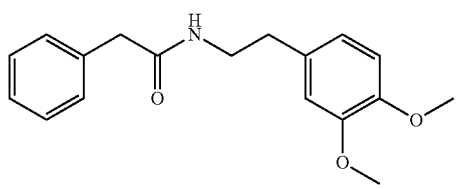 [SMILES: COc1ccc(CCNC(=O)Cc2ccccc2)cc1OC]

14.3.1) Following the general procedure using phenyl acetic acid (150 mg, 1.10 mmol), 3,4-dimethoxyphenethylamine (181 mg, 1.00 mmol) and COMU (471 mg, 1.10 mmol) in 2 ml of aqueous oligosaccharide solution (2 wt % HPMC, 40-60 cps, in degassed Millipore water), the reaction was allowed to stir for 30 min. at room temperature. After column chromatography (50-100% ethyl acetate-heptane), the product was obtained as a clear oil (243 mg, 78%).

14.3.2) Following the general procedure using phenyl acetic acid (150 mg, 1.10 mmol), 3,4-dimethoxyphenethylamine (181 mg, 1.00 mmol) and 2 ml of aqueous oligosaccharide solution (2 wt % HPMC, 40-60 cps, in degassed water), the reaction was allowed to stir for 20 min. at 50° C. After column chromatography (50-100% ethyl acetate-heptane), the product was obtained as a clear oil (258 mg, 82%).

14.3.3) Following the general procedure using phenyl acetic acid (150 mg, 1.10 mmol), 3,4-dimethoxyphenethylamine (181 mg, 1.00 mmol) and COMU (471 mg, 1.10 mmol) in 0.35 ml of aqueous oligosaccharide solution (2 wt % HPMC, 40-60 cps, in degassed Millipore water), the reaction was allowed to stir for 20 min. at room temperature. LC-MS and TLC indicated however that the reaction was already completed after 1 min. After column chromatography (50-100% ethyl acetate-heptane), the product was obtained as a clear oil (251 mg, 81%, 97% purity).

14.3.4) Following the general procedure using phenyl acetic acid (150 mg, 1.10 mmol), 3,4-dimethoxyphenethylamine (181 mg, 1.00 mmol) and COMU (471 mg, 1.10 mmol) in 0.35 ml of aqueous oligosaccharide solution (2 wt % HPMC, 40-60 cps, in degassed Millipore water), the reaction was allowed to stir for 15 min. at 50° C. LC-MS and TLC indicated however that the reaction was already completed after 1 min. After column chromatography (50-100% ethyl acetate-heptane), the product was obtained as a clear oil (255 mg, 81%, 95% purity).

ESI-MS: m/z (%): 300.10 (100, [M+H]$^+$).

$^1$H NMR (600 MHz, CDCl$_3$): δ [ppm]: 7.35-7.25 (m, 3H), 7.15 (m, 2H), 6.70 (m, 1H), 6.60 (m, 1H), 6.55 (m, 1H), 5.35 (s$_{br}$, 1H), 3.85 (s, 3H), 3.80 (s, 3H), 3.55 (s, 2H), 3.45 (m, 2H), 2.70 (t, 3H).

General Procedure for Sulfonylations

Under an argon atmosphere, a base (2.97 mmol) and the aqueous oligosaccharide solution (2 wt % HPMC, in degassed Millipore water) were weighed into a 5 mL microwave vial containing a magnetic stir bar and a Teflon-lined septum. An amine (0.99 mmol) and subsequently a sulfonyl chloride (1.98 mmol) were added to the vigorously stirred reaction mixture at room temperature. Stirring was continued for the indicated time at the indicated temperature. The reaction mixture was diluted with ethyl acetate, the solids were filtered and the aqueous phase was extracted 3× with ethyl acetate. The combined organic extracts were dried with magnesium sulfate, filtered and concentrated in vacuo. The crude product was purified by flash chromatography on silica gel.

14.4 Preparation of 1-(phenylsulfonyl)indoline

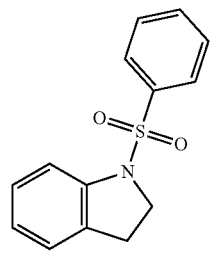 [SMILES: O=S(=O)(c1ccccc1)N1CCc2ccccc21]

14.4.1) Following the general procedure using potassium trimethylsilanolate (380 mg, 2.97 mmol), indoline (119 mg, 0.99 mmol), benzenesulfonyl chloride (364 mg, 1.98 mmol) and 3 ml of aqueous oligosaccharide solution (2 wt %

HPMC, 40-60 cps, in degassed Millipore water), the reaction was allowed to stir for 30 min room temperature. After column chromatography (40-100% n-heptane-dichloromethane), the product was obtained as a white crystalline material (233 mg, 89%).

14.4.2) Following the general procedure using potassium trimethylsilanolate (380 mg, 2.97 mmol), indoline (119 mg, 0.99 mmol), benzenesulfonyl chloride (220 mg, 1.20 mmol) and 3 ml of aqueous oligosaccharide solution (2 wt % HPMC, 4-6 cps, in degassed Millipore water), the reaction was allowed to stir for 30 min room temperature. LC-MS and TLC indicated that the reaction was already completed after 5 min. After column chromatography (40-100% n-heptane-dichloromethane), the product was obtained as a white crystalline material (262 mg, 97%, 96% purity).

ESI-MS: m/z (%): 260.20 (100, [M+H]$^+$).

$^1$H NMR (600 MHz, CDCl$_3$): δ [ppm]: 7.80 (m, 2H), 7.65 (m, 1H), 7.55 (m, 1H), 7.45 (m, 2H), 7.20 (m, 1H), 7.10 (m, 1H), 7.00 (m, 1H), 3.95 (m, 2H), 2.90 (m, 2H).

14.5 Preparation of N-(4-fluorophenyl)-4-methylbenzenesulfonamide

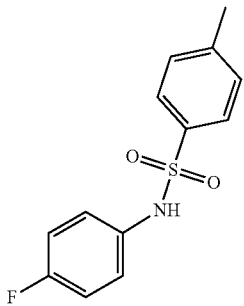 [SMILES: Cc1ccc(S(=O)(=O)Nc2ccc(F)cc2)cc1]

Following the general procedure using triethylamine (209 μl, 1.50 mmol), 4-fluoroaniline (112 mg, 1.00 mmol), 4-methylbenzene-1-sulfonyl chloride (233 mg, 1.20 mmol) and 3 ml of aqueous oligosaccharide solution (2 wt % HPMC, 4-6 cps, in degassed Millipore water), the reaction was allowed to stir for 20 min room temperature. After column chromatography (0-50% n-heptane-ethyl acetate), the product was obtained as a clear oil (222 mg, 80%).

ESI-MS: m/z (%): 266.20 (100, [M+H]$^+$).

$^1$H NMR (600 MHz, CDCl$_3$): δ [ppm]: 7.60 (m, 2H), 7.20 (m, 2H), 7.00 (m, 2H), 6.95 (m, 2H), 6.30 (s$_{br}$, 1H), 2.40 (s, 3H).

15. Nucleophilic Aromatic Substitutions

General Procedure for Nucleophilic Aromatic Substitutions

To the aryl halide (1.0 equiv.) and the nucleophile (1.0-1.1 equiv.) in a 5 mL microwave vial was added a 2 wt % solution of HPMC (40-60 cps) in Millipore water (1 mL). After the addition of sodium tert-butoxide (1.1 equiv) the mixture was vigorously stirred (1200 rpm) at room temperature until LCMS or TLC showed full conversion of the aryl halide. The mixture was diluted with EtOAc (3 mL) followed by the addition of a saturated aqueous solution of sodium sulfate (2 mL). After 5-15 min of stirring (200 rpm) the precipitated solids were filtered off and washed with EtOAc (3×15 mL). After extraction, the organic layer was dried over sodium sulfate. The crude product was purified by flash chromatography on silica gel.

15.1 Preparation of 2,5-dichloro-N-(3,4-dimethoxyphenethyl)pyrimidin-4-amine

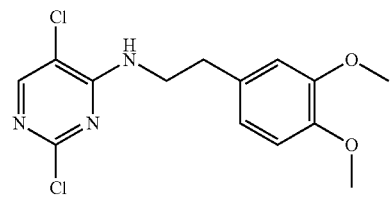 [SMILES: COc1ccc(CCNc2nc(Cl)ncc2Cl)cc1OC]

Following the general procedure using 3,4-dimethoxyphenethylamine (90.0 mg, 0.50 mmol, 1.0 equiv.), 2,4,5-trichloropyrimidine (91.5 mg, 0.50 mmol, 1.0 equiv.) and sodium tert-butoxide (52.8 mg, 0.55 mmol, 1.1 equiv) the reaction was allowed to stir for 10 min at room temperature. After column chromatography (0-30% ethyl acetate-cyclohexane), the product was obtained as a white solid (140 mg, 0.43 mmol, 86%).

ESI-MS: m/z (%): 328 (100, [M]$^+$).

$^1$H NMR (600 MHz, CDCl$_3$): δ [ppm]: 7.99 (s, 1H), 6.88-6.79 (m, 1H), 6.80-6.71 (m, 2H), 5.61 (s$_{br}$, 1H), 3.88 (s, 3H), 3.87 (s, 3H), 3.79-3.73 (m, 2H), 2.88 (t, J=6.9 Hz, 2H).

15.2 Preparation of N-benzyl-2-nitroaniline

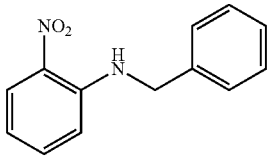 [SMILES: O=[N+]([O-])c1ccccc1NCc1ccccc1]

Following the general procedure using benzylamine (53.6 mg, 0.50 mmol, 1.0 equiv.), 1-fluoro-2-nitrobenzene (70.5 mg, 0.50 mmol, 1.0 equiv.) and sodium tert-butoxide (72.1 mg, 0.75 mmol, 1.5 equiv) the reaction was allowed to stir for 3 h at room temperature. After column chromatography (0-30% ethyl acetate-cyclohexane), the product was obtained as a white solid (89 mg, 0.39 mmol, 78%).

ESI-MS: m/z (%): 229.20 (100, [M]$^+$).

$^1$H NMR (600 MHz, CDCl$_3$): δ [ppm]: 8.44 (s, 1H), 8.20 (dd, J=8.6, 1.6 Hz, 1H), 7.44-7.27 (m, 7H), 6.83-6.79 (m, 1H), 6.69-6.64 (m, 1H), 4.55 (d, J=5.7 Hz, 2H).

15.3 Preparation of naphthalen-2-yl(2-nitrophenyl)sulfane

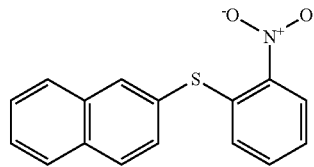

Following the general procedure using 1-fluoro-2-nitrobenzene (70.5 mg, 0.50 mmol, 1.0 equiv.), 2-naphthalenethiol (88.0 mg, 0.55 mmol, 1.1 equiv.) and sodium tert-butoxide (52.8 mg, 0.55 mmol, 1.1 equiv) the reaction was allowed to stir for 3 h at room temperature. After column chromatography (0-30% ethyl acetate-cyclohexane), the product was obtained as a yellow solid (127 mg, 0.45 mmol, 90%).

ESI-MS: m/z (%): 304.1 (40, [M+Na]$^+$), 585.2 (100, [2M+Na]$^+$).

$^1$H NMR (600 MHz, CDCl$_3$): δ [ppm]: 8.28-8.21 (m, 1H), 8.20-8.14 (m, 1H), 7.95-7.88 (m, 2H), 7.89-7.83 (m, 1H), 7.64-7.54 (m, 2H), 7.54-7.50 (m, 1H), 7.32-7.26 (m, 1H), 7.23-7.17 (m, 1H), 6.89 (dd, J=8.3, 1.2 Hz, 1H).

16. Nitro Reduction

General Procedure for Nitro Reduction Using Zinc

Under an argon atmosphere, a nitro group-containing compound (0.237 mmol) was weighed into a 5 mL microwave vial containing a magnetic stir bar and a Teflon-lined septum. Subsequently zinc dust (155 mg, 2.37 mmol), ammonium chloride (25 mg, 0.475 mmol) and the aqueous oligosaccharide solution (2 wt % HPMC, 40-60 cps, in degassed Millipore water) were added and the reaction mixture was vigorously stirred at the indicated temperature for the indicated time. The reaction mixture was diluted with ethyl acetate, the solids were filtered and the aqueous phase was extracted 3× with ethyl acetate. The combined organic extracts were dried with magnesium sulfate, filtered and concentrated in vacuo. The crude product was purified by flash chromatography on silica gel.

16.1 Preparation of 4-amino-N-(2-(diethylamino)ethyl)benzamide

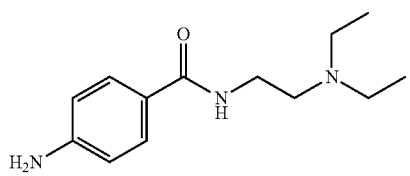 [SMILES: CCN(CC)CCNC(=O)c1ccc(N)cc1]

Following the general procedure using N-(2-diethylamino)ethyl)-4-nitrobenzamide (63 mg, 0.237 mmol), zinc (155 mg, 2.37 mmol), ammonium chloride (25 mg, 0.475 mmol) and 1.25 ml of aqueous oligosaccharide solution (2 wt % HPMC, 40-60 cps, in degassed Millipore water), the reaction was allowed to stir for 2 h at room temperature (the conversion was however already completed after 5 min, as indicated by LC-MS). After the work-up the clean product was obtained (46 mg, 82%).

ESI-MS: m/z (%): 236.10 (100, [M+H]$^+$).

$^1$H NMR (600 MHz, d$_6$-DMSO): δ [ppm]: 7.91 (d, J=6.0 Hz, 1H), 7.56-7.50 (m, 2H), 6.56-6.49 (m, 2H), 5.59 (s, 2H), 3.30-3.24 (m, 2H), 2.57-2.51 (m, 6H), 0.97 (t, J=7.1 Hz, 6H).

16. Preparation of 3-fluoro-4-methoxyaniline

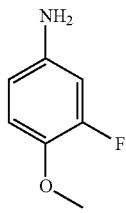

Following the general procedure using 2-fluoro-4-nitroanisole (171 mg, 1.00 mmol), zinc (327 mg, 5.00 mmol), ammonium chloride (64 mg, 1.20 mmol) and 2 ml of aqueous oligosaccharide solution (2 wt % HPMC, 40-60 cps, in degassed Millipore water), the reaction was allowed to stir for 5 min at room temperature. After column chromatography (0-100% ethyl acetate-dichloromethane), the product was obtained (110 mg, 78%).

ESI-MS: m/z (%): 142.10 (100, [M+H]$^+$).

$^1$H NMR (600 MHz, d$_6$-DMSO): δ [ppm]: 6.85-6.81 (m, 1H), 6.41-6.37 (m, 1H), 6.31-6.28 (m, 1H), 4.91 (s$_{br}$, 2H), 3.68 (s, 3H).

General Procedure for Hydrogenations of Nitro Groups Using Pd/C

To the nitro compound (1.0 equiv.) was added a 2 wt % solution of HPMC (40-60 cps) in Millipore water (0.5 M) and palladium on carbon (10%, 0.05 equiv.). The mixture was stirred vigorously under a hydrogen atmosphere for the indicated time at room temperature. The mixture was diluted with EtOAc (3 mL) and a sat. solution of Na$_2$SO$_4$ (2 mL), filtered, extracted with EtOAc (3×15 mL) and dried over MgSO$_4$. The clean product was obtained after flash chromatography on silica gel.

16.3 Preparation of 4-methoxyaniline

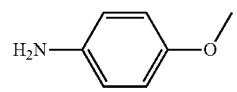

Following the general procedure using 4-nitroanisole (600 mg, 3.92 mmol, 1.0 equiv.) and palladium on carbon (10%, 208 mg, 0.2 mmol, 0.05 equiv) the reaction was allowed to stir under a hydrogen atmosphere for 18 h at room temperature. After column chromatography (dichloromethane/ethyl acetate), the product was obtained (430 mg, 3.49 mmol, 89%).

ESI-MS: m/z (%): 124.1 (100, [M+H]$^+$).

$^1$H NMR (600 MHz, CDCl$_3$): δ [ppm]: 6.79-6.71 (m, 2H), 6.68-6.63 (m, 2H), 3.75 (s, 3H), 3.52 (s$_{br}$, 2H).

17. CuH Reductions of Double Bonds

General Procedure for CuH Reductions of Double Bonds

To Cu(OAc)$_2$ (0.03 equiv.) and (6,6'-dimethoxy-[1,1'-biphenyl]-2,2'-diyl)bis(bis(3,5-dimethylphenyl)phosphine) (0.03 equiv.) under argon was given a 2 wt % solution of HPMC (4-6 cps) in Millipore water (0.25 M). After the addition of the alkene (1.0 equiv.) the mixture was stirred for 5 min at room temperature. Polymethylhydrosiloxane (0.31 equiv.) was slowly added and the mixture was stirred under argon for the indicated time at room temperature. The reaction was quenched with a NH$_4$F solution and stirred for 2 h at room temperature. The mixture was filtered through a short pad of silica which was washed with methanol (3×15 ml). The clean product was obtained after flash chromatography on silica gel.

17.1 Preparation of ethyl 3-phenylbutanoate

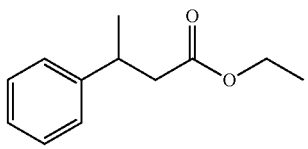

Following the general procedure using ethyl trans-beta-methylcinnamate (95 mg, 0.5 mmol, 1.0 equiv.), (6,6'-dimethoxy-[1,1'-biphenyl]-2,2'-diyl)bis(bis(3,5-dimethylphenyl)phosphine) (10.4 mg, 0.015 mmol, 0.03 equiv.), polymethylhydrosiloxane (294 mg, 0.155 mmol, 0.31 equiv.) and Cu(OAc)$_2$ (2.7 mg, 0.015 mmol, 0.03 equiv.) the reaction was allowed to stir under an argon atmosphere for 24 h at room temperature. After column chromatography (ethyl acetate/cyclohexane), the product was obtained (95 mg, 0.49 mmol, 99%).

APCI-MS: m/z (%): 193.2 (100, [M+H]$^+$).

$^1$H NMR (600 MHz, d$_6$-DMSO): δ [ppm]: 7.33-7.22 (m, 4H), 7.23-7.13 (m, 1H), 4.03-3.91 (m, 2H), 3.21-3.09 (m, 1H), 2.63-2.54 (m, 2H), 1.21 (d, J=7.0 Hz, 3H), 1.09 (t, J=7.1 Hz, 3H).

18. Reductive Amination

General Procedure for Reductive Aminations Using Aldehydes

A 5 mL microwave vial was charged with the amine (1.0 equiv.), borane-2-picoline complex (1.2 equiv.) and diphenyl phosphate (0.1 equiv.). After the addition of HPMC-solution (40-60 cps, 2 wt % in Millipore water, 1.25 mL) and the aldehyde (1.2 equiv.) the reaction mixture was vigorously stirred at room temperature until LCMS or TLC showed full conversion of the starting materials. The mixture was quenched with a saturated solution of sodium hydrogen carbonate in water (1 mL), diluted with EtOAc (3 mL) and stirred for 2 min. After the addition of a saturated solution of sodium sulfate (2 mL) the phases were separated and the aqueous phase was further extracted with EtOAc (3×). The combined organic layers were dried over sodium sulfate. The crude product was purified by flash chromatography on silica gel.

18.1 Preparation of N-benzyl-4-methoxyaniline

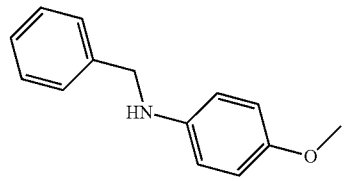 [SMILES: COc1ccc(NCc2ccccc2)cc1]

Following the general procedure using p-anisidine (62.0 mg, 0.50 mmol, 1.0 equiv.), borane-2-picoline complex (64.6 mg, 0.60 mmol, 1.2 equiv.), diphenyl phosphate (12.6 mg, 0.05 mmol, 0.1 equiv.) and freshly distilled benzaldehyde (64.1 mg, 0.60 mmol, 1.2 equiv.) the reaction was stirred for 2 h at room temperature. After column chromatography on silica gel (0-100% ethyl acetate-heptane) the product was obtained as a colorless oil (88 mg, 0.41 mmol, 82%).

ESI-MS: m/z (%): 214.1 (100, [M+H]$^+$).

$^1$H NMR (600 MHz, CDCl$_3$): δ [ppm]: 7.37-7.21 (m, 5H), 6.79-6.71 (m, 2H), 6.61-6.51 (m, 2H), 4.23 (s, 2H), 3.75 (s$_{br}$, 1H), 3.69 (s, 3H).

General Procedure for Reductive Aminations Using Ketones

A 5 mL microwave vial was charged with the amine (1.0 equiv.), borane-2-picoline complex (1.2 equiv.) and diphenyl phosphate (0.1 equiv.). After the addition of HPMC-solution (40-60 cps, 2 wt % in Millipore water, 1.25 mL) and the ketone (1.2 equiv.) the reaction mixture was vigorously stirred at room temperature until LCMS or TLC showed full conversion of the starting materials. The mixture was quenched with a saturated solution of sodium hydrogen carbonate in water (1 mL), diluted with EtOAc (3 mL) and stirred for 2 min. After the addition of a saturated solution of sodium sulfate (2 mL) the phases were separated and the aqueous phase was further extracted with EtOAc (3×). The combined organic layers were dried over sodium sulfate. The crude product was purified by flash chromatography on silica gel.

18.2 Preparation of 4-methoxy-N-(1-phenylethyl)aniline

Following the general procedure using p-anisidine (62.0 mg, 0.50 mmol, 1.0 equiv.), borane-2-picoline complex (64.6 mg, 0.60 mmol, 1.2 equiv.), diphenyl phosphate (12.6 mg, 0.05 mmol, 0.1 equiv.) and acetophenone (72.6 mg, 0.60 mmol, 1.2 equiv.) the reaction was stirred for 48 h at room temperature. After column chromatography on silica gel (0-100% ethyl acetate-heptane) the product was obtained as a colorless oil (88 mg, 0.39 mmol, 77%).

ESI-MS: m/z (%): 228.1 (100, [M+H]+).

$^1$H NMR (600 MHz, CDCl$_3$): δ [ppm]: 7.36-7.25 (m, 4H), 7.22-7.17 (m, 1H), 6.70-6.64 (m, 2H), 6.47-6.42 (m, 2H), 4.38 (q, J=6.7 Hz, 1H), 3.72 (s$_{br}$, 1H), 3.65 (s, 3H), 1.46 (d, J=6.8 Hz, 3H).

19. Introduction of Protective Groups

General Procedure for Boc-Protections of Primary Amines

A 5 mL microwave vial was charged with the amine (1.0 equiv.) and a HPMC-solution (40-60 cps, 2 wt % in Millipore water, 1.5 mL). After the addition of di-tert-butyl dicarbonate (1.1 equiv.) and trimethylamine (1.1 equiv.) the reaction mixture was stirred at room temperature until LCMS or TLC showed full conversion of the starting materials. Ethyl acetate (1 mL) was added followed by a saturated solution of sodium sulfate in water (2 mL). The mixture was filtered through a plug of neutral aluminum oxide, which was washed with ethyl acetate. The organic phase was dried over sodium sulfate and the product was obtained after removal of the solvent or after column chromatography on silica gel.

19.1 Preparation of tert-butyl (1,2,3,4-tetrahydronaphthalen-2-yl)carbamate

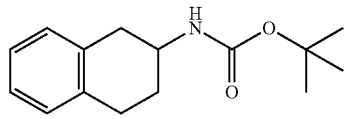 [SMILES: CC(C)(C)OC(=O)NC1CCc2ccccc2C1]

Following the general procedure using 1,2,3,4-tetrahydronaphthalen-2-amine (74.0 mg, 0.50 mmol, 1.0 equiv.), di-tert-butyl dicarbonate (121 mg, 0.55 mmol, 1.1 equiv.) and trimethylamine (56.0 mg, 0.55 mmol, 1.1 equiv) the reaction was stirred for 30 min at room temperature. The product was obtained as a white solid (80 mg, 0.32 mmol, 64%).

ESI-MS: m/z (%): 270.4 (100, [M+Na]+).

$^1$H NMR (600 MHz, CDCl$_3$): δ [ppm]: 7.14-7.02 (m, 4H), 4.70-4.60 (m, 1H), 4.03-3.92 (m, 1H), 3.15-3.06 (m, 1H), 2.93-2.82 (m, 2H), 2.66-2.58 (m, 1H), 2.10-2.02 (m, 1H), 1.78-1.69 (m, 1H), 1.45 (s, 9H).

General Procedure for Z-Protections of Primary Amines

A 5 mL microwave vial was charged with the amine (1.0 equiv.) and a HPMC-solution (40-60 cps, 2 wt % in Millipore water, 1.5 mL). After the addition of dibenzyl dicarbonate (1.0 equiv.) the reaction mixture was stirred at room temperature until LCMS or TLC showed full conversion of the starting materials. Ethyl acetate (1 mL) was added followed by a saturated solution of sodium sulfate in water (2 mL). The organic phase was dried over sodium sulfate and the product was obtained after column chromatography on silica gel.

19.2 Preparation of Benzyl (4-(cyanomethyl)phenyl)carbamate

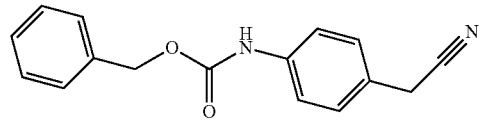 [SMILES: N#CCc1ccc(NC(=O)OCc2ccccc2)cc1]

Following the general procedure using 4-aminophenylacetonitrile (66.0 mg, 0.50 mmol, 1.0 equiv) and dibenzyl dicarbonate (143.0 mg, 0.50 mmol, 1.0 equiv) the reaction was stirred for 20 min at room temperature. After column chromatography on silica gel (0-1% dichloromethane-methanol) the product was obtained as a white solid (91 mg, 0.34 mmol, 68%).

ESI-MS: m/z (%): 267.1 (80, [M+H]+).

$^1$H NMR (600 MHz, CDCl$_3$): δ [ppm]: 7.51-6.84 (m, 10H), 5.18 (s, 2H), 3.66 (s, 2H).

General Procedure for Acetyl Protections of Primary Amines

A 5 mL microwave vial was charged with the amine (1.0 equiv.) and a HPMC-solution (40-60 cps, 2 wt % in Millipore water, 1.5 mL). After the addition of acetic anhydride (1.1 equiv.) and triethylamine (1.5 equiv.) the reaction mixture was stirred at room temperature until LCMS or TLC showed full conversion of the starting materials. Ethyl acetate (1 mL) was added followed by a saturated solution of sodium sulfate in water (1 mL). The mixture was filtered through a plug of silica, which was washed with ethyl acetate. The organic phase was dried over sodium sulfate and the product was obtained after removal of the solvent or after column chromatography on silica gel.

19.3 Preparation of N-(1,2,3,4-tetrahydronaphthalen-2-yl)acetamide

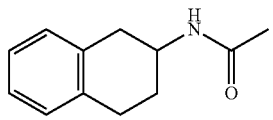

Following the general procedure using 1,2,3,4-tetrahydronaphthalen-2-amine (74.0 mg, 0.50 mmol, 1.0 equiv.), acetic anhydride (56.4 mg, 0.55 mmol, 1.1 equiv.) and trimethylamine (76.0 mg, 0.75 mmol, 1.5 equiv) the reaction was stirred for 10 min at room temperature. Ethyl acetate (1 mL) was added followed by a saturated solution of sodium sulfate in water (1 mL). The crude reaction mixture was filtered through a plug of silica. The organic phase was dried over sodium sulfate. After removal of the solvent the product was obtained as a white solid (61 mg, 0.32 mmol, 64%).

ESI-MS: m/z (%): 190.4 (100, [M+H]+).

$^1$H NMR (600 MHz, CDCl$_3$): δ [ppm]: 7.19-6.99 (m, 4H), 5.87 (s, 1H), 4.33-4.21 (m, 1H), 3.16-3.05 (m, 1H), 2.96-2.80 (m, 2H), 2.68-2.60 (m, 1H), 2.08-2.01 (m, 1H), 1.97 (s, 3H), 1.81-1.72 (m, 1H).

General Procedure for Acetyl Protections of Primary Amines in High Concentrations A 5 mL microwave vial was charged with the amine (1.0 equiv.) and a HPMC-solution (40-60 cps, 2 wt % in Millipore water, 0.165 mL). After the addition of acetic anhydride (1.1 equiv.) and triethylamine (1.2 equiv.) the reaction mixture was stirred for at room temperature until LCMS or TLC showed full conversion of the starting materials.

19.4 Preparation of N-(4-(5-cyano-4-hydroxy-6-oxo-6,7-dihydrothieno[2,3-b]pyridin-3-yl)phenylacetamide

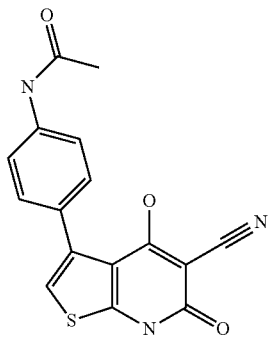 [SMILES: CC(=O)Nc1ccc(-c2csc3[nH]c(=O)c(C#N)c(O)c23)cc1]

Following the general procedure using 3-(4-aminophenyl)-4-hydroxy-6-oxo-6,7-dihydrothieno[2,3-b]pyridine-5-carbonitrile (35 mg, 0.12 mmol, 1.0 equiv.), acetic anhydride (13.9 mg, 0.14 mmol, 1.1 equiv.) and triethylamine (15.0 mg, 0.15 mmol, 1.2 equiv.) the reaction was stirred for 5 min at room temperature. After the addition of brine (0.3 mL) the formed solid was filtered off, washed with water (0.5 mL) and dried. The product was obtained as an off-white solid (40 mg, 0.12 mmol, quant.).

ESI-MS: m/z (%): 326.1 (100, [M+H]$^+$).

$^1$H NMR (600 MHz, dmso): δ [ppm]: 10.79 (s, 1H), 9.93 (s, 1H), 7.63-7.26 (m, 4H), 6.57 (s, 1H), 2.05 (s, 3H).

19.5 Preparation of N-(4-(6-cyano-7-hydroxy-5-oxo-4,5-dihydro-1H-pyrrolo[3,2-b]-pyridin-1-yl)phenyl)acetamide

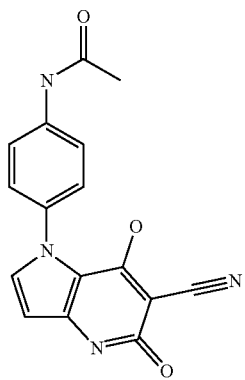

Following the general procedure using 1-(4-aminophenyl)-7-hydroxy-5-oxo-4,5-dihydro-1H-pyrrolo[3,2-b]pyridine-6-carbonitrile hydrochloride (32 mg, 0.11 mmol, 1.0 equiv.), acetic anhydride (11.9 mg, 0.12 mmol, 1.1 equiv.) and triethylamine (34.2 mg, 0.34 mmol, 3.2 equiv.) the reaction was stirred for 1 h at room temperature. After the addition of brine (1.0 mL) the formed solid was filtered off, washed with water (0.5 mL) and dried. The product was obtained as an off-white solid (20 mg, 0.07 mmol, 62%).

ESI-MS: m/z (%): 309.2 (100, [M+H]$^+$).

$^1$H NMR (500 MHz, dmso): δ [ppm]: 9.98 (s, 1H), 9.69 (s, 1H), 7.66-7.18 (m, 4H), 6.93 (d, J=2.9 Hz, 1H), 5.85 (d, J=3.0 Hz, 1H), 2.06 (s, 3H).

19.6 Preparation of ethyl 3-acetamido-1H-pyrrole-2-carboxylate (10154514-1934)

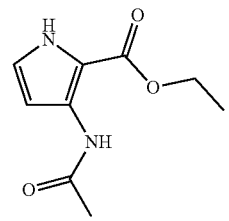

Following the general procedure using ethyl 3-amino-H-pyrrole-2-carboxylate (100 mg, 0.64 mmol, 1.0 equiv.), acetic anhydride (71.4 mg, 0.70 mmol, 1.1 equiv.) and a HPMC-solution (40-60 cps, 2 wt % in Millipore water, 0.212 mL) the reaction was stirred for 10 min at room temperature. After the addition of ethyl acetate (20.0 mL) and a saturated solution of sodium sulfate in water (0.2 mL) the phases were separated. The organic layer was dried over sodium sulfate. The product was obtained after removal of the solvent (126 mg, 0.61 mmol, 95%).

ESI-MS: m/z (%): 197.1 (100, [M+H]$^+$).

$^1$H NMR (600 MHz, CDCl$_3$): δ [ppm]: 9.17 (s, 1H), 8.55 (s, 1H), 7.07-7.04 (m, 1H), 6.85-6.78 (m, 1H), 4.35 (q, J=7.1 Hz, 2H), 2.19 (s, 3H), 1.38 (t, J=7.1 Hz, 3H).

20. One Pot Multi Step Reactions

20.1 One-Pot Two Step Reaction Including Double Nucleophilic Substitution with Ring Formation to an Azetidine and Subsequent Ester Hydrolysis

General Procedure for a One-Pot Azetidine Formation and Ester Hydrolysis

A 5 mL microwave vial was charged with the primary amine (1.0 equiv.), the bis-triflate (1.5 equiv.) and a HPMC-solution (40-60 cps, 2 wt % in Millipore water, 1.0 mL). After the addition of potassium hydroxide (6.0 equiv.) the mixture was stirred at 50° C. for the indicated time. The product was obtained reversed phase high pressure liquid chromatography of the crude reaction mixture.

20.1.1 Preparation of 3-methyl-1-(1,2,3,4-tetrahydronaphthalen-2-yl)azetidine-3-carboxylic Acid

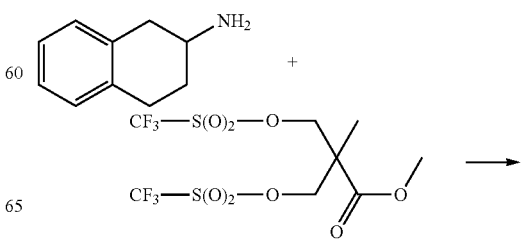

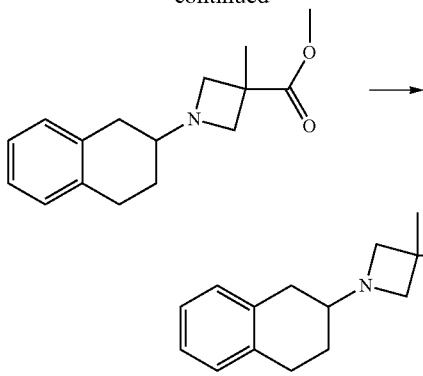

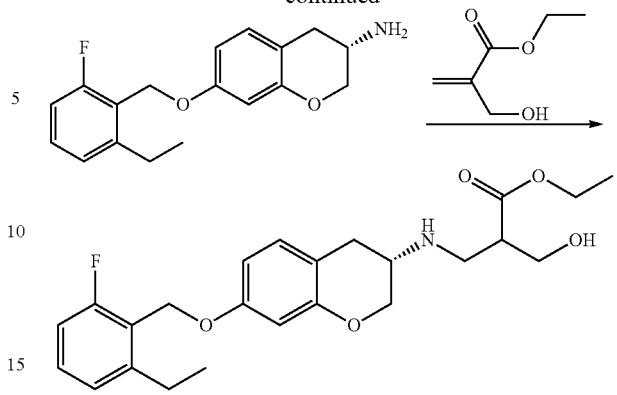

Following the general procedure for a one-pot azetidine formation and ester hydrolysis using 1,2,3,4-tetrahydronaphthalen-2-amine (73.6 mg, 0.50 mmol, 1.0 equiv.), methyl 2-methyl-3-(((trifluoromethyl)sulfonyl)oxy)-2-((((trifluoromethyl)sulfonyl)oxy)-methyl)propanoate (309 mg, 0.75 mmol, 1.5 equiv.) and potassium hydroxide (168 mg, 3.00 mmol, 6.0 equiv.) the reaction was stirred for 2 h at 50° C. After reversed phase high pressure liquid chromatography the product was obtained as a white solid (91 mg, 0.37 mmol, 74%).

ESI-MS: m/z (%): 246.4 (100, [M+H]$^+$).

$^1$H NMR (600 MHz, DMSO-d$_6$): δ [ppm]: 7.21-7.06 (m, 4H), 4.48-4.38 (m, 2H), 4.14-4.05 (m, 2H), 3.71 (s$_{br}$, 1H), 3.67-3.57 (m, 1H), 3.17-3.09 (m, 1H), 2.92-2.47 (m, 4H), 2.17-2.05 (m, 1H), 1.54 (s, 3H).

$^{13}$C NMR (126 MHz, DMSO-d$_6$) δ [ppm]: 174.78, 135.25, 132.57, 129.52, 128.98, 126.82, 126.52, 60.87, 59.63, 59.61, 38.74, 29.65, 27.23, 23.46, 21.80.

20.2 One-Pot Four Step Reaction Including Boc-Protection of an Amino Group, Nucleophilic Substitution, Deprotection and Michael Addition of an N Nucleophile 20.2.2 Preparation of ethyl 3-(((S)-7-((2-ethyl-6-fluorobenzyl)oxy)chroman-3-yl)amino)-2-(hydroxymethyl)propanoate

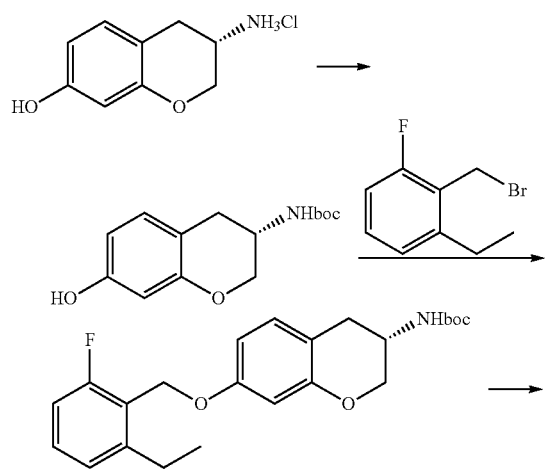

(S)-3-Aminochroman-7-ol hydrochloride (500 mg, 2.48 mmol, 1.0 eq.) and di-tert-butyl dicarbonate (635 µl, 2.76 mmol, 1.1 eq.) were loaded into a 5.0 mL microwave vial opened in the air and containing a magnetic stir bar and Teflon-lined septum. HPMC in water solution (Matrocel E5, 8.3 ml of 2 wt % in degassed Millipore water) was added followed by trimethylamine (382 µl, 2.73 mmol, 1.1 eq.). The microwave tube was close with a septa and the reaction mixture was stirred at room temperature for 5 minutes. Completion of the reaction was confirmed by LC/MS.

To the reaction mixture was added 2-(bromomethyl)-1-ethyl-3-fluorobenzene (592 mg, 2.73 mmol, 1.1 eq.) and sodium hydroxide (129 mg, 3.22 mmol, 1.3 eq.) and the suspension was stirred at 65° C. for 15 min. As the reaction did not go to completion an extra 1.0 eq. of sodium hydroxide and 0.2 eq. of 2-(bromomethyl)-1-ethyl-3-fluorobenzene were added and the reaction mixture was stirred at 65° C. for an extra 15 min. Completion of the reaction was confirmed by LC/MS.

12N HCl was added dropwise to adjust the pH of the mixture to 4. p-Toluenesulfonic acid (1.71 g, 9.92 mmol, 4.00 eq.) was added to the mixture in two portions. The mixture was then vigorously stirred and heated at 65° C. for 15 min. As no reaction was observed after 15 min extra p-toluenesulfonic acid (850 mg, 4.96 mmol, 2.00 eq.) was added and the reaction was complete after 1 h.

The mixture was cooled to room temperature and trimethylamine (1.74 mL, 12.40 mmol, 5.00 eq.) was added in order to adjust the pH to 9. Ethyl 2-(hydroxymethyl)acrylate (323 mg, 2.48 mmol, 1.00 eq.) was then added and the mixture was stirred at room temperature for 12 h. LCMS shows some starting material left. An extra 0.50 eq. of ethyl 2-(hydroxymethyl)acrylate (162 mg, 1.24 mmol) was added and the mixture was stirred for an extra 3 h.

To the reaction mixture were added ethyl acetate and saturated aqueous sodium sulfate solution. The mixture was stirred at room temperature for 10 min and filtered through celite to remove the solid. The solid was washed three times with ethyl acetate. The organic phase was separated from the aqueous layer. The combined ethyl acetate phases were dried in vacuo to give 1.00 g of crude material. After column chromatography on silica gel (0-5% dichloromethane-methanol in presence of 1% triethylamine) the product was obtained as a colorless oil (810 mg, 1.88 mmol, 76%).

ESI-MS: m/z (%): 432.0 (100, [M+H]$^+$)

$^1$H NMR (600 MHz, CDCl$_3$): δ [ppm]: 7.33-7.29 (m, 1H), 7.08 (d, J=7.6 Hz, 1H), 7.00-6.92 (m, 2H), 6.59 (d, J=8.3 Hz, 1H), 6.54 (s, 1H), 5.07 (s, 2H), 4.25-4.09 (m, 3H), 4.08-3.90

(m, 3H), 3.33-3.21 (m, 1H), 3.23-3.07 (m, 2H), 3.07-2.95 (m, 1H), 2.86-2.70 (m, 3H), 2.64 (dd, J=15.9, 6.6 Hz, 2H), 1.34-1.18 (m, 6H).

21. Cyclopropanation

General Procedure for Cyclopropanations with In-Situ Formation of the Diazo Compound from Glycine Ethyl Ester Hydrochloride A 10 mL vial was charged with the alkene (1.0 equiv.), meso-tetraphenylporphyrin iron(III) chloride complex (0.01 equiv.) and glycine ethyl ester hydrochloride (2.0 equiv.). After the addition of dichloroethane (0.4 mL per mmol of alkene), a HPMC-solution (40-60 cps, 2 wt % in Millipore water, 4 mL per mmol of alkene) and acetic acid (0.15 equiv.), the mixture was heated to 40° C. Sodium nitrite (2.4 equiv) was added and the mixture was stirred for 20 h at 40° C. The mixture was diluted with ethyl acetate (2 mL/mmol) and a saturated solution of sodium sulfate (2 mL/mmol). After extraction with ethyl acetate (3×) the combined organic layers were dried over sodium sulfate. The crude product was purified by flash chromatography on silica gel.

21.1 Preparation of ethyl 2-([1,1'-biphenyl]-4-yl) cyclopropanecarboxylate

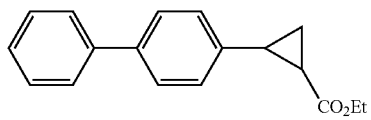 [SMILES: CCOC(=O)C1CC1c1ccc(-c2ccccc2)cc1]

Following the general procedure using 4-vinylbiphenyl (90 mg, 0.5 mmol, 1.0 equiv.), meso-tetraphenylporphyrin iron(III) chloride complex (3.5 mg, 0.005 mmol, 0.01 equiv.), glycine ethyl ester hydrochloride (140 mg, 1.0 mmol, 2.0 equiv.), acetic acid (4.5 mg, 0.075 mmol, 0.15 mmol) and sodium nitrite (83 mg, 1.2 mmol, 2.4 equiv.) the reaction mixture was stirred for 20 h at 40° C. After column chromatography on silica gel (0-100% ethyl acetate-heptane) the product was obtained as a pale yellow solid (50 mg, 0.19 mmol, 38%). The product was a mixture of trans:cis=8:1.

Analytical data for the trans product:

ESI-MS: m/z (%): 267.2 (100, [M+H]$^+$).

$^1$H NMR (600 MHz, CDCl$_3$): δ [ppm]: 7.62-7.09 (m, 9H), 4.17 (q, J=7.1 Hz, 2H), 2.60-2.51 (m, 1H), 1.98-1.90 (m, 1H), 1.70-1.58 (m, 1H), 1.38-1.31 (m, 1H), 1.28 (t, J=7.1 Hz, 3H).

We claim:

1. A method of carrying out an organic reaction in a solvent containing at least 90% by weight, based on the total weight of the solvent, of water, which method comprises reacting the reagents in said solvent in the presence of a cellulose derivative as a surfactant which is selected from the group consisting of cellulose modified with one or more alkylene oxides or other hydroxyalkyl precursors, and alkylcellulose; where the organic reaction is not a polymerization or oligomerization reaction of olefinically unsaturated compounds; and
where the organic reaction is
a transition metal catalyzed reaction in which a transition metal catalyst is used; where the transition metal catalyzed reaction is
a transition metal catalyzed C—C coupling reaction;
a transition metal catalyzed reaction involving C—N bond formation which is an Au-catalyzed cyclodehydratization of α,β-amino alcohols containing a C—C triple bond;
a transition metal catalyzed reaction involving C—O bond formation;
a transition metal catalyzed reaction involving C—S bond formation;
a transition metal catalyzed reaction involving C—B bond formation; or
a transition metal catalyzed reaction involving C-halogen bond formation; or
a C—C coupling reaction not requiring transition metal catalysis which is selected from the group consisting of reactions of carbonyl or nitrile compounds and pericyclic reactions;
a nucleophilic substitution reaction;
a reduction or an oxidation reaction; or
an ester formation reaction or an ester hydrolysis reaction.

2. The method as claimed in claim 1, where the cellulose derivative has a viscosity of from 1 to 150000 mPa·s, determined as a 2% by weight aqueous solution, relative to the weight of water.

3. The method as claimed in claim 1, where in the cellulose derivative 5 to 70% of the hydrogen atoms in the hydroxyl groups of the cellulose on which the cellulose derivative is based are replaced by a hydroxyalkyl and/or alkyl group.

4. The method as claimed in claim 1, where the cellulose modified with one or more alkylene oxides or other hydroxyalkyl precursors is selected from the group consisting of hydroxyalkylcelluloses which are celluloses in which a part of the hydrogen atoms of the OH groups is replaced by a $C_2$-$C_4$-hydroxyalkyl group; hydroxyalkylalkylcelluloses which are celluloses in which a part of the hydrogen atoms of the OH groups is replaced by a $C_2$-$C_4$-hydroxyalkyl group and a part of the hydrogen atoms of the OH groups is replaced by a $C_1$-$C_3$-alkyl group; and alkylcelluloses which are celluloses in which a part of the hydrogen atoms of the OH groups is replaced by a $C_1$-$C_3$-alkyl group.

5. The method as claimed in any claim 4, where the cellulose derivative is selected from the group consisting of hydroxypropylmethylcellulose, hydroxypropylcellulose, hydroxyethylmethylcellulose, ethylhydroxyethylcellulose, hydroxyethylcellulose, methylcellulose and ethylcellulose.

6. The method as claimed in claim 5, where the cellulose derivative is hydroxypropylmethylcellulose.

7. The method as claimed in claim 1, where the cellulose derivative is used in an amount of from 0.01 to 15% by weight, based on the weight of the solvent, or, alternatively, based on the weight of water.

8. The method as claimed in claim 1, where the weight ratio of the cellulose derivative and all reagents is from 1:1 to 1:200.

9. The method as claimed in claim 1, where at least one of the reagents has a water solubility of at most 100 g per 1 l of water at 20° C.+/−20% and 101325 Pascal+/−20%.

10. The method as claimed in claim 1, where the organic reaction is a transition metal catalyzed reaction in which a transition metal catalyst is used.

11. The method as claimed in claim 10, where the transition metal catalyst is not a catalyst supported on the cellulose derivative.

12. The method as claimed in claim 10, where the transition metal is selected from the group consisting of Fe, Ru, Co, Rh, Ir, Ni, Pd, Pt, Cu, Ag, Au, and Zn.

13. The method as claimed in claim 1, where the transition metal catalyzed C—C-coupling reaction is selected from the group consisting of the Suzuki-Miyaura reaction, Negishi coupling, Heck reaction, C—C coupling reactions involving C—H activation different from Heck reaction, Sonogashira coupling, Stille coupling, Grubbs olefin metathesis, 1,4 additions of organoborane compounds to α,β-olefinically unsaturated carbonyl compounds, Kumada coupling, Hiyama coupling, Ullmann reactions, Glaser coupling inclusive the Eglinton and the Hay coupling, Cadiot-Chodkiewicz coupling, the Fukuyama coupling, hydroformylation and cyclopropanation.

14. The method as claimed in claim 13, where the transition metal catalyzed C—C-coupling reaction is a Suzuki-Miyaura reaction in which an organoboron compound is reacted with an organic halogenide or sulfonate in the presence of a transition metal catalyst and optionally a base;
   where the organoboron compound is a compound of formula $R^1$—$BY_2$, where $R^1$ is an alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl or heteroaryl group and Y is an alkyl, O-alkyl or hydroxyl group, or the two substituents Y form together with the boron atom they are bound to a mono-, bi- or polycyclic ring; or the organoboron compound is a compound of formula $R^1$—$BF_3M$, where M is a metal equivalent; and
   the organic halogenide or sulfonate is a compound of formula $R^2$—$(Z)_n$, where $R^2$ is an alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl or heteroaryl group, Z is a halogenide or sulfonate group, and n is 1, 2, 3 or 4;
   where the alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl and heteroaryl groups $R^1$ and $R^2$ can carry one or more substituents.

15. The method as claimed in claim 13, where the transition metal catalyzed C—C-coupling reaction is a Sonogashira reaction, where an aryl, heteroaryl or vinyl halogenide or sulfonate is reacted with a terminal alkyne in the presence of a transition metal catalyst, optionally of a copper(I) salt, and optionally of a base;
   where the aryl, heteroaryl or vinyl halogenide or sulfonate is a compound of formula $R^2$—$(Z)_n$, where $R^2$ is a terminal alkenyl, aryl or heteroaryl group, Z is a halogenide or sulfonate group and n is 1, 2, 3 or 4;
   the terminal alkyne is a compound of formula H—C≡C—$R^1$, where $R^1$ is hydrogen or an alkyl, alkenyl, alkapolyenyl, alkynyl (provided that the alkyne group is not terminal), alkapolyynyl (provided there is no terminal alkyne group in this radical), mixed alkenyl/alkynyl (provided there is no terminal alkyne group in this radical), cycloalkyl, cycloalkenyl, cycloalkynyl, mixed cycloalkenyl/cycloalkynyl, polycarbocyclyl, heterocyclyl, aryl, heteroaryl or silyl group $Si(R^{14t})_3$,
   where the alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, aryl, heterocyclyl and heteroaryl groups $R^1$ and $R^2$ can carry one or more substituents; and where each $R^{14t}$ is independently selected from the group consisting of hydrogen, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, and phenyl, optionally substituted with 1, 2, 3, 4, or 5 radicals selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy.

16. The method as claimed in claim 13, where the transition metal catalyzed C—C coupling reaction is a Heck reaction, where an aryl, heteroaryl, benzyl, vinyl or alkyl halogenide or sulfonate (the alkyl group must not contain any β-hydrogen atoms) is reacted with an olefinically unsaturated compound in the presence of a transition metal catalyst and optionally in the presence of a base;
   where the aryl, heteroaryl, benzyl, vinyl or alkyl halogenide or sulfonate is a compound of the formula $R^2$—$(Z)_n$, where $R^2$ is an aryl, heteroaryl, benzyl, vinyl or alkyl group, where the alkyl group must not contain any β-hydrogen atoms, Z is a halogen atom or a sulfonate group, and n is 1, 2, 3 or 4, and
   the olefinically unsaturated compound is a compound of the formula $R^1(H)C=C(R^3)(R^4)$ where $R^1$, $R^3$, and $R^4$, independently of each other, are selected from the group consisting of hydrogen, alkyl, alkenyl, alkapolyenyl, alkynyl, alkapolyynyl, mixed alkenyl/alkynyl, halogen, cyano, nitro, azido, —SCN, —$SF_5$, $OR^{11}$, $S(O)_mR^{11}$, $NR^{12a}R^{12b}$, $C(=O)R^{13}$, $C(=S)R^{13}$, $C(=NR^{12a})R^{13}$, —$Si(R^{14})_3$, cycloalkyl, cycloalkenyl, cycloalkynyl, mixed cycloalkenyl/cycloalkynyl, polycarbocyclyl, where the five last-mentioned substituents may carry one or more substituents $R^{15}$; aryl which may be substituted by one or more radicals $R^{15}$; heterocyclyl which may be substituted by one or more radicals $R^{15}$; and heteroaryl which may be substituted by one or more radicals $R^{15}$; where
   each $R^{11}$ is independently selected from the group consisting of hydrogen, cyano, alkyl, cycloalkyl, cycloalkenyl, cycloalkynyl, mixed cycloalkenyl/cycloalkynyl, polycarbocyclyl, alkenyl, alkapolyenyl, alkynyl, alkapolyynyl, mixed alkenyl/alkynyl, where the aliphatic and cycloaliphatic moieties in the 11 last-mentioned radicals may be partially or fully halogenated and/or may be substituted by one or more radicals $R^{17}$,
   -alkyl-C(=O)$OR^{18}$, -alkyl-C(=O)N($R^{12a}$)$R^{12b}$,
   -alkyl-C(=S)N($R^{12a}$)$R^{12b}$, -alkyl-C(=N$R^{12}$)N($R^{12a}$)$R^{12b}$,
   —$Si(R^{14})_3$, —$S(O)_mR^{18}$, —$S(O)_mN(R^{12a})R^{12b}$, —$N(R^{12a})R^{12b}$, —N=C($R^{16}$)$_2$,
   —C(=O)$R^{13}$, —C(=O)N($R^{12a}$)$R^{12b}$, —C(=S)N($R^{12a}$)$R^{12b}$, —C(=O)$OR^{18}$,
   aryl, optionally substituted with one or more substituents $R^{15}$;
   heterocyclyl, optionally substituted with one or more substituents $R^{15}$; and
   heteroaryl, optionally substituted with one or more substituents $R^{15}$; and
   $R^{11}$ in the group —$S(O)_mR^{11}$ is additionally selected from the group consisting of alkoxy and haloalkoxy;
   $R^{12}$, $R^{12a}$ and $R^{12b}$, independently of each other and independently of each occurrence, are selected from the group consisting of hydrogen, cyano, alkyl, cycloalkyl, cycloalkenyl, cycloalkynyl, mixed cycloalkenyl/cycloalkynyl, polycarbocyclyl, alkenyl, alkapolyenyl, alkynyl, alkapolyynyl, mixed alkenyl/alkynyl, wherein the 11 last-mentioned aliphatic and cycloaliphatic radicals may be partially or fully halogenated and/or may be substituted by one or more substituents $R^{19}$, $-OR^{20}$, $-NR^{21a}R^{21b}$, $-S(O)_mR^{20}$, $-C(=O)N(R^{21a}R^{21b})$, $-C(=O)NR^{21}N(R^{21a}R^{21b})$, $-Si(R^{14})_3$, $-C(=O)R^{13}$, aryl which may be substituted with 1, 2, 3, 4, or 5 substituents $R^{15}$, heterocyclyl which may be substituted with one or more substituents $R^{15}$; and heteroaryl which may be substituted with one or more substituents $R^{15}$;

or $R^{12a}$ and $R^{12b}$, together with the nitrogen atom to which they are bound, form a saturated, partially unsaturated or maximally unsaturated heterocyclic or heteroaromatic ring, where the ring may further contain 1, 2, 3 or 4 heteroatoms or heteroatom-containing groups selected from the group consisting of O, S, N, SO, $SO_2$, C=O and C=S as ring members, wherein the heterocyclic or heteroaromatic ring may be substituted with 1, 2, 3, 4 or 5 independent $R^{15}$ substituents;

or $R^{12a}$ and $R^{12b}$ together form a group $=C(R^{22})_2$, $=S(O)_m(R^{20})_2$, $=NR^{21a}$ or $=NOR^{20}$;

each $R^{13}$ is independently selected from the group consisting of hydrogen, alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, where the aliphatic and cycloaliphatic moieties in the 11 last-mentioned radicals may be partially or fully halogenated and/or may be substituted by one or more radicals $R^{17}$; aryl, optionally substituted with one or more radicals $R^{15}$; heterocyclyl, optionally substituted with one or more radicals $R^{15}$; heteroaryl, optionally substituted with one or more radicals $R^{15}$; $OR^{20}$, $-S(O)_mR^{20}$, $-N(R^{21a})R^{21b}$, $-C(=O)N(R^{21a})R^{21b}$, $-C(=S)N(R^{21a})R^{21b}$ and $-C(=O)OR^{20}$;

each $R^{14}$ is independently selected from the group consisting of hydrogen, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, and phenyl, optionally substituted with 1, 2, 3, 4, or 5 radicals $R^{15}$;

each $R^{15}$ is independently selected from the group consisting of halogen, azido, nitro, cyano, $-OH$, $-SH$, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $-Si(R^{23})_3$;

$C_1$-$C_{20}$-alkyl, $C_2$-$C_{20}$-alkenyl, $C_2$-$C_{20}$-alkapolyenyl, $C_2$-$C_{20}$-alkynyl, $C_2$-$C_{20}$-alkapolyynyl, mixed $C_2$-$C_{20}$-alkenyl/alkynyl, wherein the six last-mentioned aliphatic radicals may be partially or fully halogenated and/or may carry one or more radicals selected from the group consisting of OH, $C_1$-$C_{20}$-alkoxy, $C_1$-$C_{20}$-haloalkoxy, SH, $C_1$-$C_{20}$-alkylthio, $C_1$-$C_{20}$-haloalkylthio, $C_1$-$C_{20}$-alkylsulfinyl, $C_1$-$C_{20}$-haloalkylsulfinyl, $C_1$-$C_{20}$-alkylsulfonyl, $C_1$-$C_{20}$-haloalkylsulfonyl, $-Si(R^{23})_3$, oxo, $C_3$-$C_8$-cycloalkyl, $C_3$-$C_8$-cycloalkenyl, $C_8$-$C_{20}$-cycloalkynyl, mixed $C_3$-$C_{20}$-cycloalkenyl/cycloalkynyl, polycarbocyclyl, aryl, heterocyclyl and heteroaryl, wherein the 8 last mentioned cyclic radicals may in turn be partially or fully halogenated and/or may carry one or more radicals selected from the group consisting of OH, $C_1$-$C_{20}$-alkoxy, $C_1$-$C_{20}$-haloalkoxy, SH, $C_1$-$C_{20}$-alkylthio, $C_1$-$C_{20}$-haloalkylthio, $C_1$-$C_{20}$-alkylsulfinyl, $C_1$-$C_{20}$-haloalkylsulfinyl, $C_1$-$C_{20}$-alkylsulfonyl, $C_1$-$C_{20}$-haloalkylsulfonyl, $-Si(R^{23})_3$, oxo, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-cycloalkenyl, $C_8$-$C_{20}$-cycloalkynyl, mixed $C_3$-$C_{20}$-cycloalkenyl/cycloalkynyl, polycarbocyclyl, aryl, heterocyclyl and heteroaryl, wherein the 8 last mentioned radicals may in turn be unsubstituted, partially or fully halogenated and/or carry 1, 2 or 3 substituents selected from the group consisting of cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl and $C_1$-$C_6$-haloalkoxycarbonyl;

$C_3$-$C_8$-cycloalkyl, $C_3$-$C_8$-cycloalkenyl, $C_8$-$C_{20}$-cycloalkynyl, mixed $C_3$-$C_{20}$-cycloalkenyl/cycloalkynyl, polycarbocyclyl, wherein the 5 last-mentioned cycloaliphatic radicals may be partially or fully halogenated and/or may carry one or more radicals selected from the group consisting of cyano, $C_1$-$C_4$-alkyl, $C_1$-$C_4$-haloalkyl, $C_1$-$C_4$-alkoxy, $C_1$-$C_4$-haloalkoxy and oxo;

aryl, O-aryl, heterocyclyl, O-heterocyclyl, heteroaryl and O-heteroaryl, wherein the cyclic moieties in the 6 last mentioned radicals may be unsubstituted, partially or fully halogenated and/or carry 1, 2 or 3 substituents selected from the group consisting of $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl and $C_1$-$C_6$-haloalkoxycarbonyl;

or two $R^{15}$ present together on the same atom of an unsaturated or partially unsaturated ring may be $=O$, $=S$, $=N(C_1$-$C_6$-alkyl), $=NO(C_1$-$C_6$-alkyl), $=CH(C_1$-$C_4$-alkyl) or $=C(C_1$-$C_4$-alkyl)$C_1$-$C_4$-alkyl;

or two $R^{15}$ on two adjacent carbon or nitrogen atoms form together with the carbon or nitrogen atoms they are bonded to a 4-, 5-, 6-, 7- or 8-membered saturated, partially unsaturated or maximally unsaturated, including heteroaromatic, ring, wherein the ring may contain 1, 2, 3 or 4 heteroatoms or heteroatom groups selected from the group consisting of N, O, S, NO, SO and $SO_2$, as ring members, and wherein the ring optionally carries one or more substituents selected from the group consisting of halogen, cyano, $C_1$-$C_4$-alkyl, $C_1$-$C_4$-haloalkyl, $C_1$-$C_4$-alkoxy and $C_1$-$C_4$-haloalkoxy;

each $R^{16}$ is independently selected from the group consisting of hydrogen, halogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl and $C_2$-$C_6$-haloalkynyl, wherein the six last-mentioned aliphatic radicals may carry 1 or 2 radicals selected from the group consisting of CN, $C_3$-$C_4$-cycloalkyl, $C_1$-$C_4$-alkoxy, $C_1$-$C_4$-haloalkoxy and oxo;

each $R^{17}$ is independently selected from the group consisting of cyano, nitro, $-OH$, $-SH$, $-SCN$, $-SF_5$, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $-Si(R^{14})_3$, $C_3$-$C_8$-cycloalkyl which may be unsubstituted, partially or fully halogenated and/or may carry 1 or 2 radicals selected from the group consisting of $C_1$-$C_4$-alkyl, $C_1$-$C_4$-haloalkyl, $C_3$-$C_8$-cycloalkyl, $C_3$-$C_8$-halocycloalkyl, $C_1$-$C_4$-alkoxy, $C_1$-$C_4$-haloalkoxy and oxo;

aryl, aryloxy, heterocyclyl, heterocyclyloxy, heteroaryl and heteroaryloxy, where the cyclic moiety in the 6 last-mentioned radicals may be unsubstituted, partially or fully halogenated and/or carry 1, 2, 3, 4 or 5 substituents $R^{15}$; or two $R^{17}$ present on the same carbon atom (of an alkyl, cycloalkyl, cycloalkenyl, cycloalkynyl, mixed cycloalkenyl/cycloalkynyl, polycarbocyclyl, alkenyl, alkapolyenyl, alkynyl, alkapolyynyl or mixed alkenyl/alkynyl group) may together be =O, =CH($C_1$-$C_4$-alkyl), =C($C_1$-$C_4$-alkyl)$C_1$-$C_4$-alkyl, =N($C_1$-$C_6$-alkyl) or =NO($C_1$-$C_6$-alkyl); and $R^{17}$ as a substituent on a cycloalkyl, cycloalkenyl, cycloalkynyl, mixed cycloalkenyl/cycloalkynyl or polycarbocyclyl ring is additionally selected from the group consisting of $C_1$-$C_6$-alkyl, $C_2$-$C_6$-alkenyl and $C_2$-$C_6$-alkynyl, wherein the three last-mentioned aliphatic radicals may be unsubstituted, partially or fully halogenated and/or may carry 1 or 2 substituents selected from the group consisting of CN, $C_3$-$C_4$-cycloalkyl, $C_3$-$C_4$-halocycloalkyl, $C_1$-$C_4$-alkoxy, $C_1$-$C_4$-haloalkoxy and oxo;

each $R^{18}$ is independently selected from the group consisting of hydrogen, cyano, —Si($R^{14}$)$_3$, $C_1$-$C_{20}$-alkyl, $C_2$-$C_{20}$-alkenyl, $C_2$-$C_{20}$-alkynyl, wherein the three last-mentioned aliphatic radicals may be unsubstituted, partially or fully halogenated and/or may carry 1 or 2 radicals selected from the group consisting of $C_3$-$C_8$-cycloalkyl, $C_3$-$C_8$-halocycloalkyl, $C_1$-$C_{20}$-alkoxy, $C_1$-$C_{20}$-haloalkoxy, $C_1$-$C_{20}$-alkylthio, $C_1$-$C_{20}$-haloalkylthio, $C_1$-$C_{20}$-alkylsulfinyl, $C_1$-$C_{20}$-haloalkylsulfinyl, $C_1$-$C_{20}$-alkylsulfonyl, $C_1$-$C_{20}$-haloalkylsulfonyl and oxo;

$C_3$-$C_8$-cycloalkyl which may be unsubstituted, partially or fully halogenated and/or may carry 1 or 2 radicals selected from the group consisting of $C_1$-$C_4$-alkyl, $C_1$-$C_4$-haloalkyl, $C_3$-$C_4$-cycloalkyl, $C_3$-$C_4$-halocycloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl and oxo;

aryl, heterocyclyl and heteroaryl, wherein the 3 last-mentioned radicals may be unsubstituted, partially or fully halogenated and/or carry 1, 2 or 3 substituents selected from the group consisting of $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl and $C_1$-$C_6$-haloalkoxycarbonyl; and $R^{18}$ in the group S(O)$_m R^{18}$ is additionally selected from the group consisting of $C_1$-$C_6$-alkoxy, $C_1$-$C_6$-haloalkoxy, aryloxy, heterocyclyloxy and heteroaryloxy;

each $R^{19}$ is independently selected from the group consisting of halogen, nitro, cyano, —OH, —SH, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, Si($R^{14}$)$_3$;

$C_3$-$C_8$-cycloalkyl, $C_3$-$C_8$-halocycloalkyl, wherein the two last-mentioned cycloaliphatic radicals may carry one or more radicals selected from the group consisting of cyano, $C_1$-$C_4$-alkyl, $C_1$-$C_4$-haloalkyl, $C_3$-$C_8$-cycloalkyl, $C_3$-$C_8$-halocycloalkyl, $C_1$-$C_4$-alkoxy, $C_1$-$C_4$-haloalkoxy and oxo;

aryl, aryloxy, heterocyclyl, heterocyclyloxy, heteroaryl and heteroaryloxy, wherein the 6 last mentioned radicals may be unsubstituted, partially or fully halogenated and/or carry 1, 2 or 3 substituents selected from the group consisting of $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl and $C_1$-$C_6$-haloalkoxycarbonyl;

each $R^{20}$ is independently defined as $R^{18}$;

$R^{21}$, $R^{21a}$ and $R^{21b}$, independently of each other and independently of each occurrence, are selected from the group consisting of hydrogen, cyano, alkyl, cycloalkyl, alkenyl, alkynyl, wherein the four last-mentioned aliphatic and cycloaliphatic radicals may be partially or fully halogenated, aryl, aryl-$C_1$-$C_4$-alkyl, heterocyclyl, and heteroaryl, where the rings in the 4 last mentioned radicals may be substituted with 1, 2, 3, 4, or 5 substituents $R^{15}$;

or $R^{21a}$ and $R^{21b}$, together with the nitrogen atom to which they are bound, form a 3-, 4-, 5-, 6-, 7- or 8-membered saturated, partially unsaturated or maximally unsaturated heterocyclic, inclusive heteroaromatic, ring, where the ring may further contain 1, 2, 3 or 4 heteroatoms or heteroatom-containing groups selected from the group consisting of O, S, N, SO, SO$_2$, C=O and C=S as ring members, wherein the heterocyclic ring may be substituted with 1, 2, 3, 4 or 5 independent $R^{15}$ substituents;

each $R^{22}$ is independently defined as $R^{16}$;

each $R^{23}$ is independently selected from the group consisting of hydrogen, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, and phenyl, optionally substituted with 1, 2, 3, 4, or 5 radicals selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy; and m is 0, 1 or 2;

where the alkyl, alkenyl, alkapolyenyl, alkynyl, alkapolyynyl and mixed alkenyl/alkynyl groups $R^1$, $R^3$ and $R^4$, and the aryl, heteroaryl, benzyl, vinyl and alkyl groups $R^2$ can carry one or more substituents.

17. The method as claimed in claim 13, where the transition metal catalyzed C—C-coupling reaction is a C—C coupling reaction involving C—H activation in which an aromatic or heteroaromatic halogenide or sulfonate is coupled with an aromatic or heteroaromatic compound in the presence of a transition metal catalyst and in case that an aromatic or heteroaromatic chloride, bromide or iodide is used, optionally also in the presence of a water-soluble silver(I) salt;

where the aromatic or heteroaromatic halogenide or sulfonate is a compound of formula $R^2$—Z, where $R^2$ is an aryl or heteroaryl group, Z is a halogen atom or a sulfonate group, and the aromatic or heteroaromatic is a compound of formula $R^1$—H, where $R^1$ is an aryl or heteroaryl group, where the aryl and heteroaryl groups $R^1$ and $R^2$ can carry one or more substituents.

18. The method as claimed in claim 13, where the transition metal catalyzed C—C-coupling reaction is a Stille reaction, where an organotin compound (organostannane) is reacted with an alkenyl, aryl, heteroaryl or acyl halide, sulfonate or phosphate in the presence of a transition metal catalyst and optionally also in the presence of a base, where the organostannane compound is a compound of the formula $R^1$—Sn($R^a$)$_3$, where $R^1$ is a an alkenyl, aryl or heteroaryl group and $R^a$ is an alkyl group, and the alkenyl, aryl, heteroaryl or acyl halide, sulfonate or phosphate is a compound of the formula $R^2-(Z)_n$, where $R^2$ is an alkenyl, aryl, heteroaryl or acyl group, Z is a halogen atom, a sulfonate group or a phosphate group, and n is 1, 2, 3 or 4, where the alkenyl, aryl and heteroaryl groups $R^1$ and $R^2$ can carry one or more substituents.

19. The method as claimed in claim 13, where the transition metal catalyzed C—C-coupling reaction is a Negishi reaction.

20. The method as claimed in claim 13, where the transition metal catalyzed C—C-coupling reaction is a Grubbs olefin metathesis, where two olefinic compounds $R^1R^2C=CR^3R^4$ and $R^5R^6C=CR^7R^8$ are reacted with each other in the presence of a Grubbs catalyst, where $R^1$, $R^2$, $R^3$, $R^4$, $R^5$, $R^6$, $R^7$ and $R^8$, independently of each other, are selected from the group consisting of hydrogen, alkyl, alkenyl, alkynyl, cycloalkyl, cycloalkenyl, cycloalkynyl, mixed cycloalkenyl/cycloalkynyl, polycarbocyclyl, heterocyclyl, aryl, hetaryl, halogen, cyano, nitro, azido, —SCN, —SF$_5$, $OR^{11}$, $S(O)_mR^{11}$, $NR^{12a}R^{12b}$, $C(=O)R^{13}$, $C(=S)R^{13}$, $C(=NR^{12a})R^{13}$ and —Si$(R^{14})_3$; where $R^{11}$, $R^{12a}$, $R^{12b}$, $R^{13}$ and $R^{14}$ are independently as defined in claim 17;

where the alkyl, alkenyl, alkynyl, cycloalkyl, cycloalkenyl, cycloalkynyl, mixed cycloalkenyl/cycloalkynyl, polycarbocyclyl, heterocyclyl, aryl and heteroaryl groups $R^1$, $R^2$, $R^3$, $R^4$, $R^5$, $R^6$, $R^7$ and $R^8$ can carry one or more substituents.

21. The method as claimed in claim 13, where the transition metal catalyzed C—C coupling reaction is a 1,4-addition of an organoborane compound to an α,β-olefinically unsaturated carbonyl compound in the presence of a transition metal catalyst, where the organoboron compound is a compound of formula $R^1$—$BY_2$, where $R^1$ is an alkyl, alkenyl, alkynyl, aryl or heteroaryl group and Y is an alkyl, O-alkyl or hydroxyl group, or the two substituents Y form together with the boron atom they are bound to a mono-, bi- or polycyclic ring; or the organoboron compound is a compound of formula $R^1$—$BF_3M$, where M is a metal equivalent, and the α,β-olefinically unsaturated carbonyl compound is a compound of formula $R^2R^3C=CR^4$—$C(=O)$—$R^5$, where $R^2$, $R^3$ and $R^4$, independently of each other, are hydrogen, alkyl, cycloalkyl, heterocyclyl, aryl or heteroaryl and $R^5$ is hydrogen, alkyl, cycloalkyl, aryl, heteroaryl, OH, SH, alkoxy, alkylthio, $NH_2$, alkylamino or dialkylamino, where the alkyl (also as part of alkoxy, alkylthio, alkylamino or dialkylamino), alkenyl, alkynyl, cycloalkyl, heterocyclyl, aryl or heteroaryl groups $R^1$, $R^2$, $R^3$, $R^4$ and $R^5$ can carry one or more substituents.

22. The method as claimed in claim 13, where the transition metal catalyzed C—C-coupling reaction is a cyclopropanation, where an olefinically unsaturated compound is reacted with a diazo compound in the presence of a transition metal catalyst, where the olefinically unsaturated compound is a compound of formula $R^1R^2C=CR^3R^4$ and the diazo compound is a compound of formula $N_2=CR^5R^6$, where $R^1$, $R^2$, $R^3$, $R^4$, $R^5$ and $R^6$, independently of each other, are selected from the group consisting of hydrogen, alkyl, alkenyl, alkynyl, cycloalkyl, cycloalkenyl, cycloalkynyl, mixed cycloalkenyl/cycloalkynyl, polycarbocyclyl, heterocyclyl, aryl, hetaryl, halogen, cyano, nitro, azido, —SCN, —SF$_5$, $OR^{11}$, $S(O)_mR^{11}$, $NR^{12a}R^{12b}$, $C(=O)R^{13}$, $C(=S)R^{13}$, $C(=NR^{12a})R^{13}$ and —Si$(R^{14})_3$; where $R^{11}$, $R^{12a}$, $R^{12b}$, $R^{13}$ and $R^{14}$ are independently as defined in claim 17;

where the alkyl, alkenyl, alkynyl, cycloalkyl, cycloalkenyl, cycloalkynyl, mixed cycloalkenyl/cycloalkynyl, polycarbocyclyl, heterocyclyl, aryl and heteroaryl groups $R^1$, $R^2$, $R^3$, $R^4$, $R^5$ and $R^6$ can carry one or more substituents.

23. The method as claimed in claim 1, where the transition metal catalyzed reaction is a transition metal catalyzed reaction involving C—O bond formation, where the transition metal catalyzed reaction involving C—O bond formation is an Au-catalyzed cyclodehydratization of alkyne diols, an Au-catalyzed cyclization of alkynenols, an Au-catalyzed cyclization of alkynones, an Au-catalyzed cyclization of allenones, or is the formation of alcohols or ethers via C—O coupling.

24. The method as claimed in claim 23, where the transition metal catalyzed reaction involving C—O bond formation is an Au-catalyzed cyclodehydratization of an alkyne (I) carrying in α- and β-position to the alkyne group two OH groups to the corresponding furane (II):

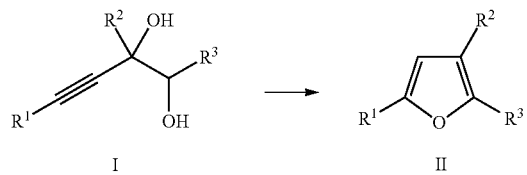

where $R^1$, $R^2$ and $R^3$ are independently of each other H, alkyl, cycloalkyl, aryl, heterocyclyl or heteroaryl, where the alkyl, cycloalkyl, aryl, heterocyclyl or heteroaryl groups $R^1$, $R^2$ and $R^3$ can carry one or more substituents.

25. The method as claimed in claim 23, where the transition metal catalyzed reaction involving C—O bond formation is the formation of alcohols or ethers via C—O coupling, where an aromatic or heteroaromatic compound $R^1$—X, where $R^1$ is an aryl or heteroaryl group and X is a halogen atom or a pseudohalide group, is reacted with a metal hydroxide to yield an alcohol $R^1$—OH; or is reacted with a hydroxyl compound $R^2$—OH, where $R^2$ is alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl or heteroaryl, to yield an ether $R^1$—O—$R^2$, where the alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl or heteroaryl groups $R^1$ and $R^2$ can carry one or more substituents.

26. The method as claimed in claim 1, where the transition metal catalyzed reaction is a transition metal catalyzed reaction involving C—B bond formation, where the transition metal catalyzed reaction involving C—B bond formation is a Miyaura borylation, where a halogenide or sulfonate $R^2-(Z)_n$, where $R^2$ is an alkenyl, aryl or heteroaryl group, Z is a halogenide or sulfonate group and n is 1, 2, 3 or 4, is reacted with a tetraalkoxydiboron $(R^1O)_2B$—$B(OR^1)_2$, where $R^1$ is alkyl or two $R^1$ bound on oxygen atoms bound in turn to the same B atom form together —$C(CH_3)_3$—$C(CH_3)_2$— (so that $B(OR^1)_2$ is the pinacolon ester of boronic acid), in the presence of a transition metal catalyst, and optionally also of a base, where the alkyl, alkenyl, aryl or heteroaryl groups $R^1$ and $R^2$ can carry one or more substituents.

27. The method as claimed in claim 1, where the transition metal catalyzed reaction is a transition metal catalyzed reaction involving C-halogen bond formation, in which an aromatic or heteroaromatic compound $R^1$—H, where $R^1$ is aryl or heteroaryl, is reacted with a halogenating agent in the presence of a transition metal catalyst, to yield a compound $R^1$—X, where X is a halogen atom, where the aryl or heteroaryl group $R^1$ can carry one or more substituents.

28. The method as claimed in claim 1, where the organic reaction is a C—C coupling reaction not requiring transition metal catalysis, and is selected from the group consisting of reactions of carbonyl or nitrile compounds and pericyclic reactions.

29. The method as claimed in claim 28, where the C—C coupling reaction not requiring transition metal catalysis is a Wittig reaction in which a phosphorous ylene or ylide (I) is reacted with a carbonyl compound (II) to an olefinically unsaturated compound (III) and a phosphorus oxide (IV)

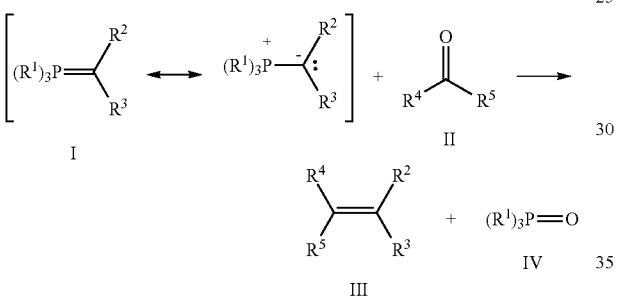

where
$R^1$ is an aryl group;
$R^2$ and $R^3$, independently of each other, are hydrogen, alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl, heteroaryl, CN, C(O)$R^{13}$, C(S)$R^{13}$ or S(O)$_2R^{11}$, where $R^{11}$ and $R^{13}$ are as defined in claim 17; and
$R^4$ and $R^5$ are independently of each other hydrogen, alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl or heteroaryl;
where the alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl and heteroaryl groups $R^1$, $R^2$, $R^3$, $R^4$ and $R^5$ can carry one or more substituents.

30. The method as claimed in claim 28, where the C—C coupling reaction not requiring transition metal catalysis is a Diels-Alder reaction in which a conjugated diene is reacted with a dienophile to a cyclohexene derivative.

31. The method as claimed in claim 28, where the C—C coupling reaction not requiring transition metal catalysis is a Baylis-Hillman reaction in which an α,β-olefinically unsaturated carbonyl compound (I) is reacted with an aldehyde or an activated ketone or derivative thereof (II) in the presence of a nucleophilic catalyst and optionally in the presence of a metal-derived Lewis acid to a compound (III):

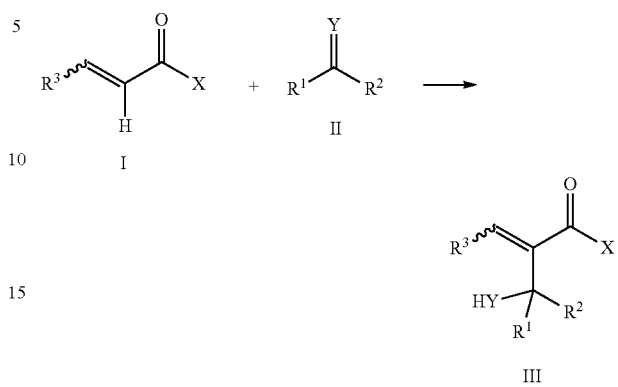

or in which α,β-olefinically unsaturated nitrile (IV) compound is reacted with a an aldehyde or an activated ketone or derivative thereof (II) in the presence of a nucleophilic catalyst and optionally in the presence of a metal-derived Lewis acid to a compound (V):

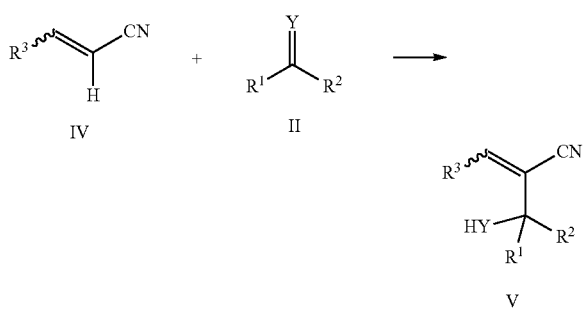

where $R^1$, $R^2$ and $R^3$ are independently of each other H, alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl or heteroaryl, or $R^1$ and $R^2$ form together with the carbon atom they are bound to a carbocyclic or heterocyclic ring;
X is OR or N(R)$_2$, where R is H, alkyl, cycloalkyl, heterocyclyl, aryl or heteroaryl,
Y is O or N substituted with an electron-withdrawing group, and
the nucleophilic catalyst is selected from the group consisting of tertiary amines and tertiary phosphines;
where the alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl and heteroaryl groups $R^1$, $R^2$, $R^3$ and R can carry one or more substituents.

32. The method as claimed in claim 1, where the organic reaction is a nucleophilic substitution reaction, where a compound $R^1$—X is reacted with an alcohol $R^2$—OH, a thiol $R^2$—SH, a primary amine $R^3NH_2$ or a secondary amine $R^3(R^4)NH$ to a compound $R^1$—O—$R^2$, $R^1$—S—$R^2$, $R^1$—NH—$R^3$ or $R^1$—N($R^4$)—$R^3$, or a compound $R^1(X)_2$ is reacted with a primary amine $R^3NH_2$ to a cyclic compound;
where $R^1$, $R^2$, $R^3$ and $R^4$, independently of each other, are an alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl or heteroaryl group; and X is a halogenide or sulfonate group;

where the alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl or heteroaryl groups $R^1$, $R^2$, $R^3$ and $R^4$ can carry one or more substituents.

33. The method as claimed in claim 1, where the organic reaction is a nucleophilic aromatic substitution reaction, where a compound $R^1$—X is reacted with an alcohol $R^2$—OH, a thiol $R^2$—SH, a primary amine $R^3NH_2$ or a secondary amine $R^3(R^4)NH$, where $R^1$ is a mono-, bi- or polycyclic aryl or heteroaryl group;

X is a halide, and $R^2$, $R^3$ and $R^4$ are independently of each other an alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl or heteroaryl group, where the alkyl, alkenyl, alkapolyenyl, alkynyl, alkapolyynyl, mixed alkenyl/alkynyl, cycloalkyl, cycloalkenyl, cycloalkynyl, mixed cycloalkenyl/cycloalkynyl, polycarbocyclyl, heterocyclyl, aryl, heteroaryl groups $R^1$, $R^2$, $R^3$ and $R^4$ can carry one or more substituents.

34. The method as claimed in claim 1, where the organic reaction is the reduction of nitro compounds to the corresponding amino compounds via reduction with a base metal, optionally in acidic solution; with a metal hydride, with a complex hydride, or with a borane; or via catalytic hydrogenation.

35. The method as claimed in claim 34, where an aromatic or heteroaromatic nitro compound $R^1$—$NO_2$, where $R^1$ is a mono-, bi- or polycyclic aryl or heteroaryl group, is reduced with Zn or Fe in acidic solution; or is reduced via catalytic hydrogenation in the presence of a hydrogenation catalyst, where the hydrogenation catalyst comprises at least one metal of group VIII and/or VIIa selected from the group consisting of ruthenium, cobalt, rhodium, nickel, palladium, platinum and rhenium, where the hydrogenation catalyst is a heterogeneous hydrogenation catalyst in which the metal is used in finely divided form, as a metal sponge or as a supported catalyst, or where the catalyst is a homogeneous hydrogenation catalysts;

where the aryl or heteroaryl group $R^1$ can carry one or more substituents.

36. The method as claimed in claim 1, where the organic reaction is the reduction of C—C double bonds.

37. The method as claimed in claim 1, where the organic reaction is a reductive amination, where a primary or secondary amine is reacted with an aldehyde or ketone in the presence of a reduction agent to an amino compound.

38. The method as claimed in claim 1, which is additionally carried out in the presence of a surfactant different from the cellulose derivative as defined in claim 1, where the surfactant is selected from the group consisting of anionic, cationic, nonionic and amphoteric surfactants, block polymers, polyelectrolytes, and mixtures thereof.

39. The method as claimed in claim 38, where the surfactant is a polyoxyethanyl-α-tocopheryl succinate derivative.

40. The method as claimed in claim 1, where after completion of the organic reaction the cellulose derivative is precipitated by heating or by adding an inorganic salt, where the inorganic salt is selected from the group consisting of sodium sulfate, potassium sulfate, magnesium sulfate, ammonium sulfate, sodium phosphate, potassium phosphate, sodium hydrogenphosphate, potassium hydrogenphosphate and sodium chloride; where precipitation of the cellulose derivative can be carried out before or after removing the reaction product and, if present, unreacted starting compounds, and where the precipitated cellulose derivative, after a reactivation step, can be reused in the method as claimed in claim 1.

\* \* \* \* \*